United States Patent
Zhang et al.

(10) Patent No.: US 7,622,585 B2
(45) Date of Patent: Nov. 24, 2009

(54) PHENYLGLYCINAMIDE DERIVATIVES USEFUL AS ANTICOAGULANTS

(75) Inventors: Xiaojun Zhang, Furlong, PA (US);
Eldon Scott Priestley, Yardley, PA (US);
Alexandra A. Nirschl, Yardley, PA (US);
Yan Zou, Levittown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 735 days.

(21) Appl. No.: 11/328,479

(22) Filed: Jan. 9, 2006

(65) Prior Publication Data

US 2006/0166997 A1    Jul. 27, 2006

Related U.S. Application Data

(60) Provisional application No. 60/642,751, filed on Jan. 10, 2005.

(51) Int. Cl.
*C07D 215/38* (2006.01)
(52) U.S. Cl. ........................ 546/148; 546/146
(58) Field of Classification Search ................ 514/307; 546/146, 148
See application file for complete search history.

(56) References Cited

U.S. PATENT DOCUMENTS

| | | | |
|---|---|---|---|
| 5,023,236 | A | 6/1991 | Edgington et al. |
| 5,475,106 | A | 12/1995 | Bourzat et al. |
| 5,602,101 | A * | 2/1997 | Schacht et al. ............. 514/18 |
| 5,843,442 | A | 12/1998 | Soule et al. |
| 5,866,542 | A | 2/1999 | Vlasuk et al. |
| 6,140,353 | A | 10/2000 | Ackermann et al. |
| 6,194,409 | B1 | 2/2001 | van Boeckel et al. |
| 6,242,644 | B1 | 6/2001 | Ackermann et al. |
| 6,335,324 | B1 | 1/2002 | Bisacchi et al. |
| 6,358,960 | B1 | 3/2002 | Senokuchi et al. |
| 6,472,393 | B1 | 10/2002 | Aliagas-Martin et al. |
| 6,642,252 | B2 | 11/2003 | Bisacchi et al. |
| 6,699,994 | B1 | 3/2004 | Babu et al. |
| 6,900,207 | B2 | 5/2005 | Ohmoto et al. |
| 2003/0166694 | A1 | 9/2003 | Dorsch et al. |
| 2004/0176375 | A1 | 9/2004 | Bisacchi et al. |
| 2004/0204412 | A1 | 10/2004 | Glunz et al. |
| 2005/0107409 | A1 | 5/2005 | Priepke et al. |
| 2006/0211720 | A1 | 9/2006 | Glunz et al. |
| 2007/0003539 | A1 | 1/2007 | Zhang et al. |

FOREIGN PATENT DOCUMENTS

| | | |
|---|---|---|
| DE | 10310278 | 9/2004 |
| WO | WO 96/20689 | 7/1996 |
| WO | WO 97/10214 | 3/1997 |
| WO | WO 01/44172 | 6/2001 |
| WO | WO 01/90051 | 11/2001 |
| WO | WO 02/09688 | 2/2002 |
| WO | WO 02/34711 | 5/2002 |
| WO | WO 03/013531 | 2/2003 |
| WO | WO 03/066588 | 8/2003 |
| WO | WO 03/084533 | 10/2003 |
| WO | WO 2004/072101 | 8/2004 |
| WO | WO 2005/054430 | 6/2005 |

OTHER PUBLICATIONS

Carson, S.D. et al., "The role of tissue factor in the production of thrombin", Blood Coagulation and Fibrinolysis, vol. 4, pp. 281-292 (1993).
Colman, R.W., Chapter 6: "Contact Activation Pathway: Inflammatory, Fibrinolytic, Anticoagulant, Antiadhesive, and Antiangiogenic Activities", Hemostasis and Thrombosis: Basic Principles and Clinical Practice, $4^{th}$ Ed., Lippincott Williams & Wilkins, publ., Colman, R.W. et al., eds., pp. 103-121 (2001).
Girard, T.J. et al., "The role of tissue factor/factor VIIa in the pathophysiology of acute thrombotic formation", Current Opinion in Pharmacology, vol. 1, pp. 159-163 (2001).
Goodnight, S.H. et al., Chapter 4: "Screening Tests of Hemostasis", Disorders of Hemostasis and Thrombosis: A Clinical Guide, The McGraw-Hill Companies, publ., pp. 41-51 (2001).
Schmaier, A.H., Chapter 5: "Contact Activation", Hemostasis and Thrombosis: Basic Principles and Clinical Practice, $4^{th}$ Ed., Lippincott Williams & Wilkins, publ., Colman, R.W. et al., eds., pp. 105-127 (2001).

* cited by examiner

*Primary Examiner*—D. Margaret Seaman
(74) *Attorney, Agent, or Firm*—Jing G. Sun

(57) ABSTRACT

The present invention relates generally to phenylglycinamide derivatives that inhibit serine proteases. In particular it0 is directed to novel phenylglycinamide derivatives, and analogues thereof, which are useful as selective inhibitors of serine protease enzymes of the coagulation cascade; for example thrombin, factor VIIa, factor Xa, factor XIa, factor IXa, and/or plasma kallikrein. In particular, it relates to compounds that are factor VIIa inhibitors. This invention also relates to pharmaceutical compositions comprising these compounds and methods of using the same.

23 Claims, No Drawings

PHENYLGLYCINAMIDE DERIVATIVES USEFUL AS ANTICOAGULANTS

CROSS-REFERENCE TO RELATED APPLICATIONS

The present application claims the priority benefit of U.S. Provisional Application No. 60/642,751, filed Jan. 10, 2005, which is expressly incorporated fully herein by reference.

FIELD OF THE INVENTION

The present invention provides novel phenylglycinamide derivatives and analogues thereof, which are selective inhibitors of serine protease enzymes of the coagulation cascade and/or contact activation system; for example thrombin, factor VIIa, factor Xa, factor XIa, factor IXa, and/or plasma kallikrein. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the initiation of the coagulation cascade. It binds with high affinity to tissue factor in the presence of calcium ions to form a complex with enhanced proteolytic activity (Carson, S. D. and Brozna, J. P. *Blood Coag. Fibrinol.* 1993, 4, 281-292). The tissue factor/factor VIIa complex initiates blood coagulation by proteolytic cleavage of factor X to factor Xa, factor IX to factor IXa and additional factor VII to VIIa. Ultimately, the activity of factor VIIa induces the conversion of prothrombin to thrombin. Thrombin coverts fibrinogen to fibrin, which forms a clot through polymerization.

While blood coagulation is essential to the regulation of an organism's hemostasis, it is also involved in many pathological conditions. For instance, thrombosis, or formation of a clot which obstructs circulation, plays a key role in unstable angina, myocardial infarction, ischemic stroke, deep vein thrombosis, peripheral occlusive arterial disease, pulmonary embolism, and other diseases.

Because of its key role in the coagulation cascade, researchers have postulated that inhibition of factor VIIa could be used to treat or prevent thrombotic disease. (Girard, T. J.; Nicholson, N. S. *Curr. Opin. Pharmacol.* 2001, 1, 159-163). Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytically active factor XII (factor XIIa and factor XIIf). Factor XIIa (or XIIf) has a number of target proteins, including plasma prekallikrein and factor XI. Active plasma kallikrein further activates factor XII, leading to an amplification of contact activation. Activated FXI acts on FIX, which acts through the coagulation cascade to produce thrombin. Thus, inhibitors of plasma kallikrein would be expected to exert an antithrombotic effect under conditions of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wiliins 2001; Schmaier A. H. *Contact Activation*, pages 105-128 in *Thrombosis and Hemorrhage*, 1998).

Plasma kallikrein is a zymogen of a trypsin-like serine protease and is present in plasma at 35 to 50 µg/mL. The gene structure is similar to that of factor XI; overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). Inhibitors of plasma kallikrein would be expected to reduce potential for bradykinin release and thus to exert an anti-inflammatory effect.

While a number of factor VIIa inhibitors have been discussed in the art, improved inhibitors, especially non-peptide inhibitors, of serine proteases for the treatment of thromboembolic disorders are always desirable. The present invention discloses phenylglycinamide derivatives and analogues thereof as inhibitors of coagulation Factor VIIa and, as such, their utility in the treatment of thromboembolic disorders.

In addition, it is also desirable to find new compounds with improved pharmacological characteristics compared with known serine protease inhibitors. For example, it is preferred to find new compounds with improved factor VIIa inhibitory activity and selectivity for factor VIIa versus other serine proteases. Also, it is preferred to find new compounds with improved plasma kallikrein inhibitory activity and selectivity for plasma kallikrein versus other serine proteases. Also, it is preferred to find new compounds with improved activity in in vitro clotting assays, such as the prothrombin time (PT) assay or activated partial thromboplastin time assay (APTT) (for a description of the PT and APTT assays see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmaceutical properties, including oral bioavailability; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

The present invention provides novel phenylglycinamide derivatives, and analogues thereof, which are useful as selective inhibitors of serine protease enzymes, especially factor VIIa.

The present invention also provides processes and intermediates for making the compounds of the present invention or stereoisomers, tautomers, pharmaceutically acceptable salts, solvates, or prodrug forms thereof.

The present invention also provides pharmaceutical compositions comprising a pharmaceutically acceptable carrier and a therapeutically effective amount of at least one of the compounds of the present invention, or a stereoisomer, tautomer, pharmaceutically acceptable salt, solvate, or prodrug thereof.

The present invention also provides a method for modulation of the coagulation cascade and/or the contact activation system comprising administering to a host in need of such treatment a therapeutically effective amount of at least one of the compounds of the present invention or a stereoisomer, tautomer, pharmaceutically acceptable salt, solvate, or prodrug thereof.

The present invention also provides a method for treating thromboembolic disorders comprising administering to a host in need of such treatment a therapeutically effective amount of at least one of the compounds of the present invention or a stereoisomer, tautomer, pharmaceutically acceptable salt, solvate, or prodrug thereof.

The present invention also provides a method for treating inflammatory disorders comprising administering to a host in need of such treatment a therapeutically effective amount of at least one of the compounds of the present invention or a stereoisomer, tautomer, pharmaceutically acceptable salt or prodrug thereof.

The present invention also provides novel phenylglycinamide derivatives, and analogues thereof, for use in therapy.

The present invention also provides the use of novel phenylglycinamide derivatives, and analogues thereof, for the manufacture of a medicament for the treatment of a thromboembolic disorder.

The present invention also provides the use of phenylglycinamide derivatives, and analogues thereof, for the manufacture of a medicament for the treatment of an inflammatory disorder.

These and other features of the invention will be set forth in the expanded form as the disclosure continues.

DETAILED DESCRIPTION OF THE INVENTION

In a first embodiment, the present invention provides, inter alia, a compound of Formula (I):

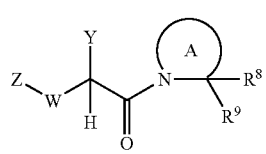

(I)

or a stereoisomer, tautomer, pharmaceutically acceptable salt, solvate, or prodrug thereof, wherein:

Y is selected from:

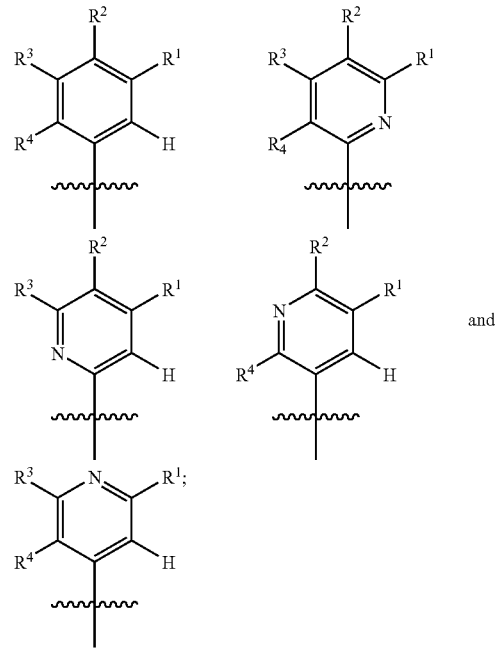

and $R^1$ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

$R^2$ and $R^3$ are, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle is substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;

W is NH or O;

Z is substituted with 0-2 R$^6$ and selected from:

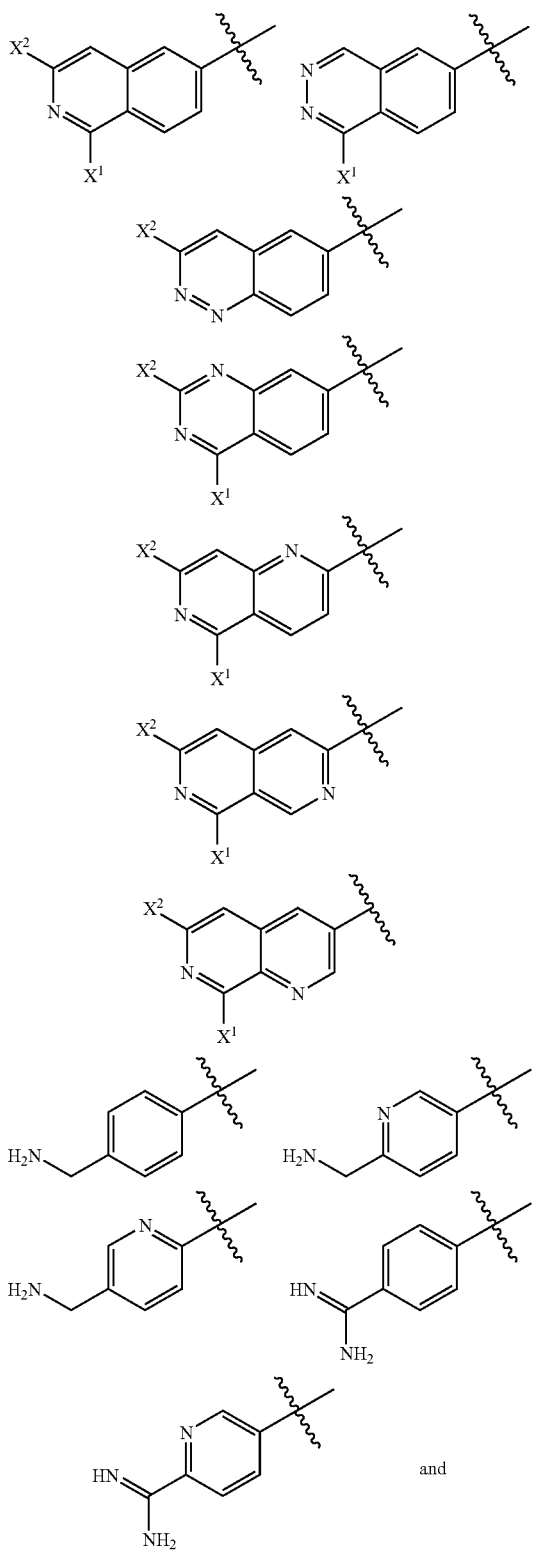

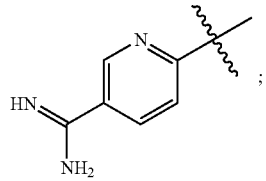

and

R$^6$ is, independently at each occurrence, F, Cl, Br, I, CN, OH, CF$_3$, C$_{1-4}$ alkyl, C$_{1-4}$ haloalkyl, or C$_{1-4}$ alkoxy;

X$^1$ and X$^2$ are, independently at each occurrence, H or NH$_2$;

ring A is a 4- to 8-membered heterocycle comprising: the nitrogen atom shown in the ring, carbon atoms and 0-1 additional heteroatom selected from N, NR$^c$, O, and S(O)$_p$, 0-1 carbonyl, and 0-2 double bonds, wherein said heterocycle is substituted with 0-2 R$^7$;

R$^7$ is, independently at each occurrence, OR$^a$, F, Cl, Br, I, CN, NO$_2$, —OCF$_3$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —SO$_2$NHC(O)R$^a$, —C(O)NHSO$_2$R$^a$, —NR$^c$SO$_2$CF$_3$, —SO$_2$CF$_3$, —S(O)$_p$R$^i$, —(CF$_2$)$_r$CF$_3$, tetrazole, —(CH$_2$)$_r$-phenyl substituted with 0-3 R$^f$, or a —(CH$_2$)$_r$-5- to 6-membered heterocycle comprising: carbon atoms and 1-4 heteroatoms selected from N, NR$^c$, O, and S(O)$_p$, wherein said heterocycle is substituted with 0-3 R$^f$;

R$^8$ is H, CN, —CO$_2$R$^a$, —C(O)NR$^c$R$^d$, tetrazolyl, or C$_{1-4}$ alkyl substituted with 0-2 R$^{8a}$;

R$^{8a}$ is, independently at each occurrence, =O, OR$^a$, F, Cl, Br, I, CN, NO$_2$, —OCF$_3$, —NR$^b$R$^c$, —C(O)R$^a$, —CO$_2$R$^a$, —OC(O)R$^a$, —OC(O)NR$^c$R$^d$, —NR$^d$C(O)R$^a$, —C(O)NR$^c$R$^d$, —NR$^c$C(O)NR$^c$R$^d$, NR$^c$C(O)OR$^a$, —SO$_2$NR$^c$R$^d$, —NR$^c$SO$_2$R$^i$, —NR$^c$SO$_2$NR$^c$R$^d$, —SO$_2$NHC(O)R$^a$, —C(O)NHSO$_2$R$^a$, —NR$^c$SO$_2$CF$_3$, —SO$_2$CF$_3$, —S(O)$_p$R$^i$, —(CF$_2$)$_r$CF$_3$, tetrazole, C$_{3-6}$ cycloalkyl substituted with 0-3 R$^f$, phenyl substituted with 0-3 R$^f$, or 5- to 6-membered heterocycle comprising: carbon atoms and 1-4 heteroatoms selected from N, NR$^c$, O, and S(O)$_p$, wherein said heterocycle is substituted with 0-3 R$^f$;

R$^9$ is phenyl substituted with 0-3 R$^{10}$, naphthyl substituted with 0-3 R$^{10}$, or a 5- to 10-membered heterocycle comprising: carbon atoms and 1-4 heteroatoms selected from N, NR$^c$, O, and S(O)$_p$, wherein said heterocycle is substituted with 0-3 R$^{11}$;

R$^{10}$ is, independently at each occurrence, F, Cl, Br, I, —(CH$_2$)$_r$OR$^a$, SR$^a$, OCF$_3$, SCF$_3$, CN, NO$_2$, —B(OH)$_2$, —(CH$_2$)$_r$—NR$^b$R$^c$, —C(O)R$^a$, —(CH$_2$)$_r$—CO$_2$R$^a$, —(CH$_2$)$_r$NR$^c$CO$_2$R$^a$, —NR$^d$C(O)R$^a$, —(CH$_2$)$_r$—C(O)NR$^c$R$^d$, —NR$^c$C(O)NR$^c$R$^d$, —SO$_2$NR$^c$R$^d$, —OSO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^f$, or —(CH$_2$)$_r$-5- to 10-membered heterocycle comprising: carbon atoms and 1-4 heteroatoms selected from N, NR$^c$, O, and S(O)$_p$, wherein said heterocycle are substituted with 0-3 R$^f$;

R$^{11}$ is, independently at each occurrence, =O, F, Cl, Br, I, —(CH$_2$)$_r$—OR$^a$, SR$^a$, OCF$_3$, SCF$_3$, CN, NO$_2$, —B(OH)$_2$, —(CH$_2$)$_r$—NR$^b$R$^c$, —C(O)R$^a$, —(CH$_2$)$_r$CO$_2$R$^a$, —(CH$_2$)$_r$NR$^c$CO$_2$R$^a$, —NR$^d$C(O)R$^a$, —(CH$_2$)$_r$—C(O)NR$^c$R$^d$, —NR$^c$C(O)NR$^c$R$^d$, —SO$_2$NR$^c$R$^d$, —OSO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$, —(CH$_2$)$_r$—C$_{3-10}$ carbocycle substituted with 0-3 R$^f$, —(CH$_2$)$_r$-5- to 10-membered heterocycle comprising: carbon atoms and 1-4 heteroatoms selected from N, NR$^c$, O, and S(O)$_p$, wherein said heterocycle are substituted with 0-3 R$^f$;

R$^a$ is, independently at each occurrence, H, C$_{1-6}$ alkyl substituted with 0-4 R$^h$, —(CH$_2$)$_r$—C$_{3-7}$ carbocycle substituted with 0-4 R$^f$, or —(CH$_2$)$_r$-5- to 10-membered heterocycle comprising: carbon atoms and 1-4 heteroatoms selected from N, NR$^g$, O, and S(O)$_p$, wherein said heteroaryl is substituted with 0-4 R$^f$;

R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$alkyl-C(O)—, (C$_{6-10}$ aryl)-(C$_{0-4}$alkyl)-C(O)—, (5- to 10-membered heteroaryl)-C$_{0-4}$ alkyl-C(O)—, (C$_{1-6}$ alkyl)-NHC(O)—, (C$_{1-6}$ alkyl)$_2$—NHC(O)—, (C$_{6-10}$ aryl)-C$_{0-4}$ alkyl-NHC(O)—, (5- to 10-membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, or (5- to 10-membered heteroaryl)-C$_{0-4}$ alkyl-SO$_2$—, wherein said phenyl, aryl and heteroaryl are substituted with 0-2 R$^f$;

R$^c$ is, independently at each occurrence, H, C$_{1-6}$ alkyl substituted with 0-3 R$^h$, —(CH$_2$)$_n$—C$_{3-7}$ cycloalkyl substituted with 0-3 R$^h$, or —(CH$_2$)$_n$-phenyl substituted with 0-3 R$^h$;

alternatively, R$^b$ and R$^c$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^d$ is, independently at each occurrence, H, C$_{1-6}$ alkyl, —(CH$_2$)$_r$—C$_{3-10}$ carbocycle substituted with 0-3 R$^f$, or a —(CH$_2$)$_r$-5- to 12-membered heterocycle comprising: carbon atoms and 1-4 heteroatoms selected from N, NR$^g$, O, and S(O)$_p$, wherein said heterocycle is substituted with 0-3 R$^f$;

alternatively, R$^c$ and R$^d$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^g$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

R$^h$ is, independently at each occurrence, =O, —(CH$_2$)$_r$ OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$ —NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$—C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;
p, at each occurrence, is selected from 0, 1, and 2; and
r, at each occurrence, is selected from 0, 1, 2, 3, and 4.

In a second embodiment, the present invention provides a compound of Formula (I) or a stereoisomer, tautomer, pharmaceutically acceptable salt, solvate, or prodrug thereof, wherein:

R$^1$ is, independently at each occurrence, H, F, Cl, Br, C$_{1-3}$ alkyl substituted with 0-1 OH, C$_{1-3}$ haloalkyl, C$_{2-3}$ alkenyl, C$_{2-3}$ alkynyl, —O—C$_{1-3}$ alkyl, or C$_{3-6}$ cycloalkyl;
W is NH or O;
Z is substituted with 0-2 R$^6$ and selected from:

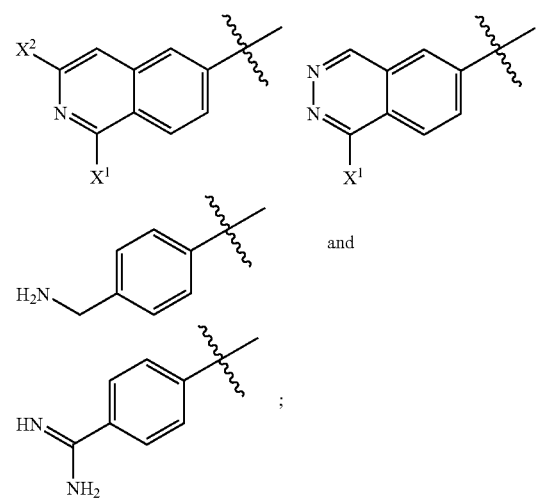

ring A is a 4- to 7-membered heterocycle comprising: the nitrogen atom shown in the ring, carbon atoms and 0-1 additional heteroatom selected from N, $NR^c$, O, and $S(O)_p$, wherein said heterocycle is substituted with 0-2 $R^7$; and $R^9$ is phenyl substituted with 0-3 $R^{10}$, naphthyl, or a heterocycle substituted With 0-3 $R^{11}$ and selected from: furyl, thienyl, thiazolyl, imidazolyl, pyrazolyl, pyridyl, dihydroindolyl, indolyl, or 2,3-dihydro-1,4-benzodioxinyl.

In a third embodiment, the present invention includes a compound of Formula (Ia):

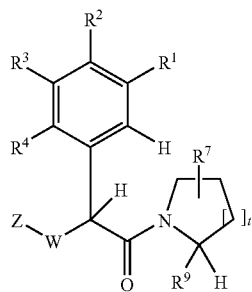

(Ia)

or a stereoisomer, tautomer, pharmaceutically acceptable salt, solvate, or prodrug thereof, wherein:

$R^1$ is H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-6}$ cycloalkyl;

$R^2$ and $R^3$ are, independently at each occurrence, H, F, Cl, Br, I, $OR^a$, $SR^a$, $OCF_3$, CN, $NO_2$, —$NR^bR^c$, —C(O)$R^a$, —$CO_2R^a$, —$NR^dC(O)R^a$, —C(O)$NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —S(O)$_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —C(O)$R^a$, —$CO_2R^a$, —$NR^dC(O)R^a$, —C(O)$NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —S(O)$_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

Z is substituted with 0-2 $R^6$ and selected from:

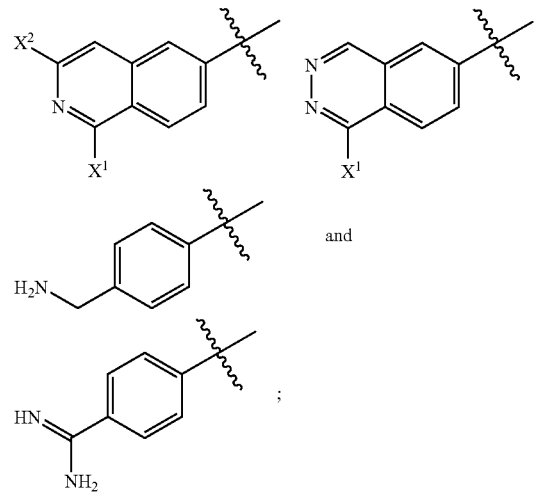

W is NH or O;

$R^6$ is, independently at each occurrence, F, Cl, $CH_3$, OH or $CF_3$;

$X^1$ and $X^2$ are, independently at each occurrence, H or $NH_2$;

$R^7$ is, independently at each occurrence, $OR^a$, F, Cl, Br, I, CN, $NO_2$, —$OCF_3$, —$NR^bR^c$, —C(O)$R^a$, —$CO_2R^a$, —$NR^dC(O)R^a$, —C(O)$NR^cR^d$, —$SO_2NR^cR^d$, —$NR^cSO_2R^i$, —$SO_2NHC(O)R^a$, —C(O)$NHSO_2R^a$, —$NR^cSO_2CF_3$, —$SO_2CF_3$, —S(O)$_pR^i$, —$(CF_2)_rCF_3$, tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is selected from:

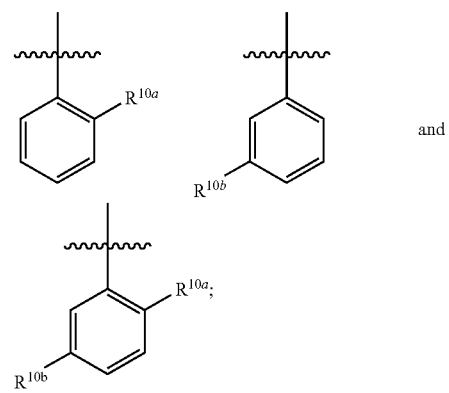

and $R^{10a}$ and $R^{10b}$ are, independently at each occurrence, H, F, Cl, Br, I, —$(CH_2)_rOR^a$, $SR^a$, $OCF_3$, $SCF_3$, CN, $NO_2$, —$B(OH)_2$, —$(CH_2)_rNR^bR^c$, —C(O)$R^a$, —$(CH_2)_r$—$CO_2R^a$, —$(CH_2)_r$—$NR^cCO_2R^a$, —$NR^dC(O)R^a$, —$(CH_2)_r$—C(O)$NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —S(O)$_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heteroaryl is substituted with 0-4 $R^f$;

$R^b$ is, independently at each occurrence, H, $C_{1-6}$ alkyl, —$(CH_2)_n$-phenyl, $(C_{1-6}$ alkyl)C(O)—, $(C_{3-6}$ cycloalkyl)-$C_{0-4}$alkyl-C(O)—, $(C_{6-10}$ aryl)-$(C_{0-4}$ alkyl)-C(O)—, (5- to 10-membered heteroaryl)-$C_{0-4}$ alkyl-C(O)—, $(C_{1-6}$ alkyl)-NHC(O)—, $(C_{1-6}$ alkyl)$_2$—NHC(O)—, $(C_{6-10}$ aryl)-$C_{0-4}$ alkyl-NHC(O)—, (5- to 10-membered heteroaryl)-$C_{0-4}$ alkyl-NHC(O)—, $(C_{1-6}$ alkyl)-$SO_2$—, $(C_{6-10}$ aryl)-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each occurrence, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each occurrence, =O, $OR^a$, F, Cl, Br, I, CN, $NO_2$, —$SR^a$, —$OCF_3$, —$NR^bR^c$, —$C(O)R^a$, —$CO_2R^a$, —$NR^dC(O)R^a$, —$C(O)NR^cR^d$, —$OC(O)R^a$, —$NR^dC(O)OR^a$, —$NR^dC(O)NR^cR^d$, —$OC(O)NR^cR^d$, —$SO_2NR^cR^d$, —$NC(O)OR^a$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, —$SR^g$, —$OCF_3$, —$NR^cR^c$, —$C(O)R^g$, —$CO_2R^g$, —$NR^cC(O)R^g$, —$C(O)NR^cR^c$, —$OC(O)R^g$, —$NR^cC(O)OR^f$, —$NR^cC(O)NR^cR^c$, —$OC(O)NR^cR^c$, —$SO_2NR^cR^c$, —$NR^cSO_2NR^cR^c$, —$NR^cSO_2R^i$, —$NR^cSO_2CF_3$, —$SO_2CF_3$, —$S(O)_pR^i$, —$(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each occurrence, H, $C_{1-6}$ alkyl, or —$(CH_2)_n$-phenyl;

$R^h$ is, independently at each occurrence, =O, —$(CH_2)_r$$OR^g$, F, Cl, Br, I, CN, $NO_2$, —$OCF_3$, —$NR^gR^g$, —$C(O)R^g$, —$CO_2R^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$SO_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, $(C_{1-6}$ alkyl)C(O)—, $(C_{3-6}$ cycloalkyl)-$C_{0-4}$ alkyl-C(O)—, $(C_{6-10}$ aryl)-$(C_{0-4}$ alkyl)-C(O)—, (5-10 membered heteroaryl)-$C_{0-4}$ alkyl-C(O)—, $(C_{1-6}$ alkyl)-NHC(O)—, $(C_{1-6}$ alkyl)$_2$—NHC(O)—, $(C_{6-10}$ aryl)-$C_{0-4}$ alkyl-NHC(O)—, (5-10 membered heteroaryl)-$C_{0-4}$ alkyl-NHC(O)—, $(C_{1-6}$ alkyl)-$SO_2$—, $(C_{6-10}$ aryl)-$C_{0-4}$ alkyl-$SO_2$—, (5-10 membered heteroaryl)-$C_{0-4}$ alkyl-$SO_2$—, —$(CH_2)_r$—$C_{3-10}$ carbocycle, or a —$(CH_2)_r$-5- to 12-membered heterocycle comprising: carbon atoms and 1-4 heteroatoms selected from N, $NR^g$, O, and $S(O)_p$;

$R^i$ is, independently at each occurrence, H, $C_{1-6}$ alkyl substituted with 0-3 $R^h$, $C_{3-6}$ cycloalkyl substituted with 0-3 $R^h$, —$(CH_2)_n$-phenyl substituted with 0-3 $R^h$, —$(CH_2)_r$-5- to 10-membered heterocycle comprising: carbon atoms and 1-4 heteroatoms selected from N, $NR^g$, O, and $S(O)_p$, wherein said heterocycle is substituted with 0-3 $R^h$;

n, at each occurrence, is selected from 0, 1, 2, 3, and 4;

p, at each occurrence, is selected from 0, 1, and 2;

r, at each occurrence, is selected from 0, 1, 2, 3, and 4; and t is selected from 0, 1, 2, and 3.

In a fourth embodiment, the present invention includes a compound of Formula (Ia) or a stereoisomer, tautomer, pharmaceutically acceptable salt, solvate, or prodrug thereof, wherein:

$R^1$ is H, F, Cl, Br, Me, Et, vinyl, 2-propenyl, ethynyl, —CH(OH)Me, OMe, OEt, cyclopropyl, —$OCHF_2$, or —$OCF_2CHF_2$;

$R^2$ and $R^3$ are, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$, $C_{3-6}$ cycloalkyl substituted with 0-3 $R^f$, phenyl substituted with 0-3 $R^f$, or a 5- to 6-membered heterocycle comprising: carbon atoms and 1-4 heteroatoms selected from N, $NR^c$, O, and $S(O)_p$, wherein said heterocycle are substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-6}$ cycloalkyl substituted with 0-3 $R^f$, phenyl substituted with 0-3 $R^f$, or a 5- to 6-membered heterocycle comprising: carbon atoms and 1-4 heteroatoms selected from N, $NR^c$, O, and $S(O)_p$, wherein said heterocycle are substituted with 0-3 $R^f$;

Z is substituted with 0-1 $R^6$ and selected from:

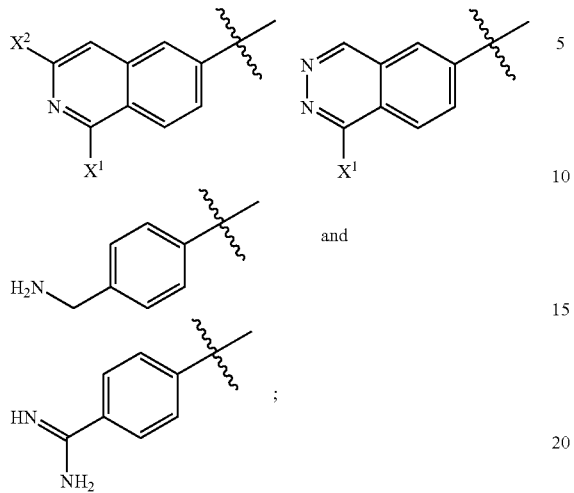

$R^a$ is, independently at each occurrence, H, $C_{1-6}$ alkyl substituted with 0-2 $R^h$, —$(CH_2)_r$—$C_{3-6}$ cycloalkyl substituted with 0-2 $R^f$, —$(CH_2)_r$-phenyl substituted with 0-3 $R^f$, or —$(CH_2)_r$-5- to 6-membered heterocycle comprising: carbon atoms and 1-4 heteroatoms selected from N, $NR^g$, O, and $S(O)_p$, wherein said heteroaryl is substituted with 0-3 $R^f$;

$R^b$ is, independently at each occurrence, H, $C_{1-6}$ alkyl, —$(CH_2)_n$-phenyl, ($C_{1-6}$ alkyl)C(O)—, ($C_{3-6}$ cycloalkyl)-$C_{0-4}$ alkyl-C(O)—, phenyl-($C_{0-4}$ alkyl)-C(O)—, (5- to 6-membered heteroaryl)-$C_{0-4}$ alkyl-C(O)—, ($C_{1-6}$ alkyl)-NHC(O)—, ($C_{1-6}$ alkyl)$_2$—NHC(O)—, phenyl-$C_{0-4}$ alkyl-NHC(O)—, (5- to 6-membered heteroaryl)-$C_{0-4}$ alkyl-NHC(O)—, ($C_{1-6}$ alkyl)-$SO_2$—, phenyl-$C_{0-4}$ alkyl-$SO_2$—, or (5- to 6-membered heteroaryl)-$C_{0-4}$ alkyl-$SO_2$—, wherein said phenyl and heteroaryl are substituted with 0-2 $R^f$;

$R^c$ is, independently at each occurrence, H, $C_{1-6}$ alkyl substituted with 0-3 $R^h$, —$(CH_2)_n$—$C_{3-6}$ cycloalkyl substituted with 0-2 $R^h$, or —$(CH_2)_n$-phenyl substituted with 0-3 $R^h$;

$R^d$ is, independently at each occurrence, H, $C_{1-6}$ alkyl, —$(CH_2)_n$—$C_{3-6}$ cycloalkyl substituted with 0-2 $R^f$, —$(CH_2)_r$-phenyl substituted with 0-3 $R^f$, or a —$(CH_2)_r$-5- to 10-membered heterocycle comprising: carbon atoms and 1-4 heteroatoms selected from N, $NR^g$, O, and $S(O)_p$, wherein said heterocycle is substituted with 0-3 $R^f$;

$R^e$ is, independently at each occurrence, =O, $OR^a$, F, Cl, Br, I, CN, $NO_2$, —$SR^a$, —$OCF_3$, —$NR^bR^c$, —$C(O)R^a$, —$CO_2R^a$, —$NR^dC(O)R^a$, —$C(O)NR^cR^d$, —$OC(O)R^a$, —$NR^dC(O)OR^a$, —$NR^dC(O)NR^cR^d$, —$OC(O)NR^cR^d$, —$SO_2NR^cR^d$, —$NC(O)OR^a$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{3-6}$ cycloalkyl substituted with 0-2 $R^f$, phenyl substituted with 0-3 $R^f$, or a 5- to 10-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, —$SR^g$, —$OCF_3$, —$NR^cR^c$, —$C(O)R^g$, —$CO_2R^g$, —$NR^cC(O)R^g$, —$C(O)NR^cR^c$, —$OC(O)R^g$, —$NR^cC(O)OR^g$, —$NR^cC(O)NR^cR^c$, —$OC(O)NR^cR^c$, —$SO_2NR^cR^c$, —$NR^cSO_2NR^cR^c$, —$NR^cSO_2R^i$, —$NR^cSO_2CF_3$, —$SO_2CF_3$, —$S(O)_pR^i$, —$(CF_2)_rCF_3$, $C_{1-6}$ alkyl, $C_{2-6}$ alkenyl, $C_{2-6}$ alkynyl, $C_{3-6}$ cycloalkyl substituted with 0-2 $R^f$, phenyl substituted with 0-3 $R^f$, or a 5- to 10-membered heterocycle comprising: carbon atoms and 1-4 heteroatoms selected from N, $NR^g$, O, and $S(O)_p$, and substituted with 0-3 $R^h$;

$R^h$ is, independently at each occurrence, =O, —$(CH_2)_r$ $OR^g$, F, Cl, Br, I, CN, $NO_2$, —$OCF_3$, —$NR^gR^g$, —$C(O)R^g$, —$CO_2R^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$SO_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, ($C_{1-6}$ alkyl)C(O)—, ($C_{3-6}$ cycloalkyl)-$C_{0-4}$ alkyl-C(O)—, ($C_{6-10}$ aryl)-($C_{0-4}$ alkyl)-C(O)—, (5-10 membered heteroaryl)-$C_{0-4}$ alkyl-C(O)—, ($C_{1-6}$ alkyl)-NHC(O)—, ($C_{1-6}$ alkyl)$_2$—NHC(O)—, ($C_{6-10}$ aryl)-$C_{0-4}$ alkyl-NHC(O)—, (5-10 membered heteroaryl)-$C_{0-4}$ alkyl-NHC(O)—, ($C_{1-6}$ alkyl)-$SO_2$—, ($C_{6-10}$ aryl)-$C_{0-4}$ alkyl-$SO_2$—, (5-10 membered heteroaryl)-$C_{0-4}$ alkyl-$SO_2$—, $C_{3-6}$ cycloalkyl, phenyl, or a —$(CH_2)_r$-5- to 10-membered heterocycle comprising: carbon atoms and 1-4 heteroatoms selected from N, $NR^g$, O, and $S(O)_p$; and $R^i$ is, independently at each occurrence, H, $C_{1-6}$ alkyl substituted with 0-3 $R^h$, $C_{3-6}$ cycloalkyl substituted with 0-3 $R^h$, —$(CH_2)_n$-phenyl substituted with 0-3 $R^h$, —$(CH_2)_r$-5- to 6-membered heterocycle comprising: carbon atoms and 1-4 heteroatoms selected from N, $NR^g$, O, and $S(O)_p$, wherein said heterocycle is substituted with 0-3 $R^h$.

In a fifth embodiment, the present invention includes a compound of Formula (Ib):

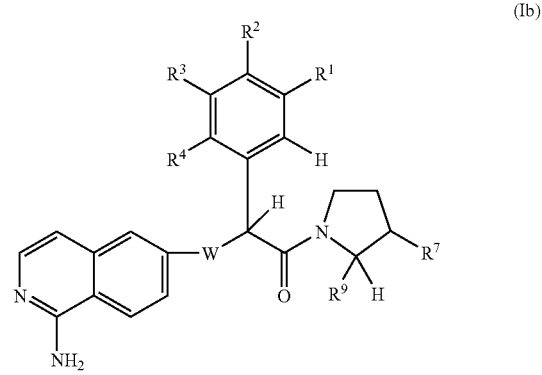

(Ib)

or a stereoisomer, tautomer, pharmaceutically acceptable salt, solvate, or prodrug thereof, wherein:

W is NH or O;

$R^1$ is H, F, Cl, Br, Me, Et, vinyl, 2-propenyl, ethynyl, —CH(OH)Me, OMe, OEt, cyclopropyl, —$OCHF_2$, or —$OCF_2CHF_2$;

$R^2$ is H, F, Cl, Me, Et, OMe, O(i-Pr), or —$OCHF_2$;

$R^3$ is H, OMe, or OEt;

$R^4$ is H or F;

$R^7$ is H, $CO_2H$, $CO_2Me$, $CO_2Et$, or $CONMe_2$;

$R^9$ is selected from:

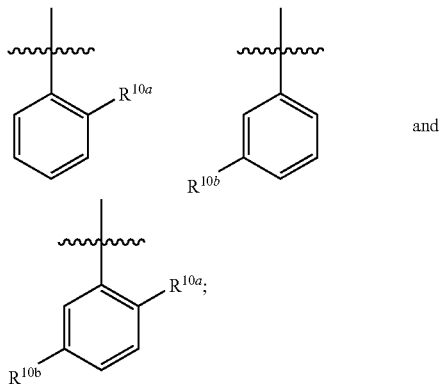

and

R[10a] and R[10b] are, independently at each occurrence, H, $C_{1-4}$ alkyl, F, Cl, OH, —O—$C_{1-4}$ alkyl, —S—$C_{1-4}$ alkyl, $CF_3$, $OCF_3$, $SCF_3$, $CO_2Me$, $CONH_2$, $NH_2$, NHMe, NHEt, $NMe_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCO-(1-azetidinyl), —NHCO-(1-pyrrolidinyl), —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, NO$_2$, or —B(OH)$_2$.

In a sixth embodiment, the present invention includes a compound of Formula (Ib) or a stereoisomer, tautomer, pharmaceutically acceptable salt, solvate, or prodrug thereof, wherein:

W is NH;

$R^1$ is H, F, Cl, Et, OMe, or OEt;

$R^{10a}$ is, independently at each occurrence, H, —SO$_2$—$C_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—$C_{1-14}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl; and $R^{10b}$ is, independently at each occurrence, H, OH, NH$_2$, —NHCOH, —NHCOMe, —NHCOEt, —NHCO$_2$Me, —NHCO$_2$Et, —NHCONHMe, —NHCONH$_2$, —NHCONMe$_2$, —NHCON(Me)Et, —NHCO-(1-azetidinyl), —NHCO-(1-pyrrolidinyl), —OSO$_2$NH$_2$, —NHSO$_2$NH$_2$, —NHSO$_2$Me, —SO$_2$NH$_2$, or NO$_2$.

In a seventh embodiment, the present invention includes a compound of Formula (Ib) or a stereoisomer, tautomer, pharmaceutically acceptable salt, solvate, or prodrug thereof, wherein:

$R^7$ is H;

$R^{10a}$ is, independently at each occurrence, —SO$_2$—$C_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—$C_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl; and $R^{10b}$ is, independently at each occurrence, OH, NH$_2$, —NHCOH, —NHCOMe, —NHCOEt, —NHCO$_2$Me, —NHCO$_2$Et, —NHCONHMe, —NHCONMe$_2$, —NHCON(Me)Et, —NHCO-(1-pyrrolidinyl), —NHCONH$_2$, —OSO$_2$NH$_2$, —NHSO$_2$NH$_2$, —NHSO$_2$Me, or —SO$_2$NH$_2$.

In an eighth embodiment, the present invention includes a compound of Formula (Ib) or a stereoisomer, tautomer, pharmaceutically acceptable salt, solvate, or prodrug thereof, wherein:

$R^7$ is CO$_2$H, CO$_2$Me, CO$_2$Et, or CONMe$_2$;

$R^{10a}$ is, independently at each occurrence, —SO$_2$—$C_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—$C_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl; and $R^{10b}$ is H.

In a ninth embodiment, the present invention includes a compound of Formula (Ib) or a stereoisomer, tautomer, pharmaceutically acceptable salt, solvate, or prodrug thereof, wherein:

$R^7$ is CO$_2$H, CO$_2$Me, CO$_2$Et, or CONMe$_2$;

$R^{10a}$ is, independently at each occurrence, —SO$_2$—$C_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—$C_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl; and $R^{10b}$ is, independently at each occurrence, OH, NH$_2$, —NHCOH, —NHCOMe, —NHCOEt, —NHCO$_2$Me, —NHCO$_2$Et, —NHCONHMe, —NHCONMe$_2$, —NHCON(Me)Et, —NHCO-(1-pyrrolidinyl), —NHCONH$_2$, —OSO$_2$NH$_2$, —NHSO$_2$NH$_2$, —NHSO$_2$Me, or —SO$_2$NH$_2$.

In a tenth embodiment, the present invention includes a compound of Formula (Ib) or a stereoisomer, tautomer, pharmaceutically acceptable salt, solvate, or prodrug thereof, wherein:

$R^7$ is CO$_2$H, CO$_2$Me, or CO$_2$Et;

$R^{10a}$ is H;

$R^{10b}$ is, independently at each occurrence, OH, NH$_2$, —NHCOH, —NHCOMe, —NHCOEt, —NHCO$_2$Me, —NHCO$_2$Et, —NHCONHMe, —NHCONMe$_2$, —NHCON(Me)Et, —NHCO-(1-pyrrolidinyl), —NHCONH$_2$, —OSO$_2$NH$_2$, —NHSO$_2$NH$_2$, —NHSO$_2$Me, or —SO$_2$NH$_2$.

In an eleventh embodiment, the present invention includes a compound of Formula (1c):

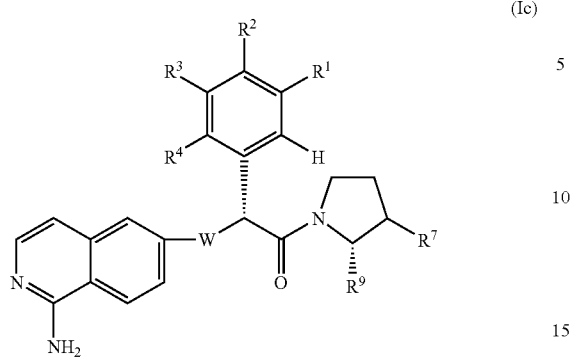

(Ic)

wherein: W, $R^1$, $R^2$, $R^3$, $R^4$, $R^7$ and $R^9$ are the same as defined in the fifth embodiment.

In a twelfth embodiment, the present invention provides a compound selected from the exemplified examples or a stereoisomer, tautomer, pharmaceutically acceptable salt, solvate, or prodrug thereof.

In another embodiment, the present invention includes a compound of Formula (Ib) or a stereoisomer, tautomer, pharmaceutically acceptable salt, solvate, or prodrug thereof, wherein:
$R^1$ is OEt;
$R^2$ is O(i-Pr);
$R^9$ is

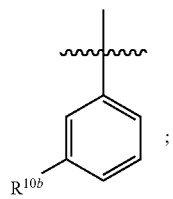

and
$R^{10b}$ is H, —NHCOMe, or —NHSO$_2$NH$_2$.

In another embodiment, the present invention includes a compound of Formula (I) or (Ia) or a stereoisomer, tautomer, pharmaceutically acceptable salt, solvate, or prodrug thereof, wherein: $R^1$ is, independently at each occurrence, F, Cl, Br, I, $C_{1-5}$ alkyl, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl.

In another embodiment, the present invention includes a compound of Formula (I) or (Ia) or a stereoisomer, tautomer, pharmaceutically acceptable salt, solvate, or prodrug thereof, wherein: $R^1$ is, independently at each occurrence, H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-6}$ cycloalkyl.

In another embodiment, the present invention includes a compound of Formula (I) or (Ia) or a stereoisomer, tautomer, pharmaceutically acceptable salt, solvate, or prodrug thereof, wherein: $R^1$ is independently at each occurrence, Cl, Br, $C_{1-3}$ alkyl, $C_{1-3}$ haloalkyl, $C_{2-3}$ alkenyl, —O—$C_{1-3}$ alkyl, or $C_{3-6}$ cycloalkyl.

In another embodiment, the present invention includes the compounds of Formula (I) or (Ia) or a stereoisomer, tautomer, pharmaceutically acceptable salt, solvate, or prodrug thereof, wherein: Z is substituted with 0-2 $R^6$ and selected from:

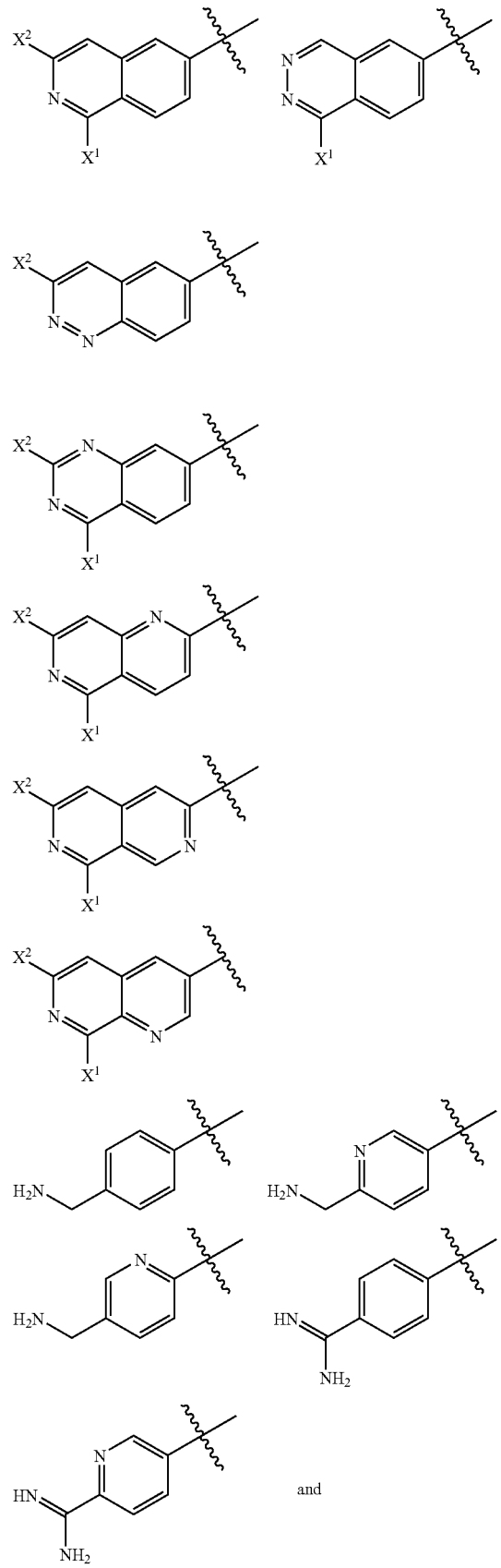

-continued

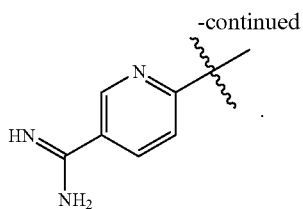

In another embodiment, the present invention includes the compounds of Formula (I) or (Ia) or a stereoisomer, tautomer, pharmaceutically acceptable salt, solvate, or prodrug thereof, wherein: Z is substituted with 0-2 $R^6$ and selected from:

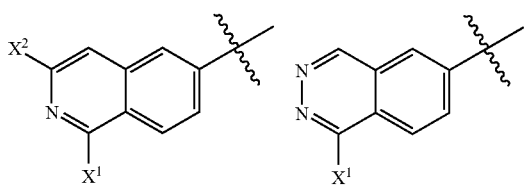

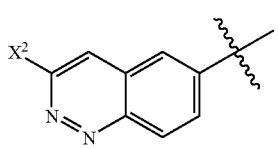

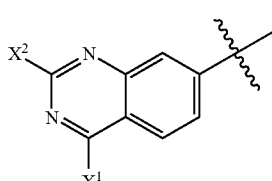

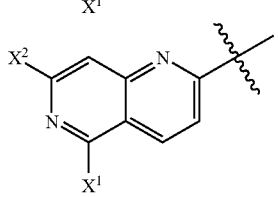

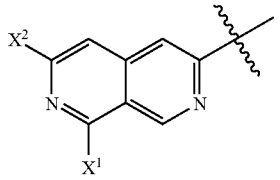

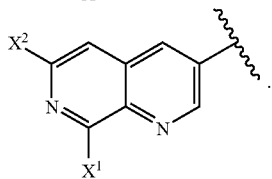

In another embodiment, the present invention includes the compounds of Formula (I) or (Ia) or a stereoisomer, tautomer, pharmaceutically acceptable salt, solvate, or prodrug thereof, wherein: Z is substituted with 0-2 $R^6$ and selected from:

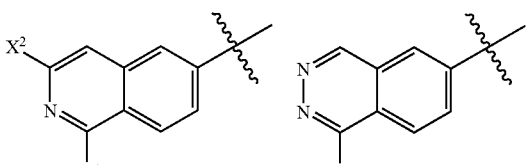

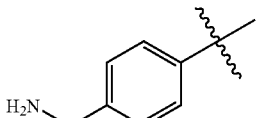

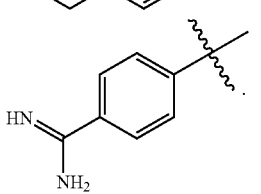

In another embodiment, the present invention includes the compounds of Formula (I) or (Ia) or a stereoisomer, tautomer, pharmaceutically acceptable salt, solvate, or prodrug thereof, wherein: Z is substituted with 0-2 $R^6$ and selected from:

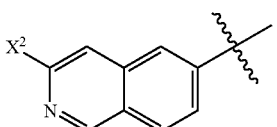

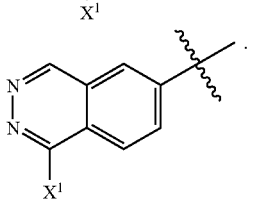

In another embodiment, the present invention includes a compound of Formula (I), (Ia) or (Ib) or a stereoisomer, tautomer, pharmaceutically acceptable salt, solvate, or prodrug thereof, wherein: W is NH.

In another embodiment, the present invention includes a compound of Formula (I) or a stereoisomer, tautomer, pharmaceutically acceptable salt, solvate, or prodrug thereof, wherein: $R^8$ is H, —$CO_2R^a$, —C(O)$NR^cR^d$, or $C_{1-4}$ alkyl substituted with 0-2 $R^{8a}$.

In another embodiment the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, pharmaceutically acceptable salt, solvate, or prodrug thereof.

In another embodiment the present invention provides a method for treating thromboembolic disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a method of treating a patient in need of inflammatory disorder treatment, comprising: administering a compound of the present invention or a stereoisomer, tautomer, pharmaceutically acceptable salt, solvate, or prodrug thereof in an amount effective to treat an inflammatory disorder.

In another embodiment, the present invention provides a method, comprising: administering a compound of the present invention or a stereoisomer, tautomer, pharmaceutically acceptable salt, solvate, or prodrug thereof in an amount effective to treat a thromboembolic and/or inflammatory disorder.

In another embodiment, the present invention provides a pharmaceutical composition further comprising at least one additional herapeutic agent selected from one or more of potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, anti-osteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In a preferred embodiment, the present invention provides a pharmaceutical composition wherein the at least one additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, an anticoagulant agent selected from thrombin inhibitors, other factor VIIa inhibitors, other plasma kallikrein inhibitors, factor IXa inhibitors, factor Xa inhibitors, and factor XIa inhibitors, or an antiplatelet agent selected from GPIIb/IIIa blockers, $P2Y_1$ and $P2Y_{12}$ antagonists, thromboxane receptor antagonists, and aspirin.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a novel method, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quarternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^f$, then said group may optionally be substituted with up to three $R^f$ groups and $R^f$ at each occurrence is selected independently from the definition of $R^f$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. Branched cycloalkyl groups such as 1-methylcyclopropyl and 2-methylcyclopropyl are included in the definition of "cycloalkyl".

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "heterocycle" or "heterocyclic group" is intended to mean a stable 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydro-benzofuranyl, chromanyl, 1,2,3,4-tetrahydro-quinoxaline, and 1,2,3,4-tetrahydro-quinazoline.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "aryl", "$C_{6-10}$ aryl" or "aromatic residue", is intended to mean an aromatic moiety containing, if specified, the specified number of carbon atoms; for example phenyl or naphthyl. Unless otherwise specified, "aryl", "$C_{6-10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, o and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

The term "counterion" is used to represent a small, negatively charged species such as chloride, bromide, hydroxide, acetate, and sulfate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfueric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Isotopically labeled compounds of the present invention, i.e., wherein one or more of the atoms described are replaced by an isotope of that atom (e.g., C replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor VIIa and/or plasma kallikrein. "Therapeutically effective amount" is also intended to include an amount of the combination of compounds claimed that is effective to inhibit factor VIIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor VIIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier. A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Alternatively, flash chromatography was carried out on an ISCO CombiFlash™ System Sq16x using prepacked $SiO_2$ cartridges eluted with gradients of the specified solvents.

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "rt" for room temperature, "atm" for atmosphere, "psi" for pounds per square inch, "MS" for mass spectrometry, "ESI" for electrospray ionization mass spectroscopy, "HR" for high resolution, "LC-MS" for liquid chromatography mass spectrometry, "HPLC" for high pressure liquid chromatography, "NMR" for nuclear magnetic resonance spectroscopy, "1H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

As used throughout the specification, the following abbreviations for chemical reagents apply:
AIBN is 2,2'-azobisisobutyrInitrile
BINAP is 2,2'-bis(diphenylphosphino)-1,1'-binaphthyl
Bn is benzyl Boc is tert-butyl oxycarbonyl
BOP is benzotriazol-1-yloxy-tris(dimethylamino)phosphonium hexafluorophosphate
Bu is butyl
iBu or i-Bu is isobutyl
t-Bu is tert-butyl
Cbz is carbonylbenzyloxy
CbzSerOtBu is (S)-2-tert-butoxycarbonylamino-3-hydroxy-propionic acid tert-butyl ester
CDI is 1,1'-carbonyldiimidazole
Davis oxaziridine is 2-benzenesulfonyl-3-phenyl-oxaziridine
DCE is 1,2-dichloroethane
DIBAH is diisobutylaluminum hydride
DIBAL is diisobutylaluminium
DIC is 1,3-diisopropylcarbodiimdie
DIEA is N,N-diisopropylethyl amine
DMAP is dimethylaminopyridine
DME is dimethyl ether
DMF is dimethylformamide
DMSO is dimethyl sulfoxide
DMPU is 1,3-dimethyl-3,4,5,6-tetrahydro-2(1H)-pyrimidone
DPPA is diphenylphosphoryl azide
EDCI is 1-(3-dimethylaminopropyl)-3-ethylcarbodiimide hydrochloride
Et is ethyl
EtOAc is ethyl acetate
HATU is O-(7-azabenzotriazol-1-yl)-N,N,N',N'-tetramethyluronium
HBTU is O-benzotriazol-1-yl-N,N,N',N'-tetramethyluronium hexafluorophosphate
HOAc or AcOH is acetic acid
HOAT is 1-hydroxy-7-azabenzotriazole
LAH is lithium aluminum hydride
LDA is lithium diisopropylamide
LiHMDS is lithium bis(trimethylsilyl)amide
Me is methyl
MeOH is methanol
mCPBA is meta-choroperbenzoic acid
MoOPH is oxodiperoxymolybdenum(pyridine)(hexamethylphosphoric triamide)
MsCl is methanesulfonyl chloride
NaOAc is sodium actetate
NBS is N-bromosuccinimide
NCS is N-chlorosuccinimide
OAc is acetate
Pd(PPh$_3$)$_4$ is tetraks (triphenylphosphine)palladium
Ph is phenyl
Pr is propyl
iPr or i-Pr is isopropyl
PyBroP is bromotripyrrolidinophosphonium hexafluorophosphate
Selectfluor™ is [1 (chloromethy)-4-fluoro-1,4-diazoniabicyclo[2,2,2]octanebis(tetrafluoroborate)]
TBAF is tetrabutylammoniumfluoride
TBAI is tetrabutylammonium iodide
TEA is triethylamine
TFA is trifluoroacetic acid
TFAA is trifluoroacetic anhydride
THF is tetrahydrofuran.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (Ia):

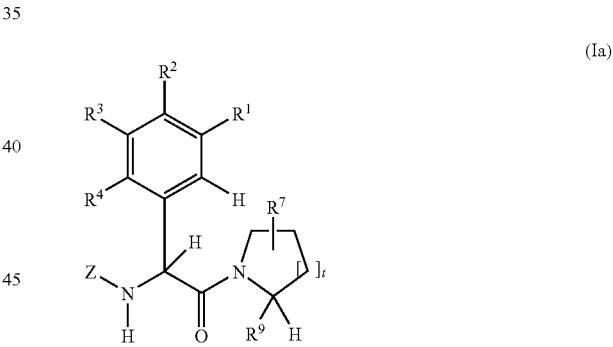

wherein R$^1$-R$^4$, R$^7$, R$^9$, t and Z are each as defined above, can be prepared by coupling an acid of Formula (Iaa):

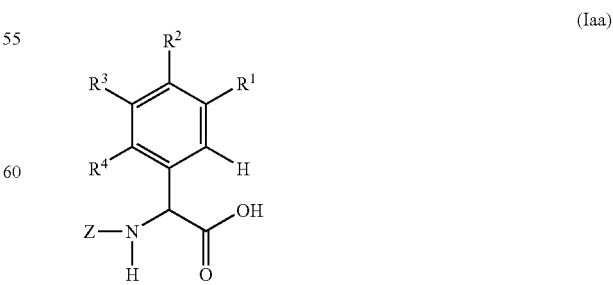

with an amine of Formula (Iab):

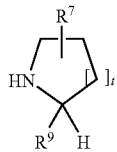

(Iab)

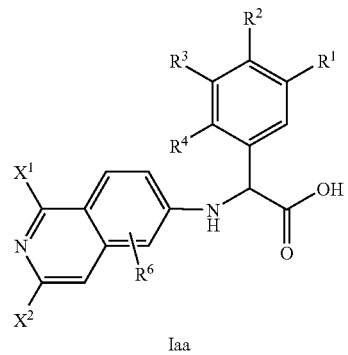

Iaa under conditions suitable for forming an amide bond between the acid and the amine. Coupling conditions can be found in Bodanszky, "Principles of Peptide Synthesis, Second Edition" Springer Verlag Ed, Berlin (1993). Coupling reagents include CDI, DIC, and EDCI. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in the presence of one equivalent of a tertiary base such as DIEA or TEA. Protection and deprotection of functional groups may be required before or after the amide formation step to afford a compound of Formula (Ia).

The intermediate acid of Formula (Iaa) can be prepared in several different ways. For example, it can be prepared according to the steps described in Scheme 1 when Z in Formula (Iaa) is a substituted isoquinoline. Thus, amines 1 (prepared following the methods shown in later Schemes and in the Examples) react with phenyl acetate derivatives 2 under basic conditions to give 3. X is a leaving group such as Cl, Br or $OSO_2Me$ and P is a protecting group such as methyl or benzyl. Deprotection of P in 3 by hydrolysis or hydrogenation gives acid intermediates Iaa.

Acids Iaa can also be prepared by a Petasis boronic acid Mannich reaction (*J. Am. Chem. Soc.* 1997, 119, 445-446) shown in Scheme 2. Amines 1 react with phenyl boronic acid derivatives 4 and glyoxaldehyde 5 in a suitable solvent such as 1,2-dichloroethane and toluene to give the acids Iaa directly. Many phenyl boronic acid derivatives are commercial available. They can also be prepared by methods known in the art.

Scheme 2

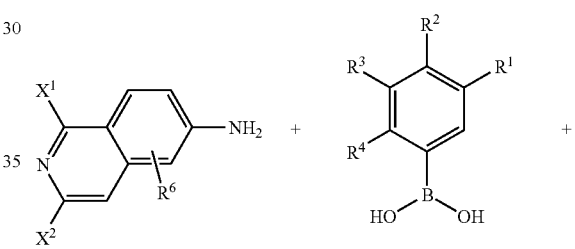

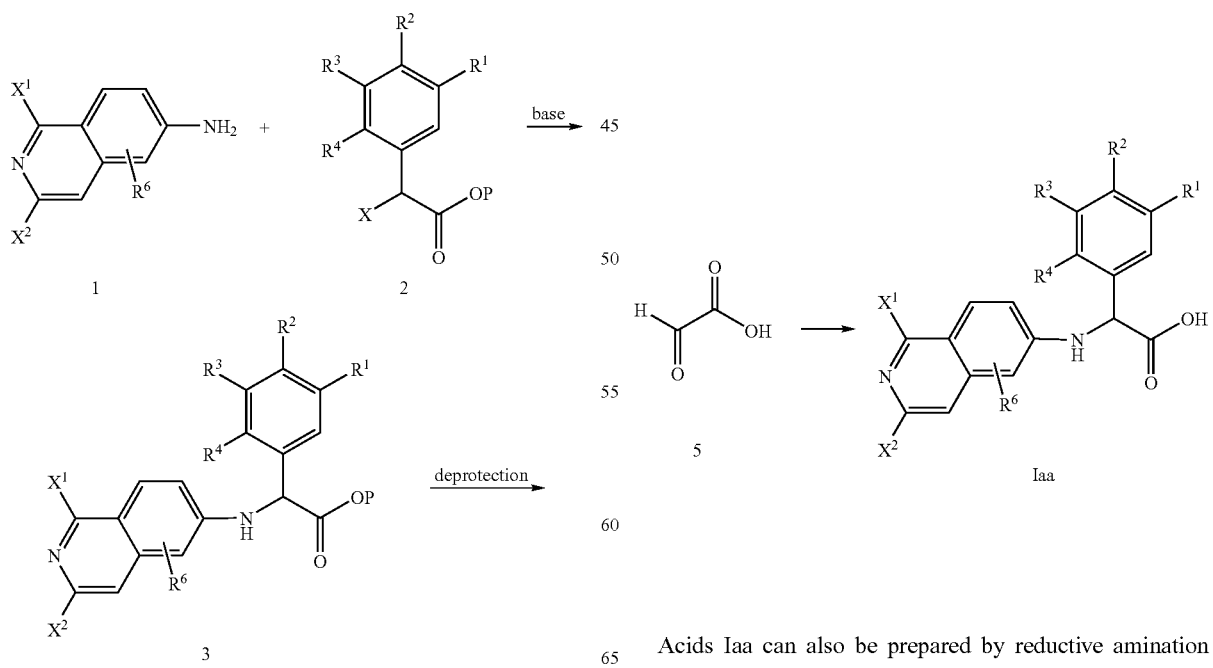

Acids Iaa can also be prepared by reductive amination (*Tetrahedron*, 1996, 52, 9777-9784) of α-keto acids 6 with amines 1 as shown in Scheme 3.

Scheme 3

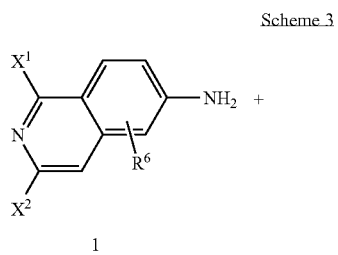

1

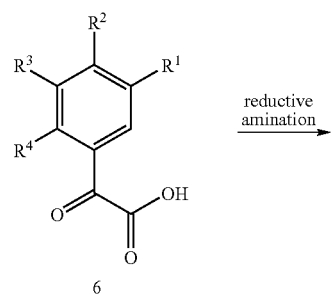

6 reductive amination →

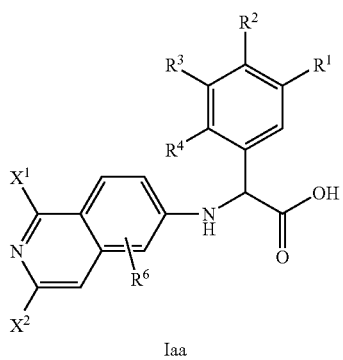

Iaa

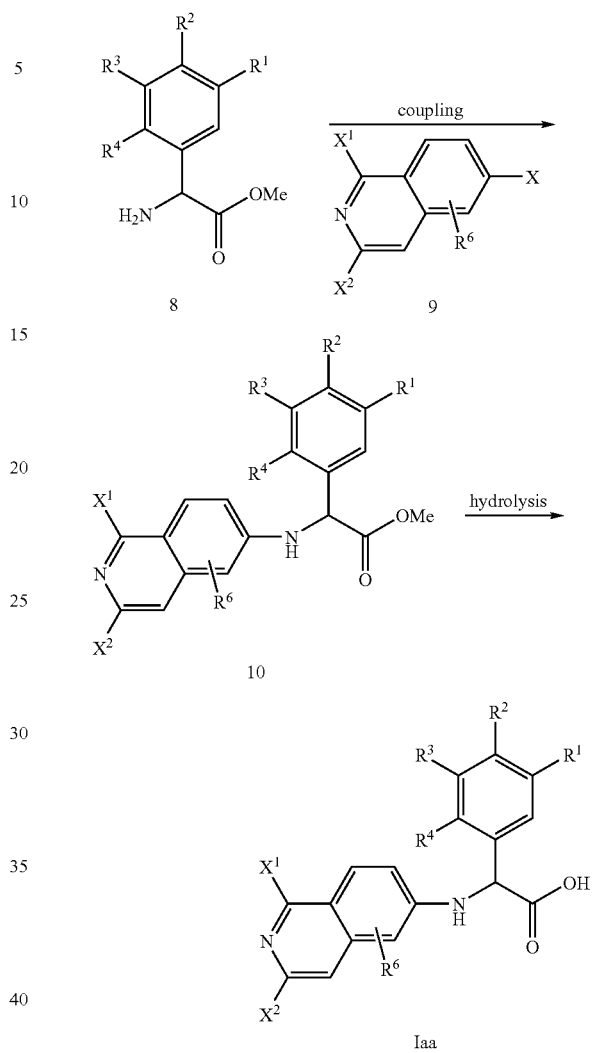

Alternatively to Schemes 1, 2 and 3, as exemplified in Scheme 4, acids Iaa can be prepared from amino-esters 8. Amino-esters 8 can be accessed through a Strecker type synthesis, by condensation of aldehydes 7 with trimethylsilylcyanide in presence of ammonia, followed by treatment with hydrochloric acid in MeOH. Compounds 8 can be converted to 10 via coupling with aryl halides or sulfonates 9 by methods known in the art. For example, amino-esters 8 may be coupled to aryl halides 9 in the presence of a palladium catalyst, an appropriate ligand, for example, BINAP, and a base such as cesium carbonate to provide esters 10. Hydrolysis of 10 gives Iaa.

Substituted isoquinoline amines 1 can be obtained from 11 as shown in Scheme 5. Anilines 11 can be treated with an electrophilic source of halogens such as, for example, NCS, NBS or Selectfluor™. Bromides 12 can further be manipulated to provide anilines 1 via, for example, reaction with tetra-alkyltins in the presence of a palladium catalyst such as $PdCl_2(PPh_3)_3$.

Scheme 4

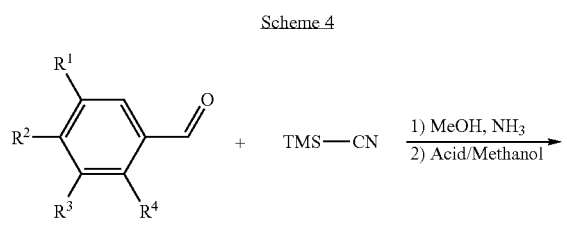

7

Scheme 5

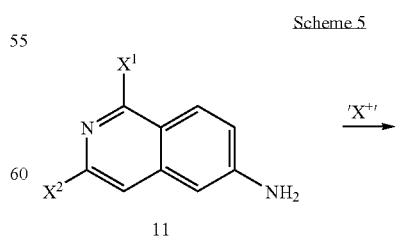

11

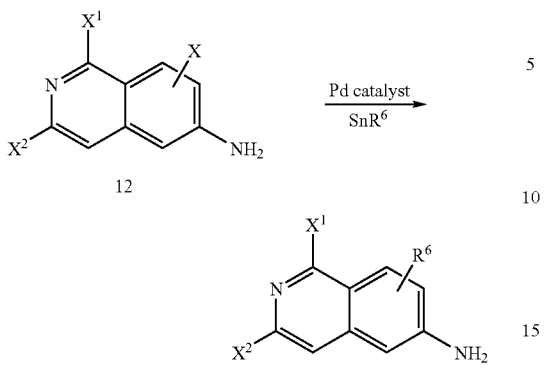

X = Cl, Br, F

Acid Iaa wherein Z in Formula (Ia) is 1-aminophthalazine may be prepared according to Scheme 6. 4-Bromobenzoic acid 13 is converted to the acid chloride and reacted with diethylamine. The resulting diethylbenzamide 14 is formylated by treatment with lithium tetramethylpiperidide at −78° C., followed by quenching with DMF. Subsequent cyclization in refluxing hydrochloric acid provides the hydroxyphthalide 15. The hydroxyphthalide 15 is refluxed with hydrazine in ethanol to afford 6-bromophthalazin-1(2H)-one 16. Treatment with phosphorous oxychloride gives 6-bromo-1-chlorophthalazine 17, which is converted to 1-amino-6-bromophthalazine 18 by reaction with ammonia saturated ethylene glycol at 130° C. The amine is protected by reaction with di-tert-butyl dicarbonate and 4-dimethylaminopyridine in acetonitrile. The resulting bromide 19 can then by coupled to a phenylglycine ester 8 with palladium-BINAP complex. Subsquent ester hydrolysis of ester 20 gives Iaa.

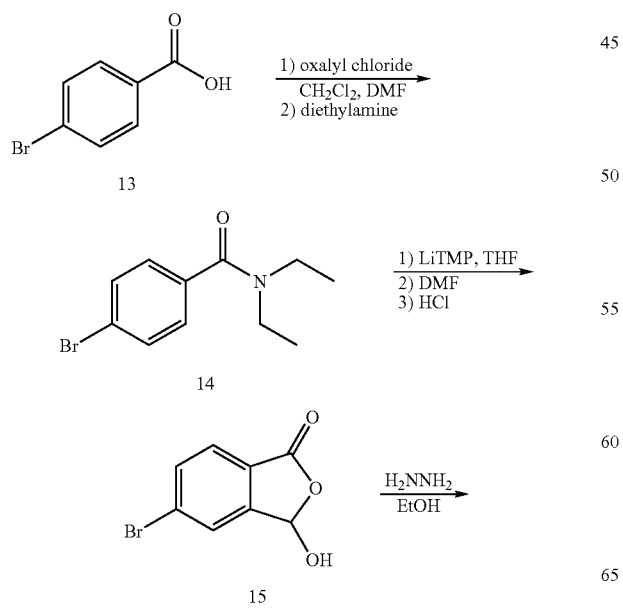

Amines of Formula (Iab) may be prepared in different ways depending on the ring size and substituents.

A general method to prepare N-heterocycles of formula Iab may be via palladium catalyzed coupling of lactam-derived ketene aminal with aryl boronic acids, as shown in Scheme 7. Thus, treatment of properly protected lactam 21 with base such as LDA at low temperature and trapping the enolate with diphenylphosphoryl chloride gives the ketene aminal diphenylphosphate 22. Diphenylphosphate 22 undergoes palladium catalyzed coupling with arylboronic acid 23 to give the coupled intermediate 24. Hydrogenation of the double bond in 24 and removal of the protecting group in 25 should give rise to x-aryl substituted N-heterocycle 26. The sequences described in scheme 7 are particularly useful for preparation of 5-, 6-, 7- and 8-membered N-heterocycles.

ration of α-aryl substituted pyrrolidine and piperidine. Condensation of benzylamine 27 with diphenylketone gives Shiff base 28. Treatment of the Schiff base 28 with 1.0 equivalent of base such as LDA and mono-alkylation with a dielectrophile 29 gives intermediate amine 30 after acid hydrolysis. Intramolecular cyclization of 30 in the presence of base such as $K_2CO_3$ should give rise to α-aryl substituted N-heterocycle 31.

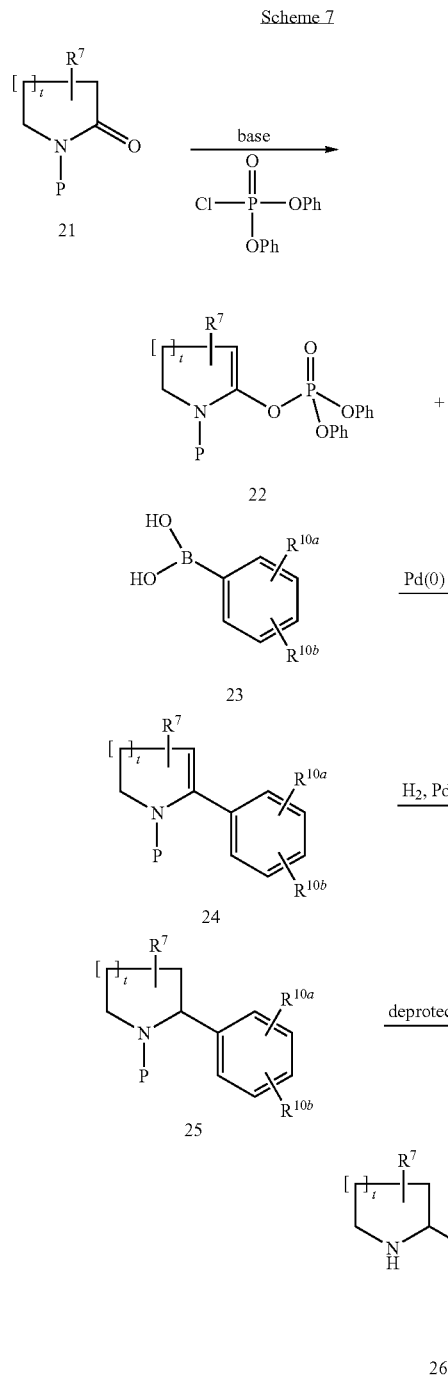

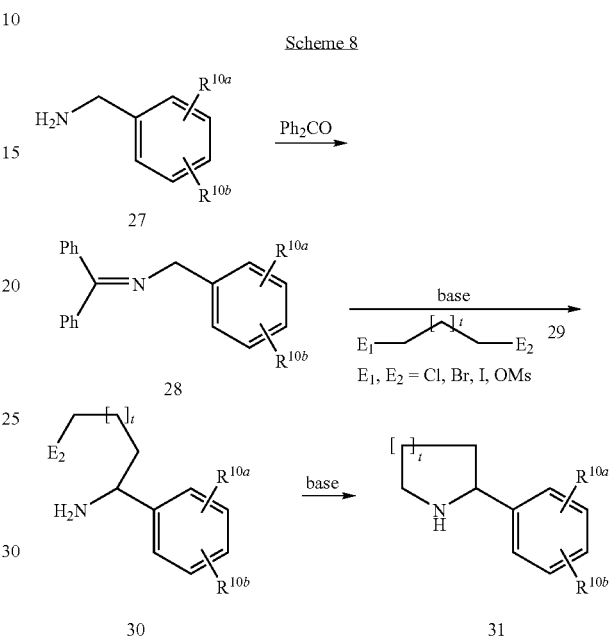

Functionalized phenylpyrrolidines are prepared by the procedures described in Schemes 9, 10 and 11. In Scheme 9, palladium catalyzed coupling of Boc protected 2-pyrrole boronic acid 32 with substituted phenyl halide 33 (X=Br or D) gives aryl pyrrole 34. Aryl pyrrole can be hydrogenated with a catalyst such as Pt/C, $PtO_2$/C and $Pd(OH)_2$/C in a solvent such as MeOH to Boc-protected aryl pyrrolidine 35. At this stage, the $R^{10a}$ and $R^{10b}$ groups can be manipulated to the desired functional groups. Treatment of the Boc protected 2-aryl pyrrolidine 35 with acid such as HCl in dioxane or TFA gives the pyrrolidine 36.

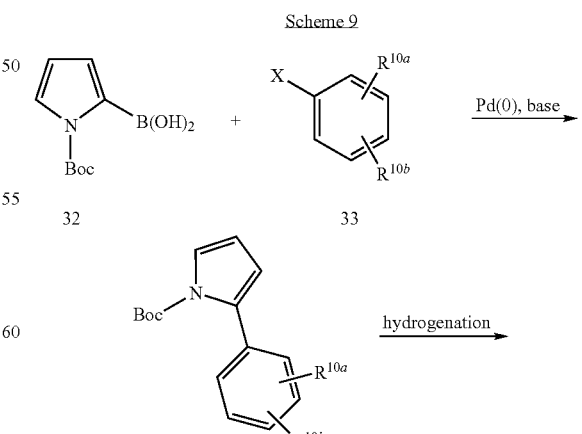

Scheme 8 illustrate another general method to prepare N-heterocycles of Formula (Iab), particularly for the prepa-

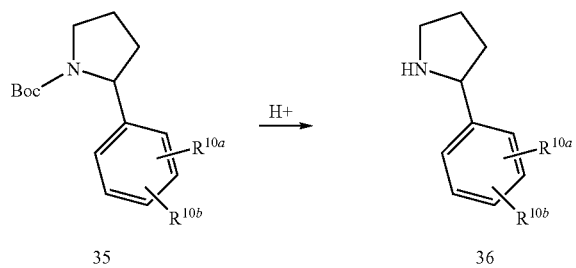

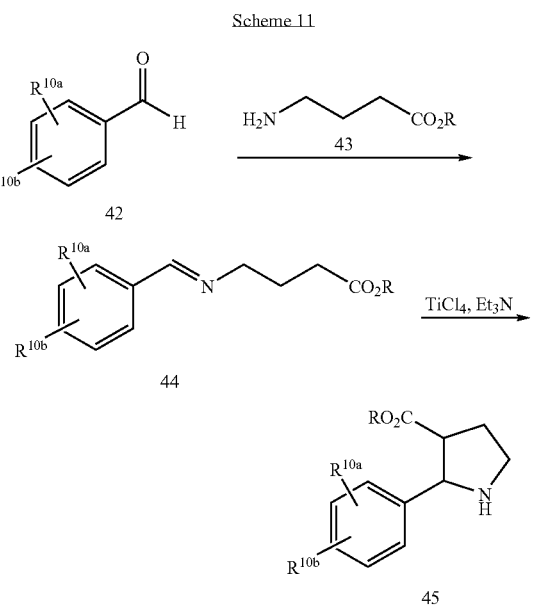

In Scheme 10, reduction of chloro ketone 37 gives hydroxy chlorides 38. Hydroxy chloride 38 can be converted to azides 39, e.g. by the action of DPPA/DBU. Reduction of the azides with $PPh_3$ to amines 40, followed by base-promoted intramolecular cyclization gives the functionalized phenylpyrrolidines 41. It is known that the reduction of the aryl ketones like 37 can be achieved enatioselectively with chiral boranes, e.g. B-chlorodiisopinocamphenyl borane (Dip-Cl, Brown, H. C. et al, *Tetrahedron Lett.* 1994, 35, 2141-2144). It is possible that both enantiomers of 41 can be prepared with the proper choice of chiral borane reagent.

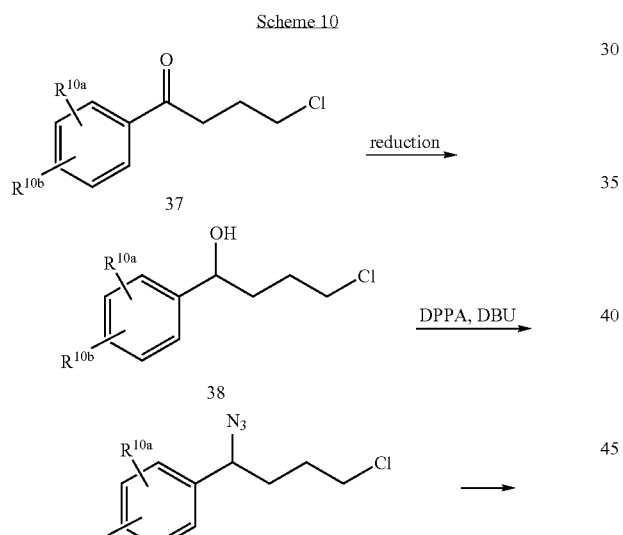

The compound of the instant invention herein described may have asymmetric centers. For example, the chiral carbon atoms in Formula (I) as indicated below, exist in either as S or R configuration.

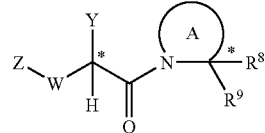

Thus, the stereoisomeric configurations of each compound of Formula (I), (Ia) or (Ib) are considered part of the invention. For example, but not limited to therein, in compounds of Formula (Ib), the following four stereoisomeric configurations are possible:

Scheme 11 illustrate the preparation of arylpyrrolidine carboxylate. Condensation of aryl aldehyde 42 with γ-aminobutyric ester 43 gives imine 44. Intramolecular cyclization of 44 in the presence of catalyst such as $TiCl_4$ and base $Et_3N$ gives rise to arylpyrrolidine carboxylate 45.

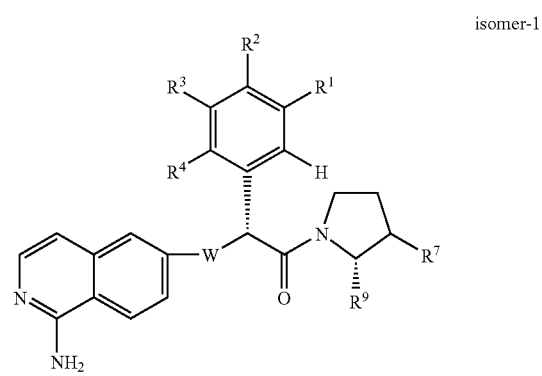

isomer-1

-continued

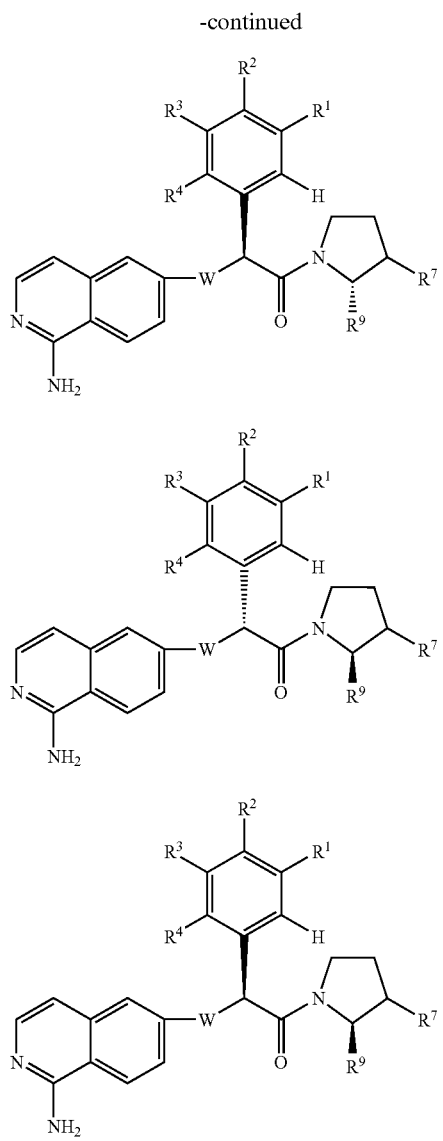

isomer-2 isomer-3 isomer-4

They are collectively, as well as individually, considered part of the invention. In a preferred stereoisomeric embodiment the present invention provides for a stereoisomeric configuration of isomer-1 for all embodiments of Formula (I), (Ia) or (Ib), or tautomer, pharmaceutically acceptable salt, solvate, or prodrug form thereof.

EXAMPLES

The following Examples have been prepared, isolated and characterized using the methods disclosed herein. The following Examples demonstrate a partial scope of the invention and are not meant to be limiting of the scope of the invention.

General Coupling-Deprotection Procedure: Most of the final compounds described in the following examples were made according to the following general coupling-deprotection scheme:

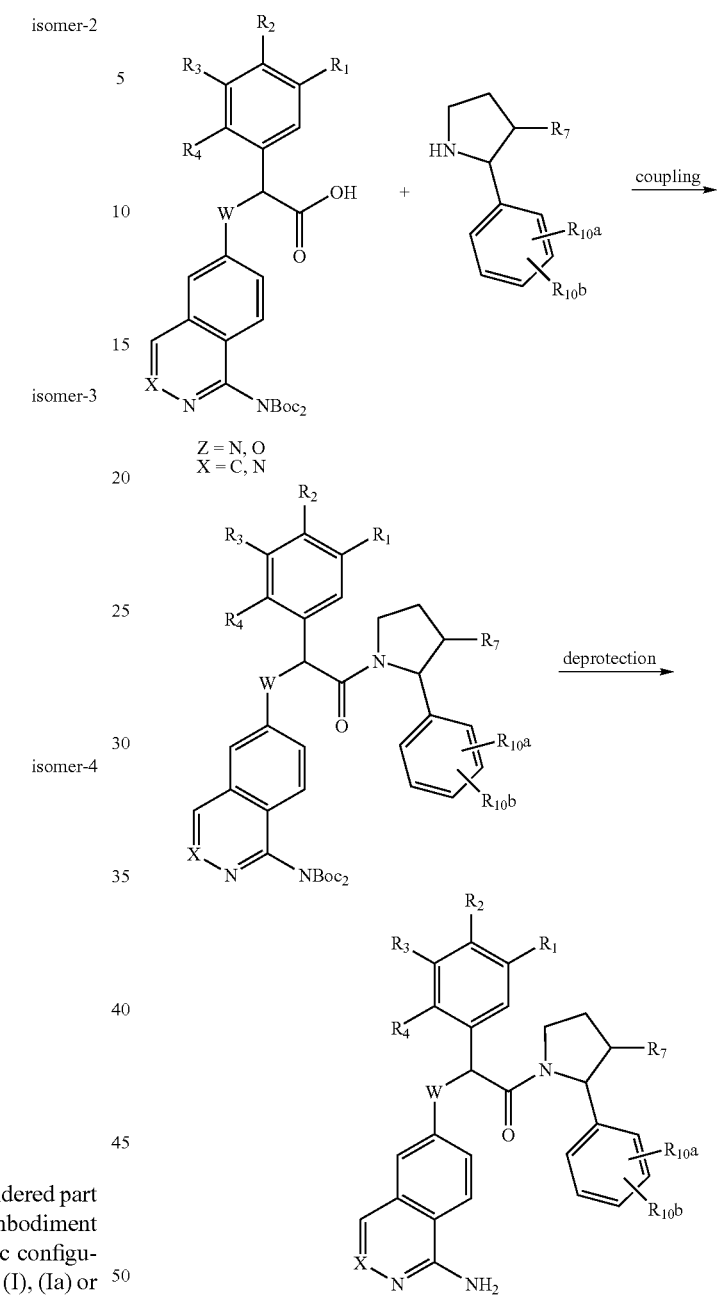

A mixture of intermediate acid (1 eq, preparation given in examples), amine (1.5-2 eq, commercial available or otherwise noted with preparation in the examples), EDCI (1.5-2.5 eq), HOAT (0.4-1.0 eq), DIEA (0-5 eq) in $CH_2Cl_2$ (0.01M) or $CH_2Cl_2$/DMF (0.03 M, 10:1) was stirred at rt for 4 h to overnight. The reaction product was concentrated and purified via preparative HPLC (MeOH/$H_2O$/TFA or $CH_3CN$/$H_2O$/TFA) to provide the desired di-Boc-protected amide. To a solution of the amide (1 eq) in EtOAc (~0.04 M) was added a 4 M solution of HCl in dioxane (~100 eq) and the reaction was stirred at rt for 4 h—overnight. The reaction product was then concentrated and purified via preparative HPLC (MeOH/$H_2O$/TFA or $CH_3CN$/$H_2O$/TFA) then lyophilized ($CH_3CN$, $H_2O$) to provide the desired final compound as a solid TFA salt.

Example 1

2-(1-Aminoisoquinolin-6-ylamino)-2-(3-ethoxy-4-isopropoxyphenyl)-1-(2-phenylpyrrolidin-1-yl)ethanone trifluoroacetic acid salt

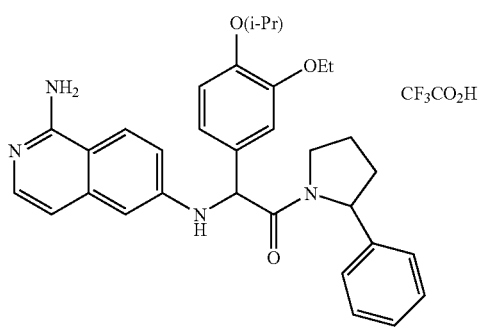

1A: 3-Ethoxy-4-isopropoxyphenylboronic acid

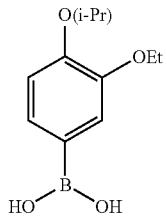

To a solution of 2-isopropoxyphenol (1.53 g, 10 mmol) in CH$_2$Cl$_2$ at 0° C., was added pyridine (1.76 mL, 22 mmol) followed by acetyl chloride (0.79 mL, 1.1 eq). The mixture was stirred at 0° C. for 1.0 h, diluted with diethyl ether, washed with 5% citric acid and brine. The organic extract was dried over Na$_2$SO$_4$, evaporated to give 2-isopropoxyphenyl acetate as an oil.

To a solution of 2-isopropoxyphenyl acetate (10 mmol) in CH$_2$Cl$_2$ at 0° C., iodine monochloride (1.0 M in CH$_2$Cl$_2$, 11.0 mL) was added dropwise in 20 min. The mixture was stirred at 0° C. for 2.0 h, diluted with ether, washed with saturated Na$_2$S$_2$O$_3$ and brine. The organic extract was dried over MgSO$_4$ and evaporated to give 5-iodo-2-isopropoxyphenyl acetate as an oil.

To a solution of 5-iodo-2-isopropoxyphenyl acetate (10 mmol) in MeOH (5 mL) and THF (15 mL), LiOH (1.0 M, 15 mL) was added at 0° C. After the mixture was stirred at rt for 3.0 h, 5% citric acid (30 mL) and diethyl ether (150 mL) was added. The organic extract was washed with brine, dried over Na$_2$SO$_4$ and evaporated to give 5-iodo-2-isopropoxyphenol (2.3 g) as an oil.

To a solution of 5-iodo-2-isopropoxyphenol (2.3 g, 8.3 mmol) in DMF (20 mL), K$_2$CO$_3$ (2.3 g, 16.5 mmol) and ethyl iodide (0.86 mL, 10.8 mmol) were added. The mixture was stirred at 40° C. for 2.0 h. It was diluted with diethyl ether, washed with brine, dried over MgSO$_4$. The crude was purified by chromatography (5:1 EtOAc/hexanes) to give 2-ethoxy-4-iodo-1-isopropoxybenzene (2.5 g, 96% yield) as an oil.

To a solution of 2-ethoxy-4-iodo-1-isopropoxybenzene (2.39 g, 7.8 mmol) in THF (25 mL) at −78° C., n-BuLi (1.6 M in hexanes, 6.83 mL, 1.4 eq) was slowly added. The reaction mixture was stirred at −78° C. for 20 min, followed by addition of triisopropyl borate (4.95 mL, 21.5 mmol). The mixture was stirred at −78° C. for 3.0 h and then warmed up to rt over 1.0 h. It was quenched by addition of 5% citric acid (20 mL), followed by a solution of Na$_2$S$_2$O$_3$. After extraction with EtOAc and drying over Na$_2$SO$_4$, the crude product was purified by chromatography to give 1A (1.2 g, 67% yield) as a white solid. $^1$H NMR (400 MHz, CDCl$_3$) δ ppm 1.41 (d, J=6.15 Hz, 6H) 1.49 (t, J=7.03 Hz, 3H) 4.21 (q, J=7.03 Hz, 2H) 4.64 (m, 1H) 7.02 (d, J=8.35 Hz, 1H) 7.70 (s, 1H) 7.79 (m, 1H).

1B: 6-Amino-1-bis(tert-butyl carbonyl)aminoisoquinoline

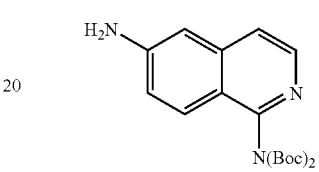

A mixture of 2-methyl-4-nitrobenzonitrile (Aldrich, 5.0 g, 31 mmol) and 1-(1,1-dimethylethoxy)-N,N,N',N'-tetramethyl-methanediamine (Aldrich, 12.2 mL, 59 mmol) in dry DMF (8 mL) was stirred at 70° C. for 2 h under N$_2$. After cooling to rt, DMF was removed in vacuo and the crude product was triturated with hexanes/ethyl acetate (5:1). The solid was collected by filtration and washed with hexane to give (E)-2-(2-(dimethylamino)vinyl)-4-nitrobenzonitrile (6.5 g, 97% yield) as a black solid. $^1$H NMR (400 MHz, CDCl$_3$) δ ppm 2.97 (s, 6H) 5.36 (d, J=513.18 Hz, 1H) 7.16 (d, J=13.62 Hz, 1H) 7.52 (d, J=8.79 Hz, 1H) 7.60 (m, 1H) 8.11 (d, J=1.76 Hz, 1H).

(E)-2-(2-(Dimethylamino)vinyl)-4-nitrobenzonitrile (4.6 g, 21.2 mmol) and 2,4-dimethoxybenzylamine (4.0 mL, 1.25 eq) in DMPU (10 mL) were heated at 140° C. for 3 h. The solvent was removed by vacuum distillation and residue was treated with hexanes/ethyl acetate (1:1). The solid was collected by filtration and washed with hexane to give 2-(2,4-dimethoxybenzyl)-6-nitroisoquinolin-1(2H)-imine (4.6 g). $^1$H NMR (400 MHz, DMSO-d$_6$) δ ppm 3.72 (s, 3H) 3.81 (s, 3H) 4.96 (s, 1H) 6.28 (d, J=6.59 Hz, 1H) 6.46 (d, J=7.47 Hz, 1H) 6.58 (d, J=1.76 Hz, 1H) 7.03 (d, J=8.79 Hz, 1H) 7.27 (d, J=6.15 Hz, 1H) 8.02 (dd, J=9.01, 2.42 Hz, 1H) 8.31 (d, J=2.20 Hz, 1H) 8.43 (d, J=8.35 Hz, 1H).

To a solution of 2-(2,4-dimethoxybenzyl)-6-nitroisoquinolin-1(2H)-imine (11.9 g, 35 mmol) in anisole (24 mL) was added TFA (24 mL). The reaction mixture was stirred at 90° C. for 6 h and the solvent was removed under reduced pressure. The residue was suspended in MeOH (30 mL) and then treated with NaOH (1.0 N, 38 mL). The mixture was stirred at rt for 10 min and pH was checked to be 9-10. The precipitate was collected by filtration and washed with water to afford 6-nitroisoquinolin-1-amine (6.0 g). $^1$H NMR (400 MHz, DMSO-d$_6$) ppm 7.20 (d, J=5.72 1H) 7.36 (s, 2H) 7.95 (d, J=5.72 Hz, 1H) 8.15 (dd, J=9.24, 2.64 Hz, 1H) 8.43 (d, J=9.24 Hz, 1H) 8.67 (d, J=2.64 Hz, 1H).

A solution of 6-nitroisoquinolin-1-amine (25.00 g, 0.132 mol), di-tert-butyl dicarbonate (63.45 g, 0.29 mol) and DMAP (750 mg, catalyst) in DMPU (125 ml) was stirred at 70° C. for 30 min. The reaction was quenched with water (300 ml). The reaction mixture was diluted with ethyl acetate (500 ml) and washed with water. The organic layer was separated and the solvent removed under vacuum. The residue was recrystallized from methanol to give 54.05 g (95.02%) of 6-nitro-1-bis(tert-butyl carbonyl)amino-isoquinoline as a solid. $^1$H NMR (400 MHz, CDCl$_3$) δ ppm 1.33 (s, 18H) 7.86 (d, J=5.27 Hz, 1H) 8.15 (d, J=9.23 Hz, 1H) 8.39 (dd, J=9.23, 2.20 Hz, 1H) 8.62 (d, J=5.71 Hz, 1H) 8.82 (d, J=2.20 Hz, 1H). LC-MS: 801 (2M+Na)$^+$.

6-Nitro-1-bis(tert-butyl carbonyl)aminoisoquinoline (75.00 g, 0.193 mol) in methanol/THF (500 ml/500 ml) was hydrogenated with a hydrogen balloon in the presence of Pd/C (5%, 5 g) for 2.0 h. Filtration of the Pd/C and concentration gave a solid, which was recrystallized from methanol to give 65.72 g (94.97%) of 1B as a white solid. $^1$H NMR (400 MHz, CDCl$_3$) δ ppm 1.33 (m, 18H) 4.18 (s, 2H) 6.89 (d, J=2.20 Hz, 1H) 6.99 (dd, J=9.01, 2.42 Hz, 1H) 7.35 (d, J=6.59 Hz, 1H) 7.75 (d, J=8.79 Hz, 1H) 8.22 (d, J=5.71 Hz, 1H). LC-MS: 741 (2M+Na)$^+$.

1C: 2-(1-Bis(1,1-dimethylethoxy)carbonylaminoisoquinolin-6-ylamino)-2-(3-ethoxy-4-isopropoxyphenyl)acetic acid

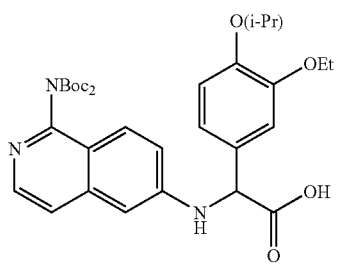

A mixture of 1A (308 mg, 1.38 mmol), 1B (494 mg, 1.38 mmol) and glyoxylic acid monohydrate (127.1 mg, 1.38 mmol) in toluene (12 mL) and methanol (2.5 mL) was heated at 60° C. for 6.0 h and then stirred at rt overnight. After removing the solvent, the crude product was purified by silica gel chromatography eluting with CH$_2$Cl$_2$/MeOH to give 1C (0.65 g, 78% yield) as a yellow solid. $^1$H NMR (400 MHz, Methanol-d$_4$) δ ppm 1.29 (m, 24H) 1.35 (t, J=7.03 Hz, 3H) 4.05 (dd, J=7.03, 5.27 Hz, 2H) 4.49 (m, 1H) 5.11 (s, 1H) 6.68 (d, J=1.76 Hz, 1H) 6.93 (d, J=8.35 Hz, 1H) 7.10 (dd, J=8.35, 2.20 Hz, 1H) 7.17 (d, J=1.76 Hz, 1H) 7.27 (dd, J=9.23, 2.20 Hz, 1H) 7.42 (d, J=5.71 Hz, 1H) 7.62 (d, J=9.23 Hz, 1H) 8.01 (d, J=6.15 Hz, 1H).

1D: Example 1

Example 1 was prepared according to the general coupling-deprotection using 1C and 2-phenylpyrrolidine (Aldrich) and it was separated by prep HPLC (YMC ODSS5 30×100 mm, 40 mL/min form 10% CH$_3$CN to 90% CH$_3$CN).

$^1$H NMR (400 MHz, Methanol-d$_4$) δ ppm 1.30 (m, 9H) 2.09 (m, 4H) 3.86 (m, 4H) 4.43 (m, 1H) 5.32 (m, 2H) 6.68 (m, 2H) 7.01 (m, 2H) 7.11 (m, 4H) 7.29 (m, 4H) 8.00 (d, J=9.29 Hz, 1H). LC-MS: 525 (M+H)$^+$.

Example 2

Diastereoisomer of Example 1

2-(1-Aminoisoquinolin-6-ylamino)-2-(3-ethoxy-4-isopropoxyphenyl)-1-(2-phenylpyrrolidin-1-yl)ethanone trifluoroacetic acid salt

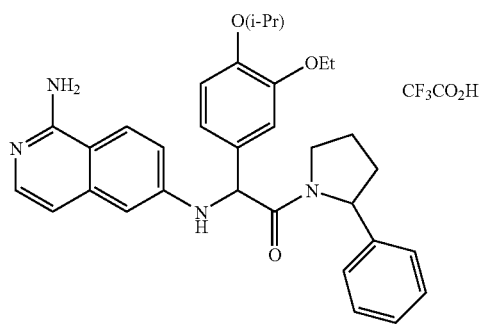

Example 2 was separated as a diastereomer of Example 1 by prep HPLC (YMC ODSS5 30×100 mm, 40 mL/min form 10% CH$_3$CN to 90% CH$_3$CN) from 1D. $^1$H NMR (400 MHz, Methanol-d$_4$) δ ppm 1.35 (m, 9H) 2.05 (m, 4H) 3.84 (m, 4H) 4.57 (m, 1H) 5.17 (m, 2H) 6.78 (m, 3H) 7.05 (m, 5H) 7.30 (t, J=6.97 Hz, 1H) 7.39 (m, 2H) 7.52 (m, 1H) 7.98 (m, J=46.95, 9.05 Hz, 1H). LC-MS: 525 (M+H)$^+$.

Example 3

3-(1-(2-(1-Aminoisoquinolin-6-ylamino)-2-(3-ethoxy-4-isopropoxyphenyl)acetyl)-pyrrolidin-2-yl) benzenesulfonamide trifluoroacetic acid salt

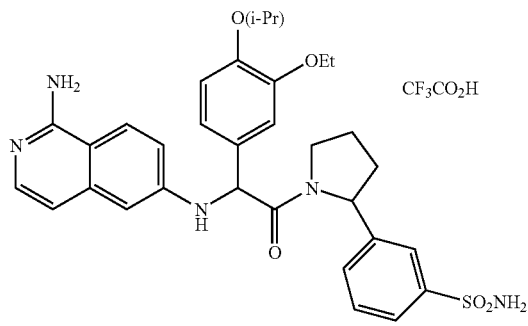

3A: 1-(tert-Butoxycarbonyl)-1H-pyrrol-2-ylboronic acid

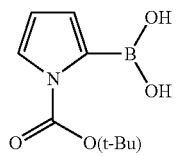

3A was prepared in 72% yield according to the procedure in Synthesis, 1991, 613-615. $^1$H NMR (400 MHz, CDCl$_3$) δ ppm 1.60 (s, 9H) 6.24 (t, J=3.30 Hz, 1H) 7.08 (m, 1H) 7.18 (s, 2H) 7.43 (m, 1H).

3B: 2-(3-Sulfamoyl-phenyl)-pyrrole-1-carboxylic acid tert-butyl ester

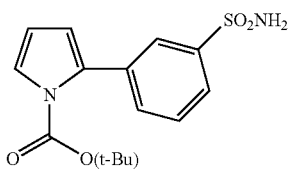

A mixture of 3A, 3-bromobenzene sulfonamide (0.1 g, 0.4 mmol) in DME (6 mL) and 2.0 M Na$_2$CO$_3$ (0.8 mL) was degassed by bubbling argon for 5 min. To this solution, Pd(PPh$_3$)$_4$ (28 mg, 0.025 mmol) was added. The mixture was heated at 92° C. for 3 h. After cooling to rt, it was extracted with EtOAc, and dried over Na$_2$SO$_4$. The crude product was purified by silica gel chromatography (hexanes/EtOAc=3/1) to give 3B (293 mg, 90% yield) as a semi-solid. $^1$H NMR (400 MHz, CDCl$_3$) δ ppm 1.37 (s, 9H) 4.88 (s, 2H) 6.23 (m, 1H) 7.36 (m, 1H) 7.47 (t, J=7.69 Hz, 1H) 7.55 (m, 1H) 7.83 (d, J=8.35 Hz, 1H) 7.90 (s, 1H).

3C: 3-Pyrrolidin-2-yl-benzenesulfonamide

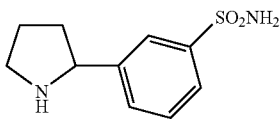

3B (290 mg, 0.9 mmol) was hydrogenated in EtOH (9.0 mL) and HOAc (0.15 mL) with Pt/C (5% wt, 100 mg) using a H$_2$ balloon for 2 days. After filtration and evaporation of solvent, the crude product was stirred in EtOAc (1.0 mL) and 4.0 N HCl/dioxane (4.3 mL, 18 eq) at rt for 1.0 h. After removal of solvent, 3C was obtained as HCl salt. $^1$H NMR (400 MHz, Methanol-d$_4$) δ ppm 2.26 (m, 3H) 2.55 (m, 1H) 3.49 (m, 2H) 4.74 (dd, J=10.11, 6.59 Hz, 1H) 7.66 (t, J=7.69 Hz, 1H) 7.74 (m, 1H) 7.97 (d, J=7.91 Hz, 1H) 8.04 (s, 1H).

3D: Example 3

Example 3 was prepared according to the general coupling-deprotection using 1C and 3C. $^1$H NMR (400 MHz, Methanol-d$_4$) δ ppm 1.35 (m, 9H) 2.05 (m, 4H) 3.82 (m, 4H) 4.58 (m, 1H) 6.76 (m, 2H) 7.05 (m, 6H) 7.29 (m, 2H) 7.60 (m, 3H) 7.91 (m, 1H) 8.03 (dd, J=9.17, 6.48 Hz, 1H). LC-MS 604 (M+H).

Example 4

N-(3-((R)-1-((R)-2-(1-aminoisoquinolin-6-ylamino)-2-(3-ethoxy-4-isopropoxyphenyl)acetyl)pyrrolidin-2-yl)phenyl)acetamide trifluoroacetic acid salt

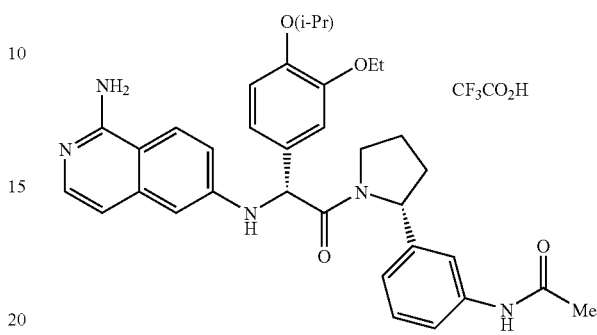

4A: tert-Butyl 2-(3-nitrophenyl)-1H-pyrrole-1-carboxylate

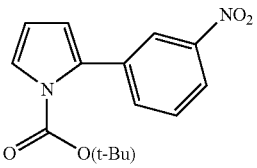

A mixture of 3A (1.46 g, 6.9 mmol) and 3-nitrobromobenzene (0.81 g, 4.0 mmol) in DME (40 mL) and 2.0 M Na$_2$CO$_3$ (8.0 mL) was degassed by bubbling argon for 5 min. To this solution, Pd(PPh$_3$)$_4$ (280 mg, 0.25 mmol) was added. The mixture was heated at 90° C. for 5 h. After cooling to rt, it was extracted with EtOAc and dried over Na$_2$SO$_4$. The product was purified by silica gel chromatography (CH$_2$Cl$_2$/hexanes=1/5) to give 4A (880 mg, 75% yield) as viscous oil. $^1$H NMR (400 MHz, Methanol-d$_4$) δ ppm 1.37 (s, 9H) 6.28 (t, J=3.52 Hz, 1H) 6.33 (dd, J=3.52, 1.76 Hz, 1H) 7.41 (dd, J=3.52, 1.76 Hz, 1H) 7.59 (m, 1H) 7.73 (d, J=7.91 Hz, 1H) 8.16 (m, 2H).

4B: N-(3-(Pyrrolidin-2-yl)phenyl)acetamide

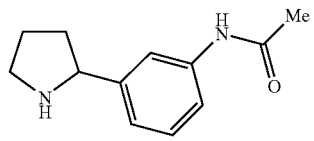

4A (870 mg, 3.0 mmol) was hydrogenated in EtOH (12 mL) and HOAc (0.7 mL) with Pt/C (5% wt, 250 mg) using a H$_2$ balloon for 2 days. After filtration and evaporation of solvent, the crude product was stirred in acetic anhydride (8.0 mL) for 20 min. After removal of acetic anhydride under high vacuum, the intermediate tert-butyl 2-(3-acetamidophenyl) pyrrolidine-1-carboxylate (316 mg, 35% yield for 2 steps) was obtained by chromatography (EtOAc/hexanes=1/1).

This intermediate (310 mg, 1.0 mmol) was stirred in EtOAc (1.0 mL) and 4.0 N HCl/dioxane (4.4 mL, 18 eq) at rt for 1.0 h. After removal of solvent, 4B was obtained as HCl salt. $^1$H NMR (400 MHz, Methanol-$d_4$) δ ppm 2.14 (s, 3H) 2.24 (m, 3H) 2.48 (m, 1H) 3.45 (m, 2H) 4.61 (m, 1H) 7.22 (d, J=7.47 Hz, 1H) 7.40 (t, J=7.69 Hz, 1H) 7.49 (m, 1H) 7.84 (s, 1H).

The enantiomers of 4B were separated using a preparative HPLC equipped with a Chiralpak®AD column (5 cm×50 cm, 20μ). The separation was performed using an isocratic method of 15% ethanol/heptane with 0.1% diethylamine for 120 min with a flow rate of 50 mL/min. (R)-4B was eluted first, followed by (S)-4B.

4C: Example 4

Example 4 was prepared according to the general coupling-deprotection using 1C and (R)-4B. It was purified by preparative HPLC (YMC ODSS5 30×100 mm, 40 mL/min from 10% $CH_3CN$ to 90% $CH_3CN$). $^1$H NMR (400 MHz, Methanol-$d_4$) δ ppm 1.35 (m, 9H) 2.03 (m, 7H) 3.85 (m, 4H) 4.56 (d, J=5.87 Hz, 1H) 5.38 (m, 2H) 6.55 (m, 1H) 6.99 (m, 6H) 7.45 (m, 4H) 7.97 (m, 1H). LC-MS: 582 $(M+H)^+$.

Example 5

Diastereoisomer of Example 4

N-(3-((R)-1-((S)-2-(1-aminoisoquinolin-6-ylamino)-2-(3-ethoxy-4-isopropoxyphenyl)acetyl)pyrrolidin-2-yl)phenyl)acetamide trifluoroacetic acid salt

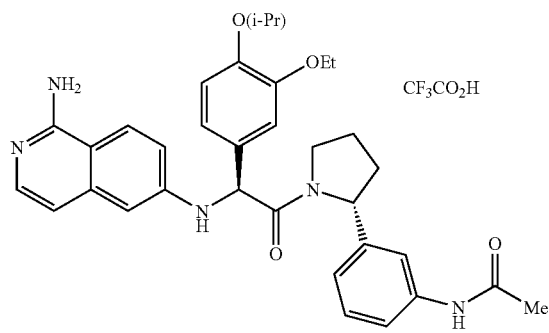

Example 5 was isolated as a diastereomer of Example 4 by preparative HPLC (YMC ODSS5 30×100 mm, 40 mL/min from 10% $CH_3CN$ to 90% $CH_3CN$) from step 4C. $^1$H NMR (400 MHz, Methanol-$d_4$) δ ppm 1.35 (m, 9H) 2.04 (m, 7H) 3.83 (m, 4H) 4.57 (m, J=5.87 Hz, 1H) 5.38 (m, 2H) 6.56 (m, 1H) 7.01 (m, 7H) 7.45 (m, 3H) 7.97 (m, 1H). LC-MS: 582 $(M+H)^+$.

Example 6

N-(3-((S)-1-((R)-2-(1-Aminoisoquinolin-6-ylamino)-2-(3-ethoxy-4-isopropoxyphenyl)acetyl)pyrrolidin-2-yl)phenyl)acetamide trifluoroacetic acid salt

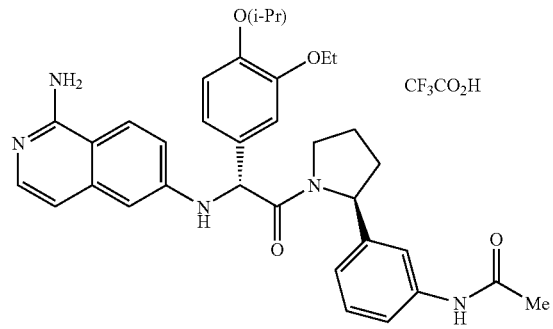

Example 6 was prepared according to the general coupling-deprotection using 1C and (S)-4B. It was purified by preparative HPLC (YMC ODSS5 30×100 mm, 40 mL/min from 10% $CH_3CN$ to 90% $CH_3CN$). $^1$H NMR (400 MHz, Methanol-$d_4$) δ ppm 1.32 (m, 9H) 2.11 (m, 7H) 4.05 (m, 4H) 4.54 (m, J=5.62 Hz, 1H) 5.36 (m, 2H) 6.64 (m, 2H) 7.00 (m, 5H) 7.33 (m, 4H) 8.01 (m, 1H). LC-MS: 582 $(M+H)^+$.

Example 7

Diastereoisomer of Example 6

N-(3-((S)-1-((S)-2-(1-Aminoisoquinolin-6-ylamino)-2-(3-ethoxy-4-isopropoxyphenyl)acetyl)pyrrolidin-2-yl)phenyl)acetamide trifluoroacetic acid salt

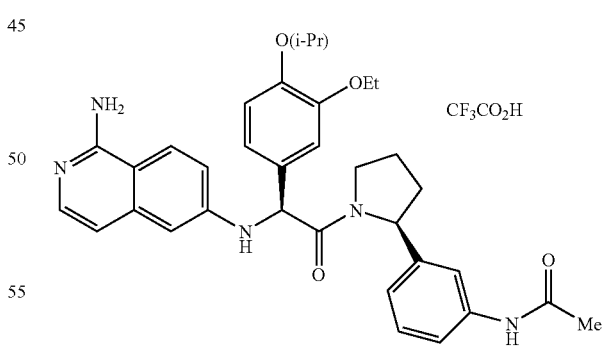

Example 7 was isolated as a diastereomer of Example 6 by preparative HPLC (YMC ODSS5 30×100 mm, 40 mL/min from 10% $CH_3CN$ to 90% $CH_3CN$). $^1$H NMR (400 MHz, Methanol-$d_4$) δ ppm 1.32 (m, 9H) 2.16 (m, 7H) 3.82 (m, 4H) 4.43 (m, 1H) 5.30 (m, 2H) 6.64 (m, 2H) 7.01 (m, 5H) 7.29 (m, 4H) 8.01 (m, 1H). LC-MS: 582 $(M+H)^+$.

Example 8

N-(3-((R)-1-(2-(1-Aminoisoquinolin-6-ylamino)-2-(3,4-dimethoxyphenyl)acetyl)pyrrolidin-2-yl)phenyl)acetamide trifluoroacetic acid salt

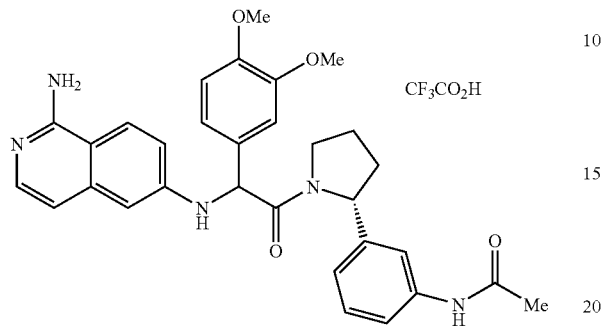

8A: 2-(1-Bis(1,1-dimethylethoxy)carbonylaminoisoquinolin-6-ylamino)-2-(3,4-dimethoxyphenyl)acetic acid

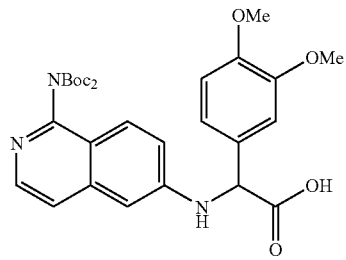

A mixture of 3,4-dimethoxyphenyl boronic acid (Aldrich, 457 mg, 2.5 mmol), 1B (900 mg, 2.5 mmol) and glyoxylic acid monohydrate (231 mg, 2.5 mmol) in toluene (20 mL) and methanol (2.5 mL) was heated at 50° C. for 3.0 h and then stirred at rt over night. After removing solvent, the crude was purified by chromatography eluting with $CH_2Cl_2$/MeOH. 8A (1.18 g, 85%) was obtained as a yellow solid. $^1$H NMR (400 MHz, Methanol-$d_4$) δ ppm 1.27 (s, 18H) 3.79 (s, 3H) 3.81 (s, 3H) 5.07 (s, 1H) 6.67 (d, J=2.20 Hz, 1H) 6.92 (d, J=8.35 Hz, 1H) 7.13 (m, 1H) 7.18 (d, J=1.76 Hz, 1H) 7.26 (dd, J=9.23, 2.20 Hz, 1H) 7.41 (d, J=6.15 Hz, 1H) 7.62 (d, J=9.23 Hz, 1H) 8.00 (d, J=5.71 Hz, 1H).

8B: Example 8

Example 8 was prepared according to the general coupling-deprotection using 8A and (R)-4B. $^1$H NMR (400 MHz, Methanol-$d_4$) δ ppm 2.18 (m, 7H) 3.74 (m, 7H) 4.11 (m, 1H) 5.28 (m, 2H) 6.69 (m, 3H) 7.17 (m, 7H) 7.54 (m, 1H). LC-MS: 540 (M+H)$^+$.

Example 9

Methyl 1-(2-(1-aminoisoquinolin-6-ylamino)-2-(3-ethoxy-4-isopropoxyphenyl)acetyl)-2-phenylpyrrolidine-3-carboxylate trifluoroacetic acid salt

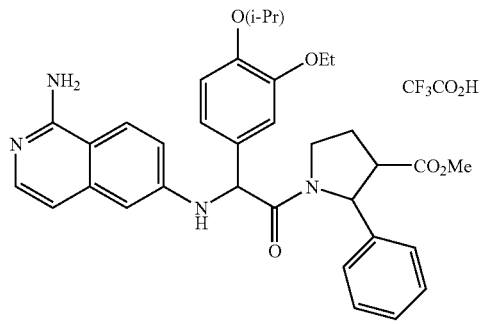

9A: (E)-Methyl 4-(benzylideneamino)butanoate

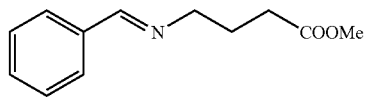

To the methyl aminobutyric ester HCl salt (1.0 g, 6.5 mmol) in dichloromethane was added triethylamine (1.36 mL, 9.75 mmol) and then the benzaldehyde (0.69 g, 6.5 mmol) and molecular sieves (0.5 g). The reaction was stirred for 26 h at rt. The reaction mixture was filtered to remove the molecular sieves and the solvent was evaporated to give 2.21 g of 9A as a white solid.

9B: (cis)-Methyl 2-phenylpyrrolidine-3-carboxylate

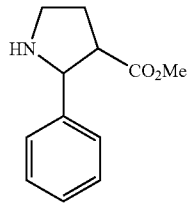

To the imine 9A (0.31 g, 1.51 mmol) and triethylamine (0.42 mL, 3.02 mmol) in dichloromethane (15 mL) at 0° C. was added titanium chloride (1.51 mL, 1.0 M in dichloromethane) dropwise under argon. The reaction was stirred at rt for 3 h and then quenched with saturated potassium carbonate. The mixture was filtered through celite and the aqueous layer was extracted with dichloromethane (2×). The organic extracts were combined, washed with brine and dried over sodium sulfate. The solvent was evaporated and the crude residue was purified by preparative HPLC equipped with a YMC ODS S5 (30×100 mm) column. The separation was performed using a linear gradient (solvent A: 10% acetonitrile-90% water-0.1% TFA; solvent B: 90% acetonitrile-90% water-0.1% TFA; 0 to 100% B in 12 min with a flow rate of 40 mL/min to give 0.095 g of 9B as a solid. $^1$H NMR (400 MHz, Methanol-$d_4$) δ ppm 2.50 (m, 2H) 3.42 (s, 3H) 3.55 (m, 1H) 3.72 (m, 2H) 4.98 (d, J=7.09 Hz, 1H) 7.36 (m, 2H) 7.44 (m, 3H).

9C: Example 9

Example 9 was prepared according to the general coupling-deprotection using 1C and 9B. $^1$H NMR (400 MHz, Methanol-$d_4$) δ ppm 1.35 (m, 6H) 1.44 (q, J=6.93 Hz, 3H) 2.35 (m, 2H) 3.35 (m, 3H) 3.74 (m, 3H) 4.12 (m, 2H) 4.62 (m, 1H) 5.42 (m, 2H) 6.75 (m, 2H) 7.10 (m, 6H) 7.37 (m, 3H) 7.57 (t, J=7.70 Hz, 1H) 8.00 (dd, J=53.31, 9.29 Hz, 1H). LC-MS: 583 (M+H)$^+$.

Example 10

1-(2-(1-Aminoisoquinoln-6-ylamino)-2-(3-ethoxy-4-isopropoxyphenyl)acetyl)-2-phenylpyrrolidine-3-carboxylic acid trifluoroacetic acid salt

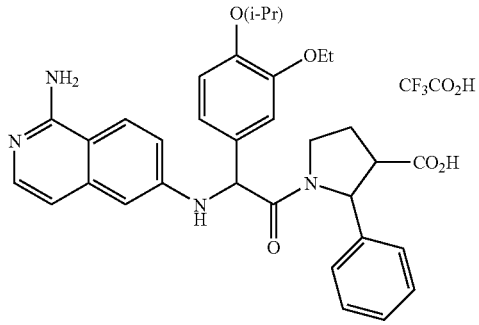

Example 9 was hydrolyzed with 3.0 equivalents of 1.0 M NaOH in MeOH/THF (1:1) to give Example 10 after prep HPLC purification. $^1$H NMR (400 MHz, Methanol-$d_4$) δ ppm 1.24 (m, 9H) 2.11 (m, 2H) 2.89 (m, 1H) 3.80 (m, 3H) 4.19 (m, J=39.62 Hz, 1H) 4.49 (m, 1H) 5.39 (m, 2H) 6.54 (m, 1H) 6.94 (m, 8H) 7.22 (m, 2H) 7.38 (m, 1H) 7.90 (m, 1H). LC-MS: 569 (M+H)$^+$.

Example 11

Methyl 1-(2-(1-aminoisoquinolin-6-ylamino)-2-(3-ethoxy-4-isopropoxyphenyl)acetyl)-2-(2-(isopropylthio)phenyl)pyrrolidine-3-carboxylate trifluoroacetic acid salt

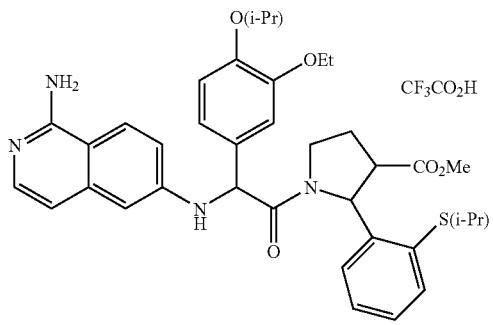

11A: 2-(Isopropylthio)benzaldehyde

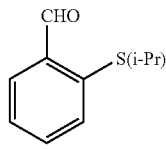

To 2-fluorobenzaldehyde (2.0 g, 16.1 mmol) and 2-thiopropane (1.35 g, 17.7 mmol) in dimethylformamide (6 mL) was added potassium carbonate (2.45 g, 17.7 mmol). The reaction mixture was stirred at 70° C. overnight. The crude reaction mixture was filtered and washed with ethyl acetate. The combined filtrate and washings were concentrated. The residue was redissolved in ethyl acetate and washed with water (3×) and then dried over sodium sulfate. Purification was performed by flash column chromatography to give 1.7 g of 11A. $^1$H NMR (400 MHz, CDCl$_3$) δ ppm 1.32 (d, J=6.85 Hz, 6H) 3.41 (m, 1H) 7.35 (d, J=4.40 Hz, 1H) 7.51 (m, 2H) 7.87 (d, J=7.34 Hz, 1H) 10.53 (s, 1H).

11B: (E)-Methyl 4-(2-(isopropylthio)benzylideneamino)butanoate

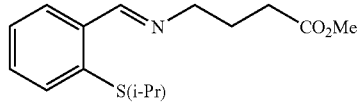

To methyl aminobutyric ester HCl salt (0.26 g, 1.66 mmol) in dichloromethane (9 mL) was added triethylamine (0.35 mL, 2.49 mmol) and then 11A (0.3 g, 1.66 mmol) and molecular sieves (0.17 g). The reaction was stirred overnight at rt and then filtered to remove the molecular sieves. The solvent was evaporated to give 0.86 g of 11B as a solid. $^1$H NMR (400 MHz, CDCl$_3$) δ ppm 1.24 (m, 6H) 1.99 (q, J=7.09 Hz, 2H) 2.38 (t, J=7.34 Hz, 2H) 3.63 (m, 6H) 7.38 (m, 2H) 7.52 (dd, J=7.83, 0.98 Hz, 1H) 7.82 (dd, J=7.83, 1.71 Hz, 1H) 8.92 (s, 1H).

11C: (cis)-Methyl 2-(2-(isopropylthio)phenyl)pyrrolidine-3-carboxylate

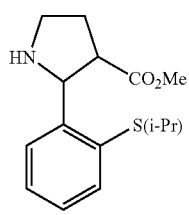

To the imine 11B (0.5 g, 1.31 mmol) and triethylamine (0.36 mL, 2.62 mmol) in dichloromethane (30 mL) at −10° C. was added titanium chloride (5.26 mL, 1.0 M in dichloromethane) dropwise under argon. The reaction was stirred at rt for 4 h and then quenched with saturated potassium carbonate. The mixture was filtered through celite and the aqueous layer was extracted with dichloromethane (2×). The organic extracts were combined, washed with brine and dried over sodium sulfate. The solvent was evaporated to give 0.32 g of crude product 11C. $^1$H NMR (400 MHz, Methanol-$d_4$) δ ppm 1.18 (d, J=6.60 Hz, 6H) 2.11 (m, 2H) 2.87 (m, J=13.94 Hz, 1H) 3.00 (m, J=18.95, 8.93 Hz, 1H) 3.16 (m, 1H) 3.56 (m, 3H) 3.69 (s, 1H) 4.88 (d, J=7.83 Hz, 1H) 5.19 (m, 1H) 7.20 (m, 2H) 7.42 (m, 2H).

11D: Example 11

Example 11 was prepared according to the general coupling-deprotection using 1C and 11C. $^1$H NMR (400 MHz, Methanol-$d_4$) δ ppm 1.33 (m, 15H) 2.20 (m, 2H) 2.91 (m, 1H) 3.67 (m, 2H) 3.82 (s, 3H) 4.00 (m, 2H) 4.17 (m, 1H) 4.61 (m, 1H) 5.78 (m, 2H) 6.48 (m, 1H) 7.07 (m, 7H) 7.42 (m, 2H) 8.00 (dd, J=49.15, 9.29 Hz, 1H). LC-MS: 657 $(M+H)^+$.

Example 12

1-(2-(1-Aminoisoquinolin-6-ylamino)-2-(3-ethoxy-4-isopropoxyphenyl)acetyl)-2-(2-(isopropylthio)phenyl)pyrrolidine-3-carboxylic acid trifluoroacetic acid salt

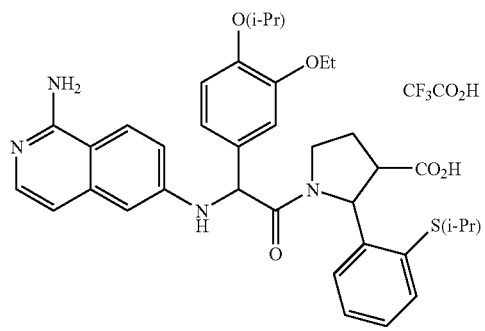

Example 11 was hydrolyzed with 3.0 equivalents of 1.0 M NaOH in MeOH/THF (1:1) to give Example 12 after prep HPLC purification. $^1$H NMR (400 MHz, Methanol-$d_4$) δ ppm 1.33 (m, 15H) 2.18 (m, 2H) 2.86 (d, J=7.58 Hz, 1H) 3.64 (m, 2H) 4.05 (m, 3H) 4.56 (m, 1H) 5.74 (m, 2H) 6.51 (dd, J=82.53, 7.70 Hz, 1H) 6.76 (m, 1H) 6.96 (m, 2H) 7.14 (m, 4H) 7.39 (m, 3H) 7.98 (m, 1H). LC-MS: 643 $(M+H)^+$.

Example 13

Methyl 1-(2-(1-aminoisoquinolin-6-ylamino)-2-(3-ethoxy-4-isopropoxyphenyl)acetyl)-2-(2-(isopropylsulfonyl)phenyl)pyrrolidine-3-carboxylate trifluoroacetic acid salt

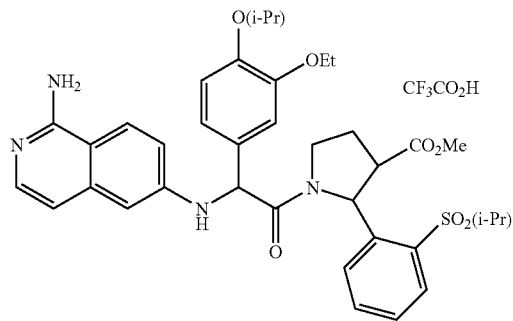

13A: (cis)-1-tert-Butyl 3-methyl 2-(2-(isopropylthio)phenyl)pyrrolidine-1,3-dicarboxylate

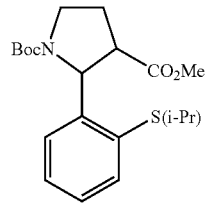

To 11C (0.25 g, 0.89 mmol) in methanol was added triethylamine (0.25 mL, 1.8 mmol) and then di-tert-butyl dicarbonate (0.29 g, 1.3 mmol). The reaction was stirred at rt for 3 h. The solvent was removed and crude residue was redissolved in ethyl acetate. The solution was washed with water and brine and dried over sodium sulfate. The solvent was evaporated and the crude residue was purified by flash column chromatography to give 0.24 g of 13A as a solid.

13B: (cis)-1-tert-Butyl 3-methyl 2-(2-(isopropylsulfonyl)phenyl)pyrrolidine-1,3-dicarboxylate

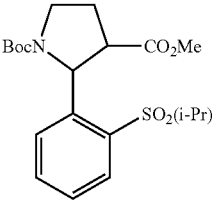

To 13A (0.24 g, 0.63 mmol) in methanol (3 mL) was added Oxone® (1.16 g, 1.90 mmol) in water (3 mL) at 0° C. The reaction was stirred for 3 h at rt. The reaction was quenched with 5% sodium bisulfite and then neutralized with 1 M sodium hydroxide. The solvent was evaporated and the aqueous layer was extracted with dichloromethane (3×). The organic extracts were combined, washed with saturated sodium chloride and dried over sodium sulfate. The solvent was evaporated and the crude residue was purified by flash column chromatography to give 0.17 g of 13B.

13C: (cis)-Methyl 2-(2-(isopropylsulfonyl)phenyl)pyrrolidine-3-carboxylate hydrochloride

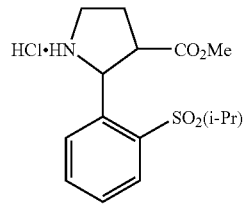

To 13B (0.27 g) was added hydrogen chloride (4M in dioxane, 2 mL). The reaction was stirred for 2 h at rt. The solvent was removed to give 0.18 g of 13C.

$^1$H NMR (400 MHz, Methanol-$d_4$) δ ppm 1.14 (d, J=6.85 Hz, 3H) 1.40 (d, J=6.85 Hz, 3H) 2.35 (m, 1H) 2.63 (m, 1H)

3.47 (m, 2H) 3.59 (m, 2H) 3.65 (m, 3H) 3.95 (m, 1H) 5.69 (d, J=9.05 Hz, 1H) 7.71 (m, 1H) 7.83 (m, 1H) 7.89 (m, 1H) 8.05 (dd, J=7.95, 1.34 Hz, 1H).

13D: Example 13

Example 13 was prepared according to the general coupling-deprotection using 1C and 13C. $^1$H NMR (400 MHz, Methanol-d$_4$) δ ppm 1.12 (d, J=6.85 Hz, 3H) 1.34 (m, 12H) 2.29 (m, 2H) 2.95 (dd, J=5.26, 2.08 Hz, 1H) 3.88 (m, 7H) 4.14 (m, 1H) 4.61 (m, 1H) 5.43 (s, 1H) 6.04 (s, 1H) 6.74 (s, 2H) 7.09 (m, 5H) 7.45 (m, 3H) 7.93 (dd, J=7.83, 1.22 Hz, 1H) 8.07 (d, J=9.29 Hz, 1H). LC-MS: 689 (M+H)$^+$.

Example 14

1-(2-(1-Aminoisoquinoln-6-ylamino)-2-(3-ethoxy-4-isopropoxyphenyl)acetyl)-2-(2-(isopropylsulfonyl)phenyl)pyrrolidine-3-carboxylic acid trifluoroacetic acid salt

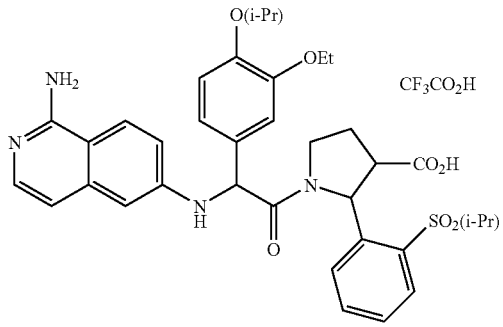

Example 13 was hydrolyzed with 3.0 equivalents of 1.0 M NaOH in MeOH/THF (1:1) to give Example 14 after prep HPLC purification. $^1$H NMR (400 MHz, Methanol-d$_4$) δ ppm 1.11 (d, J=6.60 Hz, 3H) 1.35 (m, 12H) 2.31 (m, 2H) 2.92 (d, J=7.34 Hz, 1H) 3.74 (m, 1H) 3.93 (m, 3H) 4.14 (d, J=3.42 Hz, 1H) 4.60 (m, 1H) 5.40 (s, 1H) 6.08 (s, 1H) 6.72 (m, 2H) 7.09 (m, 5H) 7.32 (d, J=6.85 Hz, 1H) 7.47 (m, 2H) 7.93 (dd, J=7.95, 1.34 Hz, 1H) 8.05 (d, J=9.29 Hz, 1H). LC-MS: 675 (M+H)$^+$.

Example 15

Methyl 1-(2-(1-aminoisoquinolin-6-ylamino)-2-(3-ethoxy-4-isopropoxyphenyl)acetyl)-2-(3-nitrophenyl)pyrrolidine-3-carboxylate trifluoroacetic acid salt

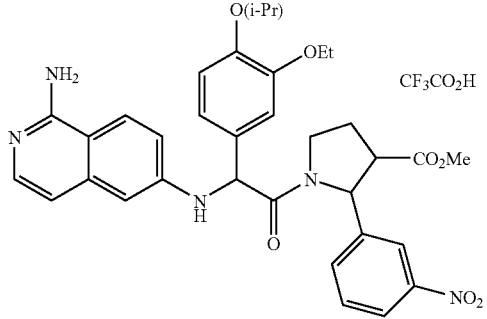

15A: (E)-Methyl 4-(3-nitrobenzylideneamino)butanoate

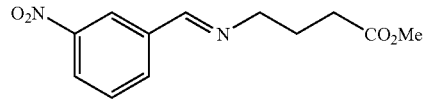

To the methyl aminobutyric ester HCl salt (2.0 g, 13.0 mmol) in dichloromethane was added triethylamine (2.7 mL, 19.5 mmol) and then the 3-nitrobenzaldehyde (1.96 g, 13.0 mmol) and molecular sieves (1.0 g). The reaction was stirred overnight at rt and then filtered to remove the molecular sieves. The solvent was evaporated to give 2.21 g of 15A as a yellow solid.

15B: (cis)-Methyl 2-(3-nitrophenyl)pyrrolidine-3-carboxylate

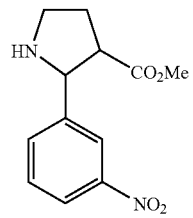

To the imine 15A (1.0 g, 2.84 mmol) and triethylamine (0.39 mL, 2.84 mmol) in dichloromethane (50 mL) at −10° C. was added titanium chloride (11.3 mL, 1.0 M in dichloromethane) dropwise under argon. The reaction was stirred at rt for 4 h and then quenched with saturated potassium carbonate. The mixture was filtered through celite and the aqueous layer was extracted with dichloromethane (2×). The organic extracts were combined, washed with brine and dried over sodium sulfate. The solvent was evaporated and the crude residue was purified by preparative HPLC equipped with a YMC ODS S5 (30×100 mm) column. The separation was performed using a linear gradient (solvent A: 10% acetonitrile-90% water-0.1% TFA; solvent B: 90% acetonitrile-90% water-0.1% TFA; 0 to 100% B in 12 min with a flow rate of 40 mL/min to give 0.32 g of 15B as a solid. $^1$H NMR (400 MHz, Methanol-d$_4$) δ ppm 2.53 (m, 2H) 3.47 (s, 3H) 3.62 (m, 1H) 3.79 (m, 2H) 5.14 (d, J=6.85 Hz, 1H) 7.76 (m, 2H) 8.33 (m, 2H).

15C: Example 15

Example 15 was prepared according to the general coupling-deprotection using 1C and 15B. $^1$H NMR (400 MHz, Methanol-d$_4$) δ ppm 1.31 (m, 9H) 2.24 (m, 2H) 3.33 (m, 3H) 3.90 (m, 5H) 4.55 (d, J=3.42 Hz, 1H) 5.53 (m, 2H) 6.69 (m, 2H) 7.17 (m, 8H) 8.05 (m, J=15.89 Hz, 2H). LC-MS: 628 (M+H)$^+$.

Example 16

1-(2-(1-Aminoisoquinolin-6-ylamino)-2-(3-ethoxy-4-isopropoxyphenyl)acetyl)-2-(3-nitrophenyl)pyrrolidine-3-carboxylic acid trifluoroacetic acid salt

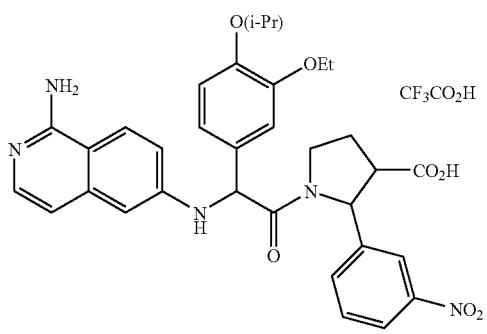

Example 15 was hydrolyzed with 3.0 equivalents of 1.0 M NaOH in MeOH/THF (1:1) to give Example 16 after prep HPLC purification. $^1$H NMR (400 MHz, Methanol-$d_4$) δ ppm 1.33 (m, 9H) 2.23 (m, 2H) 3.07 (d, J=44.02 Hz, 1H) 3.93 (m, 3H) 4.26 (m, 1H) 4.57 (m, 1H) 5.54 (m, 2H) 6.62 (m, 2H) 7.38 (m, 10H). LC-MS: 614 (M+H)$^+$.

Example 17

Methyl 2-(3-acetamidophenyl)-1-(2-(1-aminoisoquinolin-6-ylamino)-2-(3-ethoxy-4-isopropoxyphenyl)acetyl)pyrrolidine-3-carboxylate trifluoroacetic acid salt

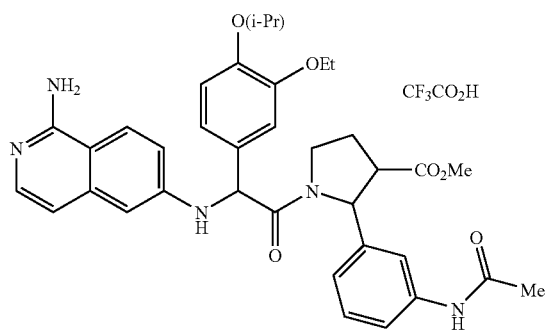

17A: (cis)-1-tert-Butyl 3-methyl 2-(3-nitrophenyl)pyrrolidine-1,3-dicarboxylate

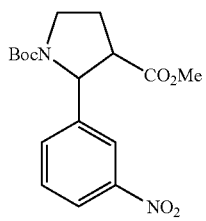

To 15B (0.15 g, 0.6 mmol) in methanol was added triethylamine (0.17 mL, 1.2 mmol) followed by di-tert-butyl dicarbonate (0.19 g, 0.9 mmol). The reaction was stirred at rt for 3 h. The solvent was removed and crude residue was redissolved in dichloromethane. The solution was washed with water and brine and dried over sodium sulfate. The solvent was evaporated to give 0.17 g of 17A as a solid.

17B: (cis)-1-tert-Butyl 3-methyl 2-(3-acetamidophenyl)pyrrolidine-1,3-dicarboxylate

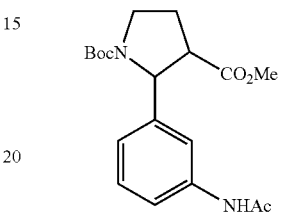

To 17A (0.17 g, 0.48 mmol) in methanol (15 mL) under nitrogen was added 10% Pd/C (0.07 g) and then a balloon filled with hydrogen gas was introduced. The reaction was stirred for 3 h at rt. The catalyst was filtered and the solvent was evaporated to give the desired amine. To the amine was added acetic anhydride (1.0 mL). The reaction was stirred at rt for 1 h. The solvent was removed and the crude residue was purified by flash column chromatography to give 0.12 g of 17B.

17C: (cis)-Methyl 2-(3-acetamidophenyl)pyrrolidine-3-dicarboxylate hydrochloride

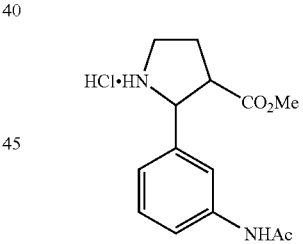

To 17B (0.12 g) in ethyl acetate (1.5 mL) was added hydrogen chloride (4M in dioxane, 2 mL). The reaction was stirred for 2 h at rt. The solvent was removed to give 0.090 g of 17C as a solid. $^1$H NMR (400 MHz, Methanol-$d_4$) δ ppm 2.01 (m, 1H) 2.13 (s, 3H) 2.49 (m, 1H) 3.56 (m, 1H) 3.66 (m, 3H) 3.71 (m, 2H) 4.95 (d, J=7.09 Hz, 1H) 7.08 (m, 1H) 7.38 (m, 2H) 7.82 (s, 1H).

17D: Example 17

Example 17 was prepared according to the general coupling-deprotection using 1C and 17C. $^1$H NMR (400 MHz, Methanol-$d_4$) δ ppm 1.33 (m, 9H) 2.11 (m, 3H) 2.28 (m, 2H) 3.40 (d, J=1.47 Hz, 3H) 3.75 (m, 3H) 4.07 (m, 2H) 4.58 (m, 1H) 5.38 (m, 2H) 6.56 (m, 2H) 7.16 (m, 10H) 7.97 (dd, J=53.92, 9.17 Hz, 1H). LC-MS: 640 (M+H)$^+$.

Example 18

2-(3-Acetamidophenyl)-1-(2-(1-aminoisoquinolin-6-ylamino)-2-(3-ethoxy-4-isopropoxyphenyl)acetyl)pyrrolidine-3-carboxylic acid trifluoroacetic acid salt

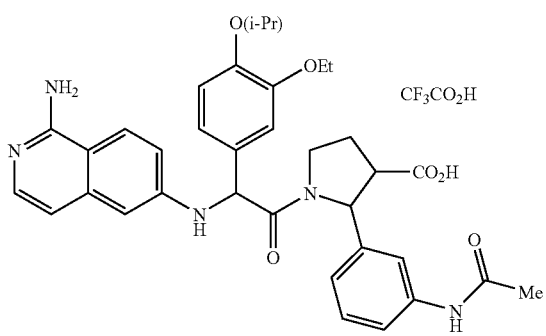

Example 17 was hydrolyzed with 3.0 equivalents of 1.0 M NaOH in MeOH/THF (1:1) to give Example 18 after prep HPLC purification. $^1$H NMR (400 MHz, Methanol-$d_4$) δ ppm 1.29 (m, 9H) 2.20 (m, 5H) 2.96 (m, 1H) 3.93 (m, 4H) 4.56 (m, 1H) 5.55 (m, 2H) 6.61 (m, 2H) 7.07 (m, 9H) 7.72 (m, 3H). LC-MS 626 (M+H)$^+$.

Example 19

1-(2-(5-Amino-2-(isopropylsulfonyl)phenyl)pyrrolidin-1-yl)-2-(1-aminoisoquinolin-6-ylamino)-2-(3-ethoxy-4-isopropoxyphenyl)ethanone trifluoroacetic acid salt

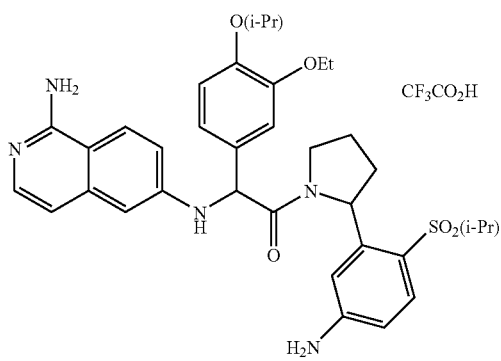

19A: (2-Bromo-4-nitrophenyl)(isopropyl)sulfane

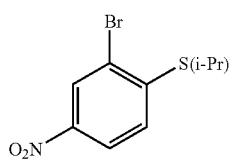

To 3-bromo-4-fluoronitrobenzene (5.0 g, 22.7 mmol) and 2-thiopropane (2.3 mL, 24.9 mmol) in DMF (15 mL) was added potassium carbonate (3.44 g, 24.9 mmol). The reaction was heated to 50° C. overnight. After cooling, the crude reaction mixture was filtered over celite and washed with ethyl acetate. The combined filtrate and washings were concentrated. The residue was redissolved in ethyl acetate and washed with water (3×) and then dried over sodium sulfate. Some of the yellow solid (2.53 g) product precipitated. The filtrate was concentrated and purified by flash column chromatography to give 3.65 g of product 19A (98% total yield). $^1$H NMR (400 MHz, CDCl$_3$) δ ppm 1.41 (d, J=6.60 Hz, 6H) 3.69 (m, 1H) 7.50 (d, J=8.80 Hz, 1H) 8.15 (dd, J=8.80, 2.45 Hz, 1H) 8.35 (d, J=2.45 Hz, 1H).

19B: 2-Bromo-1-(isopropylsulfonyl)-4-nitrobenzene

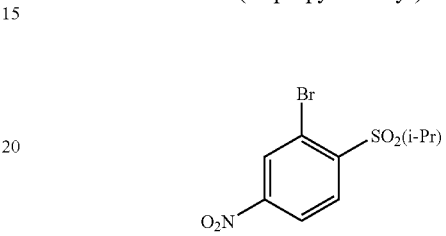

To 19A (1.6 g, 5.8 mmol) in methanol (7 mL) was added oxone® (10.7 g, 17.4 mmol) in water (10 mL). The reaction was stirred at rt overnight. The reaction was quenched with 5% NaHSO$_3$ and then neutralized with 1 M NaOH. The organic solvent was evaporated and the aqueous layer was extracted with dichloromethane (3×). The combined extracts were washed with brine and dried over sodium sulfate. The solvent was removed and the crude residue was purified by flash column chromatography to give 1.35 g of product 19B (76% yield). $^1$H NMR (400 MHz, Methanol-$d_4$) δ ppm 1.25 (d, J=6.85 Hz, 6H) 3.92 (m, 1H) 8.30 (d, J=8.56 Hz, 1H) 8.39 (m, 1H) 8.64 (d, J=11.96 Hz, 1H).

19C: tert-Butyl 2-(2-(isopropylsulfonyl)-5-nitrophenyl)-1H-pyrrole-1-carboxylate

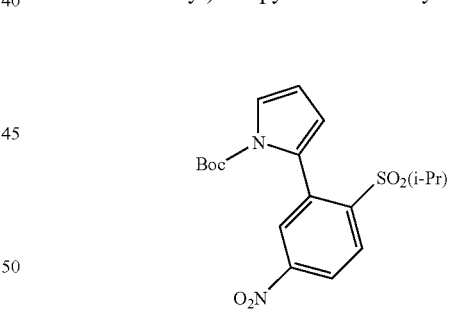

To a mixture of 19B (3.0 g, 9.7 mmol), 3A (2.5 g, 11.7 mmol) and sodium carbonate (19.5 mL, 2M, 38.9 mmol) in 1,2-dimethoxyethane (100 mL, flushed and degassed (3×) with nitrogen) was added Pd(PPh$_3$)$_4$ (2.2 g, 1.9 mmol) under nitrogen. The reaction was heated to 95° C. for 3 h. The catalyst was filtered over celite and washed with ethyl acetate. The organic layer was washed with water, brine and then dried over sodium sulfate. The solvent was removed and the crude residue was purified by flash column chromatography to give 3.68 g of product 19C (96% yield). $^1$H NMR (400 MHz, Methanol-$d_4$) δ ppm 1.01 (d, J=6.85 Hz, 3H) 1.15 (d, J=6.85 Hz, 3H) 1.20 (d, J=7.83 Hz, 9H) 3.00 (m, 1H) 6.29 (m, 2H) 7.41 (dd, J=3.18, 1.71 Hz, 1H) 8.20 (d, J=2.20 Hz, 1H) 8.25 (d, J=8.56 Hz, 1H), 8.41 (dd, J=8.68 Hz, 2.32 Hz, 1H).

19D: 4-(Isopropylsulfonyl)-3-(pyrrolidin-2-yl)benzenamine hydrochloride

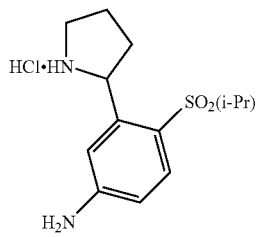

To platinum oxide (0.16 g) was added 19C (0.4 g, 1.0 mmol) in ethanol (20 mL) and hydrogen chloride (0.15 mL) under nitrogen. The reaction was placed under hydrogen (30 psi) and stirred at rt for 1.5 h. The catalyst was filtered over celite and washed with ethanol and methanol. The filtrate and washings were combined and the solvent was evaporated to give 0.35 g of yellow solid 19D.

19E: Example 19

Example 19 was prepared according to the general coupling-deprotection using 1C and 19D. $^1$H NMR (400 MHz, Methanol-$d_4$) δ ppm 1.02-1.16 (m, 3H) 1.16-1.43 (m, 12H) 1.65 (d, J=6.85 Hz, 1H) 1.83-2.07 (m, 3H) 2.43 (dd, J=12.96, 7.83 Hz, 1H) 3.42-3.79 (m, 2H) 3.84-3.99 (m, 2H) 3.97-4.16 (m, 1H) 4.40-4.61 (m, 1H) 5.44 (s, 1H) 5.53 (dd, J=8.07, 5.14 Hz, 1H) 5.69 (d, J=2.20 Hz, 1H) 6.40-6.58 (m, 1H) 6.66-6.77 (m, 1H) 6.80-7.16 (m, 6H) 7.22-7.31 (m, 1H) 7.47 (d, J=8.56 Hz, 1H) 7.99 (d, J=9.05 Hz, 1H). LC-MS: 646 (M+H)$^+$.

Example 20

Methyl 2-(5-amino-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylate trifluoroacetic acid salt

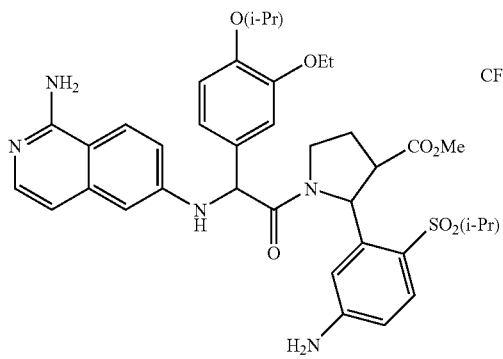

20A: 2-(Isopropylthio)-5-nitrobenzaldehyde

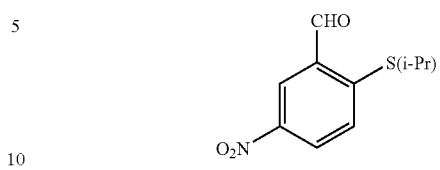

To 2-fluoro-5-nitrobenzaldehyde (5.8 g, 34.2 mmol) and 2-thiopropane (3.5 mL, 37.7 mmol) in DMF (20 mL) was added potassium carbonate (5.2 g, 37.7 mmol). The reaction mixture was stirred at 70° C. overnight. The crude reaction mixture was filtered and washed with ethyl acetate. The combined filtrate and washings were concentrated. The residue was redissolved in ethyl acetate and washed with water (3×) and then dried over sodium sulfate. Purification was performed by flash column chromatography to give 6.7 g of yellow oil product 20A. $^1$H NMR (400 MHz, DMSO-$d_6$) δ ppm 1.36 (d, J=6.60 Hz, 6H) 3.73-3.93 (m, 1H) 7.77 (d, J=9.05 Hz, 1H) 8.36 (dd, J=9.05, 2.69 Hz, 1H) 8.71 (d, J=2.69 Hz, 1H) 10.20 (s, 1H).

20B: (E)-Methyl 4-(2-(isopropylthio)-5-nitrobenzylideneamino)butanoate

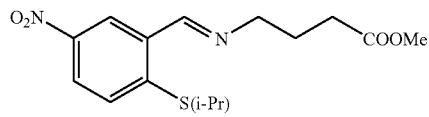

To the methyl aminobutyric ester (3.95 g, 25.7 mmol) in dichloromethane (200 mL) was added triethylamine (5.4 mL, 38.5 mmol) and then 20A (5.8 g, 25.7 mmol) and 4A molecular sieves (5.0 g). The reaction was stirred overnight at rt. The reaction mixture was filtered to remove the molecular sieves and the solvent was evaporated to give 12.0 g of a solid product 20B together with triethylamine HCl salt. $^1$H NMR (400 MHz, Methanol-$d_4$) δ ppm 1.37 (t, J=6.24 Hz, 6H) 1.93-2.11 (m, 2H) 2.45 (t, J=7.21 Hz, 2H) 7.68 (d, J=8.80 Hz, 1H) 8.21 (dd, J=8.80, 2.69 Hz, 1H) 8.61 (d, J=2.69 Hz, 1H) 8.79 (d, J=1.47 Hz, 1H).

20C: Methyl 2-(2-(isopropylthio)-5-nitrophenyl)pyrrolidine-3-carboxylate

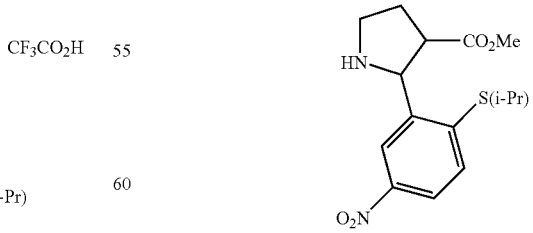

To 20B (12.0 g, 28.2 mmol) and triethylamine (7.86 mL, 56.4 mmol) in dichloromethane at −10° C. was added titanium chloride (113 mL, 1 M in dichloromethane) dropwise under argon. The reaction was stirred at rt for 4 h and then quenched with saturated potassium carbonate. The mixture was filtered through celite and the aqueous layer was extracted with dichloromethane (2×). The organic extracts were combined, washed with brine and dried over sodium sulfate. The solvent was evaporated to give 7.3 g of crude pyrrolidine 20C.

20D: 1-tert-Butyl-3-methyl 2-(2-(isopropylthio)-5-nitrophenyl)pyrrolidine-1,3-dicarboxylate

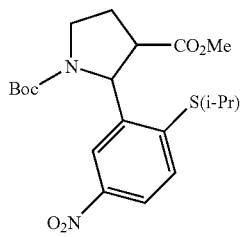

To the crude 20C (7.3 g, 22.5 mmol) in methanol (100 mL) was added triethylamine (6.3 mL, 45 mmol) and then di-tert-butyl dicarbonate (5.9 g, 27 mmol). The reaction was stirred at rt for 2 h. The solvent was removed and crude residue was redissolved in ethyl acetate. The solution was washed with water and brine and dried over sodium sulfate. The solvent was evaporated and the crude residue was purified by flash column chromatography to give 4.3 g of yellow semi-solid product 20D. $^1$H NMR analysis reveals approximately a 2:1 cis:trans ratio. $^1$H NMR (400 MHz, DMSO-$d_6$) δ ppm 0.92-1.13 (m, J=24.74 Hz, 6H) 1.24-1.47 (m, 9H) 1.99-2.25 (m, 2H) 3.19 (s, 3H) 3.51-3.64 (m, 2H) 3.63-3.71 (m, 1H) 3.73-3.89 (m, 2H) 5.17-5.48 (m, 1H) 7.50-7.71 (m, 1H) 7.72-7.92 (m, 1H) 8.07 (d, J=7.70 Hz, 1H).

20E: 1-tert-Butyl 3-methyl 2-(2-(isopropylsulfonyl)-5-nitrophenyl)pyrrolidine-1,3-dicarboxylate

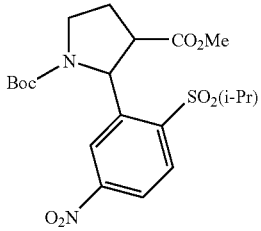

To 20D (4.0 g, 9.4 mmol) in methanol (80 mL) was added oxone® (17.3 g, 28.2 mmol) in water (70 mL) at 0° C. After stirring at rt for 4 h, the reaction was quenched with 5% sodium bisulfite and then neutralized with 1 M sodium hydroxide. The solvent was evaporated and the aqueous layer was extracted with dichloromethane (3×). The organic extracts were combined, washed with saturated sodium chloride and dried over sodium sulfate. The solvent was evaporated and the crude residue was purified by flash column chromatography to give 2.48 g of product 20E. NMR analysis reveals approximately a 2:1 cis:trans ratio. $^1$H NMR (400 MHz, DMSO-$d_6$) δ ppm 1.09-1.23 (m, 6H) 1.21-1.48 (m, 9H) 2.91-3.15 (m, J=2.20 Hz, 1H) 3.32-3.91 (m, 5H) 3.97-4.16 (m, J=6.60, 6.60, 6.60 Hz, 1H) 5.66-5.87 (m, 1H) 7.98-8.22 (m, 2H) 8.23-8.39 (m, 1H).

20F: 1-tert-Butyl 3-methyl 2-(5-amino-2-(isopropylsulfonyl)phenyl)pyrrolidine-1,3-dicarboxylate

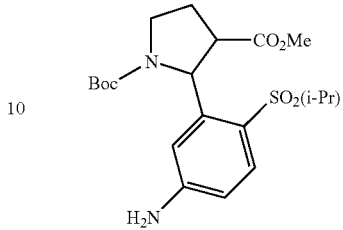

To palladium on carbon (0.5 g) was added 20E in methanol (50 mL) carefully under a stream of nitrogen. The vessel was flushed and degassed with nitrogen gas (3×) and a balloon containing hydrogen gas was introduced. The reaction was stirred at rt overnight. The catalyst was filtered through celite and washed with methanol several times. The filtrate and the combined washings were evaporated and dried to give 2.0 g of crude 20F.

20G: Methyl 2-(5-amino-2-(isopropylsulfonyl)phenyl)pyrrolidine-3-carboxylate hydrochloride

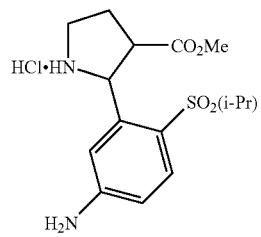

20F was treated with 4.0 N HCl in dioxane for 4.0 h. After removal of solvent, 20G was obtained as a white solid. $^1$H NMR (400 MHz, DMSO-$d_6$) δ ppm 7.62 (d, J=8.00 Hz, 1H) 6.6-6.9 (m, 2H) 5.1 and 5.0 (d, 1H) 3.2-3.5 (m, 3H) 3.0 (m, 1H) 2.1-2.4 (m, 2H) 1.32 (d, J=7.6 Hz, 3H) 1.22 (d, J=7.6 Hz, 3H).

20H: Example 20

Example 20 was prepared according to the general coupling-deprotection using 1C and 20G. $^1$H NMR (400 MHz, Methanol-$d_4$) δ ppm 0.99-1.15 (m, 3H) 1.17-1.45 (m, 12H) 2.02-2.41 (m, 2H) 3.03-3.16 (m, 3H) 3.45-3.61 (m, 1H) 3.62-3.84 (m, 2H) 3.84-4.04 (m, 2H) 4.11-4.30 (m, 1H) 4.40-4.63 (m, 1H) 5.48 (s, 1H) 5.54 (d, J=2.20 Hz, 1H) 5.87 (d, J=8.56 Hz, 1H) 6.43-6.58 (m, 1H) 6.68-6.78 (m, 1H) 6.81-7.18 (m, 5H) 7.21-7.31 (m, 1H) 7.46 (d, J=8.80 Hz, 1H) 7.99 (d, J=9.29 Hz, 1H). LC-MS: 704 (M+H)$^+$.

Example 21

2-(1-Aminoisoquinolin-6-ylamino)-2-(3-ethoxy-4-isopropoxyphenyl)-1-(2-(2-(isopropylsulfonyl)phenyl)pyrrolidin-1-yl)ethanone trifluoroacetic acid salt

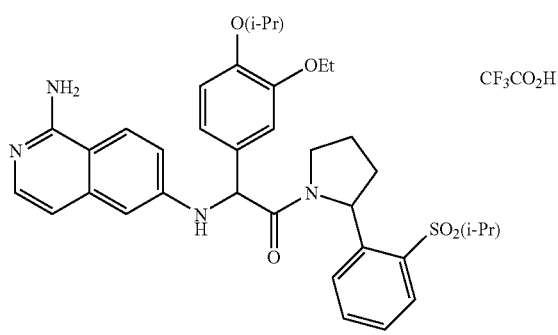

21A: (2-Bromophenyl)(isopropyl)sulfane

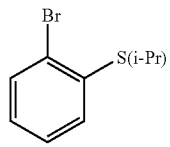

To 1-bromo-2-fluorobenzene (2.0 g, 11.4 mmol) and 2-thiopropane (1.1 mL, 12.5 mmol) in DMF (6 mL) was added potassium carbonate (1.7 g, 12.5 mmol). The reaction mixture was heated to 70° C. overnight. After cooling, the crude reaction mixture was filtered over celite and washed with ethyl acetate. The combined filtrate and washings were concentrated. The residue was redissolved in ethyl acetate and washed with water (3×) and then dried over sodium sulfate. The solvent was removed and the crude residue was purified by flash column chromatography to give 0.71 g of product 21A and recovered starting material 1-bromo-2-fluorobenzene. Note: TLC at 25% ethyl acetate in hexanes shows product and starting material sits right on top of each other. The reaction can be improve by adding more 2-thiopropane.
$^1$H NMR (400 MHz, Methanol-d$_4$) δ ppm 1.26-1.36 (m, 6H) 3.42-3.66 (m, 1H) 7.04-7.15 (m, 1H) 7.25-7.35 (m, 1H) 7.43 (dd, J=7.95, 1.59 Hz, 1H) 7.53-7.62 (m, 1H).

21B: (1-Bromo-2-(isopropylsulfonyl)benzene

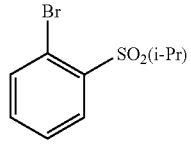

To 21A (0.7 g, 3.0 mmol) in methanol (5 mL) was added oxone®8 (5.6 g, 9.0 mmol) in water (5 mL). The reaction was stirred at rt for 4 h. The reaction was quenched with 5% NaHSO$_3$ and then neutralized with 1 M NaOH. The organic solvent was evaporated and the aqueous layer was extracted with dichloromethane (3×). The combined extracts were washed with brine and dried over sodium sulfate. The solvent was removed to give 0.53 g of product 21B (67% yield). $^1$H NMR (400 MHz, Methanol-d$_4$) δ ppm 1.26 (d, J=6.85 Hz, 6H) 3.80-4.00 (m, 1H) 7.45-7.68 (m, 2H) 7.87 (dd, J=7.46, 1.59 Hz, 1H) 8.10 (dd, J=7.34, 2.20 Hz, 1H).

21C: tert-Butyl 2-(2-(isopropylsulfonyl)phenyl)-1H-pyrrole-1-carboxylate

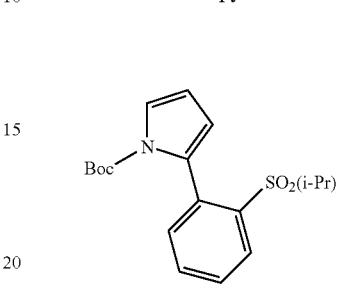

To 21B (0.53 g, 2.0 mmol), 3A (0.51 g, 2.4 mmol) and sodium carbonate (4.0 mL, 2M, 8.0 mmol) in 1,2-dimethoxyethane (25 mL, flushed and degassed (3×) with nitrogen) was added Pd(PPh$_3$)$_4$ (0.23 g, 0.2 mmol) under nitrogen. The reaction was heated to 95° C. for 3 h. The catalyst was filtered over celite and washed with ethyl acetate. The organic layer was washed with water, brine and then dried over sodium sulfate. The solvent was removed and the crude residue was purified by flash column chromatography to give 0.58 g of product 21C (69% yield).
$^1$H NMR (400 MHz, Methanol-d$_4$) δ ppm 1.00 (d, J=6.85 Hz, 3H) 1.17 (d, J=6.85 Hz, 3H) 1.19 (s, 9H) 2.93-3.07 (m, 1H) 6.19 (dd, J=3.30, 1.83 Hz, 1H) 6.26 (t, J=3.30 Hz, 1H) 7.36-7.44 (m, 1H) 7.45 (dd, J=7.46, 1.34 Hz, 1H) 7.60-7.67 (m, 1H) 7.68-7.75 (m, 1H) 8.03 (dd, J=7.70, 1.35 Hz, 1H).

21D: tert-Butyl 2-(2-(isopropylsulfonyl)phenyl)-1H-pyrrolidine-1-carboxylate

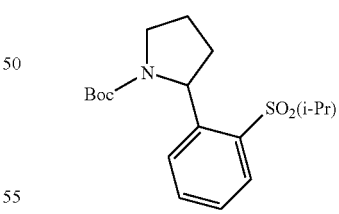

To platinum oxide (0.08 g) was added 21C in ethanol (8 mL) and hydrogen chloride (66 mL) under nitrogen. The reaction was placed under hydrogen (40 psi). After 2 h the catalyst was filtered over celite and washed with ethanol. The filtrate was neutralized with diethylamine. The solvent was evaporated and the crude residue was redissolved in dichloromethane. The organic layer was washed with water and brine, and dried over sodium sulfate. The solvent was removed to give 73 mg of crude product 21D.

21E: 2-(2-(Isopropylsulfonyl)phenyl)pyrrolidine hydrochloride

To 21D (75 mg) in ethyl acetate (1 mL) was added 4.0 N HCl in dioxane (1.5 mL). The reaction was stirred at rt for 2 h. The solvent was removed and the residue was dried under high vacuum to give 21E as a white solid. $^1$H NMR (400 MHz, Methanol-$d_4$) δ ppm 1.25 (d, J=6.60 Hz, 3H) 1.29 (d, J=6.85 Hz, 3H) 1.81-2.18 (m, 3H) 2.32-2.46 (m, 1H) 3.10-3.20 (m, 1H) 3.23-3.35 (m, 1H) 3.40-3.53 (m, 1H) 5.07 (t, J=7.83 Hz, 1H) 7.52-7.60 (m, 1H) 7.71-7.79 (m, 1H) 7.81-7.87 (m, 1H) 7.97 (dd, J=7.95, 1.35 Hz, 1H).

21F: Example 21

Example 21 was prepared according to the general coupling-deprotection using 1C and 21E. $^1$H NMR (400 MHz, Methanol-$d_4$) δ ppm 1.08-1.22 (m, 3H) 1.23-1.38 (m, 9H) 1.37-1.51 (m, 3H) 1.65 (dd, J=13.33, 6.72 Hz, 1H) 1.92-2.18 (m, 2H) 2.55 (dd, J=13.69, 6.85 Hz, 1H) 3.55-3.73 (m, 1H) 3.79-4.07 (m, 3H) 4.12-4.33 (m, 1H) 4.49-4.68 (m, 1H) 5.51 (s, 1H) 5.69 (t, J=6.85 Hz, 1H) 6.56 (d, J=7.83 Hz, 1H) 6.79 (d, J=2.20 Hz, 1H) 6.87-7.24 (m, 5H) 7.25-7.37 (m, 2H) 7.38-7.51 (m, 1H) 7.88 (dd, J=7.83, 1.22 Hz, 1H) 8.04 (d, J=9.29 Hz, 1H). LC-MS: 631 (M+H)$^+$.

Example 22

2-(5-Amino-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylic acid trifluoroacetic acid salt

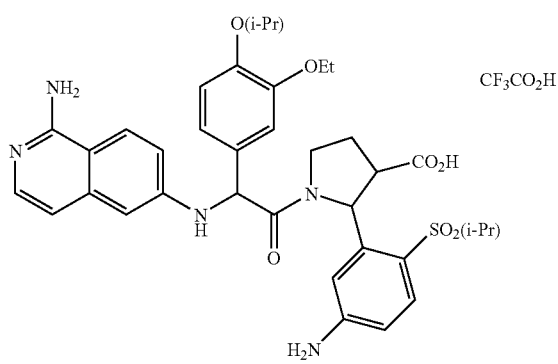

Example 22 was prepared by hydrolysis of the methyl ester Example 20 using a procedure similar to that used in the preparation of Example 12. $^1$H NMR (400 MHz, Methanol-$d_4$) δ ppm 1.01-1.23 (m, 3H) 1.20-1.50 (m, 12H) 2.10-2.45 (m, 2H) 3.48-3.66 (m, 1H) 3.72-3.92 (m, 2H) 3.90-4.05 (m, 2H) 4.02-4.35 (m, 1H) 4.47-4.67 (m, 1H) 5.47-5.72 (m, 1H) 5.84-6.03 (m, 1H) 6.41-6.64 (m, 1H) 6.62-7.20 (m, 7H) 7.30 (d, J=7.09 Hz, 1H) 7.43-7.61 (m, 1H) 8.03 (d, J=9.29 Hz, 1H). LC-MS: 690 (M+H)$^+$.

Example 23

N-(3-(1-(2-(1-Aminoisoquinolin-6-ylamino)-2-(4-fluoro-3-methoxyphenyl)acetyl)pyrrolidin-2-yl)-4-(isopropylsulfonyl)phenyl)acetamide trifluoroacetic acid salt

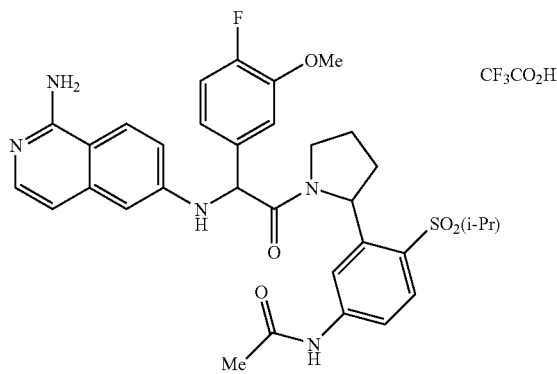

23A: 5-Bromo-2-fluorophenol

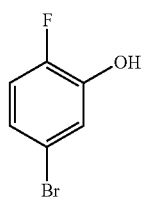

To a solution of 2,2,6,6-tetramethyl piperidine (5.6 mL, 33.2 mmol) in THF at −20° C. was added n-BuLi (1.6 M in hexanes, 18.8 mL, 30 mmol). The mixture was stirred at −20° C. for 10 min before it was cooled to −78° C. 1-Bromo-4-flurobenzene (2.95 mL, 27 mmol) was added over 10 min and the mixture was stirred at −78° C. for 2.0 h before trimethyl borate (6.0 mL, 54 mmol) was added. The mixture was stirred at −78° C. for 30 min and then at rt for 2.0 h. After it was cooled back to 0° C., glacial acetic acid (4.86 mL, 81 mmol) was added and stirred for 30 min, followed by addition of 30% $H_2O_2$ (4.86 mL, 81 mmol). The mixture was stirred at rt for 24 h, quenched by addition of $MnO_2$ (40 mg). After stirring at rt for 30 min, the cloudy solution was filtered through a pad of wet Celite® and extracted with EtOAc. The EtOAc layer was washed with aquous $NaHSO_3$, brine and dried over $Na_2SO_4$. The crude residue was purified by flash column chromatography (EtOAc:hexanes=1:5) to give 4.4 g (85%) of 23A as a liquid. ¹H NMR (400 MHz, CDCl₃) δ ppm 5.39 (s, 1H) 6.90-6.98 (m, 2H) 7.14 (dd, J=8.13, 1.98 Hz, 1H).

23B: 4-Bromo-2-methoxy-1-fluorobenzene

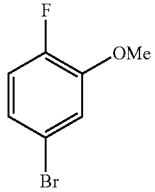

To a solution of 23A (3.3 g, 17.3 mmol) and K₂CO₃ (4.78 g, 34.6 mmol) in DMF (20 mL) was added methyl iodide (1.46 mL, 23.4 mmol) at rt. The mixture was heated at 40° C. for 2.0 h. After cooling to rt, it was diluted with diethyl ether, washed with water and brine, dried over MgSO₄. The crude residue was purified by flash column chromatography (EtOAc:hexanes=1:6) to give 2.74 g (77%) of 23B as a viscous oil. ¹H NMR (400 MHz, CDCl₃) δ ppm 3.89 (s, 3H), 6.95-7.00 (m, 3H).

23C: 3-Methoxy-4-fluorophenylboronic acid

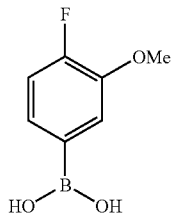

To a solution of 23B (2.7 g, 13.1 mmol) in THF (25 mL) at −78° C. was added n-BuLi (1.6 M in hexanes, 11.0 mL, 17.7 mmol). The mixture was stirred at −78° C. for 40 min before trimethyl borate (2.7 mL, 24.3 mmol) was added. The reaction was left stirring from −78° C. to rt over 18 h. It was quenched with 1.0 N HCl (40 mL), extracted with EtOAc, washed with brine and dried over Na₂SO₄. After evaporation of the solvent, the crude solid product was triturated with EtOAc/hexanes (1:4). After filtration, 23C (0.75 g, 35% yield) was collected as a white solid. ¹H NMR (400 MHz, Methanol-d₄) δ ppm 3.86 (s, 3H) 7.03-7.45 (m, 3H).

23D: 2-(1-Di-tert-butoxycarbonylaminoisoquinolin-6-ylamino)-2-(4-fluoro-3-methoxyphenyl)acetic acid

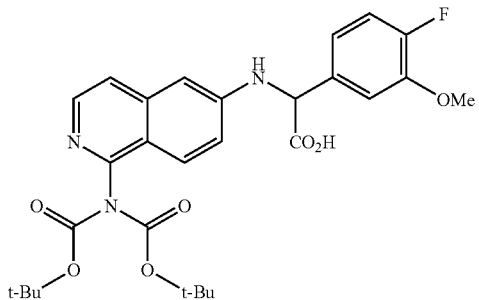

A mixture of 23C (39 mg, 0.23 mmol), 1B (72 mg, 0.2 mmol) and glyoxylic acid monohydrate (21 mg, 0.23 mmol) in 1,2-dicloroethane (0.8 mL) was heated at 85° C. for 8 min in a Microwave Reactor. The crude product was purified by flash column chromatography (CH₂Cl₂:MeOH=100:15) to give 54 mg (50%) of 23D as a solid. ¹H NMR (400 MHz, Methanol-d₄) δ ppm 1.27 (s, 18H) 3.83 (s, 3H) 4.97 (s, 1H) 6.61 (d, J=2.20 Hz, 1H) 7.00 (dd, J=10.99, 8.35 Hz, 1H) 7.12 (ddd, J=8.24, 4.28, 1.98 Hz, 1H) 7.23 (dd, J=9.23, 2.20 Hz, 1H) 7.32 (dd, J=8.35, 2.20 Hz, 1H) 7.38 (d, J=5.71 Hz, 1H) 7.61 (d, J=9.23 Hz, 1H) 7.99 (d, J=6.15 Hz, 1H); LC-MS: 542 (M+H)⁺.

23E: tert-Butyl 2-(5-amino-2-(isopropylsulfonyl)phenyl)pyrrolidine-1-carboxylate

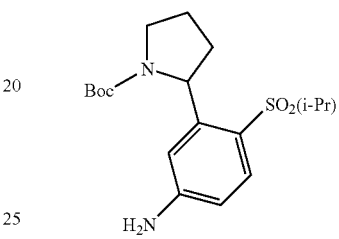

To platinum oxide (0.5 g) was added 19C in ethanol and hydrogen chloride (0.45 mL) under nitrogen. The reaction was placed under hydrogen (40 psi). After 1.5 h the reaction was half done, platinum oxide (200 mg) was added and reaction was stirred under hydrogen (40 psi) for 2 h. The catalyst was filtered over celite and washed with ethanol. The filtrate was neutralized with diethylamine. The solvent was evaporated and the crude residue was redissolved in dichloromethane. The organic layer was washed with water, brine and dried over sodium sulfate. The solvent was removed and the crude product was purified by flash column chromatography to give a white solid product 23E (1.6 g, 88%). ¹H NMR (400 MHz, Methanol-d₄) δ ppm 1.24 (m, 15H) 1.84 (m, 3H) 2.37 (m, 1H) 3.15 (m, 1H) 3.62 (m, 2H) 5.28 (s, 1H) 6.53 (d, J=19.56 Hz, 2H) 7.50 (d, J=8.56 Hz, 1H).

23F: N-(4-(Isopropylsulfonyl)-3-(pyrrolidin-2-yl)phenyl)acetamide hydrochloride

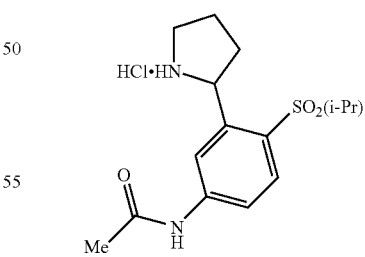

To 23E (0.15 g, 0.4 mmol) was added acetic anhydride (1.5 mL). The reaction was stirred for 1.0 h at rt. The solvent was removed and the crude residue was treated with HCl (4.0 mL, 4M in dioxane) in ethyl acetate (3.0 mL). The reaction was stirred for 2.0 h at rt. The solvent was removed and the product was placed on the high vac overnight to give 0.148 g (96% yield) of yellow solid product 23F. ¹H NMR (400 MHz, Methanol-d₄) δ ppm 1.15 (d, J=8 Hz, 3H) 1.23 (d, J=8 Hz, 3H)

2.10-2.35 (m, 6H) 2.40-2.51 (m, 1H) 3.36-3.46 (m, 3H) 5.3-5.4 (m, 1H) 7.80-7.81 (m, 1H) 8.87 (d, J=12 Hz, 1H) 8.09 (s, 1H).

23G: Example 23

Example 23 was prepared according to the general coupling-deprotection using 23D and 23F. $^1$H NMR (400 MHz, Methanol-$d_4$) δ ppm 1.17 (t, J=6.48 Hz, 3H) 1.41 (d, J=6.85 Hz, 3H) 1.56-1.85 (m, 1H) 1.97-2.24 (m, 5H) 2.39-2.66 (m, 1H) 3.58-3.68 (m, 3H) 3.66-3.80 (m, 1H) 3.83-4.03 (m, 1H) 4.10-4.30 (m, 1H) 5.53 (s, 1H) 5.68 (dd, J=7.95, 5.26 Hz, 1H) 6.79 (d, J=2.20 Hz, 1H) 6.91 (d, J=7.09 Hz, 2H) 6.99-7.09 (m, 1H) 7.07-7.24 (m, 3H) 7.23-7.43 (m, 2H) 7.72-7.84 (m, 1H) 8.04 (d, J=9.29 Hz, 1H). LC-MS: 634 (M+H)$^+$.

Example 24

Methyl 1-(2-(1-aminoisoquinolin-6-ylamino)-2-(3-ethoxy-4-isopropoxyphenyl)acetyl)-2-(2-(isopropylsulfonyl)-5-nitrophenyl)pyrrolidine-3-carboxylate trifluoroacetic acid salt

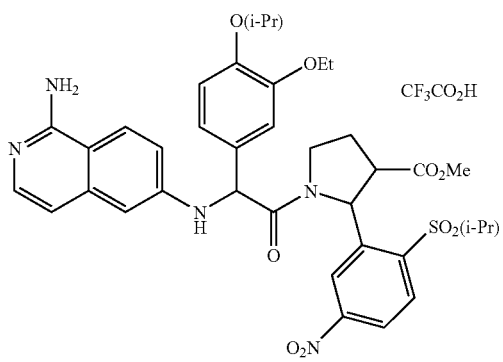

24A: Methyl 2-(2-(isopropylsulfonyl)-5-nitrophenyl)pyrrolidine-3-carboxylate hydrochloride

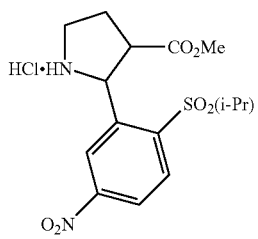

To 20E (100 mg, 0.20 mmol) was added hydrogen chloride (1 mL, 4M solution in dioxane). After stirring for 2 h at rt, the reaction was triturated with ether and filtered to give 24A (90 mg) as a white solid.

24B: Example 24

Example 24 was prepared according to the general coupling-deprotection using 1C and 24A. $^1$H NMR (400 MHz, Methanol-$d_4$) δ ppm 1.06-1.26 (m, 3H) 1.26-1.42 (m, 9H) 1.38-1.54 (m, 3H) 2.23-2.46 (m, 2H) 3.18 (s, 3H) 3.61-3.91 (m, 2H) 3.87-4.15 (m, 3H) 4.23-4.40 (m, 1H) 4.49-4.70 (m, 1H) 5.48-5.72 (m, 1H) 5.98-6.19 (m, 1H) 6.74-6.83 (m, 1H) 6.90 (d, J=7.34 Hz, 1H) 6.94-7.23 (m, 4H) 7.29-7.35 (m, 1H) 7.37 (d, J=2.20 Hz, 1H) 8.03 (t, J=8.44 Hz, 1H) 8.06-8.43 (m, 2H). LC-MS: 734 (M+H)$^+$.

Example 25

1-(2-(1-aminoisoquinolin-6-ylamino)-2-(3-ethoxy-4-isopropoxyphenyl)acetyl)-2-(2-(isopropylsulfonyl)-5-nitrophenyl)pyrrolidine-3-carboxylic acid trifluoroacetic acid salt

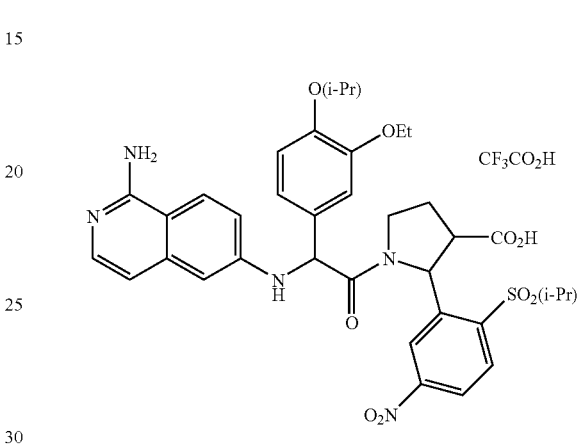

Example 25 was prepared by hydrolysis of the methyl ester Example 24 using a procedure similar to that used in the preparation of Example 12. $^1$H NMR (400 MHz, Methanol-$d_4$) δ ppm 1.06-1.22 (m, 3H) 1.23-1.56 (m, 12H) 2.21-2.48 (m, 2H) 3.01 (s, 1H) 3.70-3.91 (m, 2H) 3.91-4.07 (m, 2H) 4.06-4.26 (m, 1H) 4.50-4.69 (m, 1H) 5.38-5.58 (m, 1H) 6.11 (s, 1H) 6.61-6.80 (m, 1H) 6.94-7.20 (m, 5H) 7.23-7.38 (m, 1H) 7.43-7.62 (m, 1H) 7.96-8.12 (m, 1H) 8.14-8.26 (m, 1H) 8.27-8.38 (m, 1H). LC-MS: 720 (M+H)$^+$.

Example 26

(cis)-Methyl 2-(5-acetamido-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylate trifluoroacetic acid salt

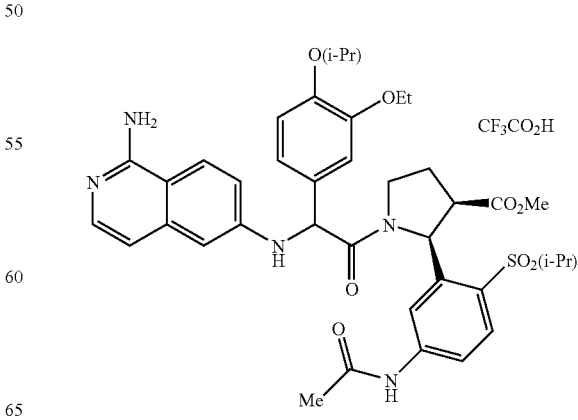

26A: cis-Methyl 2-(5-acetamido-2-(isopropylsulfonyl)phenyl)pyrrolidine-3-carboxylate trifluoroacetic acid salt and 26B: trans-Methyl 2-(5-acetamido-2-(isopropylsulfonyl)phenyl)pyrrolidine-3-carboxylate trifluoroacetic acid salt

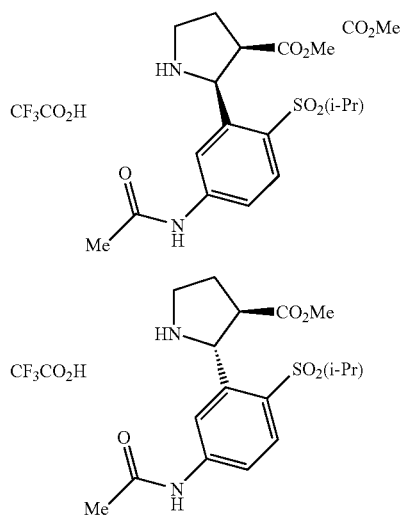

To 20F (0.3 g, 0.72 mmol) was added acetic anhydride (2.0 mL). The reaction was stirred for 1.0 h at rt. The solvent was removed and hydrogen chloride (3 mL, 4M in dioxane) was added to the crude residue. After stirring for 1.0 h at rt, the solvent was removed and the cis and trans diastereomers were separated by a preparative HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. 26A: $^1$H NMR (400 MHz, Methanol-$d_4$) δ ppm 1.28 (d, J=6.85 Hz, 3H) 1.35 (d, J=6.60 Hz, 3H) 2.18 (s, 3H) 2.47-2.61 (m, 1H) 2.63-2.80 (m, 1H) 3.39-3.50 (m, 4H) 3.49-3.63 (m, 1H) 3.63-3.77 (m, 1H) 3.82-3.99 (m, 1H) 5.88 (d, J=8.56 Hz, 1H) 7.57 (dd, J=8.80, 1.96 Hz, 1H) 8.00 (d, J=8.80 Hz, 1H). 26B: $^1$H NMR (400 MHz, methanol-$d_4$) δ ppm 1.20 (d, J=6.60 Hz, 3H) 1.44 (d, J=6.85 Hz, 3H) 2.14-2.24 (m, 3H) 2.31-2.55 (m, 1H) 2.59-2.82 (m, 1H) 3.38-3.67 (m, 3H) 3.72 (s, 3H) 3.86 (q, J=8.64 Hz, 1H) 5.73 (d, J=8.80 Hz, 1H) 7.68 (dd, J=8.68, 2.08 Hz, 1H) 8.01 (d, J=8.56 Hz, 1H) 8.34 (d, J=1.96 Hz, 1H).

26C: Example 26

Example 26 was prepared according to the general coupling-deprotection using 1C and 26A. $^1$H NMR (400 MHz, Methanol-$d_4$) δ ppm 1.13 (d, J=6.60 Hz, 3H) 1.23-1.34 (m, 9H) 1.39 (d, J=6.85 Hz, 3H) 2.05-2.18 (m, 3H) 2.22-2.49 (m, 2H) 3.15-3.28 (m, 3H) 3.50-3.73 (m, 2H) 3.76-4.05 (m, 3H) 4.22 (dd, J=7.09, 2.93 Hz, 1H) 4.46-4.66 (m, 1H) 5.47 (s, 1H) 6.07 (d, J=8.56 Hz, 1H) 6.75 (dd, J=16.02, 2.08 Hz, 2H) 6.86-7.04 (m, 3H) 7.05-7.18 (m, 2H) 7.32 (d, J=7.09 Hz, 1H) 7.53 (dd, J=8.68, 2.08 Hz, 1H) 7.76 (d, J=8.56 Hz, 1H) 8.04 (d, J=9.05 Hz, 1H). LC-MS: 746 (M+H)$^+$.

Example 27 trans-Methyl 2-(5-acetamido-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylate trifluoroacetic acid salt

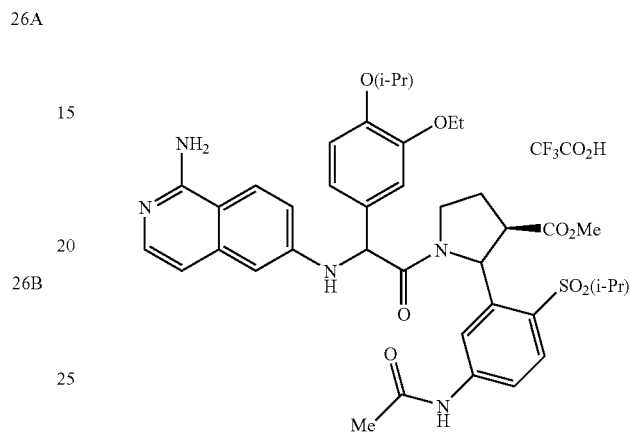

Example 27 was prepared according to the general coupling-deprotection using 1C and 26B. $^1$H NMR (400 MHz, Methanol-$d_4$) δ ppm 1.13 (d, J=6.60 Hz, 3H) 1.20-1.45 (m, 12H) 2.04-2.15 (m, 3H) 2.20-2.35 (m, 1H) 2.35-2.50 (m, 1H) 2.95 (d, J=7.58 Hz, 1H) 3.68-3.79 (m, 2H) 3.80 (s, 3H) 3.83-3.98 (m, 2H) 4.09-4.27 (m, 1H) 4.48-4.70 (m, 1H) 5.40 (s, 1H) 6.01 (s, 1H) 6.71 (d, J=2.20 Hz, 1H) 6.85 (d, J=1.96 Hz, 1H) 7.00 (d, J=8.07 Hz, 1H) 7.04-7.19 (m, 3H) 7.24 (d, J=1.96 Hz, 1H) 7.36 (d, J=7.09 Hz, 1H) 7.42 (dd, J=8.56, 2.20 Hz, 1H) 7.81 (d, J=8.80 Hz, 1H) 8.06 (d, J=9.29 Hz, 1H). LC-MS: 746 (M+H)$^+$.

Example 28 cis-Methyl 1-(2-(1-aminoisoquinolin-6-ylamino)-2-(3-ethoxy-4-isopropoxyphenyl)acetyl)-2-(2-(isopropylsulfonyl)-5-(methoxycarbonyl)phenyl)-pyrrolidine-3-carboxylate trifluoroacetic acid salt

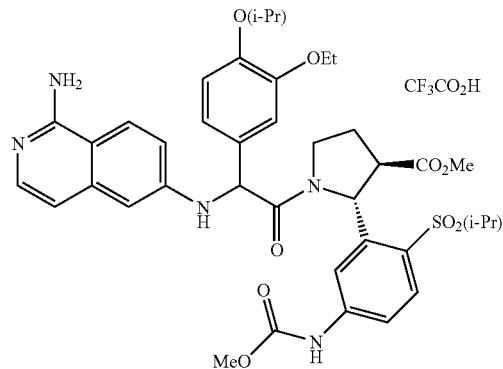

28A: cis-Methyl 2-(2-(isopropylsulfonyl)-5-(methoxycarbonyl)phenyl)pyrrolidine-3-carboxylate trifluoroacetic acid salt and 28B: trans-Methyl 2-(2-(isopropylsulfonyl)-5-(methoxycarbonyl)phenyl)pyrrolidine-3-carboxylate trifluoroacetic acid salt

28A

28B

To 20F (0.17 g, 0.39 mmol) in pyridine (2 mL) at 0° C. was added methyl chloroformate (61 μL, 0.78 mmoL). After 2.0 h of stirring at rt the reaction was acidified with 1M HCl to pH 3-4. The product was extracted with ethyl acetate and was washed with brine and dried over sodium sulfate. After evaporation of solvent, the crude product was treated with HCl (1.5 mL, 4M in dioxane) for 1.0 h at rt. The solvent was removed and the cis and trans diastereomers were separated by a preparative HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 10 to 60% B in 10 min, then 60% B for 2 min) with a flow rate of 20 mL/min. 28A. $^1$H NMR (400 MHz, Methanol-$d_4$) δ ppm 1.28 (d, J=6.85 Hz, 3H) 1.34 (d, J=6.60 Hz, 3H) 2.46-2.60 (m, 1H) 2.63-2.79 (m, 1H) 3.39-3.48 (m, 4H) 3.50-3.63 (m, 1H) 3.66-3.76 (m, 1H) 3.79 (s, 3H) 3.83-3.94 (m, 1H) 5.87 (d, J=8.31 Hz, 1H) 7.56 (dd, J=8.80, 1.96 Hz, 1H) 7.90 (d, J=1.96 Hz, 1H) 7.96 (d, J=8.56 Hz, 1H). 28B: $^1$H NMR (400 MHz, methanol-$d_4$) δ ppm 1.28 (d, J=6.85 Hz, 3H) 1.34 (d, J=6.60 Hz, 3H) 2.46-2.60 (m, 1H) 2.63-2.79 (m, 1H) 3.39-3.48 (m, 4H) 3.50-3.63 (m, 1H) 3.66-3.76 (m, 1H) 3.79 (s, 3H) 3.83-3.94 (m, 1H) 5.87 (d, J=8.31 Hz, 1H) 7.56 (dd, J=8.80, 1.96 Hz, 1H) 7.90 (d, J=1.96 Hz, 1H) 7.96 (d, J=8.56 Hz, 1H).

28C: Example 28

Example 28 was prepared according to the general coupling-deprotection using 1C and 28A. $^1$H NMR (400 MHz, Methanol-$d_4$) δ ppm 1.13 (d, J=6.60 Hz, 3H) 1.25-1.49 (m, 12H) 2.12-2.55 (m, 2H) 3.19-3.30 (m, 3H) 3.51-3.65 (m, 1H) 3.65-3.79 (m, 3H) 3.76-3.99 (m, 4H) 4.20 (d, J=2.93 Hz, 1H) 4.46-4.66 (m, 1H) 5.47 (s, 1H) 6.07 (d, J=8.31 Hz, 1H) 6.68-6.91 (m, 2H) 6.88-7.04 (m, 3H) 7.03-7.20 (m, 2H) 7.31 (t, J=7.95 Hz, 2H) 7.73 (d, J=8.56 Hz, 1H) 8.04 (d, J=9.29 Hz, 1H) 9.31 (s, 1H). LC-MS: 762 (M+H)$^+$.

Example 29 trans-Methyl 1-(2-(1-aminoisoquinolin-6-ylamino)-2-(3-ethoxy-4-isopropoxyphenyl)acetyl)-2-(2-(isopropylsulfonyl)-5-(methoxycarbonyl)phenyl)pyrrolidine-3-carboxylate trifluoroacetic acid salt

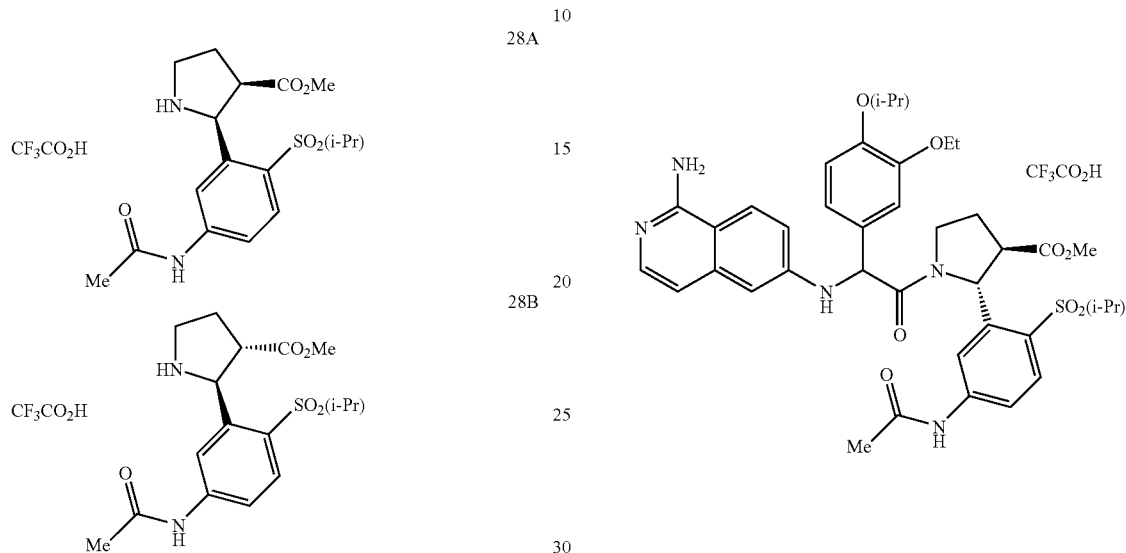

Example 29 was prepared according to the general coupling-deprotection using 1C and 28B. $^1$H NMR (400 MHz, Methanol-$d_4$) δ ppm 1.12 (d, J=6.60 Hz, 3H) 1.24-1.48 (m, 12H) 2.12-2.55 (m, 2H) 2.94 (d, J=7.34 Hz, 1H) 3.66-3.77 (m, 4H) 3.77-3.85 (m, 3H) 3.80-4.00 (m, 3H) 4.15 (d, J=7.34 Hz, 1H) 4.49-4.65 (m, 1H) 5.39 (s, 1H) 6.01 (s, 1H) 6.71 (d, J=2.20 Hz, 1H) 6.86-7.20 (m, 5H) 7.21-7.44 (m, 3H) 7.77 (d, J=8.80 Hz, 1H) 8.06 (d, J=9.29 Hz, 1H) 9.51 (s, 1H). LC-MS: 762 (M+H)$^+$.

Example 30

N-(3-(1-(2-(1-Aminoisoquinolin-6-ylamino)-2-(5-ethoxy-2-fluorophenyl)acetyl)pyrrolidin-2-yl)-4-(isopropylsulfonyl)phenyl)acetamide trifluoroacetic acid salt

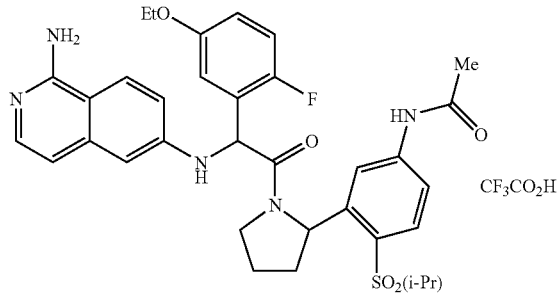

30A: 2-(1-Di-tert-butoxycarbonylaminoisoquinolin-6-ylamino)-2-(5-ethoxy-2-fluorophenyl)acetic acid

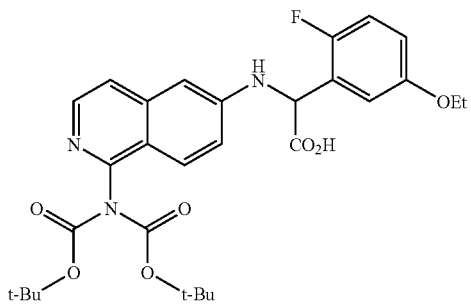

A mixture of 5-ethoxy-2-fluorophenylboronic acid (43 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography ($CH_2Cl_2$:MeOH=100:15) to give 28 mg (25%) of 30A as a solid. $^1$H NMR (400 MHz, Methanol-$d_4$) δ ppm 1.14 (s, 18H) 1.19 (t, J=6.81 Hz, 3H) 3.83 (q, J=7.03 Hz, 2H) 5.39 (s, 1H) 6.59 (d, J=2.20 Hz, 1H) 6.70-6.77 (m, 1H) 6.89-7.00 (m, 2H) 7.16 (dd, J=9.23, 2.20 Hz, 1H) 7.33 (d, J=5.71 Hz, 1H) 7.52 (d, J=9.23 Hz, 1H) 7.85 (s, 1H) 7.91 (d, J=6.15 Hz, 1H); LC-MS: 556 (M+H)$^+$.

30B: Example 30

Example 30 was prepared according to the general coupling-deprotection using 30A and 23F. $^1$H NMR (400 MHz, Methanol-$d_4$) δ ppm 1.17 (t, J=6.36 Hz, 3H) 1.32 (t, J=6.97 Hz, 3H) 1.41 (d, J=6.85 Hz, 3H) 1.71 (dd, J=12.23, 5.87 Hz, 1H) 1.97-2.28 (m, 5H) 2.51 (dd, J=13.08, 7.70 Hz, 1H) 3.60-3.81 (m, 2H) 3.83-4.07 (m, 2H) 4.07-4.35 (m, 1H) 5.54 (s, 1H) 5.69 (dd, J=7.95, 5.01 Hz, 1H) 6.79 (d, J=2.20 Hz, 1H) 6.85-6.97 (m, 2H) 7.06-7.22 (m, 3H) 7.26-7.47 (m, 3H) 7.69-7.84 (m, 1H) 8.04 (d, J=9.05 Hz, 1H). LC-MS: 648 (M+H)$^+$.

Example 31

N-(3-(1-(2-(1-Aminoisoquinolin-6-ylamino)-2-(4-chloro-3-ethoxyphenyl)acetyl)pyrrolidin-2-yl)-4-(isopropylsulfonyl)phenyl)acetamide trifluoroacetic acid salt

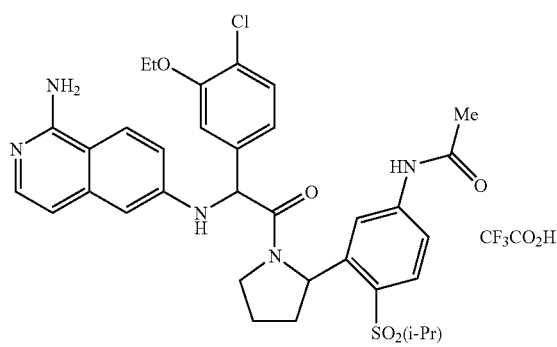

31A: 4-Bromo-1-chloro-2-ethoxybenzene

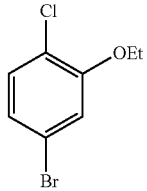

To a solution of 2-chloro-5-bromophenol (WO98/003464 which is incorporated herein by reference, 3.43 g, 16.5 mmol) and $K_2CO_3$ (4.57 g, 33.0 mmol) in DMF (20 mL) was added ethyl iodide (1.78 mL, 22.3 mmol) at rt. The mixture was heated at 55° C. for 3.0 h. After cooling to rt, the reaction was diluted with ether, washed with water and brine, and dried over $MgSO_4$. The crude residue was purified by flash column chromatography to give 3.85 g (99%) of 31A as viscous oil. $^1$H NMR (400 MHz, CDCl$_3$) δ ppm 1.48 (t, J=7.03 Hz, 3H) 4.08 (d, J=7.03 Hz, 2H) 7.03 (m, 2H) 7.22 (d, J=6.15 Hz, 2H).

31B: 4-Chloro-3-ethoxyphenylboronic acid

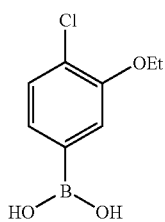

To a solution of 31A (3.8 g, 16 mmol) in THF (20 mL) at −78° C. was added n-BuLi (1.6 M in hexanes, 13.6 mL, 21.8 mmol). The mixture was stirred at −78° C. for 40 min before triisopropyl borate (7.43 mL, 32 mmol) was added. The reaction was left stirring, from −78° C. to rt over 18 h. It was quenched with 1.0 N HCl (50 mL), extracted with EtOAc, washed with brine and dried over $Na_2SO_4$. The crude residue was purified by flash column chromatography ($CH_2Cl_2$:EtOAc: MeOH=50:50:1) to give 1.85 g (57%) of 31B as a white solid. $^1$H NMR (400 MHz, CDCl$_3$) δ ppm 1.53 (t, J=7.03 Hz, 3H) 4.23 (d, J=7.03 Hz, 2H) 7.48 (d, J=7.91 Hz, 1H) 7.66 (d, J=6.15 Hz, 2H).

31C: 2-(1-Di-tert-butoxycarbonylaminoisoquinolin-6-ylamino)-2-(4-chloro-3-ethoxyphenyl)acetic acid

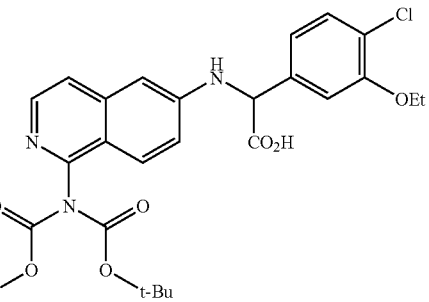

A mixture of 31B (46 mg, 0.23 mmol), 1B (72 mg, 0.2 mmol) and glyoxylic acid monohydrate (21 mg, 0.23 mmol)

in 1,2-dichloroethane (0.8 mL) was heated at 100° C. for 5 min in a Microwave Reactor. The crude product was purified by flash column chromatography (CH$_2$Cl$_2$:MeOH=100:15) to give 57 mg (50%) of 31C as a solid. $^1$H NMR (400 MHz, Methanol-d$_4$) δ ppm 1.29 (s, 18H) 1.32 (t, J=7.03 Hz, 3H) 4.10 (m, 2H) 5.52 (s, 1H) 6.81 (s, 1H) 7.21 (d, J=7.91 Hz, 1H) 7.21 (s, 1H), 7.37 (d, J=7.91 Hz, 1H) 7.50 (m, 1H), 7.69 (d, J=7.91 Hz, 1H) 7.96 (d, J=7.91 Hz, 1H) 8.00 (d, J=7.91 Hz, 1H) LC-MS: 572 (M+H)$^+$.

31D: Example 31

Example 31 was prepared according to the general coupling-deprotection using 31C and 23F. $^1$H NMR (400 MHz, Methanol-d$_4$) δ ppm 1.02-1.21 (m, 3H) 1.21-1.30 (m, 3H) 1.36-1.51 (m, 3H) 1.62-1.83 (m, 1H) 1.99-2.22 (m, 5H) 2.52 (dd, J=13.33, 7.95 Hz, 1H) 3.48-3.73 (m, 2H) 3.69-3.86 (m, 1H) 3.88-4.05 (m, 1H) 4.09-4.26 (m, 1H) 5.70 (dd, J=8.07, 5.14 Hz, 1H) 5.83 (s, 1H) 6.58 (dd, J=5.62, 3.18 Hz, 1H) 6.79 (d, J=2.45 Hz, 1H) 6.85-7.00 (m, 2H) 7.10-7.23 (m, 3H) 7.32 (d, J=7.09 Hz, 1H) 7.42 (dd, J=8.56, 2.20 Hz, 1H) 7.79 (d, J=8.56 Hz, 1H) 8.05 (d, J=9.29 Hz, 1H). LC-MS: 664 (M+H)$^+$.

Example 32

AT-3-(1-(2-(1-Aminoisoquinolin-6-ylamino)-2-(3-ethoxy-4-fluorophenyl)acetyl)pyrrolidin-2-yl)-4-(isopropylsulfonyl)phenyl)acetamide trifluoroacetic acid salt

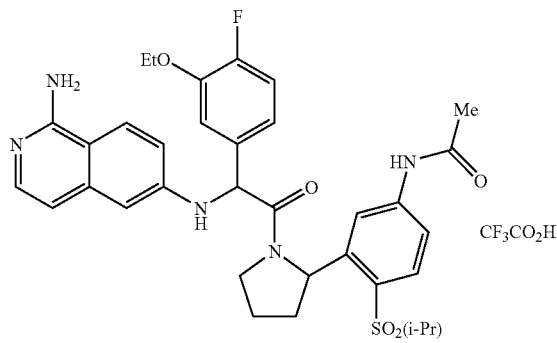

32A: 4-Bromo-2-ethoxy-1-fluorobenzene

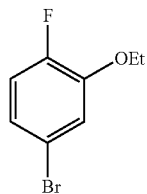

To a solution of 23A (4.4 g, 23 mmol) and K$_2$CO$_3$ (6.4 g, 46 mmol) in DMF (30 mL) was added ethyl iodide (2.49 mL, 31 mmol) at rt. The mixture was heated at 50° C. for 2.0 h. After cooling to rt, it was diluted with ether, washed with water and brine, dried over MgSO$_4$. The crude residue was purified by flash column chromatography (EtOAc:hexanes=1:5) to give 3.86 g (77%) of 32A as viscous oil.

$^1$H NMR (400 MHz, CDCl$_3$) δ ppm 1.47 (m, 3H) 4.00 (m, 2H) 6.96-7.08 (m, 3H).

32B: 3-Ethoxy-4-fluorophenylboronic acid

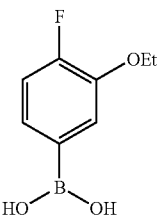

To a solution of 32A (3.86 g, 17.6 mmol) in THF (60 mL) at −78° C. was added n-BuLi (1.6 M in hexanes, 14.3 mL, 22.8 mmol). The mixture was stirred at −78° C. for 40 min before trimethyl borate (3.63 mL, 33 mmol) was added. The reaction was left stirring from −78° C. to rt over 4 h. It was quenched with 1.0 N HCl (40 mL), extracted with EtOAc, washed with brine and dried over Na$_2$SO$_4$. After evaporation of the solvent, the crude solid product was triturated with EtOAc/hexanes (1:4). After filtration, 32B (2.2 g, 69% yield) was collected as a white solid. $^1$H NMR (400 MHz, CDCl$_3$) δ ppm 1.42 (t, J=7.03 Hz, 3H) 4.11 (q, J=7.03 Hz, 2H) 7.03 (dd, J=11.42, 8.35 Hz, 1H) 7.18-7.29 (m, 2H) 7.35 (d, J=7.91 Hz, 1H).

32C: 2-(1-Di-tert-butoxycarbonylaminoisoquinolin-6-ylamino)-2-(3-ethoxy-4-fluorophenyl)acetic acid

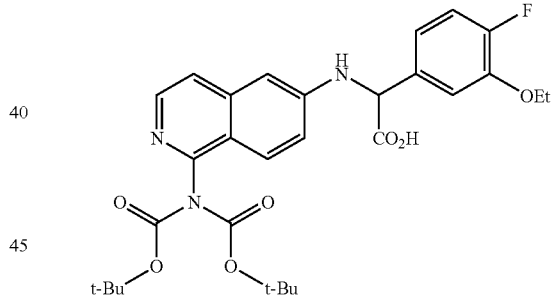

A mixture of 32B (43 mg, 0.23 mmol), 1B (72 mg, 0.2 mmol) and glyoxylic acid monohydrate (21 mg, 0.23 mmol) in 1,2-dicloroethane (0.8 mL) was heated at 100° C. for 5 min in a Microwave Reactor. The crude product was purified by flash column chromatography (CH$_2$Cl$_2$:MeOH=100:15) to give 36 mg (32%) of 32C as a solid. $^1$H NMR (400 MHz, Methanol-d$_4$) δ ppm 1.26 (s, 18H) 4.08 (dd, J=12.30, 7.03 Hz, 2H) 4.98 (s, 1H) 6.61 (d, J=2.20 Hz, 1H) 7.03 (s, 1H) 7.13 (s, 1H) 7.25 (s, 2H) 7.38 (d, J=6.15 Hz, 1H) 7.61 (d, J=9.23 Hz, 1H) 7.99 (d, J=6.15 Hz, 1H); LC-MS: 556 (M+H)$^+$.

32D: Example 32

Example 32 was prepared according to the general coupling-deprotection using 32C and 23F. $^1$H NMR (400 MHz, Methanol-d$_4$) δ ppm 1.17 (t, J=6.85 Hz, 3H) 1.25-1.37 (m, 3H) 1.35-1.50 (m, 3H) 1.63-1.83 (m, 1H) 1.99-2.23 (m, 5H) 2.40-2.63 (m, 1H) 3.65-3.81 (m, 3H) 3.82-4.32 (m, 3H) 5.52 (s, 1H) 5.68 (dd, J=8.07, 5.14 Hz, 1H) 6.73-6.83 (m, 1H)

6.84-6.99 (m, 2H) 7.03-7.11 (m, 1H) 7.07-7.23 (m, 3H) 7.25-7.42 (m, 2H) 7.70-7.84 (m, 1H) 8.04 (d, J=9.05 Hz, 1H). LC-MS: 648 (M+H)+.

Example 33 cis-2-(5-Acetamido-2-isopropylsulfonyl)phenyl)-1-(2-(1-aminoisoquinolin-6-ylamino)-2-(3-ethoxy-4-isopropoxyphenyl)acetyl)pyrrolidine-3-carboxylic acid trifluoroacetic acid salt

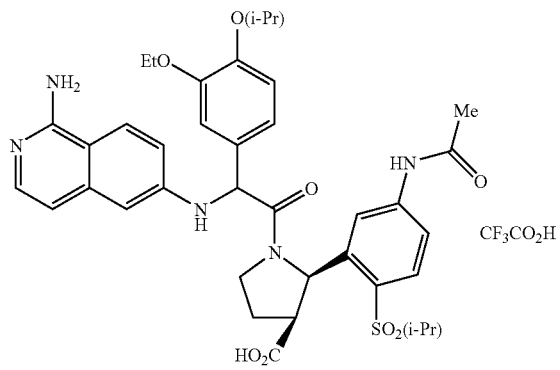

Example 33 was prepared by hydrolysis of the methyl ester Example 26 using a procedure similar to that used in the preparation of Example 12. $^1$H NMR (400 MHz, Methanol-$d_4$) δ ppm 1.03-1.19 (m, 3H) 1.18-1.44 (m, 12H) 2.03-2.16 (m, 3H) 2.21-2.55 (m, 2H) 2.91 (d, J=7.58 Hz, 1H) 3.64-3.81 (m, 2H) 3.82-4.02 (m, 2H) 4.02-4.25 (m, 1H) 4.45-4.66 (m, 1H) 5.36 (s, 1H) 6.04 (s, 1H) 6.60-6.76 (m, 1H) 6.85 (d, J=1.96 Hz, 1H) 6.93-7.03 (m, 1H) 7.00-7.18 (m, 3H) 7.23 (d, J=1.96 Hz, 1H) 7.31 (d, J=7.09 Hz, 1H) 7.41 (dd, J=8.56, 2.20 Hz, 1H) 7.80 (d, J=8.56 Hz, 1H) 7.95-8.13 (m, 1H). LC-MS: 732 (M+H)+.

Example 34 trans-2-(5-Acetamido-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylic acid trifluoroacetic acid salt

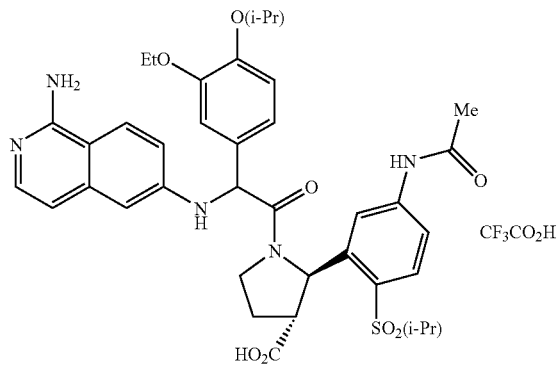

Example 34 was prepared by hydrolysis of the methyl ester Example 27 using a procedure similar to that used in the preparation of Example 12. $^1$H NMR (400 MHz, Methanol-$d_4$) δ ppm 1.13 (d, J=6.60 Hz, 3H) 1.24-1.47 (m, 12H) 2.10 (s, 3H) 2.23-2.37 (m, 1H) 2.39-2.52 (m, 1H) 2.91 (d, J=0.98 Hz, 1H) 3.65-3.82 (m, 2H) 3.82-3.99 (m, 2H) 4.13 (d, 1H) 4.59 (d, J=6.11 Hz, 1H) 5.37 (s, 1H) 6.05 (s, 1H) 6.69 (d, J=1.71 Hz, 1H) 6.86 (d, J=1.47 Hz, 1H) 6.96-7.04 (m, 1H) 7.05-7.18 (m, 3H) 7.24 (d, J=1.96 Hz, 1H) 7.32 (d, J=7.09 Hz, 1H) 7.42 (dd, J=8.44, 2.08 Hz, 1H) 7.82 (d, J=8.56 Hz, 1H) 8.05 (d, J=9.29 Hz, 1H). LC-MS: 732 (M+H)+.

Example 35 cis-1-(2-(1-aminoisoquinolin-6-ylamino)-2-(3-ethoxy-4-isopropoxyphenyl)acetyl)-2-(2-(isopropylsulfonyl)-5-(methoxycarbonyl)phenyl)pyrrolidine-3-carboxylic acid trifluoroacetic acid salt

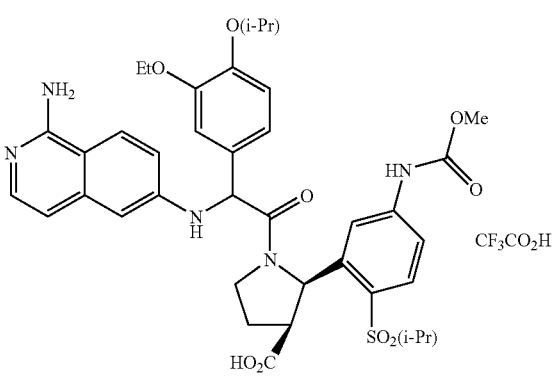

Example 35 was prepared by hydrolysis of the methyl ester Example 28 using a procedure similar to that used in the preparation of Example 12. $^1$H NMR (400 MHz, Methanol-$d_4$) δ ppm 1.08-1.20 (m, 3H) 1.24-1.45 (m, 12H) 2.18-2.57 (m, 2H) 2.76-3.10 (m, 2H) 3.65-3.78 (m, 3H) 3.80-4.01 (m, 3H) 4.07-4.24 (m, 1H) 4.44-4.65 (m, 1H) 5.37 (s, 1H) 6.04 (s, 1H) 6.61-7.18 (m, 3H) 7.21-7.39 (m, 2H) 7.68-7.84 (m, 1H) 7.90-8.62 (m, 3H) 8.75-9.60 (m, 2H). LC-MS: 748 (M+H)+.

Example 36 trans-1-(2-(1-aminoisoquinolin-6-ylamino)-2-(3-ethoxy-4-isopropoxyphenyl)acetyl)-2-(2-(isopropylsulfonyl)-5-(methoxycarbonyl)phenyl)pyrrolidine-3-carboxylic acid trifluoroacetic acid salt

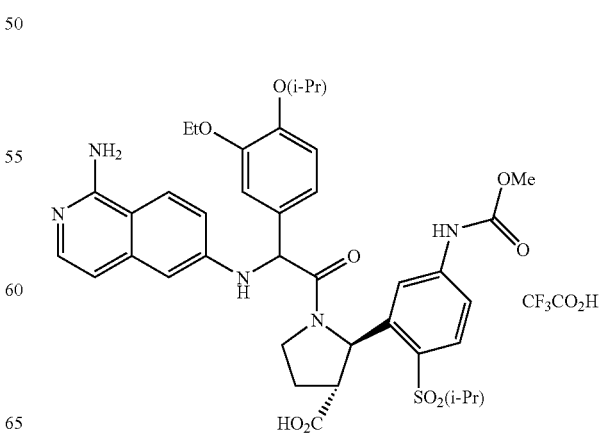

Example 36 was prepared by hydrolysis of the methyl ester Example 29 using a procedure similar to that used in the preparation of Example 12. $^1$H NMR (400 MHz, Methanol-$d_4$) δ ppm 1.03-1.19 (m, 3H) 1.20-1.45 (m, 12H) 2.19-2.52 (m, 2H) 2.76-3.09 (m, 2H) 3.64-3.78 (m, 3H) 3.75-4.02 (m, 3H) 4.03-4.28 (m, 1H) 4.44-4.66 (m, 1H) 5.41 (d, J=41.57 Hz, 1H) 5.97-6.16 (m, 1H) 6.55-7.18 (m, 5H) 7.18-7.43 (m, 1H) 7.64-8.17 (m, 3H) 8.44-8.92 (m, 2H). LC-MS: 748 (M+H)$^+$.

Example 37 cis-methyl 1-(2-(1-aminoisoquinolin-6-ylamino)-2-(3-ethoxy-4-fluorophenyl)acetyl)-2-(2-(isopropylsulfonyl)phenyl)pyrrolidine-3-carboxylate trifluoroacetic acid salt

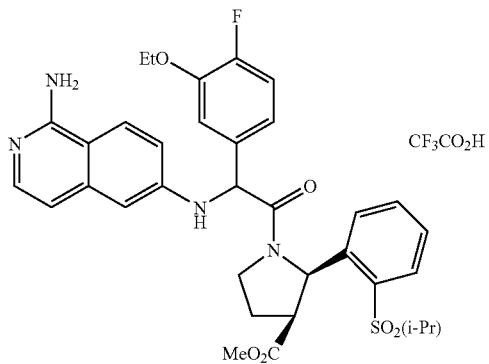

Example 37 was prepared according to the general coupling-deprotection using 32C and 13C. $^1$H NMR (400 MHz, Methanol-$d_4$) δ ppm 1.11 (d, J=6.60 Hz, 3H) 1.24-1.41 (m, 6H) 2.13-2.42 (m, 2H) 2.85-3.03 (m, 1H) 3.69-3.89 (m, 5H) 3.86-4.27 (m, 3H) 5.49 (s, 1H) 6.03 (s, 1H) 6.65-6.81 (m, 2H) 6.96-7.27 (m, 5H) 7.35 (d, J=7.09 Hz, 1H) 7.39-7.58 (m, 2H) 7.91 (d, J=7.83 Hz, 1H) 8.06 (d, J=9.05 Hz, 1H). LC-MS: 649 (M+H)$^+$.

Example 38 cis-Methyl 1-(2-(1-aminoisoquinolin-6-ylamino)-2-(4-chloro-3-ethoxyphenyl)acetyl)-2-(2-(isopropylsulfonyl)phenyl)pyrrolidine-3-carboxylate trifluoroacetic acid salt

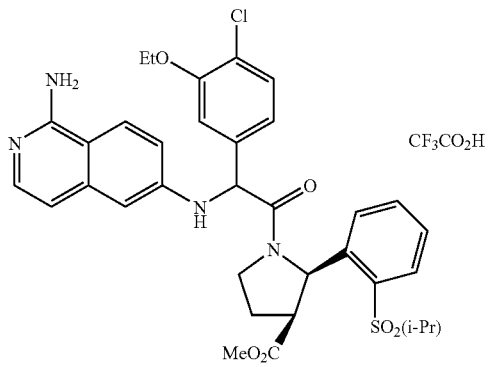

Example 38 was prepared according to the general coupling-deprotection using 31C and 13C. $^1$H NMR (400 MHz, Methanol-$d_4$) δ ppm 1.11 (d, J=6.60 Hz, 3H) 1.26-1.48 (m, 6H) 2.13-2.52 (m, 2H) 2.83-3.07 (m, 1H) 3.66-4.01 (m, 6H) 3.99-4.33 (m, 2H) 5.52 (s, 1H) 6.03 (d, J=1.71 Hz, 1H) 6.65-6.82 (m, 2H) 7.02-7.24 (m, 4H) 7.31-7.41 (m, 1H) 7.40-7.62 (m, 3H) 7.92 (dd, J=7.83, 1.22 Hz, 1H) 8.07 (d, J=9.29 Hz, 1H). LC-MS: 665 (M+H)$^+$.

Example 39 cis-Methyl 1-(2-(1-aminoisoquinolin-6-ylamino)-2-(4-fluoro-3-methoxyphenyl)acetyl)-2-(2-(isopropylsulfonyl)phenyl)pyrrolidine-3-carboxylate trifluoroacetic acid salt

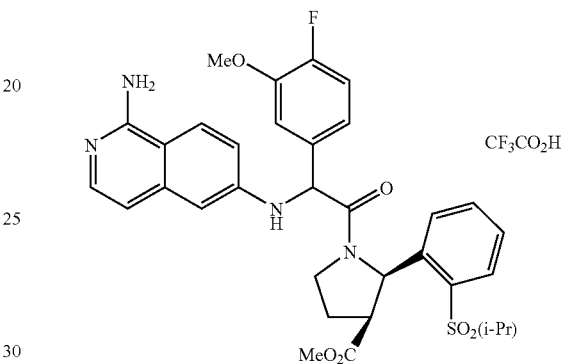

Example 39 was prepared according to the general coupling-deprotection using 23D and 13C. $^1$H NMR (400 MHz, Methanol-$d_4$) δ ppm 1.12 (d, J=6.60 Hz, 3H) 1.25-1.46 (m, 3H) 2.14-2.48 (m, 2H) 2.86-3.02 (m, 1H) 3.70-3.92 (m, 8H) 4.06-4.30 (m, 1H) 5.51 (s, 1H) 6.03 (s, 1H) 6.67-6.82 (m, 2H) 7.00-7.28 (m, 5H) 7.36 (d, J=7.09 Hz, 1H) 7.42-7.60 (m, 2H) 7.92 (dd, J=7.58, 1.47 Hz, 1H) 8.08 (d, J=9.05 Hz, 1H). LC-MS: 635 (M+H)$^+$.

Example 40

N-(3-((R)-1-((R)-2-(1-aminoisoquinolin-6-ylamino)-2-(3-ethoxy-4-isopropoxyphenyl)acetyl)pyrrolidin-2-yl)-4-(isopropylsulfonyl)phenyl)acetamide trifluoroacetic acid salt

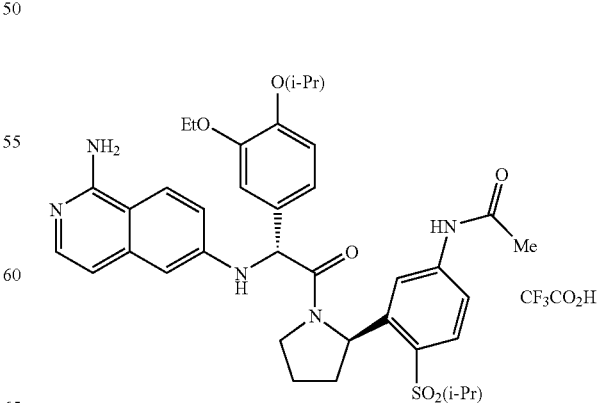

40A: (R)-tert-butyl 2-(5-amino-2-(isopropylsulfonyl)phenyl)pyrrolidine-1-carboxylate and 40B: (S)-tert-butyl 2-(5-amino-2-(isopropylsulfonyl)phenyl)pyrrolidine-1-carboxylate

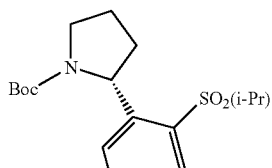

40A

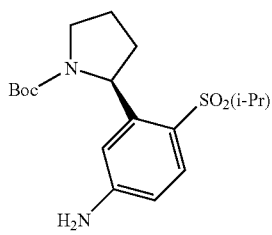

40B

Racemate 23E was separated using a preparative HPLC equipped with a Chiralpak®AD column (5 cm×50 cm, 20μ). The separation was performed using an isocratic method of 15% isopropanol/heptane with 0.1% diethylamine for 100 min with a flow rate of 50 mL/min. The first peak is 40A: $^1$H NMR (400 MHz, Methanol-$d_4$) δ ppm 1.20 (m, 15H) 1.83 (s, 3H) 2.44 (s, 1H) 3.26 (m, 1H) 3.64 (m, 2H) 5.29 (s, 1H) 6.57 (m, 2H) 7.52 (s, 1H). The second peak corresponds to isomer 40B: $^1$H NMR (400 MHz, methanol-$d_4$) δ ppm 1.25 (m, 15H) 1.77 (m, J=40.59 Hz, 3H) 2.40 (m, J=32.03 Hz, 1H) 3.22 (m, 1H) 3.63 (m, J=11.49, 7.09 Hz, 2H) 5.29 (s, 1H) 6.56 (s, 2H) 7.52 (s, 1H).

40C: (R)-N-(4-(Isopropylsulfonyl)-3-(pyrrolidin-2-yl)phenyl)acetamide hydrochloride

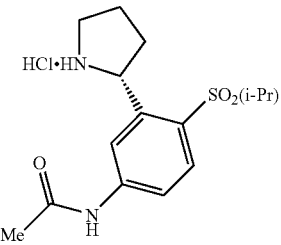

To 40A (0.03 g, 0.08 mmol) was added acetic anhydride (0.5 mL). The reaction was stirred for 1.0 h at rt. The solvent was removed and the crude residue was treated with hydrogen chloride (1 mL, 4M in dioxane) for 2.0 h at rt. The solvent was removed and the product was placed on the high vac overnight to give 0.025 g (90% yield) of yellow solid product 40C. $^1$H NMR (400 MHz, Methanol-$d_4$) δ ppm 1.23 (d, J=6.85 Hz, 3H) 1.36 (d, J=6.85 Hz, 3H) 2.14-2.28 (m, 4H) 2.32-2.44 (m, 2H) 2.45-2.59 (m, 1H) 3.36-3.55 (m, 3H) 5.43 (t, J=7.70 Hz, 1H) 7.61-7.78 (m, 1H) 7.99 (d, J=8.56 Hz, 1H) 8.32 (s, 1H).

40D: (S)-N-(4-(isopropylsulfonyl)-3-(pyrrolidin-2-yl)phenyl)acetamide hydrochloride

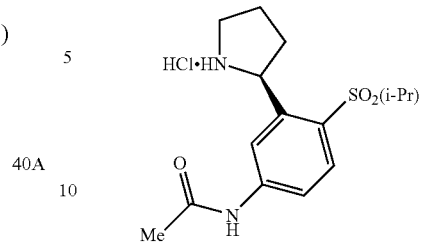

40D was prepared using a procedure similar to that used in the preparation of 40C. $^1$H NMR (400 MHz, Methanol-$d_4$) δ ppm 1.18-1.28 (m, 3H) 1.36 (d, J=6.59 Hz, 3H) 2.15-2.29 (m, 4H) 2.30-2.46 (m, 2H) 2.46-2.62 (m, 1H) 3.35-3.52 (m, 3H) 5.43 (t, J=7.69 Hz, 1H) 7.73 (dd, J=8.57, 1.98 Hz, 1H) 7.99 (d, J=8.79 Hz, 1H) 8.30 (d, J=2.20 Hz, 1H).

40E: Example 40

Example 40 was prepared according to the general coupling-deprotection using 1C and 40C. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.72 (s, 1H) 1.97-2.27 (m, 5H) 2.50 (d, J=5.14 Hz, 1H) 3.56-4.27 (m, 5H) 4.45-4.65 (m, 1H) 5.46 (s, 1H) 5.61-5.77 (m, 1H) 6.76 (s, 2H) 6.85-7.03 (m, 2H) 7.02-7.25 (m, 4H) 7.23-7.36 (m, 1H) 7.41 (dd, J=8.56, 1.47 Hz, 1H) 7.77 (d, J=8.56 Hz, 1H) 8.03 (d, J=9.29 Hz, 1H). LC-MS: 689 (M+H)$^+$.

Example 41

Diastereomer of Example 40

N-(3-((R)-1-((S)-2-(1-aminoisoquinolin-6-ylamino)-2-(3-ethoxy-4-isopropoxyphenyl)acetyl)pyrrolidin-2-yl)-4-(isopropylsulfonyl)phenyl)acetamide

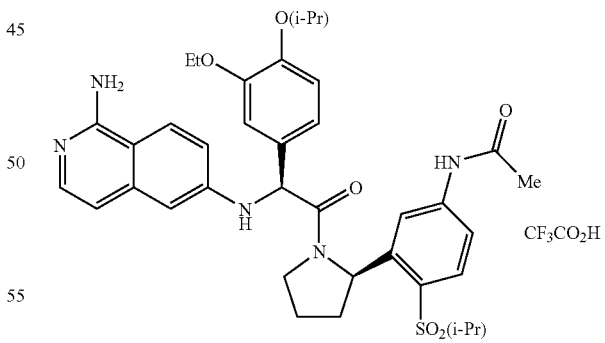

Example 41 was obtained as a diastereomer of Example 40 during its HPLC purification (see 40E). $^1$H NMR (400 MHz, Methanol-$d_4$) δ ppm 1.01 (d, J=6.60 Hz, 3H) 1.12-1.55 (m, 12H) 1.67-1.96 (m, 2H) 1.98-2.42 (m, 5H) 3.54-3.67 (m, 1H) 3.69-3.80 (m, 1H) 3.80-3.96 (m, 1H) 4.07 (q, J=7.01 Hz, 2H) 4.15-4.28 (m, 1H) 4.50-4.63 (m, 1H) 5.52-5.59 (m, 1H) 5.64 (dd, J=8.44, 3.55 Hz, 1H) 6.42-6.56 (m, 1H) 6.58-6.68 (m, 1H) 6.71-6.98 (m, 2H) 6.99-7.13 (m, 2H) 7.16 (d, J=1.96 Hz, 1H) 7.25 (d, J=6.85 Hz, 1H) 7.43 (dd, J=8.68, 2.08 Hz, 1H) 7.74-7.86 (m, 2H) 8.10 (s, 1H). LC-MS: 689 (M+H)$^+$.

Example 42

N-(3-((S)-1-((R)-2-(1-Aminoisoquinolin-6-ylamino)-2-(3-ethoxy-4-isopropoxyphenyl)acetyl)pyrrolidin-2-yl)-4-(isopropylsulfonyl)phenyl)acetamide trifluoroacetic acid salt

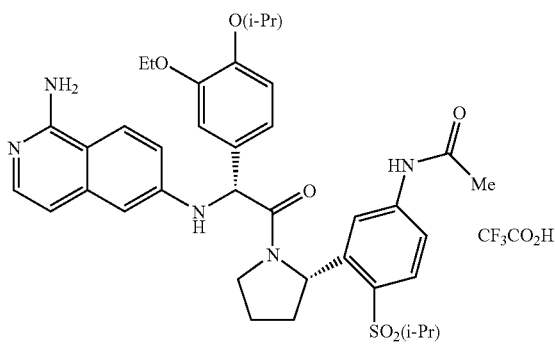

Example 42 was prepared according to the general coupling-deprotection using 1C and 40D. The diastereomers were separated by prep HPLC equipped with a C18 Luna column (21×100 mm, 5μ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.08-1.19 (m, 3H) 1.23-1.34 (m, 9H) 1.34-1.49 (m, 3H) 1.71 (dd, J=12.23, 5.87 Hz, 1H) 1.97-2.22 (m, 5H) 2.50 (dd, J=13.33, 7.70 Hz, 1H) 3.58-4.26 (m, 5H) 4.45-4.64 (m, 1H) 5.46 (s, 1H) 5.69 (dd, J=8.07, 4.89 Hz, 1H) 6.70-6.80 (m, 2H) 6.86-7.01 (m, 2H) 7.04 (d, J=1.71 Hz, 1H) 7.05-7.16 (m, 2H) 7.31 (d, J=7.09 Hz, 2H) 7.43 (dd, J=8.44, 1.83 Hz, 1H) 7.67-7.87 (m, 1H) 8.02 (d, J=9.05 Hz, 1H). LC-MS: 689 (M+H)$^+$.

Example 43

Diastereomer of Example 42

N-(3-((S)-1-((S)-2-(1-aminoisoquinolin-6-ylamino)-2-(3-ethoxy-4-isopropoxyphenyl)acetyl)pyrrolidin-2-yl)-4-(isopropylsulfonyl)phenyl)acetamide trifluoroacetic acid salt

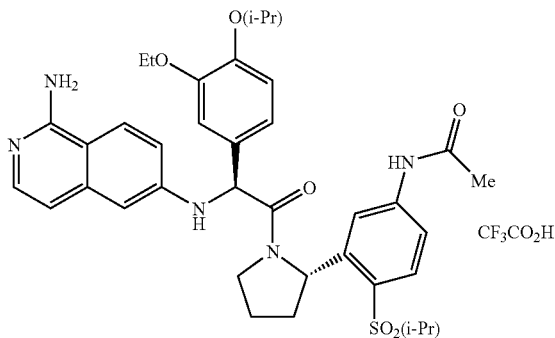

Example 43 was obtained as a diastereomer of Example 42 during its HPLC purification. $^1$H NMR (400 MHz, Methanol-$d_4$) δ ppm 0.98 (d, J=6.60 Hz, 3H) 1.12-1.55 (m, 12H) 1.67-1.97 (m, 2H) 2.01-2.27 (m, 5H) 2.25-2.42 (m, 1H) 3.52-3.64 (m, 1H) 3.66-3.77 (m, 1H) 3.80-3.96 (m, 1H) 4.00-4.14 (m, 2H) 4.16-4.28 (m, 1H) 4.49-4.63 (m, 1H) 5.52-5.58 (m, 1H) 5.64 (dd, J=8.56, 3.67 Hz, 1H) 6.40-6.56 (m, 1H) 6.57-6.68 (m, 1H) 6.73 (d, J=7.09 Hz, 1H) 6.80-6.90 (m, 1H) 6.99-7.06 (m, 1H) 7.06-7.13 (m, 1H) 7.17 (d, J=1.96 Hz, 1H) 7.20-7.29 (m, 1H) 7.40-7.49 (m, 1H) 7.71-7.87 (m, 2H) 8.08 (d, J=1.96 Hz, 1H). LC-MS: 689 (M+H)$^+$.

Example 44

Methyl 3-((R)-1-((R)-2-(1-aminoisoquinolin-6-ylamino)-2-(3-ethoxy-4-isopropoxyphenyl)acetyl)pyrrolidin-2-yl)-4-(isopropylsulfonyl)phenylcarbamate trifluoroacetic acid salt

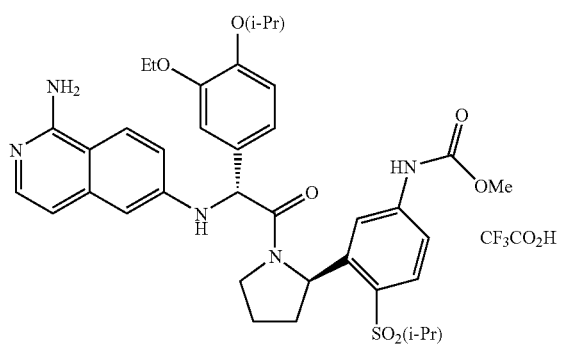

44A: (R)-Methyl(4-(isopropylsulfonyl)-3-(pyrrolidin-2-yl)phenyl)carbamate hydrochloride

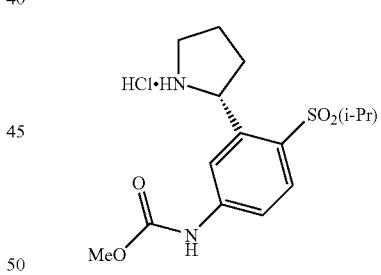

To 40A (0.1 g, 0.27 mmol) in pyridine (1 mL) at 0° C. was added methyl chloroformate (57 μL, 0.54 mmoL). After 2.0 h of stirring at rt the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.15 g white solid 44A. $^1$H NMR (400 MHz, Methanol-$d_4$) δ ppm 1.25 (t, J=7.09 Hz, 3H) 1.37 (d, J=6.85 Hz, 3H) 2.13-2.31 (m, 1H) 2.31-2.47 (m, 2H) 2.47-2.63 (m, 1H) 3.36-3.56 (m, 3H) 3.73-3.91 (m, 3H) 5.43 (t, J=7.70 Hz, 1H) 7.66 (dd, J=8.80, 2.20 Hz, 1H) 7.97 (d, J=8.80 Hz, 1H) 8.11 (d, J=1.96 Hz, 1H).

44B: (S)-Methyl(4-(isopropylsulfonyl)-3-(pyrrolidin-2-yl)phenyl)carbamate hydrochloride

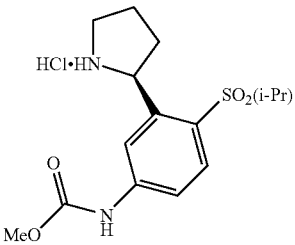

44B was prepared from 40B following a procedure similar to that used in the preparation of 44A. $^1$H NMR (400 MHz, Methanol-$d_4$) δ ppm 1.24 (d, J=6.85 Hz, 3H) 1.35 (d, J=6.85 Hz, 3H) 2.14-2.29 (m, 1H) 2.29-2.45 (m, 2H) 2.45-2.62 (m, 1H) 3.36-3.56 (m, 3H) 3.79 (s, 3H) 7.68 (dd, J=8.56, 1.96 Hz, 1H) 7.95 (d, J=8.56 Hz, 1H) 8.08 (d, J=2.20 Hz, 1H) 8.10-8.19 (m, 2H) 8.60-8.77 (m, 1H) 8.89 (d, J=5.14 Hz, 2H) 9.96 (s, 1H).

44C: Example 44

Example 44 was prepared according to the general coupling-deprotection using 1C and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.11-1.19 (m, 3H) 1.24-1.46 (m, 12H) 1.63-1.78 (m, 1H) 2.09 (dd, J=22.38, 6.72 Hz, 2H) 2.50 (dd, J=12.96, 7.83 Hz, 1H) 3.69-3.78 (m, 4H) 3.78-4.23 (m, 4H) 4.43-4.61 (m, 1H) 5.46 (s, 1H) 5.69 (dd, J=8.19, 4.77 Hz, 1H) 6.76 (d, J=2.20 Hz, 1H) 6.83-6.97 (m, 3H) 6.98-7.05 (m, 1H) 7.07-7.16 (m, 1H) 7.15-7.27 (m, 2H) 7.31 (d, J=7.09 Hz, 1H) 7.62-7.82 (m, 1H) 8.03 (d, J=9.29 Hz, 1H) 9.37 (s, 1H). LC-MS: 704 (M+H)$^+$.

Example 45

Diastereomer of Example 44

Methyl 3-((R)-1-((S)-2-(1-aminoisoquinolin-6-ylamino)-2-(3-ethoxy-4-isopropoxyphenyl)acetyl)pyrrolidin-2-yl)-4-(isopropylsulfonyl)phenylcarbamate trifluoroacetic acid salt

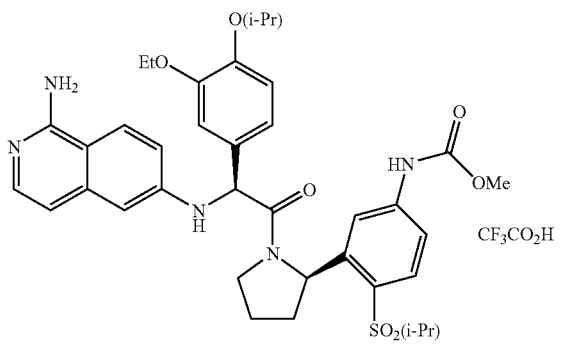

Example 45 was obtained as a diastereomer of Example 44 during its HPLC purification. $^1$H NMR (400 MHz, Methanol-$d_4$) δ ppm 1.02-1.20 (m, 3H) 1.20-1.56 (m, 12H) 1.90 (s, 2H) 2.11 (d, J=59.18 Hz, 1H) 2.35 (s, 1H) 3.51-3.67 (m, 1H) 3.68-3.97 (m, 5H) 4.07 (q, J=7.01 Hz, 2H) 4.12-4.25 (m, 1H) 4.48-4.61 (m, 1H) 5.50-5.57 (m, 1H) 5.61-5.70 (m, 1H) 6.51 (s, 1H) 6.63 (d, J=2.20 Hz, 1H) 6.77-6.95 (m, 1H) 6.98-7.17 (m, 3H) 7.21-7.35 (m, 1H) 7.39 (dd, J=8.56, 1.96 Hz, 1H) 7.68-7.87 (m, 2H) 7.89-8.05 (m, 1H). LC-MS: 704 (M+H)$^+$.

Example 46

Methyl 3-((S)-1-((R)-2-(1-aminoisoquinolin-6-ylamino)-2-(3-ethoxy-4-isopropoxyphenyl)acetyl)pyrrolidin-2-yl)-4-(isopropylsulfonyl)phenylcarbamate trifluoroacetic acid salt

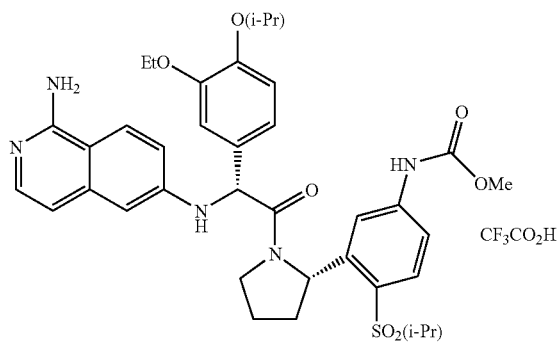

Example 46 was prepared according to the general coupling-deprotection using 1C and 44B. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.09-1.20 (m, 3H) 1.24-1.47 (m, 12H) 1.72 (dd, J=12.10, 5.75 Hz, 1H) 1.92-2.22 (m, 2H) 2.50 (dd, J=13.08, 7.70 Hz, 1H) 3.64-3.77 (m, 4H) 3.76-4.00 (m, 3H) 4.00-4.23 (m, 1H) 4.43-4.64 (m, 1H) 5.46 (s, 1H) 5.69 (dd, J=8.31, 4.89 Hz, 1H) 6.76 (d, J=2.45 Hz, 1H) 6.82-6.98 (m, 3H) 6.98-7.06 (m, 1H) 7.12 (dd, J=9.17, 2.32 Hz, 1H) 7.16-7.27 (m, 2H) 7.31 (d, J=7.09 Hz, 1H) 7.74 (d, J=8.56 Hz, 1H) 8.03 (d, J=9.29 Hz, 1H) 9.37 (s, 1H). LC-MS: 704 (M+H)$^+$.

Example 47

Diastereomer of Example 46

Methyl 3-((S)-1-((S)-2-(1-aminoisoquinolin-6-ylamino)-2-(3-ethoxy-4-isopropoxyphenyl)acetyl)pyrrolidin-2-yl)-4-(isopropylsulfonyl)phenylcarbamate trifluoroacetic acid salt

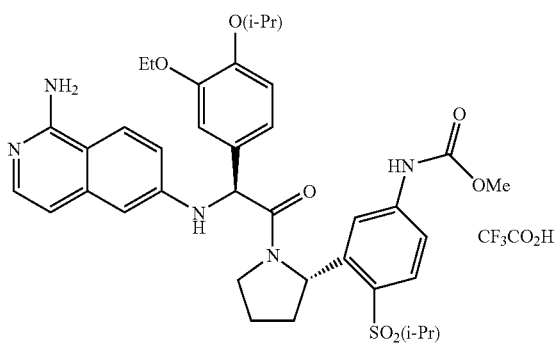

Example 47 was obtained as a diastereomer of Example 46 during its HPLC purification. $^1$H NMR (400 MHz, Methanol-$d_4$) δ ppm 0.93-1.53 (m, 15H) 1.66-2.41 (m, 4H) 3.40-3.66 (m, 1H) 3.68-3.95 (m, 4H) 4.07 (q, J=7.01 Hz, 2H) 4.23 (s, 1H) 4.44-4.63 (m, 1H) 5.42-5.61 (m, 1H) 5.64 (dd, J=8.31, 3.42 Hz, 1H) 6.34-7.34 (m, 8H) 7.31-7.51 (m, 1H) 7.65-8.10 (m, 3H). LC-MS: 704 (M+H)$^+$.

Example 50

Methyl 3-((R)-1-((R)-2-(1-aminoisoquinolin-6-ylamino)-2-(4-chloro-3-methoxyphenyl)acetyl)pyrrolidin-2-yl)-4-(isopropylsulfonyl)phenylcarbamate trifluoroacetic acid salt

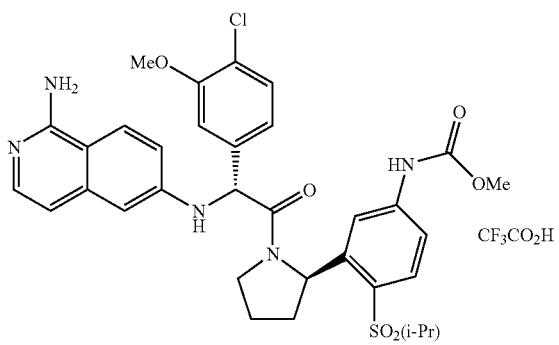

50A: 4-Chloro-3-methoxyphenylboronic acid

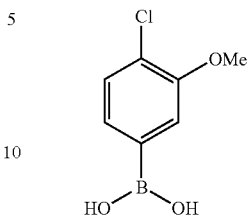

To 4-bromo-1-chloro-2-methoxybenzene (2.2 g, 9.9 mmol) in toluene/THF (16/6 mL) at −78° C. was added n-butyl lithium (8.7 mL, 1.6 M in hexane, 14 mmol) dropwise. The reaction was stirred at −78° C. for 30 min, then trimethylborate (2.2 mL, 19.8 mmol) was added. The reaction was allowed to warm to rt and stirred overnight and then quenched with 1 M HCl (15 mL). The organic layer was separated and dried over sodium sulfate. The solvent was removed and the crude product was purified by flash column chromatography to give 50A (1.2 g, 65% yield) as a white solid. $^1$H NMR (400 MHz, Methanol-$d_4$) δ ppm 3.87 (m, 3H) 7.11 (d, J=7.83 Hz, 1H) 7.20 (s, 1H) 7.29 (d, J=7.83 Hz, 1H).

50B: 2-(1-Di-tert-butoxycarbonylaminoisoquinolin-6-ylamino)-2-(4-chloro-3-methoxyphenyl)acetic acid

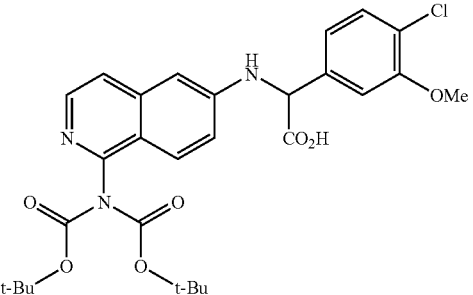

A mixture of 50A (43 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 56 mg (50%) of 50B as a solid. $^1$H NMR (400 MHz, Methanol-$d_4$) δ ppm 1.18 (s, 18H) 3.78 (s, 3H) 6.56 (d, J=2.20 Hz, 1H) 7.05 (d, J=8.35 Hz, 1H) 7.17 (dd, J=8.79, 2.20 Hz, 1H) 7.20-7.25 (m, 3H) 7.32 (d, J=5.71 Hz, 1H) 7.53 (d, J=9.23 Hz, 1H) 7.92 (d, J=5.71 Hz, 1H); LC-MS: 558 (M+H)$^+$.

50C: Example 50

Example 50 was prepared according to the general coupling-deprotection using 50B and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.02-1.26 (m, 3H) 1.33-1.53 (m, 3H) 1.61-1.85 (m, 1H) 2.12 (s, 2H) 2.52 (d, J=12.96 Hz, 1H) 3.66-3.85 (m, 7H) 3.87-4.06 (m, 1H) 4.21 (s, 1H) 5.56 (s, 1H) 5.65-5.83 (m, 1H) 6.79 (d, J=2.20 Hz, 1H) 6.86-7.05 (m, 2H) 7.04-7.24 (m, 4H) 7.34 (dd, J=16.51, 7.46 Hz, 2H) 7.73 (d, J=8.80 Hz, 1H) 8.04 (d, J=9.29 Hz, 1H) 9.42 (s, 1H). LC-MS: 666 (M+H)$^+$.

Example 51

Diastereomer of Example 50

Methyl 3-((R)-1-((S)-2-(1-aminoisoquinolin-6-ylamino)-2-(4-chloro-3-methoxyphenyl)acetyl)pyrrolidin-2-yl)-4-(isopropylsulfonyl)phenylcarbamate trifluoroacetic acid salt

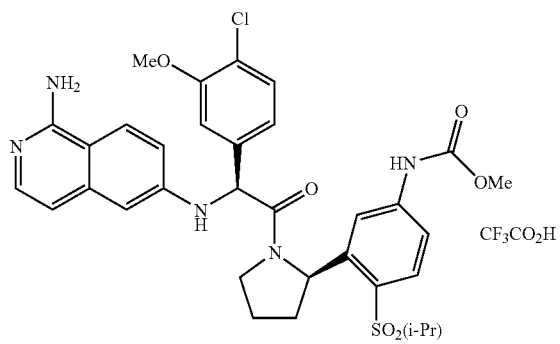

Example 51 was obtained as a diastereomer of Example 50 during its HPLC purification. $^1$H NMR (400 MHz, Methanol-d$_4$) δ ppm 1.00-1.25 (m, 3H) 1.29-1.57 (m, 3H) 1.60-2.74 (m, 4H) 3.58-4.01 (m, 8H) 4.04-4.31 (m, 1H) 5.40-5.81 (m, 2H) 6.37-7.03 (m, 3H) 7.03-7.52 (m, 5H) 7.69-7.90 (m, 2H) 7.93-8.16 (m, 1H). LC-MS: 666 (M+H)$^+$.

Example 52

Methyl 3-((R)-1-((R)-2-(1-aminoisoquinolin-6-ylamino)-2-(5-ethoxy-2-fluorophenyl)acetyl)pyrrolidin-2-yl)-4-(isopropylsulfonyl)phenylcarbamate trifluoroacetic acid salt

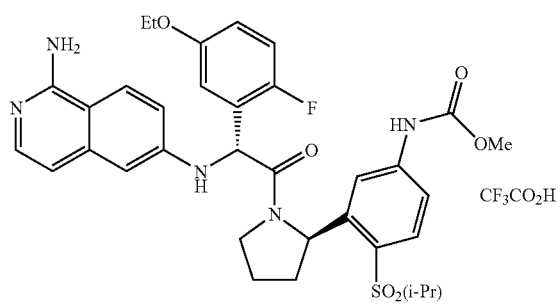

Example 52 was prepared according to the general coupling-deprotection using 30A and 44A. The diastereomers were separated by prep HPLC equipped with a C18 Luna column (21×100 mm, 5µ) The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.18 (d, J=6.60 Hz, 3H) 1.26 (q, J=6.77 Hz, 3H) 1.33-1.47 (m, 3H) 1.63-1.83 (m, 1H) 1.94-2.25 (m, 2H) 2.51 (dd, J=13.08, 7.95 Hz, 1H) 3.53-3.88 (m, 6H) 3.86-4.01 (m, 1H) 4.07-4.25 (m, 1H) 5.69 (dd, J=8.19, 5.26 Hz, 1H) 5.82 (s, 1H) 6.58 (dd, J=5.75, 3.06 Hz, 1H) 6.74-6.83 (m, 1H) 6.84-6.97 (m, 2H) 7.00-7.23 (m, 3H) 7.20-7.40 (m, 2H) 7.75 (d, J=8.80 Hz, 1H) 8.05 (d, J=9.29 Hz, 1H) 9.37 (s, 1H). LC-MS: 664 (M+H)$^+$.

Example 53

Diastereomer of Example 52

Methyl 3-(R)-1-(S)-2-(1-aminoisoquinolin-ylamino)-2-(5-ethoxy-2-fluorophenyl)acetyl)pyrrolidin-2-yl)-4-(isopropylsulfonyl)phenylcarbamate trifluoroacetic acid salt

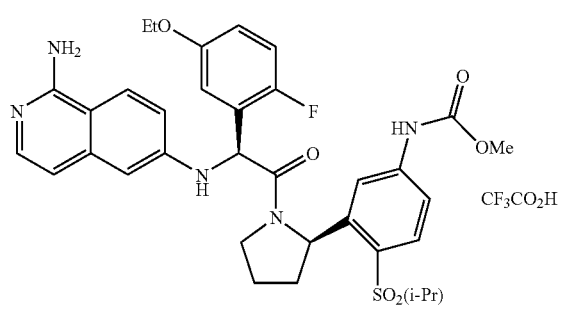

Example 53 was obtained as a diastereomer of Example 52 during its HPLC purification. $^1$H NMR (400 MHz, Methanol-d$_4$) δ ppm 1.03-1.19 (m, 3H) 1.20-1.52 (m, 6H) 1.62-2.05 (m, 2H) 2.14 (s, 1H) 2.26-2.48 (m, 1H) 3.61-4.05 (m, 7H) 4.07-4.24 (m, 1H) 5.56-5.73 (m, 1H) 5.76-5.89 (m, 1H) 6.64-7.01 (m, 4H) 7.03-7.47 (m, 4H) 7.68-7.88 (m, 2H) 7.97-8.16 (m, 1H). LC-MS: 664 (M+H)$^+$.

Example 54

N-(3-((R)-1-((R)-2-(1-aminoisoquinolin-6-ylamino)-2-phenylacetyl)pyrrolidin-2-yl)-4-(isopropylsulfonyl)phenyl)acetamide trifluoroacetic acid salt

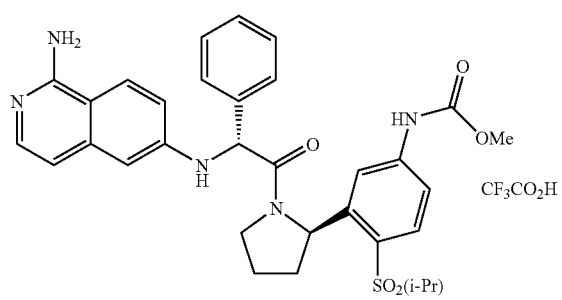

54A: 2-(1-Di-tert-butoxycarbonylaminoisoquinolin-6-ylamino)-2-phenyl acetic acid

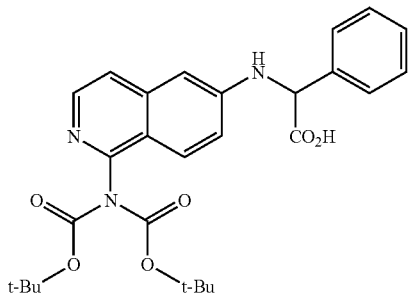

A mixture of phenylboronic acid (50 mg, 0.42 mmol), 1B (100 mg, 0.28 mmol) and glyoxylic acid monohydrate (38 mg, 0.42 mmol) in acetonitrile (0.7 mL) and DMF (0.07 mL) was heated at 85° C. for 30 min in a Microwave Reactor. The crude product was purified by flash column chromatography ($CH_2Cl_2$:MeOH =100:15) to give 46 mg (50%) of 54A as a solid. $^1$H NMR (400 MHz, Methanol-$d_4$) δ ppm 1.20-1.36 (m, 18H) 5.26 (s, 1H) 6.69 (d, J=1.96 Hz, 1H) 7.21-7.47 (m, 5H) 7.53-7.69 (m, 3H) 8.02 (d, J=5.87 Hz, 1H).

54B: Example 54

Example 54 was prepared according to the general coupling-deprotection using 54A and 40C. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.05-1.18 (m, 3H) 1.32-1.46 (m, 3H) 1.60-1.79 (m, 1H) 1.94-2.21 (m, 5H) 2.36-2.66 (m, 1H) 3.61-3.78 (m, 1H) 3.83-4.01 (m, 1H) 4.05-4.28 (m, 1H) 5.51-5.61 (m, 1H) 5.67 (dd, J=7.95, 5.26 Hz, 1H) 6.68-6.78 (m, 1H) 6.78-6.93 (m, 1H) 6.94-7.14 (m, 2H) 7.19-7.54 (m, 7H) 7.67-7.82 (m, 1H) 7.88-8.05 (m, 1H). LC-MS: 586 (M+H)$^+$.

Example 55

Diastereomer of Example 54

N-(3-((R)-1-((S)-2-(1-aminoisoquinolin-6-ylamino)-2-phenylacetyl)pyrrolidin-2-yl)-4-(isopropylsulfonyl)phenyl)acetamide trifluoroacetic acid salt

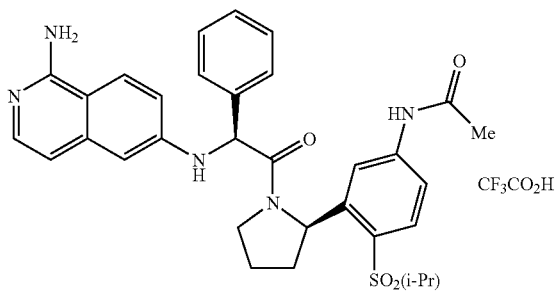

Example 55 was obtained as a diastereomer of Example 54 during its HPLC purification. $^1$H NMR (400 MHz, Methanol-$d_4$) δ ppm 1.02-1.25 (m, 3H) 1.33-1.54 (m, 3H) 1.66-1.95 (m, 2H) 1.97-2.23 (m, 4H) 2.31 (s, 1H) 3.41-3.62 (m, 1H) 3.68-3.90 (m, 1H) 4.04-4.32 (m, 1H) 5.54-5.75 (m, 2H) 6.70 (d, J=2.20 Hz, 1H) 6.80-6.88 (m, 1H) 6.98 (d, J=4.16 Hz, 1H) 7.06-7.18 (m, 1H) 7.24-7.50 (m, 4H) 7.50-7.61 (m, 2H) 7.74-7.88 (m, 1H) 7.93-8.05 (m, 1H) 8.13 (d, J=1.96 Hz, 1H). LC-MS: 586 (M+H)$^+$.

Example 56

Methyl 3-((R)-1-((R)-2-(1-aminoisoquinolin-6-ylamino)-2-(4-fluoro-3-methoxyphenyl)acetyl)pyrrolidin-2-yl)-4-(isopropylsulfonyl)phenylcarbamate trifluoroacetic acid salt

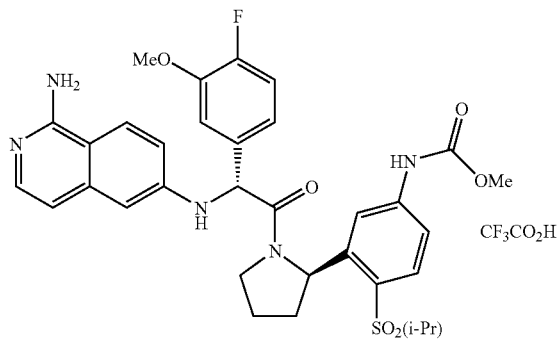

Example 56 was prepared according to the general coupling-deprotection using 23D and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.17 (t, J=6.85 Hz, 3H) 1.28-1.47 (m, 3H) 1.59-1.79 (m, 1H) 1.96-2.24 (m, 2H) 2.32-2.60 (m, 1H) 3.63-3.77 (m, 6H) 3.81-4.01 (m, 2H) 4.20 (s, 1H) 5.53 (s, 1H) 5.68 (dd, J=8.07, 5.38 Hz, 1H) 6.78 (d, J=2.20 Hz, 1H) 6.91 (d, J=7.09 Hz, 1H) 6.97-7.08 (m, 1H) 7.03-7.20 (m, 5H) 7.25-7.43 (m, 1H) 7.72 (t, J=8.68 Hz, 1H) 8.04 (d, J=9.29 Hz, 1H) 9.45 (s, 1H). LC-MS: 650 (M+H)$^+$.

Example 57

Diastereomer of Example 56

Methyl 3-((R)-1-((S)-2-(1-aminoisoquinolin-6-ylamino)-2-(4-fluoro-3-methoxyphenyl)acetyl)pyrrolidin-2-yl)-4-(isopropylsulfonyl)phenylcarbamate trifluoroacetic acid salt

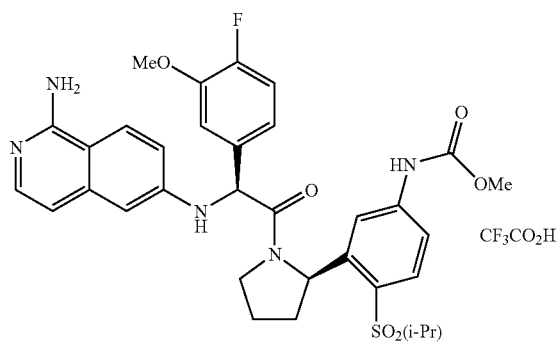

Example 57 was obtained as a diastereomer of Example 56 during its HPLC purification. $^1$H NMR (400 MHz, Methanol-$d_4$) δ ppm 1.00-1.22 (m, 3H) 1.29-1.50 (m, 3H) 1.61-2.85 (m, 4H) 3.55-3.97 (m, 8H) 4.19 (s, 1H) 5.41-5.74 (m, 2H) 6.41-6.94 (m, 2H) 7.01-7.24 (m, 4H) 7.23-7.59 (m, 3H) 7.65-7.91 (m, 1H) 7.91-8.12 (m, 1H). LC-MS: 650 (M+H)$^+$.

Example 58

(2R,3S)-Methyl 1-((S)-2-(1-aminoisoquinolin-6-ylamino)-2-(3-ethoxy-4-isopropoxyphenyl)acetyl)-2-(2-(isopropylsulfonyl)phenyl)pyrrolidine-3-carboxylate trifluoroacetic acid salt

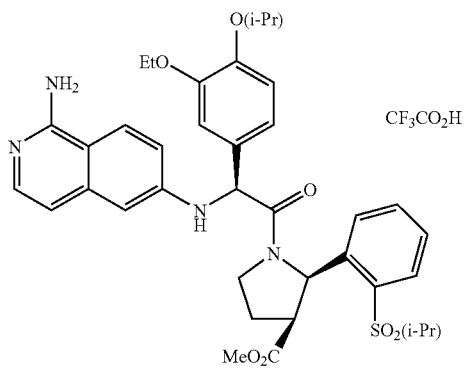

58A: (2R,3S)-Methyl 2-(2-isopropylsulfonyl)phenyl)pyrrolidine-3-carboxylate and

58B: (2S,3R)-Methyl 2-(2-isopropylsulfonyl)phenyl)pyrrolidine-3-carboxylate

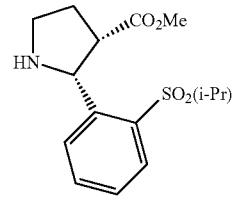
58A

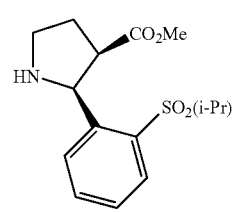
58B

The enantiomers of 13C were separated using a semi-preparative HPLC equipped with a Chiralpak®AS-H column. The separation was performed using an isocratic method of 10% isopropanol/heptane with 0.1% diethylamine for 30 min with a flow rate of 15 mL/min. The first peak is 58A: $^1$H NMR (400 MHz, Methanol-$d_4$) δ ppm 1.25 (t, J=6.97 Hz, 6H) 2.11-2.42 (m, 2H) 3.08-3.27 (m, 3H) 3.46-3.60 (m, 1H) 3.60 (s, 3H) 5.12 (d, J=7.83 Hz, 1H) 7.47-7.59 (m, 1H) 7.70-7.77 (m, 1H) 7.77-7.84 (m, 1H) 7.95 (dd, J=7.95, 1.34 Hz, 1H); The second peak corresponds to 58B: $^1$H NMR (400 MHz, Methanol-$d_4$) δ ppm 1.18-1.30 (m, 6H) 2.13-2.39 (m, 2H) 3.07-3.28 (m, 3H) 3.49-3.58 (m, 1H) 3.58-3.64 (m, 3H) 5.12 (dd, J=7.95, 1.10 Hz, 1H) 7.48-7.58 (m, 1H) 7.69-7.85 (m, 2H) 7.95 (d, J=8.07 Hz, 1H).

58C: Example 58

Example 58 was prepared according to the general coupling-deprotection using 1C and 58A. The diastereomers were separated by prep HPLC equipped with a C18 Luna column (21×100 mm, 5( ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.01-1.47 (m, 15H) 2.31 (d, J=146.97 Hz, 2H) 2.91 (d, J=7.83 Hz, 1H) 3.55-3.96 (m, 5H) 4.02-4.21 (m, 2H) 4.27-4.41 (m, 1H) 4.48-4.66 (m, 1H) 5.38-5.59 (m, 1H) 6.00 (s, 1H) 6.50-6.76 (m, 1H) 6.86-7.16 (m, 5H) 7.33-7.40 (m, 1H) 7.43-7.54 (m, 1H) 7.63-7.75 (m, 2H) 7.90 (d, J=7.58 Hz, 1H) 7.95-8.10 (m, 1H). LC-MS: 689 (M+H)$^+$.

Example 59

Diastereomer of Example 58

(2R,3S)-Methyl 1-((R)-2-(1-aminoisoquinolin-ylamino)-2-(3-ethoxy-4-isopropoxyphenyl)acetyl)-2-(2-(isopropylsulfonyl)phenyl)pyrrolidine-3-carboxylate trifluoroacetic acid salt

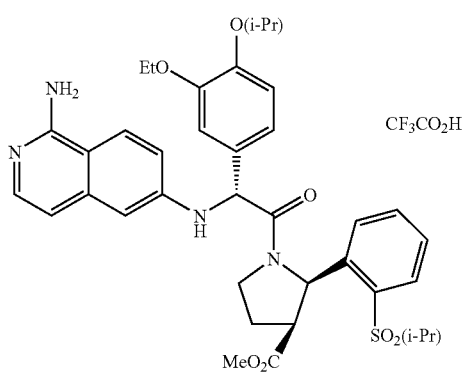

Example 59 was obtained as a diastereomer of Example 58 during its HPLC purification. $^1$H NMR (400 MHz, Methanol-$d_4$) δ ppm 1.06-1.15 (m, 3H) 1.21-1.41 (m, 12H) 2.15-2.43 (m, J=6.85 Hz, 2H) 2.83-2.99 (m, 1H) 3.53-4.04 (m, 7H) 4.13 (d, J=7.34 Hz, 1H) 4.50-4.67 (m, 1H) 5.41 (s, 1H) 6.02 (s, 1H) 6.66-6.77 (m, 2H) 6.95-7.10 (m, 4H) 7.13 (dd, J=9.17, 2.32 Hz, 1H) 7.35 (d, J=7.09 Hz, 1H) 7.37-7.45 (m, 1H) 7.45-7.55 (m, 1H) 7.91 (dd, J=7.83, 1.22 Hz, 1H) 8.06 (d, J=9.05 Hz, 1H). LC-MS: 689 (M+H)$^+$.

Example 60

(2S,3R)-Methyl 1-((R)-2-(1-aminoisoquinolin-6-ylamino)-2-(3-ethoxy-4-isopropoxyphenyl)acetyl)-2-(2-(isopropylsulfonyl)phenyl)pyrrolidine-3-carboxylate trifluoroacetic acid salt

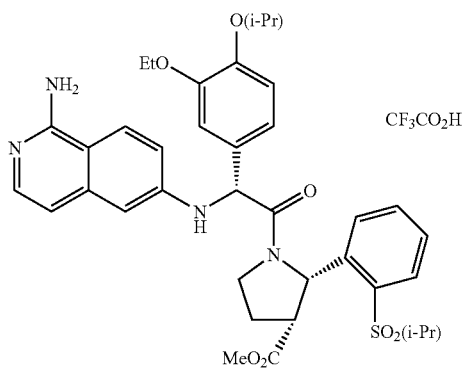

Example 60 was prepared according to the general coupling-deprotection using 1C and 58B. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.12 (d, J=6.60 Hz, 3H) 1.24-1.48 (m, 12H) 2.28 (s, 2H) 2.88-3.02 (m, 1H) 3.67-3.83 (m, 4H) 3.83-4.04 (m, 3H) 4.14 (s, 1H) 4.51-4.67 (m, 1H) 5.43 (s, 1H) 6.04 (d, J=1.71 Hz, 1H) 6.67-6.79 (m, 2H) 6.97-7.11 (m, 4H) 7.15 (dd, J=9.29, 2.45 Hz, 1H) 7.37 (d, J=7.09 Hz, 1H) 7.39-7.46 (m, 1H) 7.47-7.55 (m, 1H) 7.92 (dd, J=7.70, 1.34 Hz, 1H) 8.07 (d, J=9.05 Hz, 1H). LC-MS: 689 (M+H)$^+$.

Example 61

(2R,3S)-Methyl 2-(5-acetamido-2-(isopropylsulfonyl)phenyl)-1-((R)-2-(1-aminoisoquinolin-6-ylamino)-2-(5-ethoxy-2-fluorophenyl)acetyl)pyrrolidine-3-carboxylate trifluoroacetic acid salt

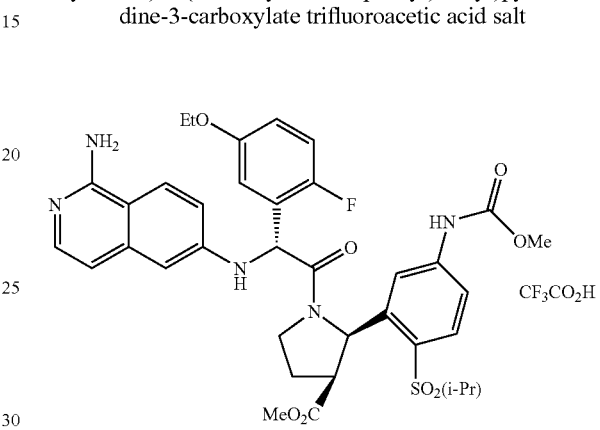

61A: (2S,3S)-1-tert-Butyl 3-methyl 2-(5-amino-2-(isopropylsulfonyl)phenyl)pyrrolidine-1,3-dicarboxylate and 61B: (2R,3R)-1-tert-Butyl 3-methyl 2-(5-amino-2-(isopropylsulfonyl)phenyl)pyrrolidine-1,3-dicarboxylate

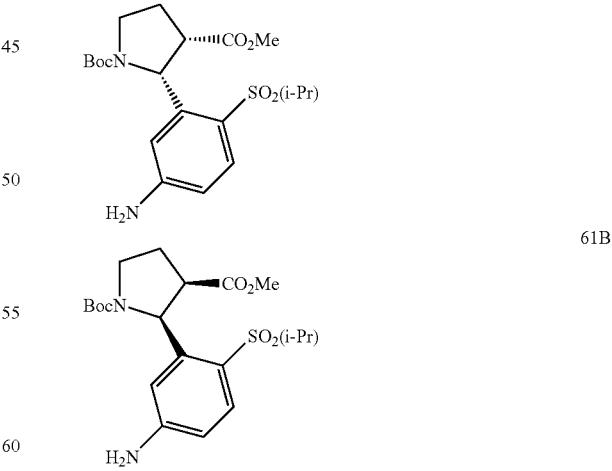

The cis and trans isomers of 20F were separated by a preparative HPLC equipped with a C18 Luna column (30× 100 mm, 5µ) The separation was performed using a linear gradient (mobile phase A:10% MeOH-90% water-0.1% TFA; mobile phase B: 90% MeOH-10% water-0.1% TFA; 50 to 65% B in 10 min, then 65% B for 2 min) with a flow rate of 40 mL/min. The enantiomers of the cis isomer were then separated using a semi-preparative HPLC equipped with a Chiralpak®AD column. The separation was performed using an isocratic method of 15% isopropanol/heptane with 0.1% diethylamine for 30 min with a flow rate of 15 mL/min. The first peak corresponds to 61A: $^1$H NMR (400 MHz, CDCl$_3$) δ ppm 1.06-1.53 (m, 15H) 1.96-2.26 (m, 3H) 3.19-3.31 (m, 3H) 3.52-4.01 (m, 3H) 5.69 (d, J=8.07 Hz, 1H) 6.41-6.67 (m, 2H) 7.66 (d, J=8.31 Hz, 1H). The second peak corresponds to 61B: $^1$H NMR (400 MHz, CDCl$_3$) δ ppm 1.01-1.52 (m, 15H) 1.95-2.30 (m, 3H) 3.19-3.31 (m, 3H) 3.47-4.01 (m, 3H) 5.69 (d, J=7.83 Hz, 1H) 6.45-6.66 (m, 2H) 7.67 (d, J=8.07 Hz, 1H).

61C: (2R,3S)-Methyl 2-(2-(isopropylsulfonyl)-5-(methoxycarbonyl)phenyl)pyrrolidine-3-carboxylate HCl salt

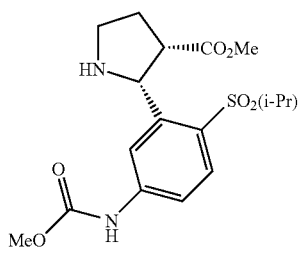

To 61A (0.09 g, 0.21 mmol) in pyridine (1 mL) at 0° C. was added methyl chloroformate (32 μL, 0.42 mmol). After 2.0 h stirring at rt the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.11 g solid 61C. $^1$H NMR (400 MHz, Methanol-d$_4$) δ ppm 1.22-1.40 (m, 6H) 2.43-2.60 (m, 1H) 2.62-2.80 (m, 1H) 3.42 (s, 3H) 3.45-3.65 (m, 2H) 3.67-3.77 (m, 1H) 3.78 (s, 3H) 3.83-3.96 (m, 1H) 5.84 (d, J=8.56 Hz, 1H) 7.55-7.67 (m, 1H) 7.81-7.90 (m, 1H) 7.94 (d, J=8.80 Hz, 1H).

61D: (2S,3R)-Methyl 2-(2-(isopropylsulfonyl)-5-(methoxycarbonyl)phenyl)pyrrolidine-3-carboxylate HCl salt

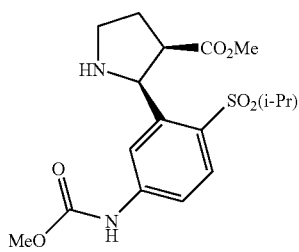

61D was prepared from 61B using a procedure similar to that used in the preparation of 61C. $^1$H NMR (400 MHz, Methanol-d$_4$) δ ppm 1.29 (d, J=6.60 Hz, 3H) 1.33 (d, J=6.85 Hz, 3H) 2.46-2.64 (m, 1H) 2.61-2.83 (m, 1H) 3.39-3.47 (m, 3H) 3.45-3.65 (m, 2H) 3.68-3.79 (m, 1H) 3.77-3.84 (m, 3H) 3.83-3.95 (m, 1H) 5.86 (d, J=8.31 Hz, 1H) 7.58 (d, J=8.80 Hz, 1H) 7.89 (s, 1H) 7.96 (d, J=8.80 Hz, 1H).

61E: Example 61

Example 61 was prepared according to the general coupling-deprotection using 30A and 61C. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.16 (dd, J=4.77, 1.83 Hz, 3H) 1.20-1.30 (m, 3H) 1.41 (dd, J=5.01, 1.83 Hz, 3H) 2.21-2.50 (m, 2H) 3.18-3.26 (m, 3H) 3.52-3.69 (m, 2H) 3.69-3.87 (m, 5H) 3.86-4.01 (m, J=11.25 Hz, 1H) 4.13-4.27 (m, 1H) 5.82 (s, 1H) 6.07 (d, J=8.31 Hz, 1H) 6.56 (s, 1H) 6.80 (d, J=1.71 Hz, 1H) 6.84-6.96 (m, 2H) 6.99 (s, 1H) 7.09-7.23 (m, 2H) 7.25-7.41 (m, 2H) 7.66-7.81 (m, 1H) 8.05 (d, J=9.54 Hz, 1H) 9.31 (s, 1H). LC-MS: 706 (M+H)$^+$.

Example 62

Diastereomer of Example 61

(2R,3S)-Methyl 2-(5-acetamido-2-(isopropylsulfonyl)phenyl)-1-((S)-2-(1-aminoisoquinolin-6-ylamino)-2-(5-ethoxy-2-fluorophenyl)acetyl)pyrrolidine-3-carboxylate trifluoroacetic acid salt

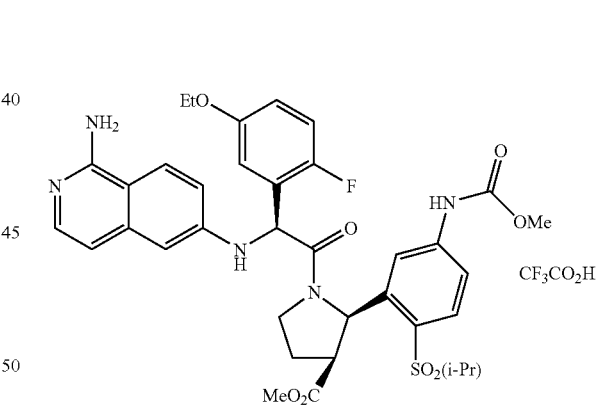

Example 62 was obtained as a diastereomer of Example 61 during its HPLC purification. $^1$H NMR (400 MHz, Methanol-d$_4$) δ ppm 1.04-1.16 (m, 3H) 1.20-1.47 (m, 6H) 2.04-2.22 (m, J=7.09 Hz, 1H) 2.31-2.53 (m, 1H) 3.22-3.28 (m, 3H) 3.42-3.58 (m, 1H) 3.63-3.84 (m, 5H) 3.88-4.04 (m, 2H) 4.21-4.42 (m, 1H) 5.84 (s, 1H) 6.00 (d, J=8.31 Hz, 1H) 6.73 (d, J=2.20 Hz, 1H) 6.84 (d, J=7.34 Hz, 1H) 6.86-6.99 (m, 2H) 7.07-7.23 (m, 2H) 7.25-7.35 (m, 1H) 7.41 (dd, J=8.68, 2.08 Hz, 1H) 7.69-7.80 (m, 2H) 8.04 (d, J=9.29 Hz, 1H). LC-MS: 706 (M+H)$^+$.

Example 63

(2S,3R)-Methyl 1-((R)-2-(1-aminoisoquinolin-6-ylamino)-2-(3-ethoxy-4-isopropoxyphenyl)acetyl)-2-(2-(isopropylsulfonyl)phenyl)pyrrolidine-3-carboxylate trifluoroacetic acid salt

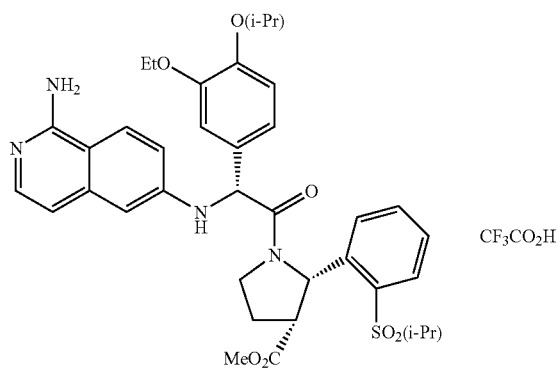

Example 63 was prepared according to the general coupling-deprotection using 1C and 58B. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.03-1.16 (m, 3H) 1.18-1.51 (m, 12H) 1.95-2.07 (m, 1H) 2.14-2.57 (m, 2H) 2.91 (d, J=7.83 Hz, 1H) 3.56-3.94 (m, 4H) 4.01-4.22 (m, 2H) 4.35 (s, 1H) 4.47-4.62 (m, 1H) 5.56 (s, 1H) 6.00 (s, 1H) 6.48-6.80 (m, 1H) 6.86-7.17 (m, 5H) 7.32-7.42 (m, 1H) 7.45-7.53 (m, 1H) 7.65-7.77 (m, 2H) 7.82-7.94 (m, 1H) 7.97-8.09 (m, 1H). LC-MS: 689 (M+H)$^+$.

Example 64

Methyl 3-((R)-1-((R)-2-(1-aminoisoquinolin-6-ylamino)-2-(5-ethoxy-2-fluoro-4-methoxyphenyl)acetyl)pyrrolidin-2-yl)-4-(isopropylsulfonyl)phenyl-carbamate trifluoroacetic acid salt

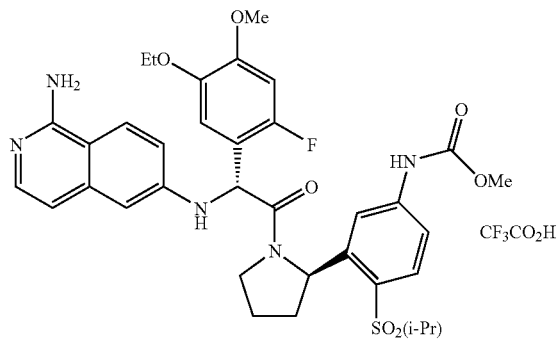

64A: 4-Fluoro-2-methoxyphenyl acetate

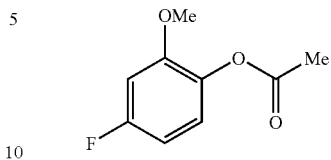

To a solution of 4-fluoro-2-methoxyphenol (569 mg, 4.0 mmol) and pyridine (0.56 mL, 7.0 mmol) in CH$_2$Cl$_2$ (8.0 mL) at 0° C. was added acetyl chloride (0.33 mL, 4.6 mmol). The mixture was stirred at rt for 2.0 h and then diluted with EtOAc and washed with 4.0 N HCl. The organic layer was washed with brine and dried over Na$_2$SO$_4$. After evaporation of the solvent, 64A (680 mg, 92% yield) was obtained as a solid used in the next step without further purification. $^1$H NMR (400 MHz, CDCl$_3$) δ ppm 2.29 (s, 3H) 3.79 (s, 3H) 6.62 (m, 1H) 6.68 (dd, J=10.33, 2.86 Hz, 1H) 6.95 (dd, J=8.79, 5.71 Hz, 1H).

64B: 4-Fluoro-5-iodo-2-methoxyphenyl acetate

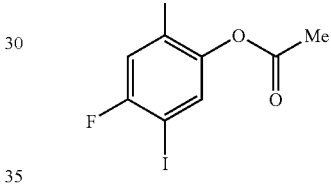

To a solution of 64A (850 mg, 4.6 mmol) in CH$_2$Cl$_2$ (5.0 mL) was added ICl (1.0 M in CH$_2$Cl$_2$, 10.2 mL, 10.2 mmol). The mixture was stirred at 50° C. for 4 h and then at rt for 18 h. The reaction was quenched by a sat. solution of NaHCO$_3$. After extraction with CH$_2$Cl$_2$, the organic layer was washed with a solution of Na$_2$S$_2$O$_3$, brine and dried over Na$_2$SO$_4$. After evaporation of the solvent, the crude product was purified by column chromatography (EtOAc:hexanes=1:4) to give 64B (1.22 g, 80% yield) as a solid. $^1$H NMR (400 MHz, CDCl$_3$) δ ppm 2.29 (s, 3H) 3.81 (s, 3H) 6.73 (d, J=9.23 Hz, 1H) 7.35 (d, J=6.59 Hz, 1H).

64C: 4-Fluoro-5-iodo-2-methoxyphenol

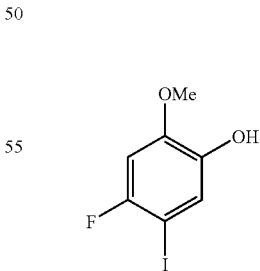

To a solution of 64B (680 mg, 2.19 mmol) in THF (3.0 mL) and MeOH (1.0 mL) was added 1.0 N NaOH (2.74 mL, 2.74 mmol). The reaction was stirred at rt for 2.0 h before it was acidified by addition of 5% citric acid. The mixture was extracted with EtOAc, washed with brine and dried over Na$_2$SO$_4$. After evaporation of the solvent, 64C (586 mg, 100% yield) was obtained as a solid and used for next step without further purification. ¹H NMR (400 MHz, CDCl₃) δ ppm 3.85 (s, 3H) 6.62 (d, J=8.79 Hz, 1H) 7.21 (d, J=6.15 Hz, 1H).

64D: 1-Ethoxy-4-fluoro-5-iodo-2-methoxybenzene

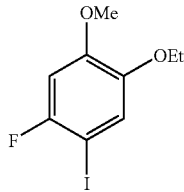

A mixture of 64C (580 mg, 2.16 mmol), ethyl iodide (0.23 mL, 2.92 mmol) and K₂CO₃ (598 mg, 4.32 mmol) in DMF (5.0 mL) was heated at 40° C. for 3.0 h. It was diluted with diethyl ether, washed with brine and dried over Na₂SO₄. After evaporation of the solvent, the crude product was purified by silica gel chromatography (EtOAc:hexanes=1:5) to give 64D (540 mg, 85% yield) as a white solid. ¹H NMR (400 MHz, CDCl₃) δ ppm 1.42 (t, J=7.03 Hz, 3H) 3.82 (s, 3H) 4.01 (q, J=7.03 Hz, 2H) 6.64 (d, J=9.23 Hz, 1H) 7.09 (d, J=6.15 Hz, 1H).

64E: 5-Ethoxy-2-fluoro-4-methoxyphenylboronic acid

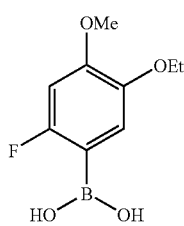

To a solution of 64D (324 mg, 1.1 mmol) in THF (5 mL) at −78° C. was slowly added n-BuLi (1.6 M in hexanes, 1.40 mL, 2.2 mmol). The reaction mixture was stirred at −78° C. for 20 min, followed by addition of trimethyl borate (0.31 mL, 2.8 mmol). The mixture was stirred at −78° C. for 3.0 h and then warmed up to rt over 18 h. It was quenched by addition of 1.0 N HCl (2.0 mL). After extraction with EtOAc, washing with a solution of Na₂S₂O₃, brine and drying over Na₂SO₄, the crude product was purified by silica gel chromatography (eluting with 5% methanol in CH₂Cl₂) to give 64E (210 mg, 80% yield) as a white solid. ¹H NMR (400 MHz, Methanol-d₄) δ ppm 1.36 (t, J=6.81 Hz, 3H) 3.86 (s, 3H) 4.00 (q, J=7.03 Hz, 2H) 6.72 (d, J=10.11 Hz, 1H) 6.89 (d, J=5.27 Hz, 1H).

64F: 2-(1-Di-tert-butoxycarbonylaminoisoquinolin-6-ylamino)-2-(5-ethoxy-2-fluoro-4-methoxyphenyl) acetic acid

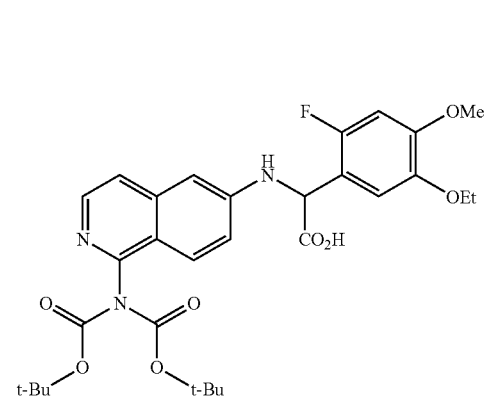

A mixture of 64E (118 mg, 0.55 mmol), 1B (180 mg, 0.5 mmol) and glyoxylic acid monohydrate (51 mg, 0.55 mmol) in acetonitrile (1.3 mL) and DMF (0.13 mL) was heated at 85° C. for 25 min in a microwave oven. After removing the solvent, the crude product was purified by silica gel chromatography eluting with CH₂Cl₂:MeOH 100:20 to give 64F (190 mg, 65% yield) as a yellow solid. ¹H NMR (400 MHz, acetonitrile-d₃) δ ppm 1.91 (m, 21H) 3.76 (s, 3H) 3.92 (dd, J=10.11, 7.03 Hz, 2H) 5.45 (s, 1H) 6.70 (d, J=2.20 Hz, 1H) 6.79 (d, J=11.86 Hz, 1H) 6.92 (d, J=7.03 Hz, 1H) 7.17 (dd, J=9.01, 2.42 Hz, 1H) 7.38 (d, J=5.27 Hz, 1H) 7.63 (d, J=8.79 Hz, 1H) 8.08 (d, J=5.71 Hz, 1H); LC-MS: 586 (M+H)⁺.

64G: Example 64

Example 64 was prepared according to the general coupling-deprotection using 64F and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. ¹H NMR (400 MHz, Methanol-d₄) δ ppm 1.17 (d, J=6.60 Hz, 3H) 1.20-1.29 (m, 3H) 1.41 (d, J=6.85 Hz, 3H) 1.62-1.79 (m, 1H) 1.95-2.21 (m, 2H) 2.51 (dd, J=13.08, 7.70 Hz, 1H) 3.51-3.67 (m, 2H) 3.67-3.76 (m, 4H) 3.81-3.90 (m, 3H) 3.90-4.03 (m, 1H) 4.07-4.22 (m, 1H) 5.68 (dd, J=7.95, 5.50 Hz, 1H) 5.75 (s, 1H) 6.51 (d, J=6.85 Hz, 1H) 6.78 (d, J=2.20 Hz, 1H) 6.84-6.97 (m, 2H) 7.13 (dd, J=9.17, 2.32 Hz, 1H) 7.16-7.24 (m, 2H) 7.32 (d, J=7.09 Hz, 1H) 7.74 (d, J=9.05 Hz, 1H) 8.04 (d, J=9.05 Hz, 1H) 9.42 (s, 1H). LC-MS: 694 (M+H)⁺.

Example 65

Diastereomer of Example 64

Methyl 3-((R)-1-((S)-2-(1-aminoisoquinolin-6-ylamino)-2-(5-ethoxy-2-fluoro-4-methoxyphenyl)acetyl)pyrrolidin-2-yl)-4-(isopropylsulfonyl)phenylcarbamate trifluoroacetic acid salt

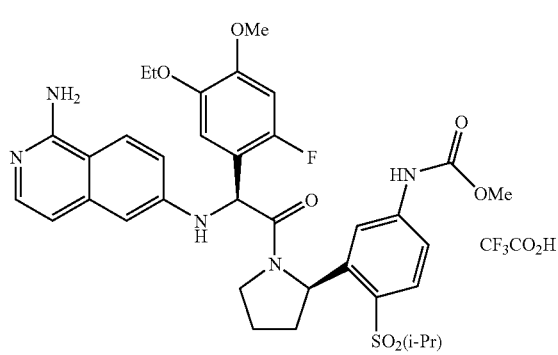

Example 65 was obtained as a diastereomer of Example 64 during its HPLC purification. $^1$H NMR (400 MHz, Methanol-$d_4$) δ ppm 1.00-1.21 (m, 3H) 1.24-1.49 (m, 6H) 1.68-1.98 (m, J=57.22 Hz, 2H) 2.00-2.42 (m, J=78.99 Hz, 2 H) 3.42-3.56 (m, 1H) 3.63-3.89 (m, 7H) 3.89-4.04 (m, 2H) 4.06-4.23 (m, J=6.97, 5.99 Hz, 1H) 5.56-5.68 (m, 1H) 5.70-5.80 (m, 1H) 6.68 (d, J=2.20 Hz, 1H) 6.77-6.96 (m, 3H) 7.05-7.19 (m, 1H) 7.20-7.47 (m, 2H) 7.66-7.85 (m, 2H) 7.94-8.09 (m, 1H) 9.68 (s, 1H). LC-MS: 694 (M+H)$^+$.

Example 66

Methyl 3-((R)-1-((R)-2-(1-aminoisoquinolin-6-ylamino)-2-(2-fluoro-5-methoxyphenyl)acetyl)pyrrolidin-2-yl)-4-(isopropylsulfonyl)phenylcarbamate trifluoroacetic acid salt

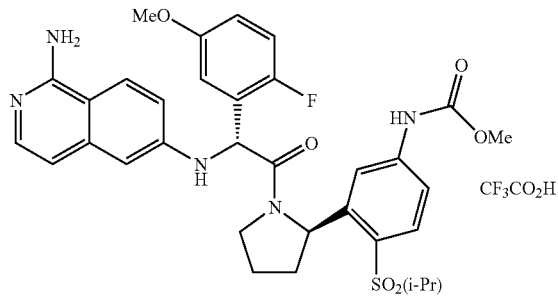

66A: 2-(1-Di-tert-butoxycarbonylaminoisoquinolin-6-ylamino)-2-(3-ethoxy-4-fluorophenyl)acetic acid

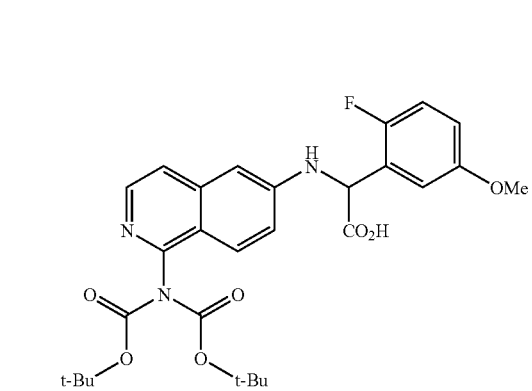

A mixture of 2-fluoro-5-methoxyphenylboronic acid (38 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 27 mg (25%) of 66A as a solid.

$^1$H NMR (400 MHz, Methanol-$d_4$) δ ppm 1.17 (s, 18H) 3.63 (s, 3H) 5.43 (s, 1H) 6.62 (d, J=2.20 Hz, 1H) 6.74-6.91 (m, 2H) 6.93-7.04 (m, 2H) 7.18 (dd, J=9.23, 2.20 Hz, 1H) 7.36 (d, J=5.71 Hz, 1H) 7.54 (d, J=9.23 Hz, 1H) 7.94 (d, J=5.71 Hz, 1H); LC-MS: 542 (M+H)$^+$.

66B: Example 66

Example 66 was prepared according to the general coupling-deprotection using 66A and 44A. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.12-1.23 (m, 3H) 1.35-1.48 (m, 3H) 1.64-1.80 (m, 1H) 1.97-2.21 (m, 2H) 2.52 (dd, J=12.96, 7.83 Hz, 1H) 3.50-3.65 (m, 4H) 3.67-3.79 (m, 3H) 3.88-4.02 (m, 1H) 4.05-4.25 (m, J=3.67 Hz, 1H) 5.62-5.73 (m, 1H) 5.82 (s, 1H) 6.52-6.69 (m, 1H) 6.80 (d, J=2.45 Hz, 1H) 6.85-6.95 (m, 2H) 7.01-7.10 (m, 1H) 7.10-7.23 (m, 2H) 7.24-7.37 (m, 2H) 7.68-7.83 (m, 1H) 8.05 (d, J=9.29 Hz, 1H) 9.35 (s, 1H). LC-MS: 650 (M+H)$^+$.

Example 67

Diastereomer of Example 66

Methyl 3-((R)-1-((S)-2-(1-aminoisoquinolin-6-ylamino)-2-(2-fluoro-5-methoxyphenyl)acetyl)pyrrolidin-2-yl)-4-(isopropylsulfonyl)phenylcarbamate trifluoroacetic acid salt

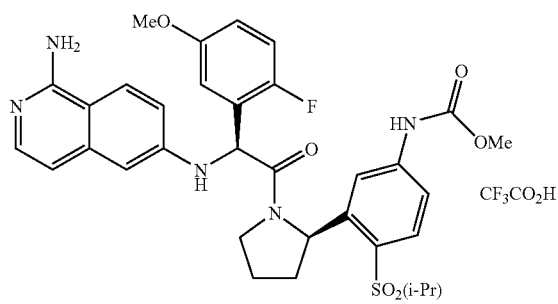

Example 67 was obtained as a diastereomer of Example 66 during its HPLC purification. $^1$H NMR (400 MHz, Methanol-d$_4$) δ ppm 1.00-1.23 (m, 3H) 1.32-1.51 (m, 3H) 1.66-2.02 (m, 2H) 2.08-2.26 (m, 1H) 2.24-2.50 (m, 1H) 3.47-3.87 (m, 8H) 4.05-4.25 (m, 1H) 5.57-5.75 (m, 1H) 5.85 (s, 1H) 6.60-7.06 (m, 4H) 7.07-7.24 (m, 2H) 7.24-7.50 (m, 2H) 7.63-7.88 (m, 2H) 7.96-8.14 (m, 1H). LC-MS: 650 (M+H)$^+$.

Example 68

Methyl 3-((R)-1-((R)-2-(1-aminoisoquinolin-6-ylamino)-2-(2-fluoro-5-methylphenyl)acetyl)pyrrolidin-2-yl)-4-(isopropylsulfonyl)phenylcarbamate trifluoroacetic acid salt

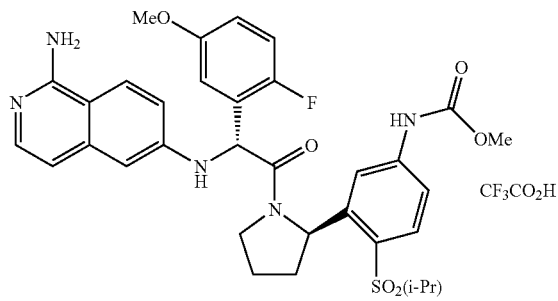

68A: 2-(1-Di-tert-butoxycarbonylaminoisoquinolin-6-ylamino)-2-(2-fluoro-5-methylphenyl)acetic acid

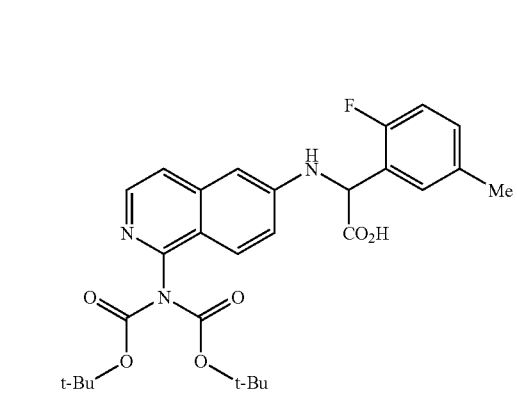

A mixture of 2-fluoro-5-methylphenylboronic acid (34 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 52 mg (50%) of 68A as a solid.

$^1$H NMR (400 MHz, Methanol-d$_4$) δ ppm 1.18 (s, 18H) 2.19 (s, 3H) 5.44 (s, 1H) 6.62 (d, J=2.20 Hz, 1H) 6.93-7.00 (m, 1H) 7.03-7.09 (m, 1H) 7.19 (dd, J=9.23, 2.20 Hz, 1H) 7.22-7.27 (m, 1H) 7.37 (d, J=5.71 Hz, 1H) 7.55 (d, J=9.23 Hz, 1H) 7.95 (d, J=5.71 Hz, 1H); LC-MS: 526 (M+H)$^+$.

68B: Example 68

Example 68 was prepared according to the general coupling-deprotection using 68A and 44A. The diastereomers were separated by prep HPLC equipped with a C18 Luna column (21×100 mm, 5µ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.13-1.24 (m, 3H) 1.40 (t, J=7.09 Hz, 3H) 1.72 (dd, J=12.84, 5.75 Hz, 1H) 1.97-2.19 (m, 5H) 2.51 (dd, J=12.84, 7.70 Hz, 1H) 3.54-3.65 (m, 1H) 3.67-3.77 (m, 3H) 3.85-4.02 (m, 1H) 4.05-4.23 (m, 1H) 5.68 (dd, J=7.95, 5.26 Hz, 1H) 5.81 (s, 1H) 6.77 (d, J=2.20 Hz, 1H) 6.83-6.97 (m, 2H) 7.04 (s, 1H) 7.08-7.21 (m, 3H) 7.26 (dd, J=8.68, 1.83 Hz, 1H) 7.31 (d, J=7.09 Hz, 1H) 7.75 (d, J=8.80 Hz, 1H) 8.04 (d, J=9.29 Hz, 1H) 9.42 (s, 1H). LC-MS: 634 (M+H)$^+$.

Example 69

Diastereomer of Example 68

Methyl 3-((R)-1-((S)-2-(1-aminoisoquinolin-6-ylamino)-2-(2-fluoro-5-methylphenyl)acetyl)pyrrolidin-2-yl)-4-(isopropylsulfonyl)phenylcarbamate trifluoroacetic acid salt

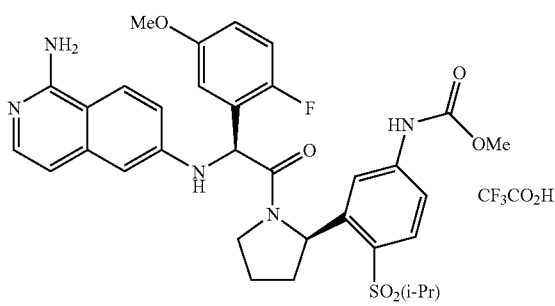

Example 69 was obtained as a diastereomer of Example 68 during its HPLC purification. $^1$H NMR (400 MHz, Methanol-$d_4$) δ ppm 1.04-1.17 (m, 3H) 1.34-1.47 (m, 3H) 1.66-1.97 (m, 2H) 2.11-2.41 (m, 5H) 3.41-3.54 (m, 1H) 3.64-3.90 (m, 4H) 4.09-4.23 (m, 1H) 5.66 (dd, J=8.56, 3.42 Hz, 1H) 5.70-5.87 (m, 1H) 6.69 (d, J=2.45 Hz, 1H) 6.78-6.92 (m, 1H) 7.05-7.15 (m, 2H) 7.17-7.35 (m, 3H) 7.41 (dd, J=8.56, 2.20 Hz, 1H) 7.69-7.86 (m, 2H) 7.93-8.07 (m, 1H). LC-MS: 634 (M+H)$^+$.

Example 70

(2S,3R)-1-((R)-2-(1-Aminoisoquinolin-6-ylamino)-2-(3-ethoxy-4-isopropoxyphenyl)acetyl)-2-(2-(isopropylsulfonyl)phenyl)pyrrolidine-3-carboxylic acid trifluoroacetic acid salt

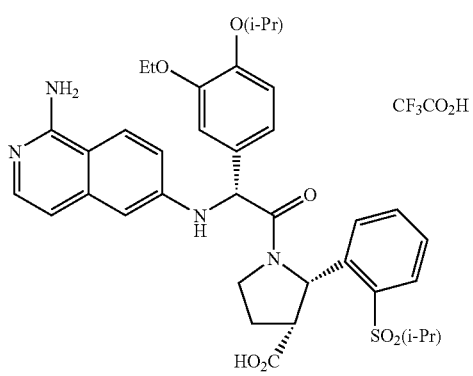

Example 70 was prepared by hydrolysis of the methyl ester Example 60 using a procedure similar to that used in the preparation of Example 12. $^1$H NMR (400 MHz, Methanol-$d_4$) δ ppm 1.10 (d, J=6.11 Hz, 3H) 1.24-1.44 (m, 12H) 2.20-2.42 (m, 2H) 2.90 (d, J=8.31 Hz, 1H) 3.69-4.03 (m, 4H) 4.08-4.19 (m, 1H) 4.54-4.66 (m, 1H) 5.40 (s, 1H) 6.08 (s, 1H) 6.71 (d, J=13.21 Hz, 2H) 6.98-7.17 (m, 5H) 7.32 (d, J=6.11 Hz, 1H) 7.38-7.55 (m, 2H) 7.92 (d, J=7.83 Hz, 1H) 8.04 (d, J=9.29 Hz, 1H). LC-MS: 675 (M+H)$^+$.

Example 71

Methyl 3-(R)-1-((R)-2-(1-aminoisoquinolin-6-ylamino)-2-(2-fluorophenyl)acetyl)pyrrolidin-2-yl)-4-(isopropylsulfonyl)phenylcarbamate trifluoroacetic acid salt

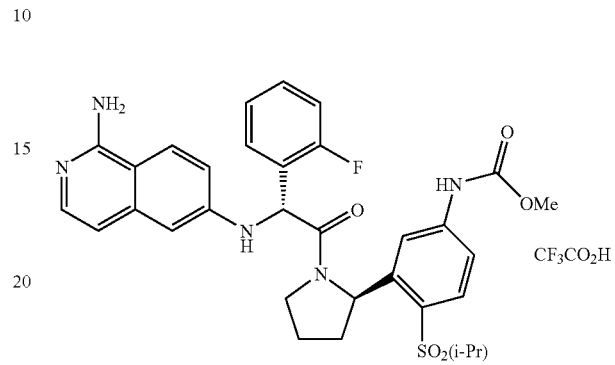

71A: 2-(1-Di-tert-butoxycarbonylaminoisoquinolin-6-ylamino)-2-(2-fluorophenyl)acetic acid

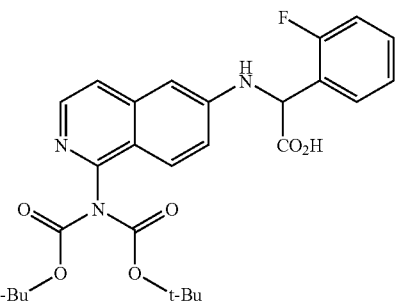

A mixture of 2-fluorophenylboronic acid (50 mg, 0.42 mmol), 1B (100 mg, 0.28 mmol) and glyoxylic acid monohydrate (38 mg, 0.42 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 20 mg (14%) of 71A as a solid. $^1$H NMR (400 MHz, Methanol-$d_4$) δ ppm 1.19-1.37 (m, 18H) 5.50 (s, 1H) 6.69 (d, J=2.20 Hz, 1H) 7.10-7.21 (m, 2H) 7.25 (dd, J=9.17, 2.32 Hz, 1H) 7.28-7.37 (m, 1H) 7.42 (d, J=5.87 Hz, 1H) 7.48-7.58 (m, 1H) 7.61 (d, J=9.29 Hz, 1H) 8.01 (d, J=5.87 Hz, 1H).

71B: Example 71

Example 71 was prepared according to the general coupling-deprotection using 71A and 44A. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.16 (d, J=6.60 Hz, 3H) 1.40 (d, J=6.85 Hz, 3H) 1.64-1.83 (m, 1H) 1.95-2.22 (m, 2H) 2.52 (dd, J=13.08, 7.70

Hz, 1H) 3.60 (d, J=10.03 Hz, 1H) 3.68-3.78 (m, 3H) 3.84-4.03 (m, 1H) 4.14 (d, J=9.54 Hz, 1H) 5.68 (dd, J=7.95, 5.50 Hz, 1H) 5.86 (s, 1H) 6.78 (d, J=2.20 Hz, 1H) 6.89 (d, J=7.09 Hz, 1H) 7.02-7.28 (m, 6H) 7.32 (d, J=7.09 Hz, 1H) 7.34-7.44 (m, 1H) 7.74 (d, J=8.80 Hz, 1H) 8.04 (d, J=9.05 Hz, 1H) 9.35 (s, 1H). LC-MS: 620 (M+H)$^+$.

Example 72

Diastereomer of Example 71

Methyl 3-((R)-1-((S)-2-(1-Aminoisoquinolin-6-ylamino)-2-(2-fluorophenyl)acetyl)pyrrolidin-2-yl)-4-(isopropylsulfonyl)phenylcarbamate trifluoroacetic acid salt

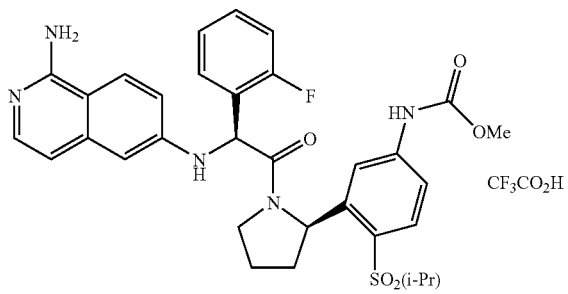

Example 72 was obtained as a diastereomer of Example 71 during its HPLC purification. $^1$H NMR (400 MHz, Methanol-d$_4$) δ ppm 1.06-1.15 (m, 3H) 1.40 (t, J=6.36 Hz, 3H) 1.70-1.82 (m, 1H) 1.90 (d, J=17.12 Hz, 1H) 2.07-2.23 (m, 1H) 2.25-2.45 (m, 1H) 3.49 (d, J=8.07 Hz, 1H) 3.62-3.84 (m, 4H) 4.07-4.20 (m, 1H) 5.65 (dd, J=8.31, 3.67 Hz, 1H) 5.87 (s, 1H) 6.71 (d, J=2.45 Hz, 1H) 6.82 (d, J=7.09 Hz, 1H) 7.15 (dd, J=9.17, 2.32 Hz, 1H) 7.17-7.29 (m, 3H) 7.34-7.50 (m, 3H) 7.71-7.85 (m, 2H) 8.01 (d, J=9.29 Hz, 1H). LC-MS: 620 (M+H)$^+$.

Example 73

(S)-2-(1-Aminoisoquinolin-6-ylamino)-2-(5-ethoxy-2-fluorophenyl)-1-((R)-2-(2-(isopropylsulfonyl)phenyl)pyrrolidin-1-yl)ethanone trifluoroacetic acid salt

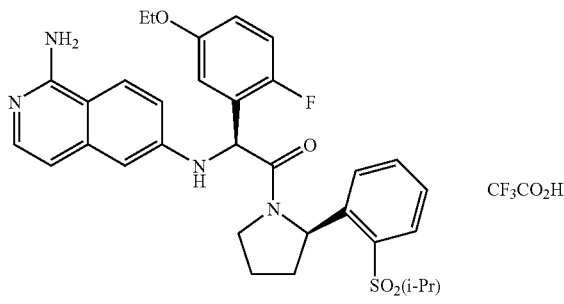

73A: (R)-2-(2-isopropylsulfonyl)phenyl)pyrrolidine

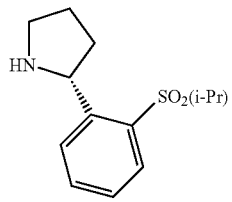

The enantiomers of 21E were separated using a semi-preparative HPLC equipped with a Chiralpak®AS-H column. The separation was performed using an isocratic method of 10% isopropanol/heptane with 0.1% diethylamine for 25 min with a flow rate of 15 mL/min. The first peak is 73A: $^1$H NMR (400 MHz, Methanol-d$_4$) δ ppm. 1.25 (d, J=6.60 Hz, 3H) 1.29 (d, J=6.85 Hz, 3H) 1.81-2.18 (m, 3H) 2.32-2.46 (m, 1H) 3.10-3.20 (m, 1H) 3.23-3.35 (m, 1H) 3.40-3.53 (m, 1H) 5.07 (t, J=7.83 Hz, 1H) 7.52-7.60 (m, 1H) 7.71-7.79 (m, 1H) 7.81-7.87 (m, 1H) 7.97 (dd, J=7.95, 1.35 Hz, 1H).

73B: Example 73

Example 73 was prepared according to the general coupling-deprotection using 30A and 73A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.05-1.17 (m, 3H) 1.24-1.49 (m, 6H) 1.68-1.82 (m, 1H) 1.83-1.96 (m, 1H) 2.06-2.23 (m, 1H) 2.41 (dd, J=13.08, 7.46 Hz, 1H) 3.42-3.56 (m, 1H) 3.72-3.91 (m, 1H) 3.99 (q, J=6.85 Hz, 2H) 4.19-4.32 (m, 1H) 5.66 (dd, J=8.56, 4.16 Hz, 1H) 5.85 (s, 1H) 6.78 (d, J=2.20 Hz, 1H) 6.90-7.01 (m, 3H) 7.08-7.21 (m, 2H) 7.36 (d, J=6.85 Hz, 1H) 7.39-7.50 (m, 1H) 7.56-7.69 (m, 2H) 7.89 (d, J=8.07 Hz, 1H) 8.03 (d, J=9.05 Hz, 1H). LC-MS: 591 (M+H)$^+$.

Example 74

Diastereomer of Example 73

(R)-2-(1-Aminoisoquinolin-6-ylamino)-2-(5-ethoxy-2-fluorophenyl)-1-((R)-2-(2-(isopropylsulfonyl)phenyl)pyrrolidin-1-yl)ethanone trifluoroacetic acid salt

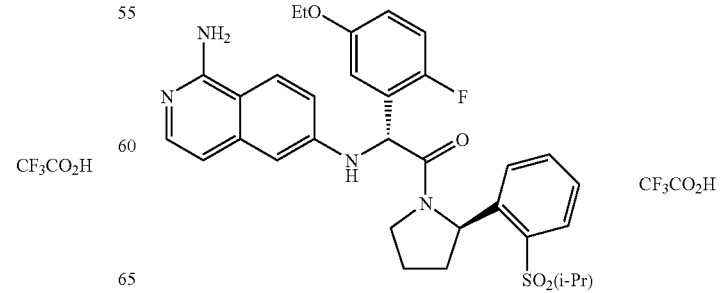

Example 74 was obtained as a diastereomer of Example 73 during its HPLC purification. ¹H NMR (400 MHz, Methanol-d₄) δ ppm 1.15 (t, J=6.48 Hz, 3H) 1.26-1.35 (m, 3H) 1.42 (t, J=6.48 Hz, 3H) 1.66 (dd, J=13.33, 6.72 Hz, 1H) 1.95-2.12 (m, 2H) 2.47-2.65 (m, 1H) 3.44-3.60 (m, 1H) 3.72-4.03 (m, 3H) 4.07-4.23 (m, 1H) 5.68 (t, J=7.21 Hz, 1H) 5.85 (s, 1H) 6.60-6.74 (m, 2H) 6.81 (d, J=1.96 Hz, 1H) 6.89 (d, J=7.34 Hz, 1H) 6.92-7.02 (m, 1H) 7.10-7.24 (m, 2H) 7.32 (d, J=7.09 Hz, 1H) 7.36-7.49 (m, 2H) 7.84-7.95 (m, 1H) 8.06 (d, J=9.05 Hz, 1H). LC-MS: 591 (M+H).

Example 75

(2S,3R)-Methyl 1-((R)-2-(1-aminoisoquinolin-6-ylamino)-2-(5-ethoxy-2-fluorophenyl)acetyl)-2-(2-(isopropylsulfonyl)-5-(methoxycarbonyl)phenyl)-pyrrolidine-3-carboxylate trifluoroacetic acid salt

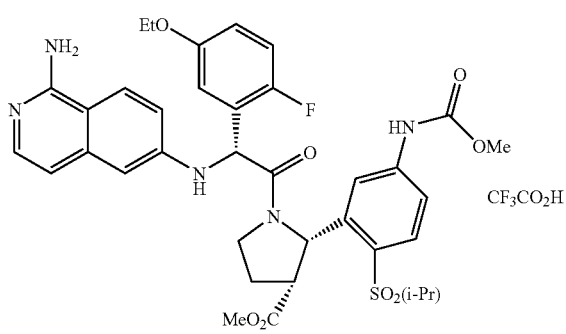

Example 75 was prepared according to the general coupling-deprotection using 30A and 61D. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. ¹H NMR (400 MHz, Methanol-d₄) δ ppm 1.16 (d, J=6.60 Hz, 3H) 1.20-1.32 (m, 3H) 1.41 (d, J=7.09 Hz, 3H) 2.18-2.47 (m, 2H) 3.19-3.26 (m, 3H) 3.51-3.69 (m, 2H) 3.68-3.86 (m, 5H) 3.87-4.04 (m, 1H) 4.20 (dd, J=8.31, 1.71 Hz, 1H) 6.56 (dd, J=5.62, 3.18 Hz, 1H) 6.70-6.95 (m, 3H) 6.94-7.03 (m, 1H) 7.11-7.22 (m, 2H) 7.26-7.41 (m, 2H) 7.74 (d, J=8.80 Hz, 1H) 8.05 (d, J=9.29 Hz, 1H) 9.30 (s, 1H). LC-MS: 722 (M+H)⁺.

Example 76

Diastereomer of Example 75

(2S,3R)-Methyl 1-((S)-2-(1-aminoisoquinolin-6-ylamino)-2-(5-ethoxy-2-fluorophenyl)acetyl)-2-(2-(isopropylsulfonyl)-5-(methoxycarbonyl)phenyl)-pyrrolidine-3-carboxylate trifluoroacetic acid salt

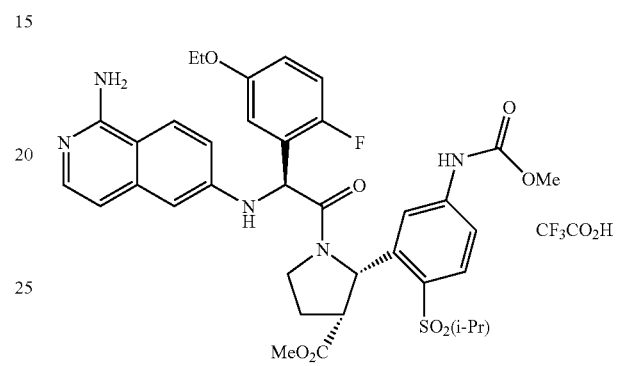

Example 76 was obtained as a diastereomer of Example 75 during its HPLC purification. ¹H NMR (400 MHz, Methanol-d₄) δ ppm 1.11 (d, J=6.60 Hz, 3H) 1.33 (t, J=6.97 Hz, 3H) 1.40 (d, J=6.85 Hz, 3H) 2.02-2.30 (m, 1H) 2.42 (dd, J=12.59, 7.46 Hz, 1H) 3.21-3.29 (m, 3H) 3.44-3.57 (m, 1H) 3.64-3.84 (m, 5H) 3.97 (q, J=6.85 Hz, 2H) 4.26-4.38 (m, 1H) 5.84 (s, 1H) 6.01 (d, J=8.56 Hz, 1H) 6.74 (d, J=2.20 Hz, 1H) 6.85 (d, J=7.09 Hz, 1H) 6.89-6.99 (m, 2H) 7.07-7.24 (m, 2H) 7.30 (d, J=7.09 Hz, 1H) 7.42 (dd, J=8.68, 2.08 Hz, 1H) 7.68-7.82 (m, 2H) 8.05 (d, J=9.29 Hz, 1H). LC-MS: 722 (M+H)⁺.

Example 77

Methyl 3-((R)-1-((R)-2-(4-(aminomethyl)-3-fluorophenylamino)-2-(5-ethoxy-2-fluorophenyl)acetyl)pyrrolidin-2-yl)-4-isopropylsulfonyl)phenylcarbamate trifluoroacetic acid salt

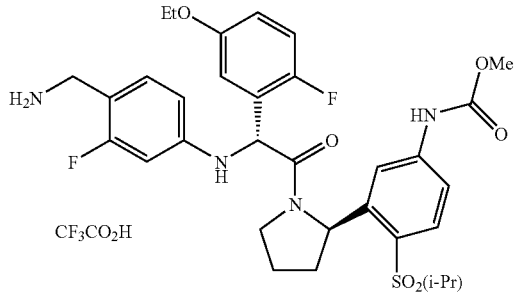

77A: 4-(Aminomethyl)-3-fluoroaniline

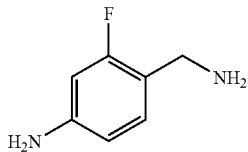

A solution of 2-fluoro-4-nitrobenzonitrile (0.541 g, 2.43 mmol) in methanol (20 mL) and 6N hydrochloric acid (3 mL) was hydrogenated (55 psi) over 10% palladium on carbon (164 mg) for 22 h. The reaction mixture was filtered and concentrated in vacuo to afford 77A (0.65 g, 100%). $^1$H NMR (400 MHz, CD$_3$OD) δ 4.23 (s, 2H), 7.29 (d, J=8.79 Hz, 2H), 7.68 (t, J=7.91 Hz, 1H).

77B: tert-Butyl 4-amino-2-fluorobenzylcarbamate

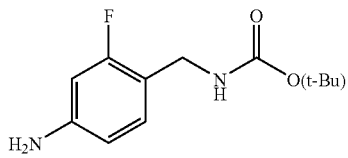

Di-tert-butyl di-carbonate (0.517 g, 2.1 mmol) was added to a solution of 77A (0.28 g, 2.0 mmol) and triethylamine (0.60 mL, 4.0 mmol) in THF (5 mL). The reaction mixture was stirred at rt overnight and then diluted with saturated NaHCO$_3$ solution and dichloromethane. The aqueous layer was extracted with dichloromethane (2×) and the combined organics were extracted with brine, dried (MgSO$_4$), and concentrated in vacuo. The residue was purified by silica gel chromatography (hexane/ethyl acetate) to give 77B (0.287 g, 60%) as a white solid.

$^1$H NMR (400 MHz, CDCl$_3$) δ ppm 1.44 (s, 9H) 3.74 (s, 2H) 4.22 (d, J=5.71 Hz, 2H) 4.78 (s, 1H) 6.39 (dd, J=15.38, 2.20 Hz, 1H) 6.37 (dd, 1H) 7.09 (t, J=8.35 Hz, 1H).

77C: 2-(4-((tert-Butoxycarbonyl)methyl)-3-fluorophenylamino)-2-(5-ethoxy-2-fluorophenyl)acetic acid

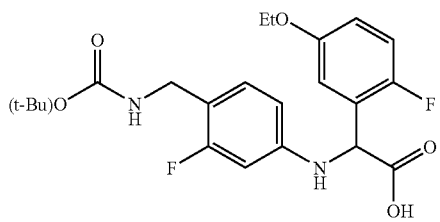

A mixture of 77B (120 mg, 0.500 mmol), 5-ethoxy-2-fluorophenylboronic acid (146 mg, 0.793 mmol) and glyoxylic acid monohydrate (55 mg, 0.60 mmol) in 1,2-dichloroethane (4 mL) was heated at 100I C for 10 min in a microwave. The reaction mixture was purified by silica gel chromatography (dichloromethane/methanol) to give 77C (0.181 g, 83%) as a brown oil. MS (ESI) m/z 437.3 (M+H)$^+$.

77D: Example 77

Example 77 was prepared according to the general coupling-deprotection using 77C and 44A and it was separated by prep HPLC to afford a white solid (10 mg, 11%). $^1$H NMR (400 MHz, CD$_3$OD) δ 1.12 (d, J=7.03 Hz, 3H), 1.33 (t, J=7.03 Hz, 3H), 1.41 (d, J=6.59 Hz, 3H), 1.71-1.82 (m, 1H), 1.86-2.06 (m, 2H), 2.14 (d, J=7.47 Hz, 1H), 2.31-2.41 (m, 1H), 3.53 (q, 1H), 3.66-3.79 (m, 2H), 3.81 (s, 3H), 3.89-4.02 (m, 3H), 4.05-4.18 (m, 1H), 5.58-5.65 (m, 2H), 6.44-6.58 (m, 3H), 6.84-6.92 (m, 2H), 7.10 (q, 2H), 7.37 (d, J=8.79 Hz, 1H), 7.78 (d, J=8.35 Hz, 1H), 7.86 (s, 1H) 9.75 (s, 1H); MS (ESI) m/z 628.2 (M-NH$_2^-$)$^+$.

Example 78

Diastereomer of Example 77

Methyl 3-((R)-1-((S)-2-(4-(aminomethyl)-3-fluorophenylamino)-2-(5-ethoxy-2-fluorophenyl)acetyl)pyrrolidin-2-yl)-4-(isopropylsulfonyl)phenylcarbamate trifluoroacetic acid salt

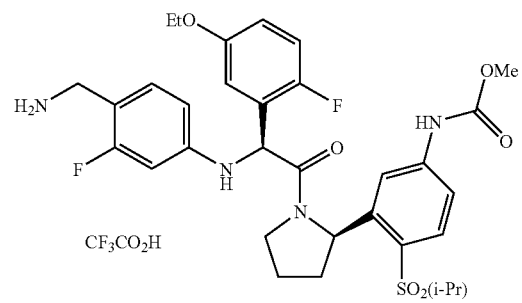

Example 78 was obtained as a diastereomer of Example 77 during its HPLC purification (24 mg, 27%, off-white solid). $^1$H NMR (400 MHz, CD$_3$OD) δ 1.18 (d, J=6.59 Hz, 3H), 1.25 (t, J=7.03 Hz, 3H), 1.43 (d, J=7.03 Hz, 3H), 1.65-1.76 (m, 1H), 1.97-2.17 (m, 2H), 2.49 (dd, J=13.18, 7.47 Hz, 1H), 3.57-3.68 (m, 2H), 3.72 (s, 3H), 3.74-3.81 (m, 1H), 3.89-4.00 (m, 2H), 4.04-4.14 (m, 1H), 5.64 (s, 1H), 6.43-6.55 (m, 3H), 6.80-6.88 (m, 1H), 7.00-7.19 (m, 3H), 7.28 (dd, J=8.79, 2.20 Hz, 1H), 7.74 (d, J=8.79 Hz, 1H), 9.38 (s, 1H); MS (ESI) m/z 628.2 (M-NH$_2^-$)$^+$.

Example 79

(R)-1-((R)-2-(5-Amino-2-(isopropylsulfonyl)phenyl)pyrrolidin-1-yl)-2-(1-aminoisoquinolin-6-ylamino)-2-(5-ethoxy-2-fluorophenyl)ethanone trifluoroacetic acid salt

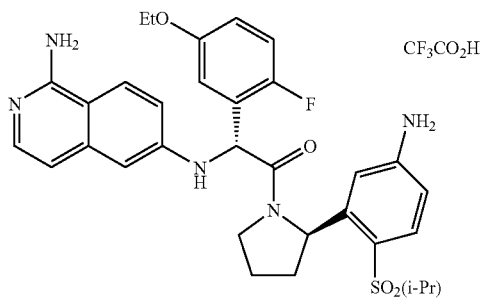

79A: (R)-4-(Isopropylsulfonyl)-3-(pyrrolidin-2-yl)benzeneamine and

79B: (S)-4-(Isopropylsulfonyl)-3-(pyrrolidin-2-yl)benzeneamine

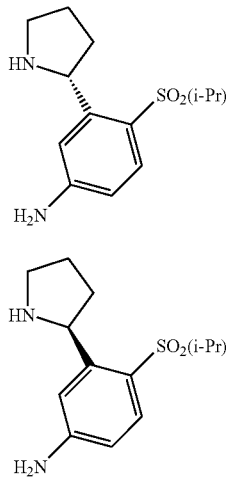

The enantiomers of 19D were separated using a preparative HPLC equipped with a Chiralpak®AS column (5 cm×50 cm, 20μ). The separation was performed using an isocratic method of 20% isopropanol/heptane with 0.1% diethylamine for 100 min with a flow rate of 60 mL/min. 79A: $^1$H NMR (400 MHz, Methanol-$d_4$) δ ppm 1.16-1.36 (m, 6H) 2.22-2.41 (m, 1H) 2.94-3.12 (m, 1H) 3.13-3.24 (m, 1H) 3.35-3.42 (m, J=1.71 Hz, 1H) 6.62 (dd, J=8.68, 2.32 Hz, 1H) 6.88 (d, J=2.20 Hz, 1H) 7.58 (d, J=8.56 Hz, 1H); 79B: $^1$H NMR (400 MHz, Methanol-$d_4$) δ ppm 1.18-1.31 (m, 6H) 1.78-2.18 (m, 3H) 2.25-2.40 (m, 1H) 3.05-3.19 (m, 1H) 3.18-3.28 (m, 1H) 3.32-3.42 (m, 1H) 4.92 (t, J=7.70 Hz, 1H) 6.65 (dd, J=8.68, 2.32 Hz, 1H) 6.89 (d, J=2.20 Hz, 1H) 7.60 (d, J=8.80 Hz, 1H).

79C: Example 79

Example 79 was prepared according to the general coupling-deprotection using 30A and 79A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.15 (d, J=6.60 Hz, 3H) 1.24-1.41 (m, 6H) 1.58-1.76 (m, 1H) 1.90-2.10 (m, 2H) 2.38-2.56 (m, 1H) 3.37-3.52 (m, 1H) 3.68-3.83 (m, 1H) 3.83-3.97 (m, 2H) 4.00-4.14 (m, 1H) 5.54 (t, 1H) 5.82 (s, 1H) 5.87 (d, J=1.47 Hz, 1H) 6.56 (d, J=8.56 Hz, 1H) 6.72-6.84 (m, 2H) 6.89 (d, J=7.34 Hz, 1H) 6.93-7.01 (m, 1H) 7.11-7.23 (m, 2H) 7.31 (d, J=7.09 Hz, 1H) 7.52 (d, J=8.80 Hz, 1H) 8.05 (d, J=9.29 Hz, 1H). LC-MS: 606 (M+H)$^+$.

Example 80

Methyl 3-((R)-1-((R)-2-(1-aminoisoquinolin-6-ylamino)-2-phenylacetyl)pyrrolidin-2-yl)-4-(isopropylsulfonyl)phenylcarbamate trifluoroacetic acid salt

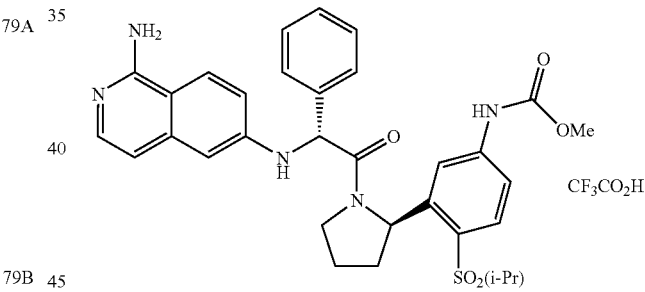

Example 80 was prepared according to the general coupling-deprotection using 54A and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.15 (d, J=6.60 Hz, 3H) 1.35-1.45 (m, 3H) 1.64-1.79 (m, 1H) 2.09 (dd, J=12.96, 6.60 Hz, 2H) 2.51 (dd, J=113.21, 7.83 Hz, 1H) 3.64-3.76 (m, 4H) 3.83-4.00 (m, 1H) 4.08-4.23 (m, J=4.16 Hz, 1H) 5.56 (s, 1H) 5.67 (dd, J=8.07, 5.38 Hz, 1H) 6.76 (d, J=2.20 Hz, 1H) 6.88 (d, J=7.09 Hz, 1H) 6.95 (s, 1H) 7.13 (dd, J=9.17, 2.32 Hz, 1H) 7.23 (dd, J=8.68, 2.08 Hz, 1H) 7.26-7.49 (m, 6H) 7.73 (d, J=8.80 Hz, 1H) 8.02 (d, J=9.29 Hz, 1H) 9.22 (s, 1H). LC-MS: 602 (M+H)$^+$.

Example 81

Diastereomer of Example 80

Methyl 3-((R)-1-((S)-2-(1-aminoisoquinolin-6-ylamino)-2-phenylacetyl)pyrrolidin-2-yl)-4-(isopropylsulfonyl)phenylcarbamate trifluoroacetic acid salt

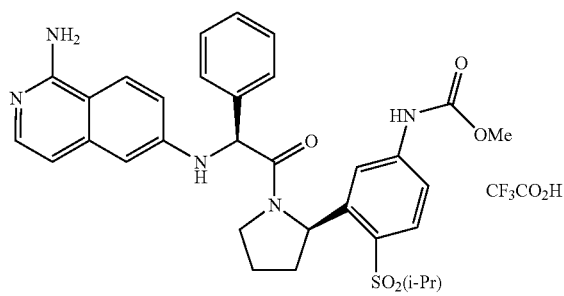

Example 81 was obtained as a diastereomer of Example 80 during its HPLC purification. $^1$H NMR (400 MHz, Methanol-$d_4$) δ ppm 1.06-1.20 (m, 3H) 1.37-1.51 (m, 3H) 1.68-1.94 (m, 2H) 2.09-2.23 (m, 1H) 2.24-2.39 (m, J=6.60 Hz, 1H) 3.46-3.57 (m, 1H) 3.75-3.85 (m, 4H) 4.12-4.25 (m, 1H) 5.53-5.69 (m, 2H) 6.68 (d, J=2.20 Hz, 1H) 6.84 (d, J=7.34 Hz, 1H) 7.12 (dd, J=9.17, 2.32 Hz, 1H) 7.27 (d, J=7.09 Hz, 1H) 7.35-7.50 (m, 4H) 7.52-7.60 (m, 1H) 7.77 (d, J=8.80 Hz, 1H) 7.81-7.87 (m, 1H) 7.97 (d, J=9.05 Hz, 1H). LC-MS: 602 (M+H)$^+$.

Example 82

Diastereomer of Example 79

(R)-1-((S)-(5-Amino-2-(isopropylsulfonyl)phenyl)pyrrolidin-1-yl)-2-(1-aminoisoquinolin-6-ylamino)-2-(5-ethoxy-2-fluorophenyl)ethanone trifluoroacetic acid salt

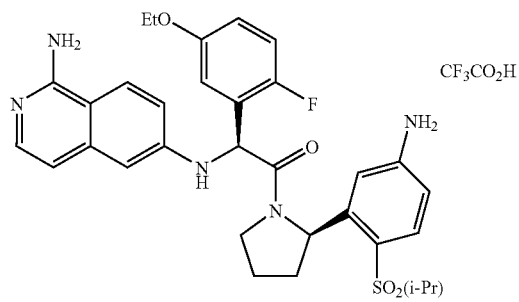

Example 82 was obtained as a diastereomer of Example 79 during its HPLC purification. $^1$H NMR (400 MHz, Methanol-$d_4$) δ ppm 1.12 (d, J=6.60 Hz, 3H) 1.29-1.42 (m, 6H) 1.71-1.95 (m, 2H) 2.08-2.20 (m, 1H) 2.23-2.36 (m, 1H) 3.39-3.49 (m, 1H) 3.63-3.75 (m, 1H) 3.98 (q, 2H) 4.09-4.22 (m, 1H) 5.58 (dd, J=8.44, 3.06 Hz, 1H) 5.80 (s, 1H) 6.58 (dd, J=8.68, 2.32 Hz, 1H) 6.68-6.76 (m, 2H) 6.92-7.01 (m, 3H) 7.10-7.22 (m, 2H) 7.28-7.35 (m, 1H) 7.47-7.58 (m, 1H) 8.04 (d, J=9.29 Hz, 1H). LC-MS: 606 (M+H)$^+$.

Example 83

Methyl 3-((R)-1-((R)-2-(1-aminoisoquinolin-6-yloxy)-2-(3-ethoxy-4-isopropoxyphenyl)acetyl)pyrrolidin-2-yl)-4-(isopropylsulfonyl)phenylcarbamate trifluoroacetic acid salt

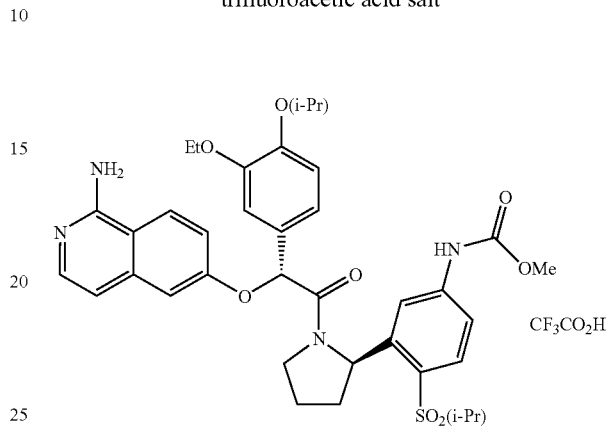

83A: 4-Methoxy-2-methylbenzoic acid

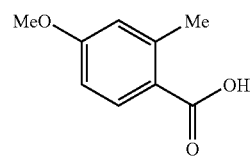

A flask equipped with a mechanical stirrer, reflux condenser and addition funnel was charged with magnesium (61.4 g) and THF (1 L) and put under a nitrogen atmosphere. The magnesium was treated with 4-bromo-3-methylanisole (500 g) and the reaction flask was warmed to 40° C. until reaction was well initiated. The remaining 4-bromo-3-methylanisole (9.5 kg) was added continuously over the next 1.5 h. The reaction temperature was maintained between 50-60° C. with an ice/water bath. The ice bath was removed during the last 10% of the addition. Once the last of the bromide was added, the reaction was allowed to stir for 1.5 h, during which time the temperature droped to 35° C. At this point, there was very little unconsumed magnesuim remaining, however the reaction solution was heated to 60° C. for 30 min to ensure completion. The reaction was cooled to −10° C. and excess carbon dioxide was added into the reaction mixture through the condenser. The reaction became quite thick, and the temperature rose to −30° C. At this point an additional 1 L of THF was added. The carbon dioxide was added until the reaction was complete and the temperature began to drop. A total of 350 mL THF was removed under reduced pressure. The resulting thick slurry was quenched with a mixture of 4.4 L ice cold water and 320 mL concentrated HCl. To the resulting thick white slurry an additional 4 L water was added. The resulting precipitate was filtered and washed with 1.5 L water, dried on the funnel overnight, and dried at 60° C. under high vacuum to provide 386.05 g of 83A as a white powder. HPLC showed a peak at the expected retention time 15.67 min and a purity of 97.45% at 220 nm, and 98.98% at 254 nm.

83B: 4-Methoxy-2-methylbenzamide

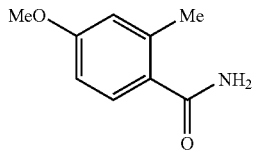

A mixture of 83A (386.05 g) in dichloromethane (3 L) was combined in a flask equipped with a mechanical stirrer, reflux condenser and addition funnel to provide a very thick slurry. DMF (1 mL) was added as catalyst, followed by oxalyl chloride (330 g) dropwise over about 2 h. The acidic effluent gasses were scrubbed through a $K_2CO_3$ scrubber. The slurry slowly dissolved during the addition to provide a red solution of acid chloride. Dichloromethane (1.3 L) was distilled off at 30° C. with slight vacuum, and the resulting concentrated solution of acid chloride was polish filtered through a course sintered glass funnel to remove some insoluble matter. This filtered solution was concentrated to a crystalline residue and pumped down under high vacuum for 30 min to remove any excess oxalyl chloride. The crystalline residue was dissolved in THF (550 mL) and titrated into a large flask containing ice cold concentrated ammonium hydroxide (1 L) over ~15 min. The temperature quickly rose to –30° C. with the formation of a thick slurry of product. To this oily slurry of product, water (3 L) was added over ~15 min to provide a thick white slurry of product. This product was filtered over course sintered glass and washed with water (1.5 L) and dried under nitrogen/vacuum for 36 h. 367.8 g of 83B was isolated as an off-white solid. HPLC showed a peak at the expected retention time of 11.85 min, with a purity of 95.15% at 220 nm, and 97.29% at 254 nm.

83C: 4-Methoxy-2-methylbenzoyl(N,N-dimethyl)formamidine

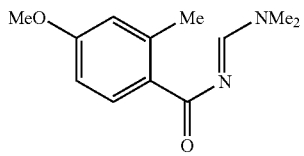

83B (296.15 g, 1.794 mol) was dissolved in THF (1.5 L) in a flask equipped with a mechanical stirrer and distilation head to give a thick slurry. DMF-DMA (263 mL, 1.1 eq) was added in one portion and slowly heated to gentle reflux. After 30 min at reflux, the reaction mixture became a homogeneous solution. The reaction was maintained at reflux for 1.5 h, and checked by HPLC and TLC (10:1 $CH_2Cl_2$/MeOH). At atmospheric pressure, 1150 mL THF was distilled out and replaced with 1500 mL heptane (Note that if the solution is not quite saturated, remaining THF should be removed by distillation). The remaining solution was cooled slowly to rt overnight with stirring, seeded at 68° C. Rapid crystallization was observed. The resulting slurry was cooled to 0° C., filtered and washed with heptanes (500 mL) and dried under vacuum at rt for 48 h. 384.6 g (97.4%) of 83C was isolated as a light tan crystalline solid. HPLC-MS using a neutral buffer ammonium acetate buffer system showed only a single peak, with the expected mass.

83D: 6-Methoxyisoquinolin-1-ol

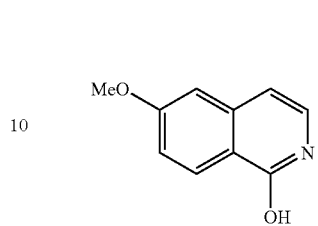

A slurry of 83C (16.33 g) in a small amount of THF (25 mL) was heated to 60° C. in a flask equipped with a stir bar, reflux condenser, and addition funnel. A solution of (1 M potassium tert-butoxide in THF, 105 mL) was titrated in over a period of 30 min. The reaction turned a light yellow, and began to precipitate a solid product after about 10 min and became a thick suspension after 30 min. The reaction was cooled to 30° C. and neutralized to pH 7 with 9.5 mL conc. HCl. Water (about 25 mL) was added to dissolve all the salts, and still an easy phase split remained. The phases were split and the aqueous phase was back extracted with 25 mL ethyl acetate. The organic phases were combined and slowly concentrated at 60° C. to provide a crystalline residue. 12.16 g (93.6%) of 83D was isolated as a light orange solid. An analytical sample was prepared by recrystallization from ethyl acetate. LC retention time=13.533 min. $^1$H NMR (DMSO-$d_6$) δ 3.86 (s, 3H); 6.46 (d, 1H); 7.02-7.13 (m, 3H); 8.08 (d, 1H); 11.03 (s, 1H).

83E: 1-Chloro-6-methoxyisoquinoline

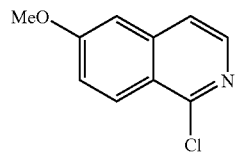

A slurry of 6-methoxyisoquinolone (116 g, 662 mmol) in phosphorous oxychloride (200 mL, 2.14 mol) was charged to a rotavap flask. The resulting thick paste was heated on the rotovap to 90° C. for ~30 min. The reaction thinned to a thick black solution with gas evolution then became pasty again, heated continuously at 90° C. for an additional 30 min and checked by TLC. An additional quantity of $POCl_3$ (100 mL, 1.07 mol) was added and heated continuously for another 2 h. The reaction was complete (checked by TLC; complete consumption of starting material with some production of a polar impurity) so the excess $POCl_3$ was stripped off under high vacuum to leave a solid mass of crude product. This solid mass was triturated with ethyl acetate (500 mL) at 0° C. for 3.5 h. The solid product was filtered off and washed with cold ethyl acetate (250 mL). Mother liquors contained essentially no product and were discarded. The weight of this crude solid salt was –208 grams. This salt was dissolved in a mixture of cold ethyl acetate (1000 mL) and water (1000 mL) and neutralized to pH=6.75 with $NaHCO_3$ (209 g, 2.49 mol, 3.75 eq based on starting material). The phases were split, and the aqueous phase was back extracted with ethyl acetate (500 mL) and combined with the first product containing ethyl acetate phase. The ethyl acetate was stripped off to yield 110.8 g crude residue. In order to remove the polar impurity, this residue was dissolved in a mixture of ethyl acetate 200 mL and heptanes 100 mL and passed through a silica gel plug (500 g) and eluted with a mixture of ethyl acetate/heptanes 1:1. The product containing fractions was concentrated to a residue to provide pinkish-yellow solids. These solids were recrystallized from hot (~75° C.) heptanes (1000 mL) and cooled to rt then to 0° C. Filtration and washing with cold heptanes (250 mL) followed by drying under vacuum provided purified 83E as a off-white crystalline solid. (98.02 g, 506 mmol, 76.5%).

83F: 6-Methoxyisoquinolin-1-amine

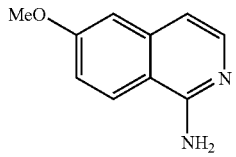

A sealable tube was charged with 83E (770 mg, 3.98 mmol), copper (I) oxide (30 mg) and ~12M $NH_3$ in ethylene glycol (5 mL). The tube was sealed and the reaction was heated to 120° C. for 72 h. After cooling to rt, the reaction was diluted with methanol and was purified via preparative HPLC (MeOH/water/TFA) to provide 83F (832 mg, 72%). LC-MS: 175.23 $(M+H)^+$.

83G: 1-Aminoisoquinolin-6-ol

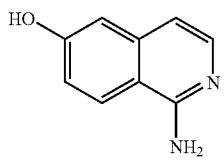

To 83F (345 mg, 2.0 mmol) in $CH_2Cl_2$ (10 mL) at 0° C. was added boron tribromide (8.0 mL, 1M solution in $CH_2Cl_2$). After warming to rt and stirring overnight, the reaction was concentrated and purified via preparative HPLC (MeOH/water/TFA) to provide 1-aminoisoquinolin-6-ol trifluoroacetic acid salt (240 mg, 44%). LC-MS: 161.2 $(M+H)^+$. The product (83 mg, 0.30 mmol) was dissolved in methanol (10 mL), and dianion WA21J Resin (2 g) was added. After stirring for 1 h, the reaction was filtered to provide the free amine 83G (41 mg, 85%). LC-MS: 161.18 $(M+H)^+$.

83H: Benzyl 2-(1-aminoisoquinolin-6-yloxy)-2-(3-ethoxy-4-isopropoxyphenyl)acetate trifluoroacetic acid salt

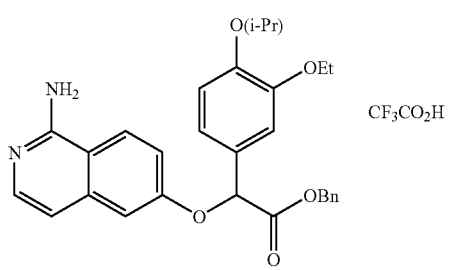

A mixture of 83G (93 mg, 0.58 mmol) in DMF (5 mL) and 60% NaH (32 mg, 0.80 mmol) was stirred for 20 min. To this mixture was added chloro-(3-ethoxy-4-isopropoxy-phenyl)-acetic acid benzyl ester (WO 2004072101, which is incorporated herein by reference) (265 mg, 0.73 mmol) in DMF (2 mL). After stirring for 1 h, the reaction was diluted with ethyl acetate, washed with water and brine then dried ($Na_2SO_4$), filtered and concentrated. The resulting residue was purified via preparative HPLC (MeOH/water/TFA) to provide 83H (160 mg, 46%). LC-MS: 487.25 $(M+H)^+$.

83I: 2-(1-Aminoisoquinolin-6-yloxy)-2-(3-ethoxy-4-isopropoxyphenyl)acetic acid trifluoroacetic acid salt

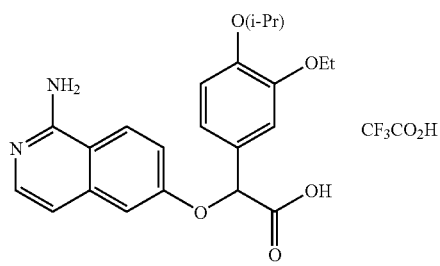

To 83H (131 mg, 0.22 mmol) in THF (8 mL) was added 10% Pd/C (cat.) and the mixture was hydrogenated at 50 psi for 3 h, then at 60 psi for 2 h. The reaction was filtered and concentrated to provide 83I (85 mg, 76%). LC-MS: 397.10 $(M+H)^+$.

83J: Example 83

A mixture of 83I (32 mg, 0.080 mmol), 44A (31 mg, 0.085 mmol), EDCI (35 mg, 0.18 mmol), HOAT (11 mg, 0.080 mmol), DIEA (0.07 mL, 0.06 mmol) in DMF (2 mL) was stirred at 60° C. for 2 h, then at rt overnight. The reaction was diluted with brine and ethyl acetate, and the layers were separated. The organic layer was concentrated and purified via preparative HPLC (MeOH/$H_2O$/TFA) to provide Example 83 (14 mg, 22%). $^1$H NMR (400 MHz, Methanol-$d_4$) δ ppm 1.13 (d, J=6.59 Hz, 3H) 1.26-1.42 (m, 12H) 1.65-1.79 (m, 1H) 2.00-2.22 (m, 2H) 2.39-2.59 (m, 1H) 3.70 (s, 3H) 3.77-4.01 (m, 4H) 4.11-4.22 (m, 1H) 4.51-4.66 (m, 1H) 5.71 (dd, J=8.13, 5.05 Hz, 1H) 6.18 (s, 1H) 6.94-7.01 (m, 2H) 7.03-7.14 (m, 2H) 7.17-7.23 (m, 2H) 7.26 (d, J=2.20 Hz, 1H) 7.40 (dd, J=9.23, 2.64 Hz, 1H) 7.48 (d, J=7.03 Hz, 1H) 7.73 (d, J=9.23 Hz, 1H) 8.32 (d, J=9.23 Hz, 1H) 9.40 (s, 1H); LC-MS: 705.57 $(M+H)^+$.

83F: 6-Methoxyisoquinolin-1-amine

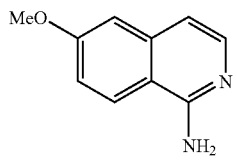

A sealable tube was charged with 83E (770 mg, 3.98 mmol), copper (I) oxide (30 mg) and 12M $NH_3$ in ethylene glycol (5 mL). The tube was sealed and the reaction was heated to 120° C. for 72 h. After cooling to rt, the reaction was diluted with methanol and was purified via preparative HPLC (MeOH/water/TFA) to provide 83F (832 mg, 72%). LC-MS: 175.23 (M+H)⁺.

83G: 1-Aminoisoquinolin-6-ol

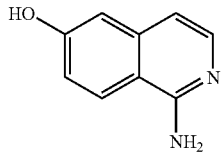

To 83F (345 mg, 2.0 mmol) in CH₂Cl₂ (10 mL) at 0° C. was added boron tribromide (8.0 mL, 1M solution in CH₂Cl₂). After warming to rt and stirring overnight, the reaction was concentrated and purified via preparative HPLC (MeOH/water/TFA) to provide 1-aminoisoquinolin-6-ol trifluoroacetic acid salt (240 mg, 44%). LC-MS: 161.2 (M+H)⁺. The product (83 mg, 0.30 mmol) was dissolved in methanol (10 mL), and dianion WA21J Resin (2 g) was added. After stirring for 1 h, the reaction was filtered to provide the free amine 83G (41 mg, 85%). LC-MS: 161.18 (M+H)⁺.

83H: Benzyl 2-(1-aminoisoquinolin-6-yloxy)-2-(3-ethoxy-4-isopropoxyphenyl)acetate trifluoroacetic acid salt

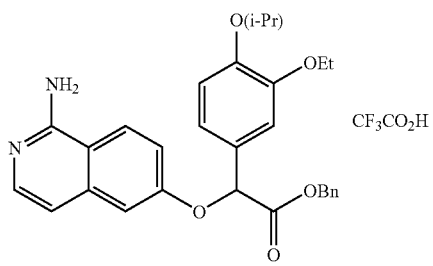

A mixture of 83G (93 mg, 0.58 mmol) in DMF (5 mL) and 60% NaH (32 mg, 0.80 mmol) was stirred for 20 min. To this mixture was added chloro-(3-ethoxy-4-isopropoxy-phenyl)-acetic acid benzyl ester (WO 2004072101, which is incorporated herein by reference) (265 mg, 0.73 mmol) in DMF (2 mL). After stirring for 1 h, the reaction was diluted with ethyl acetate, washed with water and brine then dried (Na₂SO₄), filtered and concentrated. The resulting residue was purified via preparative HPLC (MeOH/water/TFA) to provide 83H (160 mg, 46%). LC-MS: 487.25 (M+H)⁺.

83I: 2-(1-Aminoisoquinolin-yloxy)-2-(3-ethoxy-4-isopropoxyphenyl)acetic acid trifluoroacetic acid salt

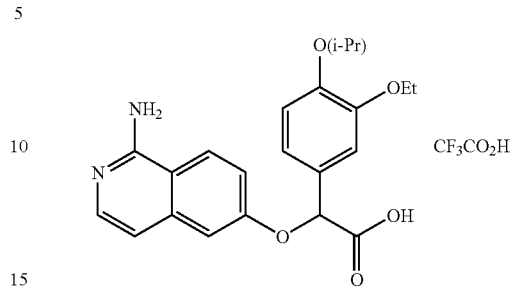

To 83H (131 mg, 0.22 mmol) in THF (8 mL) was added 10% Pd/C (cat.) and the mixture was hydrogenated at 50 psi for 3 h, then at 60 psi for 2 h. The reaction was filtered and concentrated to provide 83I (85 mg, 76%). LC-MS: 397.10 (M+H)⁺.

83J: Example 83

A mixture of 83I (32 mg, 0.080 mmol), 44A (31 mg, 0.085 mmol), EDCI (35 mg, 0.18 mmol), HOAT (11 mg, 0.080 mmol), DIEA (0.07 mL, 0.06 mmol) in DMF (2 mL) was stirred at 60° C. for 2 h, then at rt overnight. The reaction was diluted with brine and ethyl acetate, and the layers were separated. The organic layer was concentrated and purified via preparative HPLC (MeOH/H₂O/TFA) to provide Example 83 (14 mg, 22%). ¹H NMR (400 MHz, Methanol-d₄) δ ppm 1.13 (d, J=6.59 Hz, 3H) 1.26-1.42 (m, 12H) 1.65-1.79 (m, 1H) 2.00-2.22 (m, 2H) 2.39-2.59 (m, 1H) 3.70 (s, 3H) 3.77-4.01 (m, 4H) 4.11-4.22 (m, 1H) 4.51-4.66 (m, 1H) 5.71 (dd, J=8.13, 5.05 Hz, 1H) 6.18 (s, 1H) 6.94-7.01 (m, 2H) 7.03-7.14 (m, 2H) 7.17-7.23 (m, 2H) 7.26 (d, J=2.20 Hz, 1H) 7.40 (dd, J=9.23, 2.64 Hz, 1H) 7.48 (d, J=7.03 Hz, 1H) 7.73 (d, J=9.23 Hz, 1H) 8.32 (d, J=9.23 Hz, 1H) 9.40 (s, 1H); LC-MS: 705.57 (M+H)⁺.

Example 84

Methyl 3-((R)-1-((R)-2-(1-aminoisoquinolin-6-ylamino)-2-(5-ethyl-2-fluorophenyl)acetyl)pyrrolidin-2-yl)-4-(isopropylsulfonyl)phenylcarbamate trifluoroacetic acid salt

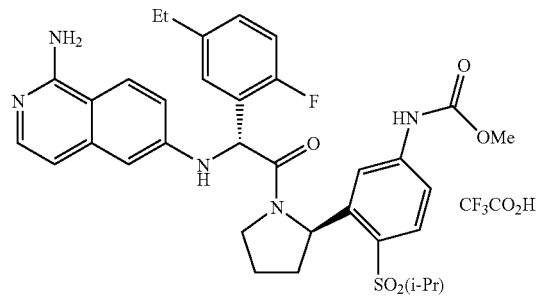

84A: 1-(3-Bromo-4-fluorophenyl)ethanol

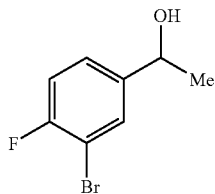

To a solution of 3-bromo-4-fluoroacetophenone (10 g, 46 mmol) in THF (100 mL) and methanol (1.0 mL) was added sodium borohydride (2.1 g, 55.5 mmol). The mixture was heated up to 70° C. for 1 h, then cooled down to rt. The reaction was quenched by 100 ml of 1N HCl solution and extracted with EtOAc (3×100 mL). The combined organic layers were washed with brine, dried over $MgSO_4$, and concentrated. The crude product was purified by column chromatography to give 9.8 g of 84A (97% yield). $^1$H NMR (400 MHz, $CDCl_3$) δ ppm 1.48 (d, J=6.15 Hz, 3H) 7.24-7.33 (m, 1H) 7.59 (dd, J=6.59, 2.20 Hz, 1H).

84B: 2-Bromo-4-ethyl-1-fluorobenzene

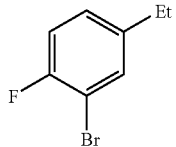

To 84A (9.8 g, 45 mmol) in trifluoroacetic acid (20 mL) was added triethylsilane (14.3 mL, 90 mmol). After stirring at 50° C. for 6 h, the reaction was quenched with 100 mL of saturated $NaHCO_3$ solution and extracted with diethyl ether (3×). The combined organic layers were washed with brine, dried over $MgSO_4$, and concentrated. The resulting residue was distilled at 200° C. to give 84B (85% purity).

$^1$H NMR (400 MHz, $CDCl_3$) δ ppm 1.22 (t, J=7.69 Hz, 3H) 2.60 (q, J=7.47 Hz, 2H) 7.02 (t, J=8.57 Hz, 1H) 7.06-7.12 (m, 1H) 7.37 (dd, J=6.59, 2.20 Hz, 1H).

84C: 5-Ethyl-2-fluorophenylboronic acid

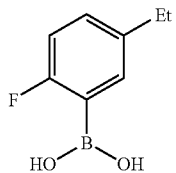

To 84B (550 mg, 2.3 mmol) in THF (10 mL) was added 1.6 M n-butyllithium in hexane (2.2 ml, 3.5 mmol) at −78° C. After stirring for 1 h, trimethylborate (0.52 mL, 4.6 mmol) was introduced at −78° C. The reaction mixture was warmed up to rt overnight. It was then quenched by 1.0 N HCl (10 mL) and extracted with EtOAc (3×30 mL). The combined organic layers were washed with brine, dried over $MgSO_4$, and concentrated. The crude product was purified by column chromatography to give 255 mg white solid of 84C. $^1$H NMR (400 MHz, Methanol-$d_4$) δ ppm 1.15-1.27 (m, 3H) 2.61 (q, J=7.76 Hz, 2H) 6.94 (t, J=8.57 Hz, 1H) 7.17-7.27 (m, 2H).

84D: 2-(1-Di-tert-butoxycarbonylaminoisoquinolin-6-ylamino)-2-(5-ethyl-2-fluoro-phenyl)acetic acid

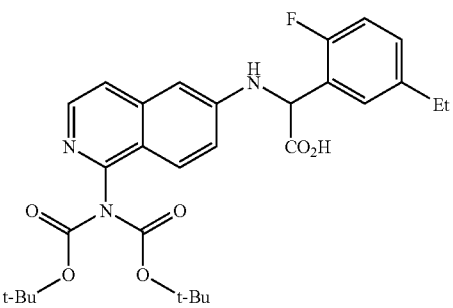

A mixture of 84C (36 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography ($CH_2Cl_2$:MeOH=100:15) to give 54 mg (51% yield) of 84D as a solid. $^1$H NMR (400 MHz, Methanol-$d_4$) δ ppm 1.05 (t, J=7.47 Hz, 3H) 1.16 (s, 18H) 2.48 (q, J=7.62 Hz, 2H) 5.44 (s, 1H) 6.61 (d, J=2.20 Hz, 1H) 6.93-7.00 (m, 1H) 7.03-7.10 (m, 1H) 7.18 (dd, J=9.23, 2.20 Hz, 1H) 7.25 (dd, J=7.03, 2.20 Hz, 1H) 7.35 (d, J=5.71 Hz, 1H) 7.54 (d, J=9.23 Hz, 1H) 7.93 (d, J=6.15 Hz, 1H) LC-MS: 540 $(M+H)^+$.

84E: Example 84

Example 84 was prepared according to the general coupling-deprotection using 84D and 44A. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.05 (t, J=7.58 Hz, 3H) 1.18 (t, J=6.48 Hz, 3H) 1.43 (d, J=6.85 Hz, 3H) 1.66-1.81 (m, J=4.16 Hz, 1H) 2.01-2.19 (m, 2H) 2.40-2.60 (m, 3H) 3.63-3.69 (m, J=9.54 Hz, 1H) 3.71 (s, 3H) 3.87-4.04 (m, 1H) 4.11-4.24 (m, 1H) 5.72 (dd, J=8.44, 5.01 Hz, 1H) 5.83 (s, 1H) 6.79 (d, J=2.20 Hz, 1H) 6.90 (d, J=7.09 Hz, 1H) 7.00 (d, J=7.09 Hz, 1H) 7.04-7.10 (m, 1H) 7.10-7.29 (m, 4H) 7.33 (d, J=7.09 Hz, 1H) 7.76 (d, J=8.56 Hz, 1H) 8.06 (d, J=9.29 Hz, 1H) 9.41 (s, 1H). LC-MS: 648 $(M+H)^+$.

Example 85

Diastereomer of Example 84

Methyl 3-((R)-1-((S)-2-(1-aminoisoquinolin-6-ylamino)-2-(5-ethyl-2-fluorophenyl)acetyl)pyrrolidin-2-yl)-4-(isopropylsulfonyl)phenylcarbamate trifluoroacetic acid salt

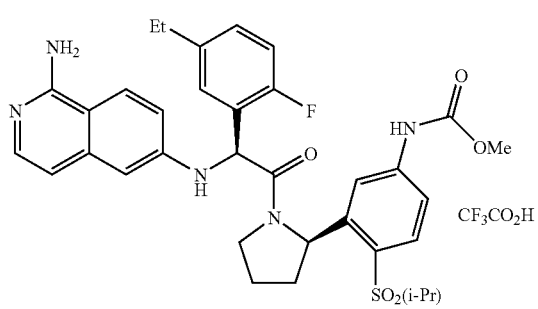

Example 85 was obtained as a diastereomer of Example 84 during its HPLC purification. $^1$H NMR (400 MHz, Methanol-d$_4$) δ ppm 1.03-1.23 (m, 6H) 1.33-1.44 (m, 3H) 1.64-1.80 (m, 1H) 1.98-2.15 (m, 2H) 2.41-2.66 (m, 2H) 2.70 (d, J=22.74 Hz, 1H) 3.55-3.67 (m, 1H) 3.74-3.90 (m, 1H) 4.08-4.23 (m, J=10.03 Hz, 1H) 5.65 (dd, J=8.31, 4.65 Hz, 1H) 5.78 (d, J=2.45 Hz, 1H) 5.85 (s, 1H) 6.49 (dd, J=8.93, 2.57 Hz, 1H) 6.73-6.81 (m, J=2.45 Hz, 1H) 6.89 (d, J=7.09 Hz, 1H) 7.10-7.19 (m, 3H) 7.20-7.29 (m, 1H) 7.32 (d, J=7.09 Hz, 1H) 7.54 (d, J=8.80 Hz, 1H) 8.06 (d, J=9.05 Hz, 1H). LC-MS: 648 (M+H)$^+$.

Example 86

Methyl 3-((R)-1-((R)-2-(1-aminoisoquinolin-6-ylamino)-2-(2-fluoro-4,5-dimethoxyphenyl)acetyl)pyrrolidin-2-yl)-4-(isopropylsulfonyl)phenylcarbamate trifluoroacetic acid salt

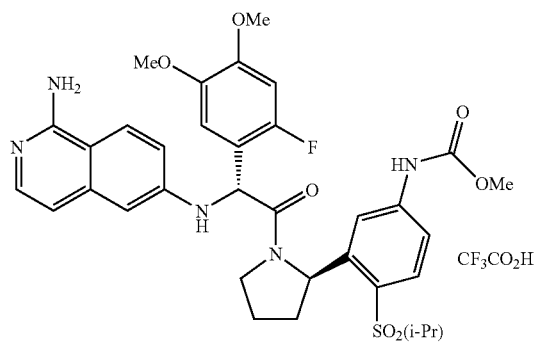

86A: 1-Fluoro-2-iodo-4,5-dimethoxybenzene

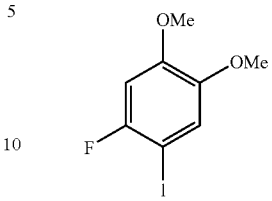

86A (656 mg, 66% yield) was obtained from 64C (960 mg, 3.58 mmol) and methyl iodide (0.3 mL, 4.83 mmol) in a procedure similar to that used in the preparation of 64D. $^1$H NMR (400 MHz, CDCl$_3$) δ ppm 3.86 (s, 6H) 6.67 (m, 1H) 7.10 (m, 1H).

86B: 2-Fluoro-4,5-dimethoxyphenylboronic acid

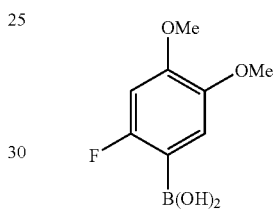

86B (330 mg, 72% yield) was obtained from 86A (650 mg, 2.3 mmol) using a procedure similar to that used in the preparation of 64E. $^1$H NMR (400 MHz, CDCl$_3$) δ ppm 3.80 (s, 3H) 3.83 (s, 3H) 6.72 (m, 1H) 6.89 (m, 1H).

86C: 2-(1-Di-tert-butoxycarbonylaminoisoquinolin-6-ylamino)-2-(4,5-dimethoxy-2-fluoro-phenyl)acetic acid

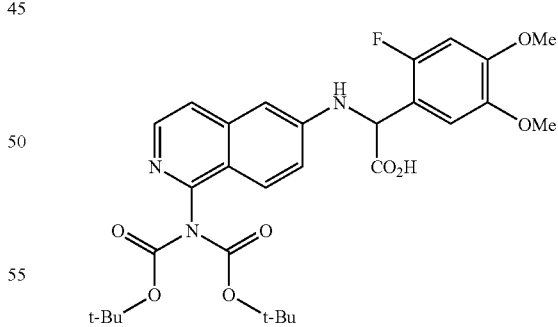

A mixture of 86B (46 mg, 0.23 mmol), 1B (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 92 mg (70% yield) of 86C as a solid. $^1$H NMR (400 MHz, Methanol-d$_4$) δ ppm 1.26 (s, 18H) 3.71 (s, 3H) 3.76 (s, 3H) 5.46 (s, 1H) 6.71 (d, J=2.20 Hz, 1H) 6.78

(d, J=11.42 Hz, 1H) 6.93 (d, J=7.03 Hz, 1H) 7.18 (dd, J=9.23, 2.20 Hz, 1H) 7.39 (d, J=5.27 Hz, 1H) 7.64 (d, J=8.79 Hz, 1H) 8.08 (d, J=5.71 Hz, 1H).

86D: Example 86

Example 86 was prepared according to the general coupling-deprotection using 86C and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.15-1.24 (m, 3H) 1.36-1.47 (m, 3H) 1.65-1.82 (m, 1H) 2.00-2.19 (m, 2H) 2.40-2.60 (m, 1H) 3.46-3.53 (m, 3H) 3.56-3.66 (m, 1H) 3.68-3.75 (m, 3H) 3.83-3.89 (m, 3H) 3.92-4.02 (m, 1H) 4.06-4.21 (m, 1H) 5.69 (dd, J=8.07, 5.62 Hz, 1H) 5.77 (s, 1H) 6.53 (d, J=6.85 Hz, 1H) 6.79 (d, J=2.20 Hz, 1H) 6.86-6.97 (m, 2H) 7.08-7.25 (m, 3H) 7.33 (d, J=7.09 Hz, 1H) 7.76 (d, J=9.05 Hz, 1H) 8.05 (d, J=9.05 Hz, 1H) 9.42 (s, 1H). LC-MS: 680 (M+H)$^+$.

Example 87

Diastereomer of Example 86

Methyl 3-(R)-1-((S)-2-(1-aminoisoquinolin-6-ylamino)-2-(2-fluoro-4,5-dimethoxyphenyl)acetyl) pyrrolidin-2-yl)-4-(isopropylsulfonyl)phenylcarbamate trifluoroacetic acid salt

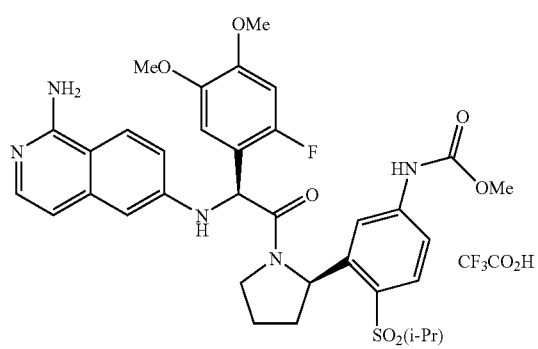

Example 87 was obtained as a diastereomer of Example 86 during its HPLC purification. $^1$H NMR (400 MHz, Methanol-$d_4$) δ ppm 0.94-1.24 (m, 3H) 1.30-1.51 (m, 3H) 1.77 (dd, J=15.04, 3.06 Hz, 1H) 1.95-2.25 (m, 2H) 2.25-2.58 (m, 1H) 3.41-3.64 (m, 2H) 3.63-3.94 (m, 9H) 4.04-4.28 (m, 1H) 5.57-5.71 (m, 1H) 5.72-5.86 (m, 1H) 6.59-7.03 (m, 4H) 7.09-7.24 (m, 2H) 7.21-7.42 (m, 2H) 7.69-7.87 (m, 1H) 8.03 (d, J=9.29 Hz, 1H) 9.69 (s, 1H). LC-MS: 680 (M+H)$^+$.

Example 88

(2R,3S)-Methyl 1-((S)-2-(1-aminoisoquinolin-6-ylamino)-2-(5-ethoxy-2-fluorophenyl)acetyl)-2-(2-(isopropylsulfonyl)phenyl)pyrrolidine-3-carboxylate trifluoroacetic acid salt

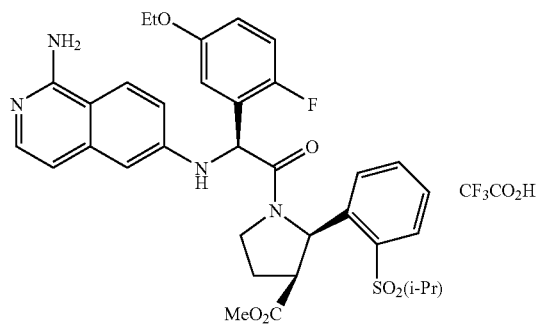

Example 88 was prepared according to the general coupling-deprotection using 30A and 58A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.06-1.17 (m, 3H) 1.34-1.47 (m, 6H) 2.11 (dd, J=13.69, 6.60 Hz, 1H) 2.49 (dd, J=13.33, 11.13 Hz, 1H) 2.83-2.98 (m, 1H) 3.22-3.30 (m, 1H) 3.61 (s, 3H) 3.70-3.83 (m, 1H) 3.93-4.17 (m, 2H) 4.27-4.43 (m, 1H) 5.88 (s, 1H) 6.00 (s, 1H) 6.80 (d, J=2.20 Hz, 1H) 6.90-7.04 (m, 3H) 7.06-7.21 (m, 2H) 7.37 (d, J=7.09 Hz, 1H) 7.46-7.57 (m, 1H) 7.62-7.78 (m, 2H) 7.88-7.95 (m, 1H) 8.02 (d, J=9.29 Hz, 1H). LC-MS: 649 (M+H)$^+$.

Example 89

Diastereomer of Example 88

(2R,3S)-Methyl 1-((R)-2-(1-aminoisoquinolin-6-ylamino)-2-(5-ethoxy-2-fluorophenyl)acetyl)-2-(2-(isopropylsulfonyl)phenyl)pyrrolidine-3-carboxylate trifluoroacetic acid salt

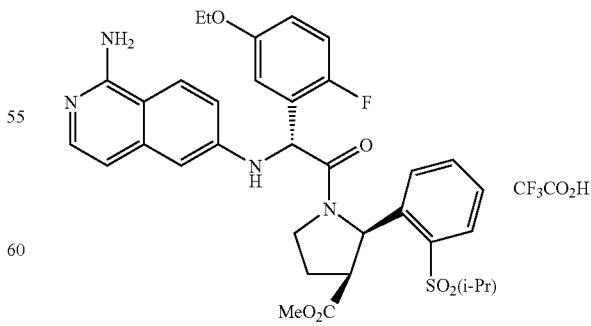

Example 89 was obtained as a diastereomer of Example 88 during its HPLC purification. $^1$H NMR (400 MHz, Methanol-$d_4$) δ ppm 1.14 (d, J=6.60 Hz, 3H) 1.24-1.33 (m, 3H) 1.33-

1.42 (m, 3H) 2.15-2.42 (m, 2H) 2.89-3.03 (m, 1H) 3.66-3.97 (m, 7H) 4.04-4.21 (m, 1H) 5.77 (s, 1H) 6.03 (d, J=2.45 Hz, 1H) 6.63-6.89 (m, 3H) 6.92-7.07 (m, 2H) 7.11-7.25 (m, 2H) 7.36 (d, J=7.09 Hz, 1H) 7.41-7.58 (m, 2H) 7.93 (dd, J=7.83, 1.47 Hz, 1H) 8.08 (d, J=9.29 Hz, 1H). LC-MS: 649 (M+H)$^+$.

Example 90

Diastereomer of Example 83

Methyl 3-((R)-1-((S)-2-(1-aminoisoquinolin-6-yloxy)-2-(3-ethoxy-4-isopropoxyphenyl)acetyl)pyrrolidin-2-yl)-4-(isopropylsulfonyl)phenylcarbamate trifluoroacetic acid salt

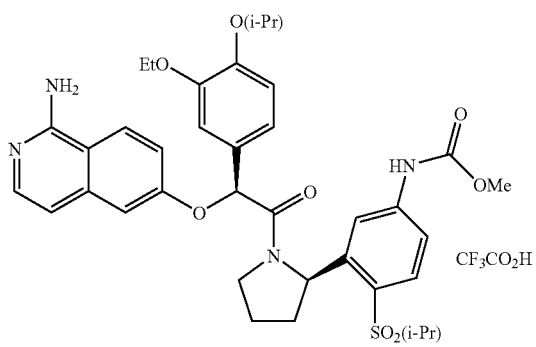

Example 90 was obtained as a diastereomer of Example 83 during its HPLC purification. $^1$H NMR (400 MHz, Methanol-d$_4$) δ ppm 1.08 (d, J=6.59 Hz, 3H) 1.30-1.43 (m, 12H) 1.66-1.79 (m, 1H) 1.82-1.96 (m, 1H) 2.10-2.23 (m, 1H) 2.23-2.40 (m, 1H) 3.48-3.60 (m, 1H) 3.72-3.82 (m, 1H) 3.84 (s, 3H) 4.06 (q, J=7.03 Hz, 2H) 4.11-4.20 (m, 1H) 4.53-4.63 (m, 1H) 5.65 (dd, J=8.35, 3.95 Hz, 1H) 6.26 (s, 1H) 6.97-7.21 (m, 5H) 7.32 (dd, J=8.79, 2.20 Hz, 1H) 7.37 (dd, J=9.23, 2.20 Hz, 1H) 7.43 (d, J=7.03 Hz, 1H) 7.74 (d, J=8.79 Hz, 1H) 7.89 (s, 1H) 8.24 (d, J=9.23 Hz, 1H) 9.79 (s, 1H); 705.57 (M+H)$^+$.

Example 91

(2R,3S)-Methyl 1-((S)-2-(1-aminoisoquinolin-6-ylamino)-2-(2-fluoro-4,5-dimethoxyphenyl)acetyl)-2-(2-(isopropylsulfonyl)phenyl)pyrrolidine-3-carboxylate trifluoroacetic acid salt

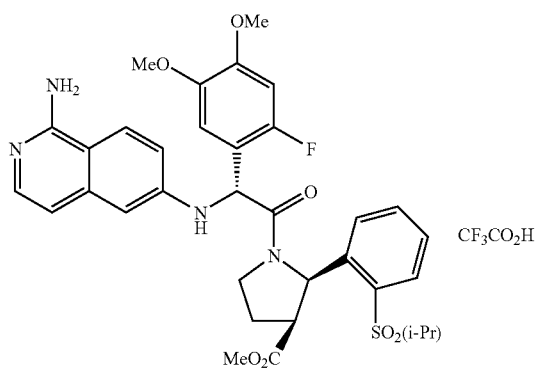

Example 91 was prepared according to the general coupling-deprotection using 86C and 58A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 ml-min. $^1$H NMR (400 MHz, Methanol-d$_4$) δ ppm 1.08-1.19 (m, 3H) 1.37-1.47 (m, 3H) 2.11 (dd, J=13.45, 6.60 Hz, 1H) 2.36-2.60 (m, 1H) 2.92 (d, J=7.83 Hz, 1H) 3.16-3.27 (m, 1H) 3.56-3.66 (m, 3H) 3.73-3.85 (m, 1H) 3.84-3.92 (m, 6H) 4.35 (t, J=9.05 Hz, 1H) 5.83 (s, 1H) 6.01 (s, 1H) 6.74-6.82 (m, 1H) 6.86-7.01 (m, 3H) 7.10 (dd, J=9.17, 2.32 Hz, 1H) 7.38 (t, J=7.34 Hz, 1H) 7.45-7.57 (m, 1H) 7.65-7.77 (m, 2H) 7.88-7.95 (m, 1H) 8.02 (d, J=9.29 Hz, 1H). LC-MS: 665 (M+H)$^+$.

Example 92

Diastereomer of Example 91

(2R,3S)-Methyl 1-((R)-2-(1-aminoisoquinolin-6-ylamino)-2-(2-fluoro-4,5-dimethoxyphenyl)acetyl)-2-(2-(isopropylsulfonyl)phenyl)pyrrolidine-3-carboxylate trifluoroacetic acid salt

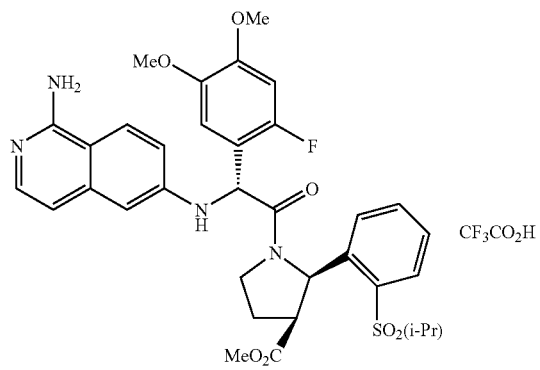

Example 92 was obtained as a diastereomer of Example 91 during its HPLC purification. $^1$H NMR (400 MHz, Methanol-d$_4$) δ ppm 1.13 (d, J=6.60 Hz, 3H) 1.37 (d, J=6.85 Hz, 3H) 2.17-2.42 (m, 2H) 2.87-3.03 (m, 1H) 3.59 (s, 3H) 3.68-3.85 (m, 5H) 3.84-3.92 (m, 3H) 4.02-4.20 (m, 1H) 5.72 (s, 1H) 6.03 (d, J=2.20 Hz, 1H) 6.61-6.84 (m, 3H) 6.97 (d, J=11.25 Hz, 1H) 7.04 (d, J=7.09 Hz, 1H) 7.15 (dd, J=9.17, 2.32 Hz, 1H) 7.36 (d, J=7.09 Hz, 1H) 7.41-7.58 (m, 2H) 7.93 (dd, J=7.83, 1.47 Hz, 1H) 8.08 (d, J=9.29 Hz, 1H). LC-MS: 665 (M+H)$^+$.

Example 93

(2R,3S)-1-((R)-2-(1-Aminoisoquinolin-6-ylamino)-2-(2-fluoro-4,5-dimethoxyphenyl)acetyl)-2-(2-(isopropylsulfonyl)phenyl)pyrrolidine-3-carboxylic acid trifluoroacetic acid salt

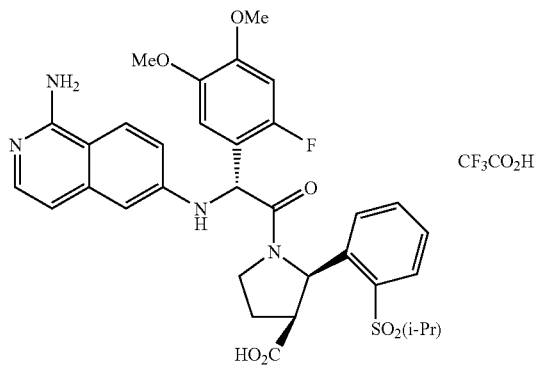

Example 93 was prepared by hydrolysis of the methyl ester Example 92 in a procedure similar to that used in Example 12. $^{1}$H NMR (400 MHz, Methanol-$d_4$) δ ppm 1.13 (d, J=6.60 Hz, 3H) 1.37 (d, J=6.85 Hz, 3H) 2.15-2.45 (m, 2H) 2.92 (d, J=7.34 Hz, 1H) 3.59 (s, 3H) 3.69-3.85 (m, 2H) 3.88 (s, 3H) 3.99-4.20 (m, 1H) 5.69 (s, 1H) 6.08 (s, 1H) 6.69-6.84 (m, 3H) 6.97 (d, J=11.25 Hz, 1H) 7.05 (d, J=6.85 Hz, 1H) 7.14 (dd, J=9.17, 2.32 Hz, 1H) 7.33 (d, J=7.09 Hz, 1H) 7.42-7.58 (m, 2H) 7.94 (dd, J=7.58, 1.47 Hz, 1H) 8.06 (d, J=9.29 Hz, 1H). LC-MS: 651 (M+H)$^+$.

Example 94

Methyl 3-((R)-1-((R)-2-(1-aminoisoquinolin-6-ylamino)-2-(2,4-difluoro-5-methylphenyl)acetyl)pyrrolidin-2-yl)-4-(isopropylsulfonyl)phenylcarbamate trifluoroacetic acid salt

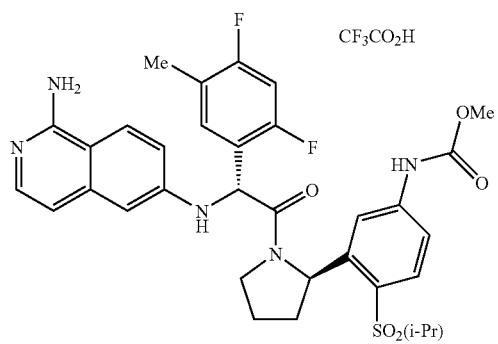

94A: 1,5-Difluoro-2-iodo-4-methylbenzene

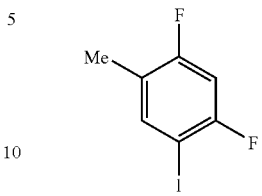

To a solution of 2,4-difluoro-1-methylbenzene (6 g, 47 mmol) in trifluoroacetic acid (15 mL) was added N-iodosuccinimide (12.1 g). The mixture was stirred at rt overnight before it was poured into ice and extracted with hexanes. The organic layer was separated and washed with saturated Na$_2$S$_2$O$_3$, NaHCO$_3$, brine and then dried over MgSO$_4$. The crude product was purified by silica gel chromatography to give 94A (10.7 g, 90% yield) as a colorless oil. $^{1}$H NMR (400 MHz, CDCl$_3$) δ ppm 2.15-2.30 (m, 3H) 6.73-6.85 (m, 1H) 7.55 (t, J=7.69 Hz, 3H).

94B: 2,4-Difluoro-5-methylphenylboronic acid

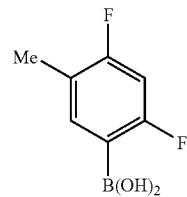

To 94A (2.8 g, 11 mmol) in THF (50 mL) was added n-BuLi (1.6M in hexane, 8.9 mL) at –78° C. After 10 min stirring, trimethyl borate (2.5 mL) was introduced. The mixture was stirred from –78° C. to rt overnight. The reaction was quenched by 1N HCl and extracted with EtOAc. The organic layer was separated and washed with saturated Na$_2$S$_2$O$_3$, brine and dried over MgSO$_4$. Evaporation of solvent gave product 94B (1.66 g, 88% yield) as a white solid. $^{1}$H NMR (400 MHz, CDCl$_3$) δ ppm 2.22 (s, 3H) 6.82 (t, J=9.23 Hz, 1H) 7.26 (t, J=7.69 Hz, 1H).

94C: 2-(1-Di-tert-butoxycarbonylaminoisoquinolin-6-ylamino)-2-(2,4-di-fluoro-5-methylphenyl)acetic acid

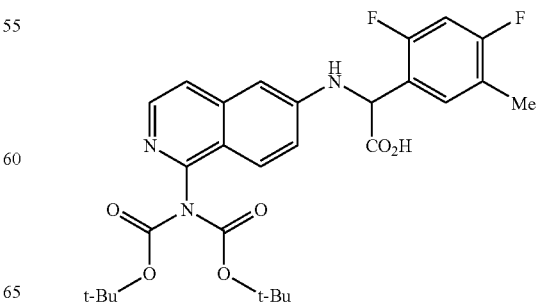

A mixture of 94C (62 mg, 0.36 mmol), 1B (108 mg, 0.3 mmol) and glyoxylic acid monohydrate (33 mg, 0.36 mmol) in acetonitrile (0.7 mL) and DMF (0.07 mL) was heated at 85° C. for 30 min in a Microwave Reactor. The crude product was purified by flash column chromatography ($CH_2Cl_2$:MeOH=100:15) to give 66 mg (41% yield) of 94C as a solid. $^1$H NMR (400 MHz, Methanol-$d_4$) δ ppm 1.27 (s, 18H) 2.20 (s, 3H) 5.50 (s, 1H) 6.71 (d, J=2.20 Hz, 1H) 6.98 (t, J=9.67 Hz, 1H) 7.28 (dd, J=9.23, 2.20 Hz, 1H) 7.41 (t, J=8.35 Hz, 1H) 7.47 (d, J=5.71 Hz, 1H) 7.65 (d, J=8.79 Hz, 1H) 7.97 (s, 1H) 8.05 (d, J=5.71 Hz, 1H). LC-MS: 544 (M+H)$^+$.

94D: Example 94

Example 94 was prepared according to the general coupling-deprotection using 94C and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.18 (d, J=6.60 Hz, 3H) 1.42 (d, J=6.85 Hz, 3H) 1.57-1.76 (m, 1H) 1.92-2.12 (m, 2H) 2.20 (s, 3H) 2.40-2.63 (m, 1H) 3.71 (s, 3H) 3.90-4.12 (m, 2H) 5.67 (t, J=7.09 Hz, 1H) 5.87 (s, 1H) 6.71-6.99 (m, 3H) 7.06-7.38 (m, 5H) 7.75 (d, J=8.80 Hz, 1H) 7.95-8.11 (m, 1H) 9.49 (s, 1H). LC-MS: 652 (M+H)$^+$.

Example 95

Diastereomer of Example 94

Methyl 3-((R)-1-((S)-2-(1-aminoisoquinolin-6-ylamino)-2-(2,4-difluoro-5-methylphenyl)acetyl)pyrrolidin-2-yl)-4-(isopropylsulfonyl)phenylcarbamate trifluoroacetic acid salt

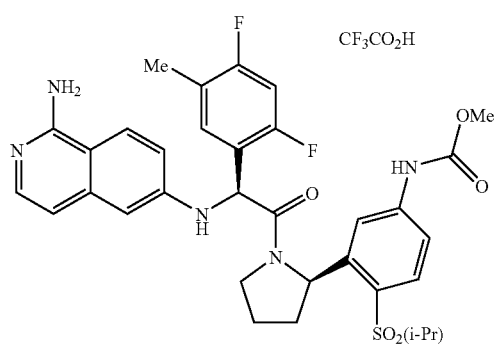

Example 95 was obtained as a diastereomer of Example 94 during its HPLC purification. $^1$H NMR (400 MHz, Methanol-$d_4$) δ ppm 1.06-1.19 (m, 3H) 1.34-1.46 (m, 3H) 1.68-1.83 (m, J=17.12 Hz, 1H) 1.86-2.01 (m, J=13.69, 13.69 Hz, 1H) 2.02-2.18 (m, 1H) 2.26 (s, 3H) 2.29-2.47 (m, J=12.23 Hz, 1H) 3.33-3.41 (m, 1H) 3.64-3.78 (m, 2H) 3.82 (s, 3H) 3.96-4.17 (m, 1H) 5.65 (dd, J=8.31, 3.42 Hz, 1H) 5.90 (s, 1H) 6.73-6.91 (m, 2H) 6.92-7.06 (m, 1H) 7.17-7.46 (m, 4H) 7.79 (d, J=8.56 Hz, 1H) 7.88 (d, J=2.20 Hz, 1H) 8.06 (d, J=9.05 Hz, 1H). LC-MS: 652 (M+H)$^+$.

Example 96

(2R,3S)-1-((R)-2-(1-aminoisoquinolin-6-ylamino)-2-(5-ethoxy-2-fluoro-4-isopropoxyphenyl)acetyl)-2-(2-(isopropylsulfonyl)phenyl)pyrrolidine-3-carboxylic acid trifluoroacetic acid salt

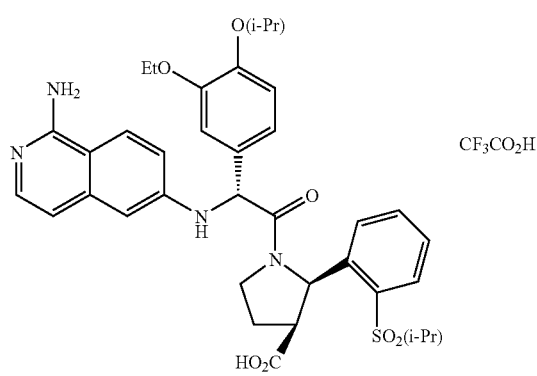

Example 96 was prepared by hydrolysis of the methyl ester Example 59 using a procedure similar to that used in the preparation of Example 12. $^1$H NMR (400 MHz, Methanol-$d_4$) δ ppm 1.06-1.20 (m, 3H) 1.23-1.43 (m, 12H) 2.19-2.47 (m, 2H) 2.92 (d, J=7.09 Hz, 1H) 3.65-3.83 (m, 1H) 3.80-4.07 (m, 3H) 4.06-4.22 (m, 1H) 4.50-4.70 (m, 1H) 5.40 (s, 1H) 6.08 (s, 1H) 6.62-6.81 (m, 2H) 6.95-7.21 (m, 5H) 7.32 (d, J=7.09 Hz, 1H) 7.38-7.48 (m, 1H) 7.47-7.59 (m, 1H) 7.93 (dd, J=7.83, 1.22 Hz, 1H) 8.05 (d, J=9.29 Hz, 1H). LC-MS: 693 (M+H)$^+$.

Example 97

Methyl 3-((R)-1-((R)-2-(1-aminoisoquinolin-6-ylamino)-2-(5-ethoxy-2,4-difluorophenyl)acetyl)pyrrolidin-2-yl)-4-(isopropylsulfonyl)phenylcarbamate trifluoroacetic acid salt

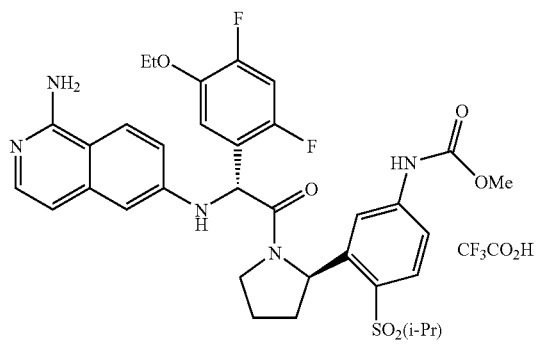

97A: Bis(2,4-difluorophenyl)carbonate

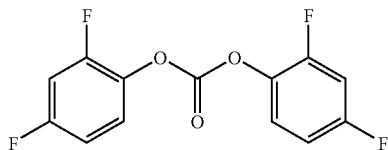

To a solution of 2,4-difluorophenol (3.3 g, 25.4 mmol) in toluene (7.0 mL) was added pyridine (4.5 mL) and phosgene (1.9M in toluene, 6.7 mL) at 0° C. The mixture was stirred overnight at rt before it was quenched by water and extracted with EtOAc. The combined organic extracts were washed with brine, dried over MgSO$_4$ and concentrated to give product 97A as a white solid (3.4 g, 94% yield). $^1$H NMR (400 MHz, CDCl$_3$) δ ppm 6.89-6.95 (m, 2H) 6.95-7.02 (m, 2H) 7.27-7.34 (m, 2H).

97B: Bis(5-bromo-2,4-difluorophenyl)carbonate

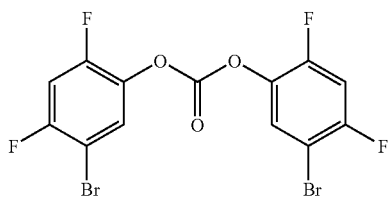

To 97A (4.4 g, 15.38 mmol) in conc. H$_2$SO$_4$ (75 mL) was added bromine (2.3 mL) at rt. The mixture was heated to 50° C. and chlorine was bubbled through for 2 h before it was cooled to rt and poured into ice. The mixture was extracted with EtOAc, washed with brine, dried over MgSO$_4$ and concentrated to give 97B as a off-white solid (6.6 g, 81% yield). $^1$H NMR (400 MHz, CDCl$_3$) δ ppm 7.09 (dd, J=9.67, 7.91 Hz, 2H) 7.55-7.60 (m, 2H).

97C: 5-Bromo-2,4-difluorophenol

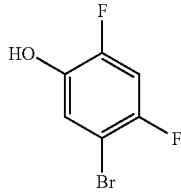

To a suspension of 97B (6.6 g, 15 mmol) in methanol (15 mL) was added NaOH (1.2 g as a 50% aqueous solution) at 0° C. After TLC (10% EtOAc/Hexane) indicated the reaction was complete (1.0 h), the mixture was diluted with diethyl ether, washed with 1N HCl, saturated NaHCO$_3$ and brine. The organic layer was dried over MgSO$_4$ and concentrated to give 97C as an colorless oil (6.3 g, 100% yield). $^1$H NMR (400 MHz, CDCl$_3$) δ ppm 6.94 (dd, J=110.11, 7.91 Hz, 1H) 7.20 (dd, J=8.79, 6.59 Hz, 1H).

97D: 1-Bromo-5-ethoxy-2,4-difluorobenzene

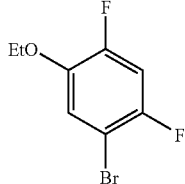

To 97C (2.0 g, 10 mmol) in acetone (30 mL) was added K$_2$CO$_3$ (4.1 g) and iodoethane (2.4 mL). The mixture was stirred at rt overnight. After TLC (10% EtOAc/Hexane) indicated the reaction was complete, the mixture was diluted with diethyl ether, washed with water and brine. The organic layer was dried over MgSO$_4$ and concentrated to give 97D as an colorless oil (1.7 g, 72% yield). $^1$H NMR (400 MHz, CDCl$_3$) δ ppm 1.44 (t, J=7.03 Hz, 3H) 4.07 (q, J=7.03 Hz, 2H) 6.94 (dd, J=10.77, 8.13 Hz, 1H) 7.11 (dd, J=8.35, 6.59 Hz, 1H).

97E: 5-Ethoxy-2,4-difluorophenylboronic acid

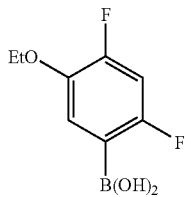

To 97D (670 mg, 2.83 mmol) in THF (10 mL) was added n-BuLi (1.6M in hexane, 2.3 mL) at −78° C. After stirring for 15 min, trimethyl borate (0.634 mL) was introduced. The mixture was stirred from −78° C. to rt for 5 h before it was quenched by 1N HCl. It was extracted with ethyl acetate. The organic extract was washed with saturated Na$_2$S$_2$O$_3$, brine and dried over MgSO$_4$. The crude product was purified by column chromatography to give 97E (400 mg, 70% yield) as a solid.

$^1$H NMR (400 MHz, CDCl$_3$) δ ppm 1.38 (t, J=7.03 Hz, 3H) 3.91-4.25 (m, 2H) 6.72-6.98 (m, 1H) 6.97-7.17 (m, 1H).

97F: 2-(1-Di-tert-butoxycarbonylaminoisoquinolin-6-ylamino)-2-(2,4-di-fluoro-5-ethoxyphenyl)acetic acid

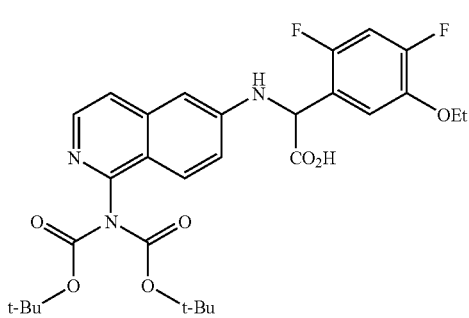

A mixture of 97E (51 mg, 0.15 mmol), 1B (54 mg, 0.15 mmol) and glyoxylic acid monohydrate (17 mg, 0.18 mmol) in acetonitrile (0.7 mL) and DMF (0.07 mL) was heated at 85° C. for 30 min in a Microwave Reactor. The crude product was purified by flash column chromatography ($CH_2Cl_2$: MeOH=100:15) to give 37 mg (43% yield) of 97F as a solid. $^1$H NMR (400 MHz, Methanol-$d_4$) o ppm 1.27 (s, 18H) 1.32 (t, J=6.81 Hz, 3H) 3.96-4.09 (m, 2H) 5.52 (s, 1H) 6.73 (d, J=2.20 Hz, 1H) 7.02-7.10 (m, 1H) 7.21 (dd, J=9.23, 7.03 Hz, 1H) 7.29 (dd, J=9.01, 2.42 Hz, 1H) 7.47 (d, J=6.59 Hz, 1H) 7.66 (d, J=9.23 Hz, 1H) 7.98 (s, 1H) 8.05 (d, J=5.71 Hz, 1H), LC-MS: 574 (M+H)$^+$.

97G: Example 97

Example 97 was prepared according to the general coupling-deprotection using 97F and 44A. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 nun, then 50% B for 2 min) with a flow rate of 20 mL/min. $^1$H NMR (400 MHz, Methanol-$d_4$) δ ppm 1.16 (d, J=6.60 Hz, 3H) 1.25 (t, J=6.97 Hz, 3H) 1.40 (t, J=6.97 Hz, 3H) 1.71 (dd, J=12.72, 6.11 Hz, 1H) 2.09 (dd, J=16.26, 6.97 Hz, 2H) 2.41-2.61 (m, J=7.83 Hz, 1H) 3.51-3.66 (m, 2H) 3.67-3.84 (m, 4H) 3.89-4.02 (m, 1H) 4.06-4.25 (m, J=9.05 Hz, 1H) 5.68 (dd, J=7.83, 5.38 Hz, 1H) 5.80 (s, 1H) 6.69 (dd, J=9.05, 6.85 Hz, 1H) 6.78 (d, J=2.45 Hz, 1H) 6.90 (d, J=7.09 Hz, 1H) 7.06-7.19 (m, 3H) 7.27 (d, J=2.20 Hz, 1H) 7.32 (d, J=7.09 Hz, 1H) 7.74 (d, J=8.56 Hz, 1H) 8.05 (d, J=9.29 Hz, 1H) 9.54 (s, 1H). LC-MS: 682 (M+H)$^+$.

Example 98

Methyl 3-((R)-1-((R)-2-(1-aminoisoquinolin-6-ylamino)-2-(2,4-difluoro-5-methoxyphenyl)acetyl)pyrrolidin-2-yl)-4-(isopropylsulfonyl)phenylcarbamate trifluoroacetic acid salt

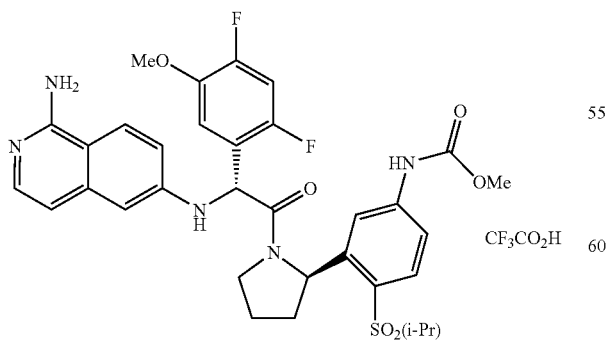

98A: 2,4-Difluoro-5-methoxybenzaldehyde

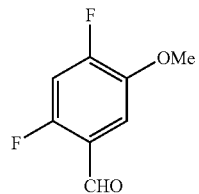

To 2,4-difluoro-1-methoxybenzene (1.14 g, 7.9 mmol) at 0° C. was added titanium tetrachloride (1.73 mL, 15.8 mmol) and dichloro(methoxy)methane (1.40 mL, 15.8 mmol). The mixture was stirred at 0° C. for 10 min. At this point, stirring became difficult. $CH_2Cl_2$ (1.5 mL) was added and the mixture was allowed to warm up to rt over night. After dilution with $CH_2Cl_2$ (50 mL), the mixture was poured into crushed ice. The organic layer was collected and washed with brine, and dried over $Na_2SO_4$. After removal of the solvent, the product 98A precipitated out from hexanes as a white solid (900 mg, 80% yield). $^{19}$F NMR (376 MHz, CDCl$_3$) δ ppm −128.47 (s, 1 F)-118.08 (s, 1 F).

98B: 2-(2,4-Difluoro-5-methoxyphenyl)-2-hydroxyacetonitrile

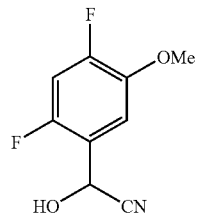

To 98A (506 mg, 2.94 mmol) in ethyl acetate (10 mL) was added a solution of KCN (574 mg, 8.82 mmol) and NaHSO$_3$ (917 mg, 8.82 mmol) dissolved in $H_2O$ (10 mL). The reaction was stirred at rt for 48 h. It was extracted with ethyl acetate (2×50 mL). The combined organic extracts were dried and concentrated to give 98B as an oil. It was used for next step without purification.

98C: Methyl 2-(2,4-difluoro-5-methoxyphenyl)-2-hydroxyacetate

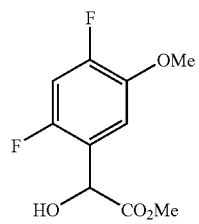

To 98B (427 mg, 2.1 mmol) in anhydrous diethyl ether (10 mL) at 0° C. was added MeOH (0.87 mL, 10 eq.) and 4.0 N HCl in dioxane (4.2 mL, 16.8 mmol). The mixture was stirred at 4° C. for 24 h. Solvent was removed to give methyl 2-(2, 4-difluoro-5-methoxyphenyl)-2-hydroxyacetimidate HCl salt. To this salt in CH$_2$Cl$_2$ (8.0 mL) was added H$_2$O (8.0 mL). The mixture was stirred at rt for 30 min, then extracted with CH$_2$Cl$_2$ (2×50 mL). The combined organic extracts were dried and concentrated to give product 98C (493 mg, 99% yield) as a white solid. $^1$H NMR (400 MHz, CDCl$_3$) δ ppm 3.41 (d, J=4.83 Hz, 1H) 3.72 (s, 3H) 3.80 (s, 3H) 5.32 (d, J=4.83 Hz, 1H) 6.78-6.84 (m, 1H) 6.90 (dd, J=9.01, 6.81 Hz, 1H).

98D: Methyl 2-(1-di-tert-butoxycarbonylaminoisoquinolin-6-ylamino)-2-(2,4-di-fluoro-5-methoxyphenyl)acetic ester

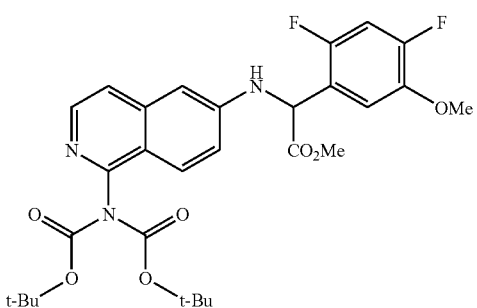

To 98C (188 mg, 0.81 mmol) in CH$_2$Cl$_2$ (2.0 mL) at 0° C. was added trifluoromethanesulfonic anhydride (0.15 mL, 0.9 mmol) and 2,6-lutidine (0.14 mL, 1.2 mmol). The mixture was stirred for 15 min before 1B (203 mg, 0.57 mmol) was added. The reaction was left stirring from 0° C. to rt for 3.0 h. It was diluted with ethyl acetate, and washed with 0.5 N HCl (3×20 mL). The organic extract was dried and concentrated. A column chromatography purification (ethyl acetate/hexanes=1/2) gave product 98D (134 mg, 40% yield). $^1$H NMR (400 MHz, CDCl$_3$) δ ppm 1.26 (s, 18H) 3.75 (s, 3H) 3.78 (s, 3H) 5.64 (s, 1H) 6.76 (d, J=2.20 Hz, 1H) 7.01-7.08 (m, 1H) 7.23 (dd, J=9.23, 7.03 Hz, 1H) 7.30 (dd, J=9.23, 2.20 Hz, 1H) 7.47 (d, J=5.71 Hz, 1H) 7.68 (d, J=9.23 Hz, 1H) 8.06 (d, J=6.15 Hz, 1H). $^{19}$F NMR (376 MHz, CDCl$_3$) δ ppm −131.50 (s, 1 F)-126.14 (s, 1 F).

98E: 2-(1-Di-tert-butoxycarbonylaminoisoquinolin-6-ylamino)-2-(2,4-di-fluoro-5-methoxyphenyl)acetic acid

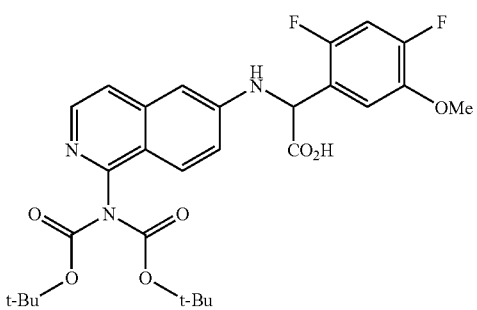

98D (175 mg, 0.3 mmol) was hydrolyzed with NaOH (1.0 N, 0.44 mL, 0.44 mmol) in THF (1.0 mL) and MeOH (2.0 mL) at rt for 3.0 h. After acidification with 5% KHSO$_4$, it was extracted with ethyl acetate (2×30 mL). The organic extract was dried and concentrated to give a solid product 98E. LC-MS: 560 (M+H)$^+$.

98F: Example 98

Example 98 was prepared according to the general coupling-deprotection using 98E and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.18 (d, J=6.60 Hz, 3H) 1.42 (d, J=6.85 Hz, 3H) 1.72 (dd, J=13.08, 5.75 Hz, 1H) 1.93-2.23 (m, 2H) 2.45-2.61 (m, 1H) 3.53 (s, 3H) 3.55-3.63 (m, 1H) 3.67-3.76 (m, 3H) 3.86-4.05 (m, 1H) 4.08-4.26 (m, 1H) 5.69 (dd, J=7.95, 5.50 Hz, 1H) 5.82 (s, 1H) 6.72 (dd, J=9.05, 6.85 Hz, 1H) 6.79 (d, J=2.45 Hz, 1H) 6.91 (d, J=6.85 Hz, 1H) 7.08-7.20 (m, 3H) 7.24 (d, J=1.96 Hz, 1H) 7.33 (d, J=7.09 Hz, 1H) 7.75 (d, J=8.80 Hz, 1H) 8.06 (d, J=9.29 Hz, 1H) 9.53 (s, 1H). LC-MS: 668 (M+H)$^+$.

Example 99

(2R,3S)-1-((R)-2-(1-aminoisoquinolin-6-ylamino)-2-(5-ethoxy-2-fluorophenyl)acetyl)-2-(2-(isopropylsulfonyl)-5-(methoxycarbonyl)phenyl)-pyrrolidine-3-carboxylic acid trifluoroacetic acid salt

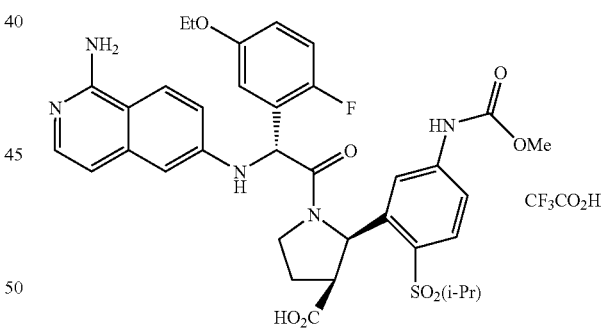

Example 99 was prepared by hydrolysis of the methyl ester Example 61 using a procedure similar to that used in the preparation of Example 12. $^1$H NMR (400 MHz, Methanol-d$_4$) δ ppm 1.10-1.19 (m, 3H) 1.20-1.31 (m, 3H) 1.31-1.43 (m, 3H) 2.23-2.38 (m, 1H) 2.37-2.55 (m, 1H) 2.92 (d, J=8.07 Hz, 1H) 3.59-3.92 (m, 7H) 4.04-4.25 (m, J=7.09 Hz, 1H) 5.71 (s, 1H) 6.05 (s, 1H) 6.67 (dd, J=5.75, 3.06 Hz, 1H) 6.73 (d, J=2.20 Hz, 1H) 6.86-7.01 (m, 1H) 7.05 (d, J=7.09 Hz, 1H) 7.09-7.23 (m, 2H) 7.24-7.38 (m, 3H) 7.79 (d, J=8.56 Hz, 1H) 8.00-8.14 (m, 1H) 9.51 (s, 1H). LC-MS: 708 (M+H)$^+$.

Example 100

Methyl 3-((S)-1-((R)-2-(1-aminoisoquinolin-6-ylamino)-2-(3-ethoxy-4-isopropoxyphenyl)acetyl)pyrrolidin-2-yl)-4-(ethylsulfonyl)phenylcarbamate trifluoroacetic acid salt

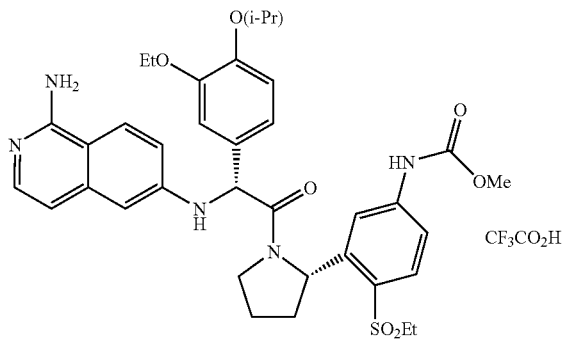

100A: (2-Bromo-4-nitrophenyl)(ethyl)sulfane

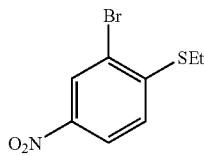

To 3-bromo-4-fluoronitrobenzene (7.05 g, 32.0 mmol) and ethanethiol (2.6 mL, 35.2 mmol) in DMF (20 mL) was added potassium carbonate (4.87 g, 35.2 mmol). The reaction mixture was heated to 60° C. overnight. After cooling, the mixture was filtered over celite and washed with ethyl acetate. The combined filtrate and washings were concentrated. The residue was redissolved in ethyl acetate and washed with water (3×) and then dried over sodium sulfate. The filtrate was concentrated and purified by flash column chromatography to give 100A (8.09 g, 96% yield) as a solid. $^1$H NMR (400 MHz, Methanol-$d_4$) δ ppm 1.41 (t, J=7.34 Hz, 3H) 3.11 (q, J=7.42 Hz, 2H) 7.45 (d, J=9.05 Hz, 8H) 8.17 (dd, J=8.80, 2.45 Hz, 7H) 8.37 (d, J=2.45 Hz, 7H).

100B: (2-Bromo-1-(ethylsulfonyl)-4-nitrobenzene

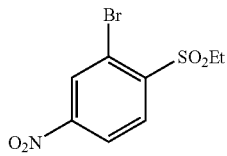

To 100A (6.4 g, 24 mmol) in methanol (50 mL) was added oxone (45 g, 73 mmol) in water (90 mL). After stirring at rt overnight, the reaction was quenched with 5% NaHSO$_3$ and then neutralized with 1 M NaOH. The organic solvent was evaporated and the aqueous layer was extracted with dichloromethane (3×). The combined extracts were washed with brine and dried over sodium sulfate. The solvent was removed and the crude residue was purified by flash column chromatography to give 6.0 g of product 100B (83% yield). $^1$H NMR (400 MHz, CDCl$_3$) δ ppm 1.26 (t, J=7.46 Hz, 3H) 3.49 (q, J=7.58 Hz, 2H) 8.34 (d, J=1.22 Hz, 2H) 8.48-8.70 (m, 1H).

100C: tert-Butyl 2-(2-(ethylsulfonyl)-5-nitrophenyl)-1H-pyrrole-1-carboxylate

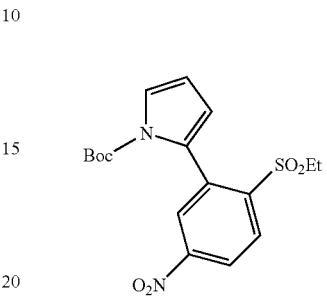

To 100B (3.48 g, 11.8 mmol), 3A (3.0 g, 14.2 mmol) and sodium carbonate (23.7 mL, 2M, 47.4 mmol) in 1,2 dimethoxyethane (100 mL, flushed and degassed (3×) with nitrogen) was added Pd(PPh$_3$)$_4$ (2.74 g, 2.37 mmol). The reaction was heated to 97° C. for 3 h. The catalyst was filtered over celite and washed with ethyl acetate. The organic layer was washed with water, brine and then dried over sodium sulfate. The solvent was removed and the crude residue was purified by flash column chromatography to give 4.11 g of product 10° C. (91% yield). $^1$H NMR (400 MHz, Methanol-$d_4$) δ ppm 1.09 (t, J=7.46 Hz, 3H) 1.25 (s, 9H) 2.87-3.04 (m, 2H) 6.24-6.44 (m, 2H) 7.46 (dd, J=3.30, 1.83 Hz, 1H) 8.24 (d, J=2.20 Hz, 1H) 8.31 (d, J=8.56 Hz, 1H) 8.45 (dd, J=8.80, 2.45 Hz, 1H).

100D: tert-Butyl 2-(5-amino-2-(ethylsulfonyl)phenyl)pyrrolidine-1-carboxylate

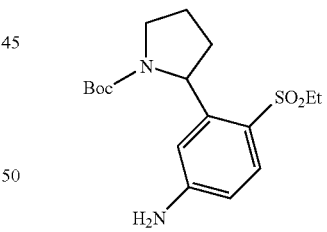

To platinum oxide (1.0 g) was added 100C in ethanol (70 mL) and hydrogen chloride (0.6 ml) under nitrogen. The reaction was placed under hydrogen (40 psi). After 3 h the reaction was half done, the catalyst was filtered and the solvent was removed. Fresh platinum oxide was added (1.0 g) and the reaction was stirred under hydrogen (40 psi) for 2 h. The catalyst was filtered over celite and washed with ethanol. The filtrate was neutralized with diethylamine. The solvent was evaporated and the crude residue was redissolved in dichloromethane. The organic layer was washed with water, brine and dried over sodium sulfate. The solvent was removed and the crude product was dried under vacuum to give a white solid 100D (2.0 g).

100E: (R)-tert-Butyl 2-(5-amino-2-(ethylsulfonyl)phenyl)pyrrolidine-1-carboxylate and 100F: (S)-tert-Butyl 2-(5-amino-2-(ethylsulfonyl)phenyl)pyrrolidine-1-carboxylate

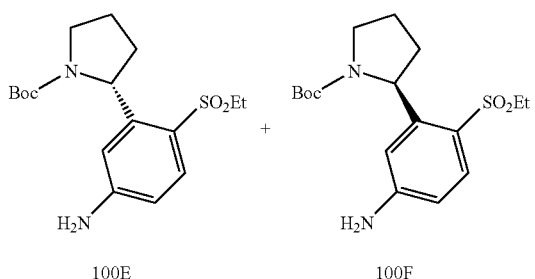

100E   100F

The enantiomers of 100D were separated using a preparative HPLC equipped with a Chiralpak®AD column (5 cm×50 cm, 20μ). The separation was performed using an isocratic method of 20% isopropanol/heptane with 0.1% diethylamine for 100 min with a flow rate of 50 mL/min. The first peak to elute is the enantiomer 100E. $^1$H NMR (400 MHz, Methanol-d$_4$) (ppm 1.17-1.32 (m, 9H) 1.38-1.50 (m, 3H) 1.67-2.05 (m, 3H) 2.32-2.56 (m, 1H) 3.07-3.24 (m, 1H) 3.30-3.36 (m, 1H) 3.51-3.79 (m, 2H) 5.25-5.42 (m, J=8.68, 4.03 Hz, 1H) 6.46-6.67 (m, 2H) 7.48-7.67 (m, J=7.34 Hz, 1H). The second peak corresponds to isomer 100F: $^1$H NMR (400 MHz, Methanol-d$_4$) (ppm 0.97-1.50 (m, 12H) 1.49-1.99 (m, 2H) 2.19-2.45 (m, 1H) 2.92-3.35 (m, 3H) 3.39-3.62 (m, 2H) 5.21 (d, J=30.08 Hz, 1H) 6.06 (d, J=12.47 Hz, 1H) 6.49 (d, J=7.09 Hz, 1H) 7.33-7.57 (m, 1H).

100G: (R)-Methyl(4-(ethylsulfonyl)-3-(pyrrolidin-2-yl)phenylcarbamate hydrochloride

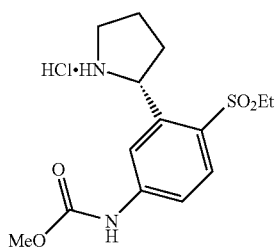

To 100E (0.28 g, 0.78 mmol) in pyridine (2 mL) at 0° C. was added methyl chloroformate (0.12 mL, 1.55 mmoL). After stirring for 2 h at rt, the reaction was acidified with 1M HCl to pH 3-4. The product was extracted with ethyl acetate and was washed with brine and dried over sodium sulfate. After evaporation of solvent, the crude residue product was redissolved in ethyl acetate (1.5 mL), and hydrogen chloride (2 mL, 4M in dioxane) was added. The reaction was stirred for 3 h at rt. The solvent was removed and placed on the lyophilizer to give 0.19 g of 100G as a white solid. $^1$H NMR (400 MHz, Methanol-d$_4$) δ ppm 1.22-1.34 (m, 3H) 2.12-2.63 (m, 4H) 3.33-3.55 (m, 4H) 3.73-3.85 (m, 3H) 5.42 (t, J=7.58 Hz, 1H) 7.64 (dd, J=8.68, 2.08 Hz, 1H) 7.99 (d, J=8.80 Hz, 1H) 8.10 (d, J=2.20 Hz, 1H).

100H: (R)-Ethyl(4-(ethylsulfonyl)-3-(pyrrolidin-2-yl)phenylcarbamate hydrochloride

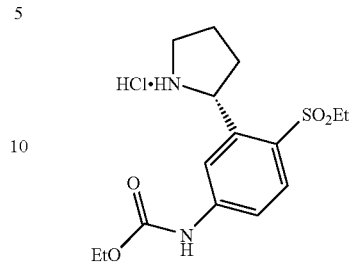

To 100E (0.28 g, 0.78 mmol) in pyridine (1 mL) at 0° C. was added ethyl chloroformate (27 μL, 0.28 mmoL). After 2.0 h stirring at rt the reaction was acidified with 1 M HCl to pH 3-4. The product was extracted with ethyl acetate and was washed with brine and dried over sodium sulfate. After evaporation of the solvent, the crude residue was redissolved in ethyl acetate (1.0 mL) and hydrogen chloride (1.5 mL, 4M in dioxane) was added. The reaction was stirred for 2 h at rt. The solvent was removed and placed on the lyophilizer to give 0.05 g of 100H as a white solid. $^1$H NMR (400 MHz, Methanol-d$_4$) δ ppm 1.17-1.37 (m, 6H) 2.10-2.68 (m, 4H) 3.34-3.52 (m, 4H) 4.12-4.36 (m, 2H) 5.41 (t, J=7.58 Hz, 1H) 7.63 (dd, J=8.80, 2.20 Hz, 1H) 7.97 (d, J=8.80 Hz, 1H) 8.08 (d, J=2.20 Hz, 1H).

100I: (S)-Methyl(4-(ethylsulfonyl)-3-(pyrrolidin-2-yl)phenylcarbamate hydrochloride

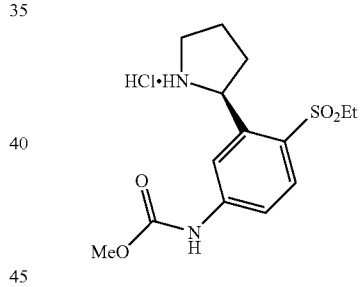

To 100F (0.1 g, 0.28 mmol) in pyridine (1.5 mL) at 0° C. was added methyl chloroformate (59 μL, 0.56 mmoL). After stirring for 2 h at rt, the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 1.5 h at rt. The solvent was removed and placed on the lyophilizer to give 0.09 g of 100I as a white solid. $^1$H NMR (400 MHz, Methanol-d$_4$) δ ppm 1.27 (t, J=7.34 Hz, 3H) 2.11-2.66 (m, 4H) 3.38-3.52 (m, 4H) 3.80 (s, 3H) 5.42 (t, J=7.58 Hz, 1H) 7.66 (dd, J=8.68, 2.08 Hz, 1H) 7.99 (d, J=8.80 Hz, 1H) 8.09 (d, J=1.96 Hz, 1H).

100J: Example 100

Example 100 was prepared according to the general coupling-deprotection using 1C and 100I. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.15-1.47 (m, 12H) 1.63-1.79 (m, 1H) 1.96-2.22 (m, 2H) 2.41-2.59 (m, 1H) 3.36-3.49 (m, 1H) 3.51-3.66 (m, 1H) 3.67-3.78 (m, 4H) 3.78-3.98 (m, 2H) 4.06-4.23 (m, 1H) 4.45-4.62 (m, 1H) 5.46 (s, 1H) 5.71 (dd, J=8.07, 5.14 Hz, 1H) 6.72-6.79 (m, 1H) 6.82-6.97 (m, 3H) 6.97-7.06 (m, 1H) 7.06-7.17 (m, 1H) 7.15-7.27 (m, 2H) 7.30 (t, J=6.48 Hz, 1H) 7.78 (t, J=8.56 Hz, 1H) 8.03 (d, J=9.29 Hz, 1H) 9.37 (s, 1H). LC-MS: 690 (M+H)$^+$.

Example 101

Diastereomer of Example 100

Methyl 3-((S)-1-((S)-2-(1-aminoisoquinolin-6-ylamino)-2-(3-ethoxy-4-isopropoxyphenyl)acetyl)pyrrolidin-2-yl)-4-(ethylsulfonyl)phenylcarbamate trifluoroacetic acid salt

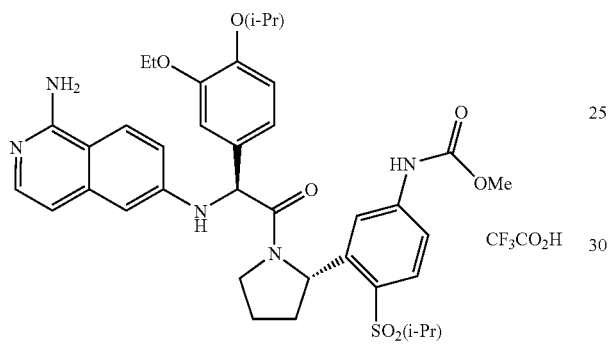

Example 101 was obtained as a diastereomer of Example 100 during its HPLC purification. $^1$H NMR (400 MHz, Methanol-$d_4$) δ ppm 1.15-1.25 (m, 3H) 1.25-1.34 (m, 6H) 1.34-1.44 (m, 3H) 1.64-1.95 (m, 2H) 2.11-2.41 (m, 2H) 3.35-3.64 (m, 2H) 3.76-3.94 (m, 4H) 4.07 (q, J=7.09 Hz, 2H) 4.12-4.24 (m, 1H) 4.45-4.62 (m, 1H) 5.51 (s, 1H) 5.67 (dd, J=8.44, 3.79 Hz, 1H) 6.46-6.65 (m, 1H) 6.79-6.86 (m, 1H) 6.96-7.15 (m, 4H) 7.20-7.43 (m, 2H) 7.73-7.87 (m, 2H) 7.90-8.05 (m, 1H). LC-MS: 690 (M+H)$^+$.

Example 102

Methyl 3-((R)-1-((R)-2-(1-aminoisoquinolin-6-ylamino)-2-(3-ethoxy-4-isopropoxyphenyl)acetyl)pyrrolidin-2-yl)-4-(ethylsulfonyl)phenylcarbamate trifluoroacetic acid salt

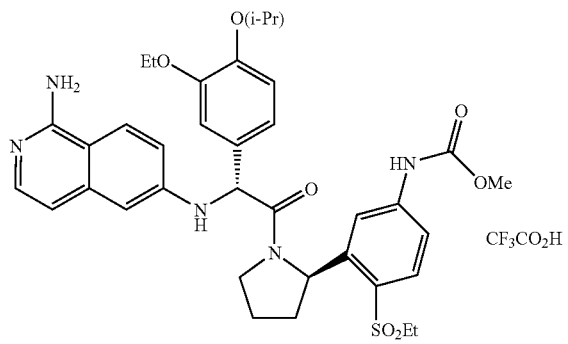

Example 102 was prepared according to the general coupling-deprotection using 1C and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.07-1.37 (m, 12H) 1.54-1.74 (m, 1H) 1.87-2.14 (m, 2H) 2.31-2.51 (m, 1H) 3.27-3.56 (m, 2H) 3.56-3.70 (m, 4H) 3.69-3.88 (m, 2H) 4.01-4.13 (m, 1H) 4.37-4.54 (m, 1H) 5.38 (s, 1H) 5.62 (dd, J=8.19, 5.01 Hz, 1H) 6.67 (d, J=2.45 Hz, 1H) 6.73-6.79 (m, 1H) 6.83 (dd, J=12.35, 7.70 Hz, 2H) 6.87-6.96 (m, 1H) 6.97-7.06 (m, 1H) 7.06-7.12 (m, 1H) 7.12-7.18 (m, 1H) 7.18-7.27 (m, 1H) 7.60-7.76 (m, 1H) 7.94 (d, J=9.29 Hz, 1H) 9.29 (s, 1H). LC-MS: 690 (M+H)$^+$.

Example 103

Diastereomer of Example 102

Methyl 3-((R)-1-((S)-2-(1-aminoisoquinolin-6-ylamino)-2-(3-ethoxy-4-isopropoxyphenyl)acetyl)pyrrolidin-2-yl)-4-(ethylsulfonyl)phenylcarbamate trifluoroacetic acid salt

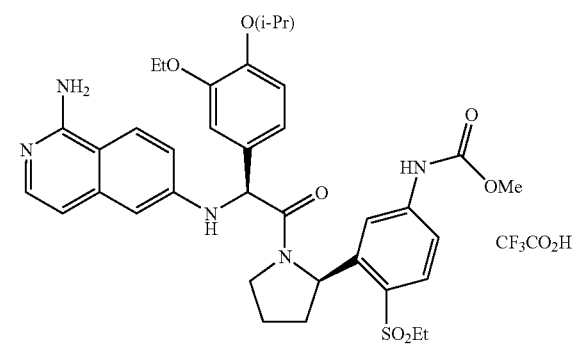

Example 103 was obtained as a diastereomer of Example 102 during its HPLC purification. $^1$H NMR (400 MHz, Methanol-$d_4$) δ ppm 1.17-1.44 (m, 12 H) 1.69-1.94 (m, 2H) 2.08-2.24 (m, 1H) 2.32 (d, J=6.85 Hz, 1H) 3.36-3.62 (m, 3H) 3.67-3.84 (m, 3H) 3.83-3.93 (m, 1H) 4.00-4.23 (m, 2H) 4.49-4.62 (m, 1H) 5.45-5.55 (m, 1H) 5.67 (dd, J=8.56, 4.16 Hz, 1H) 6.50 (s, 1H) 6.59-6.68 (m, 1H) 6.77-6.94 (m, 1H) 6.96-7.15 (m, 3H) 7.21-7.44 (m, 2H) 7.74-7.83 (m, 1H) 7.83-7.90 (m, 1H) 7.93-8.05 (m, 1H). LC-MS: 690 (M+H)$^+$.

Example 104

Methyl 3-((R)-1-((R)-2-(1-aminoisoquinolin-6-ylamino)-2-(5-ethoxy-2-fluorophenyl)acetyl)pyrrolidin-2-yl)-4-(ethylsulfonyl)phenylcarbamate trifluoroacetic acid salt

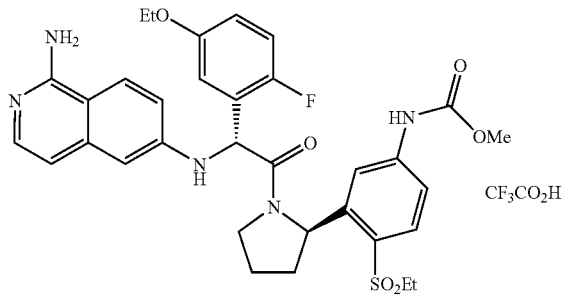

Example 104 was prepared according to the general coupling-deprotection using 30A and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.13-1.35 (m, 6H) 1.58-1.84 (m, 1H) 1.94-2.20 (m, 2H) 2.40-2.58 (m, 1H) 3.39-3.50 (m, 1H) 3.54-3.71 (m, 3H) 3.70-3.87 (m, 4H) 4.07-4.23 (m, 1H) 5.72 (dd, J=8.19, 5.26 Hz, 1H) 5.82 (s, 1H) 6.57 (dd, J=5.62, 3.18 Hz, 1H) 6.79 (d, J=2.45 Hz, 1H) 6.83-6.95 (m, 2H) 7.02-7.22 (m, 3H) 7.24-7.38 (m, 2H) 7.78 (d, J=8.80 Hz, 1H) 8.05 (d, J=9.29 Hz, 1H) 9.38 (s, 1H). LC-MS: 650 (M+H)$^+$.

Example 105

Diastereomer of Example 104

Methyl 3-((R)-1-((S)-2-(1-aminoisoquinolin-6-ylamino)-2-(5-ethoxy-2-fluorophenyl)acetyl)pyrrolidin-2-yl)-4-(ethylsulfonyl)phenylcarbamate trifluoroacetic acid salt

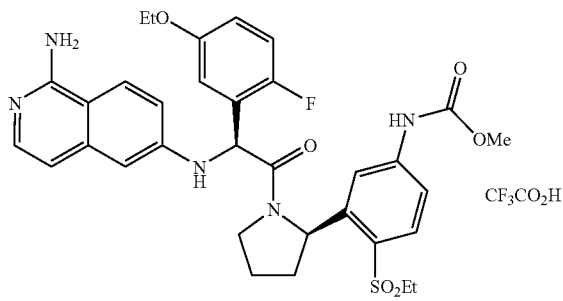

Example 105 was obtained as a diastereomer of Example 104 during its HPLC purification. $^1$H NMR (400 MHz, Methanol-$d_4$) δ ppm 1.12-1.41 (m, 6H) 1.69-1.82 (m, 1H) 1.85-2.04 (m, 1H) 2.10-2.27 (m, 1H) 2.31-2.44 (m, 1H) 3.33-3.58 (m, 3H) 3.64-3.75 (m, 1H) 3.75-3.83 (m, 3H) 3.91-4.04 (m, 2H) 4.09-4.25 (m, 1H) 5.58-5.74 (m, 1H) 5.77-5.89 (m, 1H) 6.38-7.01 (m, 4H) 7.04-7.21 (m, 2H) 7.22-7.36 (m, 1H) 7.41 (dd, J=8.80, 2.20 Hz, 1H) 7.71-7.86 (m, 2H) 7.92-8.08 (m, 1H) 9.71 (s, 1H). LC-MS: 650 (M+H)$^+$.

Example 106

Methyl 3-((R)-1-((R)-2-(1-aminoisoquinolin-6-ylamino)-2-(2,4-difluoro-5-methoxyphenyl)acetyl)pyrrolidin-2-yl)-4-(ethylsulfonyl)phenylcarbamate trifluoroacetic acid salt

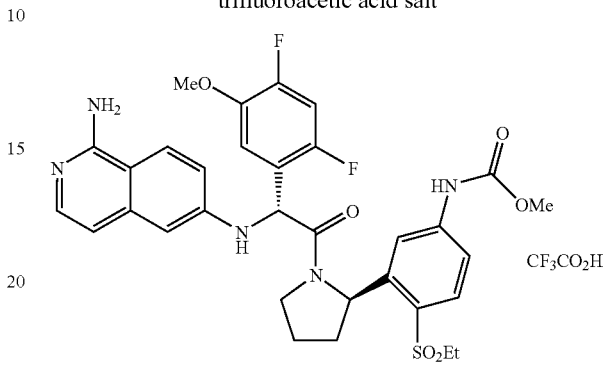

Example 106 was prepared according to the general coupling-deprotection using 98E and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.27 (t, J=7.34 Hz, 3H) 1.72 (dd, J=12.96, 5.87 Hz, 1H) 2.00-2.20 (m, 2H) 2.46-2.58 (m, 1H) 3.39-3.51 (m, 1H) 3.52-3.66 (m, 5H) 3.71 (s, 3H) 4.05-4.25 (m, 1H) 5.71 (dd, J=8.07, 5.62 Hz, 1H) 5.82 (s, 1H) 6.70 (dd, J=9.29, 6.85 Hz, 1H) 6.79 (d, J=2.20 Hz, 1H) 6.90 (d, J=7.09 Hz, 1H) 7.09-7.19 (m, 3H) 7.25 (d, J=1.96 Hz, 1H) 7.33 (d, J=7.09 Hz, 1H) 7.78 (d, J=8.56 Hz, 1H) 8.06 (d, J=9.29 Hz, 1H) 9.54 (s, 1H). LC-MS: 654 (M+H)$^+$.

Example 107

Diastereomer of Example 106

Methyl 3-((R)-1-((S)-2-(1-aminoisoquinolin-6-ylamino)-2-(2,4-difluoro-5-methoxyphenyl)acetyl)pyrrolidin-2-yl)-4-(ethylsulfonyl)phenylcarbamate trifluoroacetic acid salt

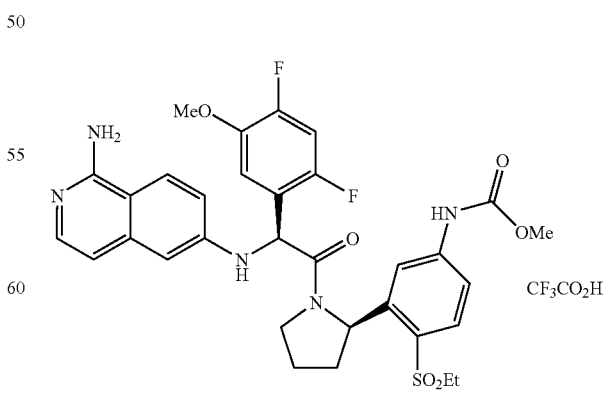

Example 107 was obtained as a diastereomer of Example 106 during its HPLC purification. $^1$H NMR (400 MHz, Methanol-$d_4$) δ ppm 1.08-1.42 (m, 3H) 1.76 (t, J=18.46 Hz, 1H) 1.84-2.28 (m, 2H) 2.29-2.47 (m, 1H) 3.36-3.65 (m, 3H) 3.65-3.91 (m, 6H) 4.15 (d, J=5.38 Hz, 1H) 5.55-5.96 (m, 2H) 6.39-7.00 (m, 3H) 7.01-7.24 (m, 3H) 7.24-7.45 (m, 2H) 7.81 (d, J=8.56 Hz, 1H) 8.06 (d, J=7.58 Hz, 1H). LC-MS: 654 $(M+H)^+$.

Example 108

Ethyl 3-((R)-1-((R)-2-(1-aminoisoquinolin-6-ylamino)-2-(5-ethoxy-2-fluorophenyl)acetyl)pyrrolidin-2-yl)-4-(ethylsulfonyl)phenylcarbamate trifluoroacetic acid salt

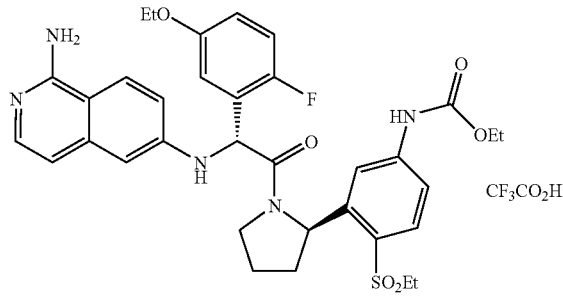

Example 108 was prepared according to the general coupling-deprotection using 30A and 100H. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.72 (dd, J=12.96, 5.62 Hz, 1H) 1.92-2.29 (m, 2H) 2.51 (dd, J=12.96, 7.83 Hz, 1H) 3.38-3.54 (m, 1H) 3.54-3.70 (m, 3H) 3.73-3.86 (m, 1H) 4.15 (q, J=7.09 Hz, 3H) 5.71 (dd, J=8.07, 5.38 Hz, 1H) 5.82 (s, 1H) 6.57 (dd, J=5.62, 3.18 Hz, 1H) 6.79 (d, J=2.45 Hz, 1H) 6.84-6.96 (m, 2H) 7.02-7.21 (m, 3H) 7.23-7.39 (m, 2H) 7.77 (d, J=8.80 Hz, 1H) 8.05 (d, J=9.05 Hz, 1H) 9.33 (s, 1H). LC-MS: 664 $(M+H)^+$.

Example 109

Diastereomer of Example 108

Ethyl 3-((R)-1-((S)-2-(1-aminoisoquinolin-6-ylamino)-2-(5-ethoxy-2-fluorophenyl)acetyl)pyrrolidin-2-yl)-4-(ethylsulfonyl)phenylcarbamate trifluoroacetic acid salt

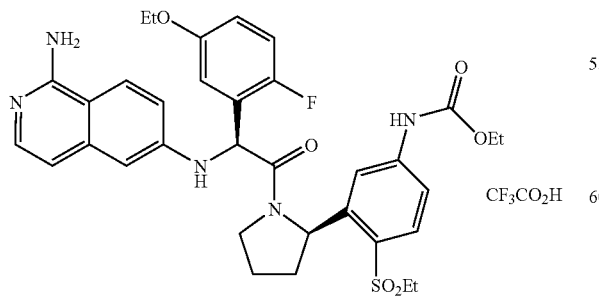

Example 109 was obtained as a diastereomer of Example 108 during its HPLC purification. $^1$H NMR (400 MHz, Methanol-$d_4$) δ ppm 1.16-1.44 (m, 9H) 1.69-1.87 (m, 1H) 1.84-2.07 (m, 1H) 2.11-2.28 (m, 1H) 2.29-2.47 (m, 1H) 3.35-3.69 (m, 3H) 3.79-4.36 (m, 5H) 5.60-5.76 (m, 1H) 5.78-5.89 (m, 1H) 6.48-7.05 (m, 4H) 7.07-7.25 (m, 2H) 7.23-7.46 (m, 2H) 7.67-7.90 (m, 2H) 7.96-8.11 (m, 1H). LC-MS: 664 $(M+H)^+$.

Example 110

Methyl 3-((R)-1-((R)-2-(1-aminoisoquinolin-6-ylamino)-2-(2-fluoro-4,5-dimethoxyphenyl)acetyl)pyrrolidin-2-yl)-4-(ethylsulfonyl)phenylcarbamate trifluoroacetic acid salt

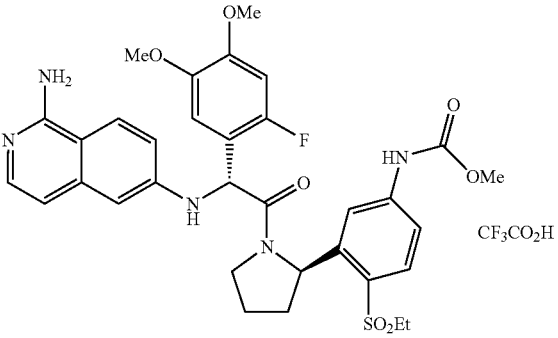

Example 110 was prepared according to the general coupling-deprotection using 86C and 100G. The diastereomers were separated by prep HPLC equipped with a C18 Luna column (21×100 mm, 5μ). The separation was performed using a linear gradient (mobile phase A: 10% MeOH-90% water-0.1% TFA, mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.22-1.32 (m, 3H) 1.72 (dd, J=12.72, 5.87 Hz, 1H) 1.99-2.19 (m, 2H) 2.51 (dd, J=13.08, 7.95 Hz, 1H) 3.42-3.52 (m, 4H) 3.56-3.67 (m, 2H) 3.68-3.74 (m, 3H) 3.81-3.87 (m, 3H) 4.07-4.21 (m, 1H) 5.66-5.75 (m, 2H) 6.53 (d, J=6.85 Hz, 1H) 6.66 (d, J=2.45 Hz, 1H) 6.74 (d, J=6.36 Hz, 1H) 6.88 (d, J=11.49 Hz, 1H) 6.97 (dd, J=59.05, 2.45 Hz, 1H) 7.13-7.25 (m, 2H) 7.49 (d, J=6.11 Hz, 1H) 7.80 (dd, J=16.87, 8.80 Hz, 2H). LC-MS: 666 $(M+H)^+$.

Example 111 trifluoroacetic acid salt

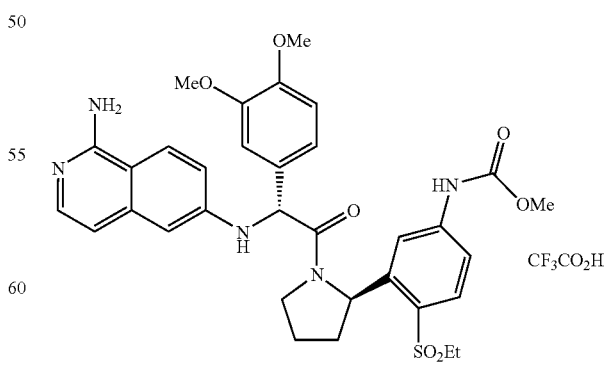

Example 111 was prepared according to the general coupling-deprotection using 8A and 100G. The diastereomers were separated by prep HPLC equipped with a C18 Luna column (21×100 mm, 5μ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.18-1.35 (m, 3H) 1.63-1.79 (m, 1H) 1.96-2.22 (m, 2H) 2.37-2.59 (m, 1H) 3.37-3.64 (m, 2H) 3.63-3.77 (m, 7H) 3.78-3.90 (m, 3H) 4.18 (dd, J=6.72, 3.55 Hz, 1H) 5.48 (s, 1H) 5.62-5.78 (m, 1H) 6.77 (d, J=2.20 Hz, 1H) 6.84-6.95 (m, 3H) 6.98-7.08 (m, 2H) 7.12 (dd, J=9.29, 2.45 Hz, 1H) 7.17-7.24 (m, 1H) 7.31 (d, J=7.09 Hz, 1H) 7.70-7.80 (m, 1H) 8.03 (d, J=9.29 Hz, 1H) 9.34 (s, 1H). LC-MS: 648 (M+H)$^+$.

Example 112

Diastereomer of Example 111

Methyl 3-((R)-1-((S)-2-(1-aminoisoquinolin-6-ylamino)-2-(3,4-dimethoxyphenyl)acetyl)pyrrolidin-2-yl)-4-(ethylsulfonyl)phenylcarbamate trifluoroacetic acid salt

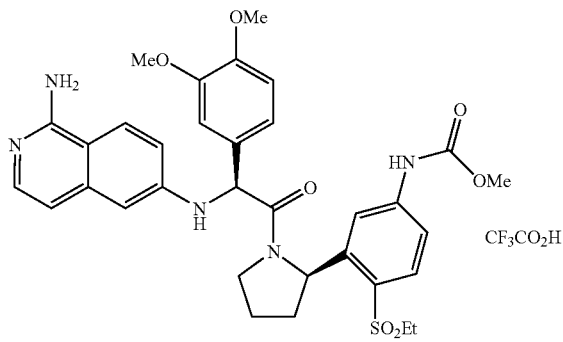

Example 112 was obtained as a diastereomer of Example 111 during its HPLC purification. $^1$H NMR (400 MHz, Methanol-$d_4$) δ ppm 1.17-1.37 (m, 3H) 1.65-2.39 (m, 4H) 3.36-3.61 (m, 2H) 3.65-3.76 (m, 3H) 3.77-3.91 (m, 7H) 4.19 (d, J=7.34 Hz, 1H) 5.44-5.59 (m, 1H) 5.59-5.81 (m, 1H) 6.35-6.74 (m, 2H) 6.77-6.97 (m, 2H) 6.97-7.09 (m, 1H) 7.06-7.19 (m, 2H) 7.21-7.47 (m, 2H) 7.73-7.90 (m, 1H) 7.91-8.12 (m, 1H). LC-MS: 648 (M+H)$^+$.

Example 113

(R)-2-(1-Aminoisoquinolin-6-ylamino)-2-(3-ethoxy-4-isopropoxyphenyl)-1-((2R,4R)-4-hydroxy-2-phenylpyrrolidin-1-yl)ethanone trifluoroacetic acid salt

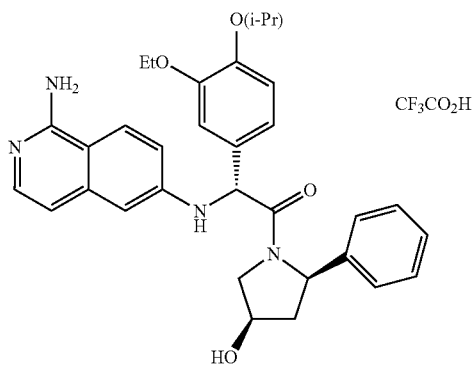

113A: 2-(1-Aminoisoquinolin-6-ylamino)-2-(3-ethoxy-4-isopropoxyphenyl)acetic acid hydrochloride

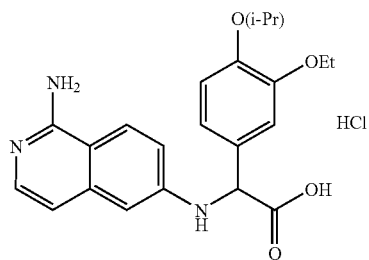

1C (1.04 g, 1.75 mmol) was dissolved in ethyl acetate (26 mL) and was treated with a 4N HCl solution in 1,4-dioxane (26 mL, 105 mmol). After stirring at rt overnight, the reaction was concentrated, diluted with diethyl ether and filtered to provide 113A (747 mg) as a yellow solid. $^1$H NMR (400 MHz, DMSO-$d_6$) δ ppm 1.22 (d, J=7.03 Hz, 6H), 1.30 (t, J=7.03 Hz, 3H), 4.00 (q, J=7.03 Hz, 2H), 4.37-4.53 (m, 2H), 5.19-5.33 (m, 1H), 6.75 (s, 1H), 6.81 (d, J=7.03 Hz, 1H), 6.90-7.04 (m, 2H), 7.13 (d, J=2.20 Hz, 1H), 7.24 (d, J=8.79 Hz, 1H), 7.43 (dd, 1H), 7.43 (dd, J=7.03, 5.71 Hz, 1H), 7.63 (s, 1H), 8.20 (d, J=9.23 Hz, 1H), 8.50 (s, 2H), 12.52 (d, J=5.27 Hz, 1H). LC-MS: 396.30 (M+H)$^+$.

113B: 2-(1-Aminoisoquinolin-ylamino)-1-((2R,4R)-4-(tert-butyldimethylsilyloxy)-2-phenylpyrrolidin-1-yl)-2-(3-ethoxy-4-isopropoxyphenyl)ethanone trifluoroacetic acid salt

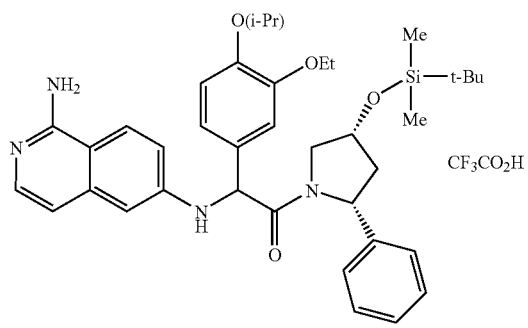

A mixture of 113A (40 mg, 0.090 mmol), (2R,4R)-4-(tert-butyldimethylsilyloxy)-2-phenylpyrrolidine (Synlett. 2001, 1808-1810, 60 mg, 0.185 mmol), EDCI (40 mg, 0.2 mmol), HOAT (30 mg, 0.2 mmol), Et$_3$N (0.03 mL, 0.18 mmol) in DMF (1 mL) was stirred at 40° C. for 5 h, then at rt overnight. The organic layer was concentrated and purified via preparative HPLC (CH$_3$CN/H$_2$O/TFA) to provide 113B (30 mg, 50%). LC-MS 655 (M+H)$^+$.

113C: Example 113

113B (30 mg, 0.045 mmol) in THF (1.0 mL) was treated with TBAF (1.0 M in THF, 0.1 mL, 0.1 mmol) for 1.0 h. Example 113 was purified via HPLC equipped with a C18 Luna column (21×100 mm, 5μ). The separation was performed using a linear gradient (mobile phase A: 10% MeOH- 90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.24 (d, J=7.18 Hz, 6H) 1.34 (t, J=7.18 Hz, 3H) 1.68-1.84 (m, 1H) 2.34-2.51 (m, 1H) 3.70 (dd, J=10.55, 5.71 Hz, 1H) 3.86 (dd, J=10.77, 4.17 Hz, 1H) 4.03 (q, J=7.03 Hz, 1H) 4.19-4.28 (m, 1H) 4.45-4.58 (m, 1H) 4.97 (dd, J=9.01, 5.05 Hz, 1H) 5.38 (s, 1H) 6.72 (d, J=2.20 Hz, 1H) 6.82 (d, J=7.03 Hz, 1H) 6.87-7.17 (m, 5H) 7.16-7.37 (m, 4H) 7.73 (d, J=9.23 Hz, 1H). LC-MS: 527 (M+H)$^+$.

Example 114

(2R,3S)-Ethyl 1-(S)-2-(1-aminoisoquinolin-6-ylamino)-2-(2-fluoro-4,5-dimethoxyphenyl)acetyl)-2-(2-(ethylsulfonyl)phenyl)pyrrolidine-3-carboxylate trifluoroacetic acid salt

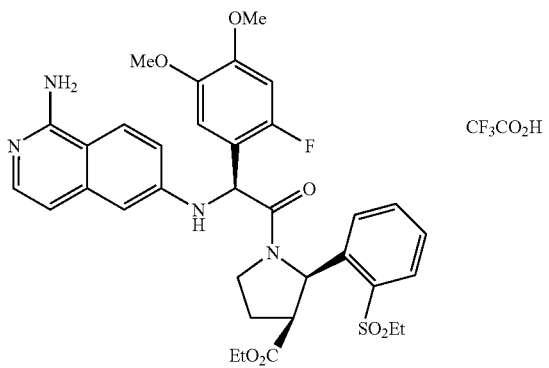

114A: 2-(Ethylthio)benzaldehyde

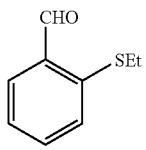

114A (10.4 g, 78% yield) was prepared from 2-fluorobezaldehyde (10 g, 81 mmol) and thioethane (5.5 g, 89 mmol) using a procedure similar to that used in the preparation of 11A. $^1$H NMR (400 MHz, Methanol-d$_4$) δ ppm 1.23-1.42 (m, 3H) 2.98 (q, J=7.34 Hz, 2H) 7.17-7.37 (m, 1H) 7.38-7.64 (m, 2H) 7.81 (dd, J=7.70, 1.59 Hz, 1H) 10.30 (s, 1H).

114B: (E)-Ethyl 4-(2-(ethylthio)benzylideneamino)butanoate

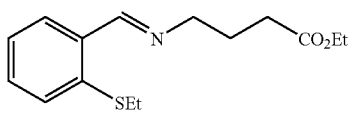

114B (>95% yield) was obtained from 114A (5.0 g, 30 mmol) and ethyl aminobutyric ester HCl salt (5.0 g, 30 mmol) using a procedure similar to that used in the preparation of 11B. $^1$H NMR (400 MHz, Methanol-d$_4$) δ ppm 1.14-1.28 (m, 6H) 1.93-2.11 (m, 2H) 2.40 (t, J=7.34 Hz, 2H) 2.93 (q, J=7.34 Hz, 2H) 3.58-3.75 (m, 2H) 4.03-4.21 (m, 2H) 7.28 (t, J=7.46 Hz, 1H) 7.36-7.46 (m, 1H) 7.44-7.54 (m, 1H) 7.81 (dd, J=7.83, 1.47 Hz, 1H) 8.87 (s, 1H).

114C: cis-Ethyl 2-(2-(ethylthio)phenyl)pyrrolidine-3-carboxylate

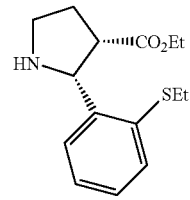

114C (3.17 g, 86% yield) was obtained from 114B using a procedure similar to that used in the preparation of 11C.

114D: cis-1-tert-Butyl 3-ethyl 2-(2-(ethylthio)phenyl)pyrrolidine-1,3-dicarboxylate

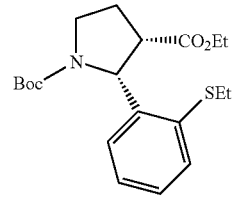

114D was obtained from 114C using a procedure similar to that used in the preparation of 13A. $^1$H NMR (400 MHz, DMSO-d$_6$) δ ppm 0.95-1.46 (m, 15H) 1.98-2.14 (m, 2H) 2.63-2.83 (m, 1H) 2.85-3.06 (m, 2H) 3.38-3.50 (m, 1H) 3.59-3.70 (m, 1H) 4.12 (q, J=6.93 Hz, 2H) 5.35 (s, 1H) 7.01-7.14 (m, 1H) 7.11-7.29 (m, 2H) 7.29-7.44 (m, 1H).

114E: cis-1-tert-Butyl 3-ethyl 2-(2-(ethylsulfonyl)phenyl)pyrrolidine-1,3-dicarboxylate

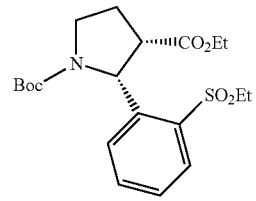

114E was obtained from 114D using a procedure similar to that used in the preparation of 13B. $^1$H NMR (400 MHz, DMSO-d$_6$) δ ppm 1.06-1.21 (m, 9H) 1.82-2.32 (m, 28H) 2.80 (dd, J=61.31, 6.87 Hz, 1H) 3.11-3.48 (m, 3H) 3.70-3.83 (m, 1H) 4.02-4.17 (m, 2H) 5.63 (d, J=20.90 Hz, 1H) 7.45 (dd, J=116.50, 7.70 Hz, 1H) 7.49-7.62 (m, 1H) 7.69-7.79 (m, 1H) 7.83-7.96 (m, 1H).

114F: cis-Ethyl 2-(2-ethylsulfonyl)phenyl)pyrrolidine-3-carboxylate HCl salt

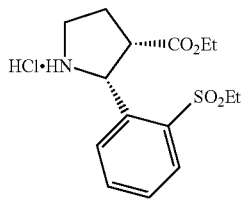

114 F was prepared from 114E using a procedure similar to that used in the preparation of 13C. $^1$H NMR (400 MHz, DMSO-$d_6$) δ ppm 0.96-1.14 (m, 6H) 1.93-2.07 (m, 1H) 2.09-2.24 (m, 1H) 2.86-3.01 (m, 2H) 3.05-3.19 (m, 1H) 3.31-3.46 (m, 2H) 3.96 (q, J=7.09 Hz, 2H) 4.99 (d, J=7.09 Hz, 1H) 7.43-7.58 (m, 1H) 7.65-7.77 (m, 1H) 7.80-7.91 (m, 2H).

114G: (2R,3S)-Ethyl 2-(2-(ethylsulfonyl)phenyl)pyrrolidine-3-carboxylate

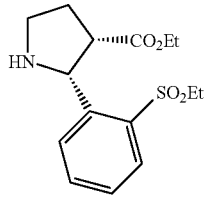

114F were separated using a preparative HPLC equipped with a Chiralpak®AS column. The separation was performed using an isocratic method of 10% isopropanol/heptane with 0.1% diethylamine for 100 min with a flow rate of 50 mL/min. The first peak corresponds to 114G. $^1$H NMR (400 MHz, DMSO-$d_6$) o ppm 0.96-1.14 (m, 6H) 1.93-2.07 (m, 1H) 2.09-2.24 (m, 1H) 2.86-3.01 (m, 2H) 3.05-3.19 (m, 1H) 3.31-3.46 (m, 2H) 3.96 (q, J=7.09 Hz, 2H) 4.99 (d, J=7.09 Hz, 1H) 7.43-7.58 (m, 1H) 7.65-7.77 (m, 1H) 7.80-7.91 (m, 2H).

114H: Example 114

Example 114 was prepared according to the general coupling-deprotection using 86C and 114G. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ 1.05-1.39 (m, 6H) 2.03-2.23 (m, 1H) 2.43-2.62 (m, 1H) 2.88 (d, J=8.07 Hz, 1H) 3.37-3.53 (m, 3H) 3.78-3.94 (m, 6H) 4.00-4.12 (m, 2H) 4.36 (t, J=9.05 Hz, 1H) 5.83 (s, 1H) 6.03 (s, 1H) 6.73-6.82 (m, 1H) 6.85-7.05 (m, 3H) 7.11 (dd, i=9.29, 2.45 Hz, 1H) 7.32-7.41 (m, 1H) 7.45-7.58 (m, 1H) 7.64-7.79 (m, 2H) 7.94 (dd, J=7.83, 1.22 Hz, 1H) 8.03 (d, J=9.29 Hz, 1H). LC-MS: 665 (M+H)$^+$.

Example 115

Diastereomer of Example 114

(2R,3S)-Ethyl 1-((R)-2-(1-aminoisoquinolin-6-ylamino)-2-(2-fluoro-4,5-dimethoxyphenyl)acetyl)-2-(2-(ethylsulfonyl)phenyl)pyrrolidine-3-carboxylate trifluoroacetic acid salt

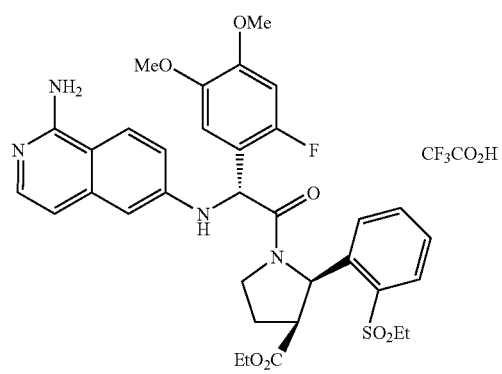

Example 115 was obtained as a diastereomer of Example 114 during its HPLC purification. $^1$H NMR (400 MHz, Methanol-$d_4$) δ ppm 1.16-1.35 (m, 6H) 2.18-2.44 (m, 2H) 2.89-2.98 (m, 1H) 3.34-3.54 (m, 2H) 3.59 (s, 3H) 3.66-3.81 (m, 1H) 3.84-3.92 (m, 3H) 4.05-4.33 (m, 3H) 5.73 (s, 1H) 6.05 (d, J=2.20 Hz, 1H) 6.70 (d, J=7.09 Hz, 1H) 6.76 (d, J=2.20 Hz, 1H) 6.81 (dd, J=7.70, 1.34 Hz, 1H) 6.97 (d, J=11.49 Hz, 1H) 7.03 (d, J=7.09 Hz, 1H) 7.15 (dd, J=9.05, 2.45 Hz, 1H) 7.36 (d, J=7.09 Hz, 1H) 7.42-7.59 (m, 2H) 7.96 (dd, J=7.58, 1.71 Hz, 1H) 8.08 (d, J=9.29 Hz, 1H). LC-MS: 665 (M+H)$^+$.

Example 116

(2R,3S)-1-((R)-2-(1-Aminoisoquinolin-6-ylamino)-2-(2-fluoro-4,5-dimethoxyphenyl)acetyl)-2-(2-(ethylsulfonyl)phenyl)pyrrolidine-3-carboxylic acid trifluoroacetic acid salt

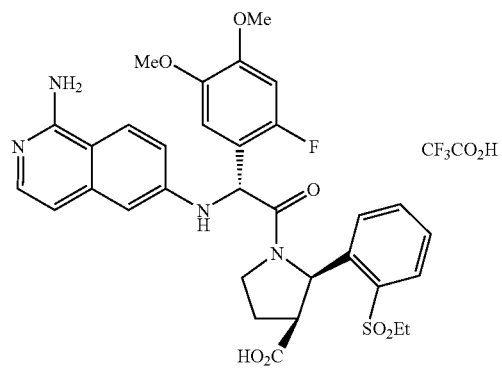

Example 116 was prepared by hydrolysis of the ethyl ester Example 115 using a procedure similar to that used in the preparation of Example 12. $^1$H NMR (400 MHz, Methanol-$d_4$) δ ppm 1.23 (t, J=7.34 Hz, 3H) 2.22-2.47 (m, 2H) 2.93 (d, J=7.34 Hz, 1H) 3.36-3.55 (m, 2H) 3.59 (s, 3H) 3.75-3.85 (m, 1H) 3.89 (s, 3H) 4.02-4.19 (m, 1H) 5.70 (s, 1H) 6.10 (s, 1H) 6.68-6.76 (m, 2H) 6.78-6.86 (m, 1H) 6.98 (d, J=11.25 Hz, 1H) 7.06 (d, J=6.85 Hz, 1H) 7.15 (dd, J=9.17, 2.32 Hz, 1H) 7.34 (d, J=6.85 Hz, 1H) 7.43-7.60 (m, 2H) 7.98 (dd, J=7.70, 1.34 Hz, 1H) 8.07 (d, J=9.05 Hz, 1H). LC-MS: 637 (M+H).

Example 117

(2R,3S)-1-((S)-2-(1-Aminoisoquinolin-6-ylamino)-2-(2-fluoro-4,5-dimethoxyphenyl)acetyl)-2-(2-(ethylsulfonyl)phenyl)pyrrolidine-3-carboxylic acid trifluoroacetic acid salt

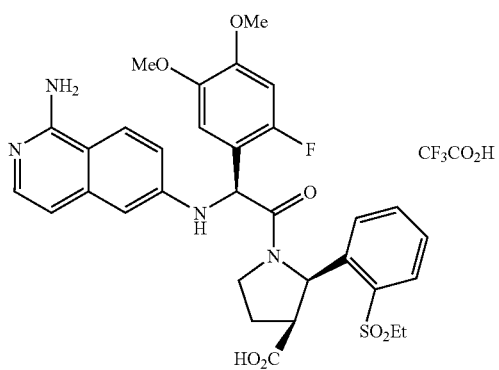

Example 117 was prepared by hydrolysis of the methyl ester Example 114 using a procedure analogous to that used in the preparation of Example 12. $^1$H NMR (400 MHz, Methanol-$d_4$) δ ppm 1.17-1.37 (m, 3H) 2.14 (dd, J=13.82, 6.72 Hz, 1H) 2.45-2.59 (m, 1H) 2.85 (d, J=7.83 Hz, 1H) 3.13-3.26 (m, 1H) 3.38-3.51 (m, 2H) 3.77-3.88 (m, 6H) 4.35 (t, J=9.29 Hz, 1H) 5.82 (s, 1H) 6.06 (s, 1H) 6.72-6.81 (m, 1H) 6.85-7.01 (m, 3H) 7.05-7.16 (m, 1H) 7.30-7.38 (m, 1H) 7.45-7.55 (m, 1H) 7.64-7.78 (m, 2H) 7.84-7.97 (m, 1H) 7.97-8.07 (m, 1H). LC-MS: 637 (M+H).

Example 118

Methyl 3-((R)-1-((R)-2-(1-aminoisoquinolin-6-ylamino)-2-(3-ethoxy-5-ethyl-2-fluorophenyl)acetyl) pyrrolidin-2-yl)-4-(ethylsulfonyl)phenylcarbamate trifluoroacetic acid salt

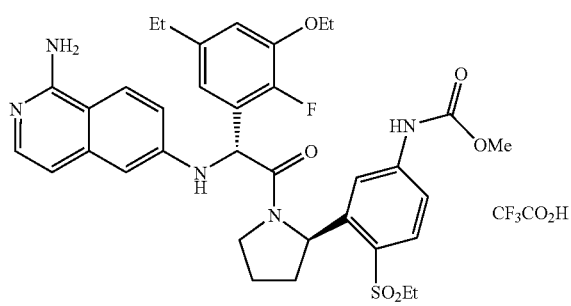

118A: 5-Ethyl-2-fluorophenol

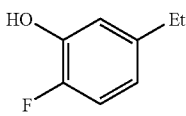

To a solution of 1-ethyl-4-fluorobenzene (7.2 g, 58 mmol) in THF (30 mL) and N,N,N',N'',N''-pentamethyldiethylenetriamine (3.0 mL) was added n-BuLi (1.6M in hexane, 42 mL) at −78° C. After 1 h stirring, trimethyl borate (13 mL) was added. The mixture was stirred from −78° C. to rt overnight. It was quenched by acetic acid (5.0 mL) and hydrogen peroxide solution (30% in water) at 0° C. The mixture was stirred for 2 h before extracted with EtOAc. The organic extracts were washed with brine, dried over MgSO$_4$ and concentrate to give 118A (7.6 g, 94% yield) as an oil. $^1$H NMR (400 MHz, CDCl$_3$) δ ppm 1.19 (t, J=7.69 Hz, 3H) 2.56 (q, J=7.62 Hz, 2H) 6.60-6.71 (m, 1H) 6.83 (dd, J=8.79, 2.20 Hz, 1H) 6.95 (dd, J=10.55, 8.35 Hz, 1H).

118B: tert-Butyl(5-ethyl-2-fluorophenoxy)dimethylsilane

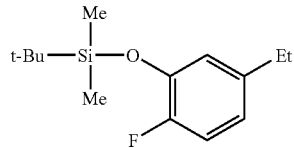

To 118A (3.75 g, 26.8 mmol) in DMF (20 mL) was added tert-butyldimethylsilyl chloride (6.1 g) and imidazole (2.6 g). The mixture was stirred at rt for overnight. It was then diluted with EtOAc/hexanes (1:4) and washed with water and brine. The organic extracts were dried and concentrated. The crude product was purified by column chromatography to give 118B (4.46 g, 66% yield) as an oil. $^1$H NMR (400 MHz, CDCl$_3$) δ ppm 0.21 (none, 6H) 0.99 (s, 9H) 1.18 (t, J=7.69 Hz, 3H) 2.54 (q, J=7.76 Hz, 2H) 6.64-6.76 (m, 2H) 6.93 (dd, J=10.55, 8.35 Hz, 1H).

118C: 3-(tert-Butyldimethylsilyloxy)-5-ethyl-2-fluorobenzaldehyde

To 118B (625 mg, 2.46 mmol) in THF (10 mL) and N,N,N',N'',N''-pentamethyldiethylenetriamine (0.77 mL) was added n-BuLi (1.6M in hexane, 1.77 mL) at −78° C. After stiiring for 45 min at −35° C., DMF (0.94 mL) was added at at −78° C. and the reaction was slowly warmed up to rt. The mixture was stirred at rt for 1 h, diluted with EtOAc. The organic extracts were washed with saturated NaHCO$_3$, brine and dried. The crude product was purified by column chromatography to give 118C (615 mg, 89% yield) as an oil. ¹H NMR (400 MHz, CDCl₃) δ ppm 0.21 (s, 6H) 1.01 (s, 9H) 1.21 (t, J=7.47 Hz, 3H) 2.59 (q, J=7.47 Hz, 2H) 6.99 (dd, J=7.91, 2.20 Hz, 1H) 7.21-7.27 (m, 1H) 10.30 (s, 1H).

118D: 3-Ethoxy-5-ethyl-2-fluorobenzaldehyde

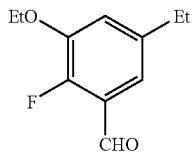

To 118C (244 mg, 0.87 mmol) in DMF (2.0 mL) was added potassium fluoride (100 mg) and iodoethane (0.13 mL). The mixture was stirred at rt overnight. It was diluted with EtOAc and the organic extracts were washed with brine and dried. The crude product was purified by column chromatography to give 118D (158 mg, 100% yield) as an oil. ¹H NMR (400 MHz, CDCl₃) δ ppm 1.22 (t, J=7.69 Hz, 3H) 1.46 (t, J=7.03 Hz, 3H) 2.62 (q, J=7.47 Hz, 2H) 4.13 (q, J=7.03 Hz, 2H) 7.02 (dd, J=7.91, 2.20 Hz, 1H) 7.22 (dd, J=5.27, 2.20 Hz, 1H) 10.35 (s, 1H).

118E: 2-(3-ethoxy-5-ethyl-2-fluorophenyl)-2-hydroxyacetonitrile

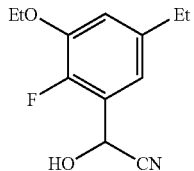

To 118D (630 mg, 3.46 mmol) in ethyl acetate (10 mL) was added a solution of KCN (676 mg) and NaHSO₃ (1.08 g) dissolved in H₂O (10 mL). It was left stirring overnight before extracted with ethyl acetate (2×50 mL). The combined organic extracts were dried and concentrated. The crude producte was purified by column chromatography to give 118E (685 mg, 92% yield) as an oil. ¹H NMR (400 MHz, CDCl₃) δ ppm 1.23 (t, J=7.69 Hz, 3H) 1.44 (t, J=7.03 Hz, 3H) 2.62 (q, J=7.76 Hz, 2H) 4.11 (q, J=7.03 Hz, 2H) 5.75 (s, 1H) 6.85 (dd, J=7.91, 2.20 Hz, 1H) 6.96 (dd, J=5.93, 1.98 Hz, 1H).

118F: Methyl 2-(3-ethoxy-5-ethyl-2-fluorophenyl)-2-hydroxyacetate

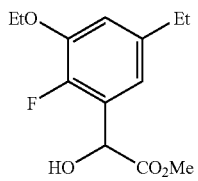

To 118E (630 mg, 2.93 mmol) in anhydrous diethyl ether (10 mL) at 0° C. was added MeOH (1.2 mL) and 4.0 N HCl in dioxane (2.9 mL). The mixture was stirred at 0° C. for 30 min and then at rt over night. Solvent was removed to give methyl 2-(3-ethoxy-5-ethyl-2-fluorophenyl)-2-hydroxyacetimidate HCl salt. To this salt in CH₂Cl₂ (5.0 mL) was added H₂O (8.0 mL). The mixture was stirred at rt for 30 min, then extracted with CH₂Cl₂ (2×50 mL). The combined organic extracts were dried and concentrated. The crude was purified by column chromatography to give 118F (632 mg, 89% yield) as a viscous oil. ¹H NMR (400 MHz, CDCl₃) δ ppm 1.20 (t, J=7.69 Hz, 3H) 1.43 (t, J=7.03 Hz, 3H) 2.58 (q, J=7.76 Hz, 2H) 3.76 (s, 3H) 4.04-4.13 (m, 2H) 5.37 (s, 1H) 6.68-6.81 (m, 2H).

118G: Methyl 2-(1-di-tert-butoxycarbonylaminoisoquinolin-6-ylamino)-2-(3-ethoxy-5-ethyl-2-fluorophenyl)acetic ester

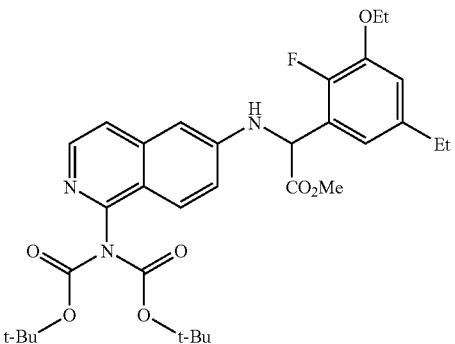

To 118F (257 mg, 1.06 mmol) in CH₂Cl₂ (5.0 mL) at 0° C. was added trifluoromethanesulfonic anhydride (0.2 mL) and 2,6-lutidine (0.19 mL). The mixture was stirred for 15 min before 1B (343 mg, 0.57 mmol) and 2,6-lutidine (0.37 mL) in CH₂Cl₂ (2.0 mL) was added. The reaction was left stirring from 0° C. to rt for 3.0 h. It was diluted with ethyl acetate, washed with 0.5 N HCl (3×20 mL). The organic extract was dried and concentrated. A column chromatography purification gave product 118G (520 mg, 84% yield). ¹H NMR (400 MHz, CDCl₃) δ ppm 1.05 (t, J=7.69 Hz, 3H) 1.16 (s, 18H) 1.31 (t, J=7.03 Hz, 3H) 2.45 (q, J=7.47 Hz, 2H) 3.65 (s, 3H) 3.95-4.04 (m, 2H) 5.49-5.56 (m, 1H) 6.62 (d, J=2.20 Hz, 1H) 6.74-6.79 (m, 2H) 7.18 (dd, J=9.23, 2.20 Hz, 1H) 7.36 (d, J=5.71 Hz, 1H) 7.53 (d, J=9.23 Hz, 1H) 7.94 (d, J=5.71 Hz, 1H).

118H: 2-(1-Di-tert-butoxycarbonylaminoisoquinolin-6-ylamino)-2-(3-ethoxy-5-ethyl-2-fluorophenyl)acetic acid

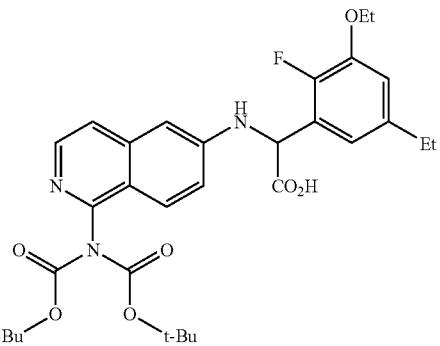

118G (77 mg, 0.13 mmol) was hydrolyzed with NaOH (1.0 N, 0.19 mL, 0.19 mmol) in THF (0.6 mL) and MeOH (0.3 mL) at rt for 2 h. After acidification with 5% KHSO$_4$, it was extracted with ethyl acetate (2×30 mL). The organic extract was dried and concentrated to give a solid product 118H (64 mg, 84% yield). $^1$H NMR (400 MHz, Methanol-d$_4$) δ ppm 1.17 (t, J=7.47 Hz, 3H) 1.34 (s, 18H) 1.42 (t, J=7.03 Hz, 3H) 2.58 (q, J=7.62 Hz, 2H) 4.12 (q, J=7.03 Hz, 2H) 5.67 (s, 1H) 6.76-7.07 (m, 3H) 7.53 (dd, J=9.67, 2.20 Hz, 1H) 7.78 (d, J=6.59 Hz, 1H) 7.91 (d, J=9.23 Hz, 1H) 8.10 (d, J=6.15 Hz, 1H).

118I: Example 118

Example 118 was prepared according to the general coupling-deprotection using 118H and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.05 (t, J=7.58 Hz, 3H) 1.20-1.36 (m, 3H) 1.39-1.50 (m, 3H) 1.61-1.83 (m, 1H) 2.00-2.23 (m, 2H) 2.36-2.61 (m, 3H) 3.40-3.55 (m, 1H) 3.53-3.69 (m, 2H) 3.68-3.79 (m, 3H) 4.06-4.25 (m, 3H) 5.73 (dd, J=8.31, 5.14 Hz, 1H) 5.82 (s, 1H) 6.53 (dd, J=5.50, 1.83 Hz, 1H) 6.79 (d, J=2.45 Hz, 1H) 6.91 (d, J=7.09 Hz, 2H) 7.07 (dd, 1H) 7.15 (dd, J=9.17, 2.32 Hz, 1H) 7.25-7.39 (m, 2H) 7.79 (d, J=8.80 Hz, 1H) 8.06 (d, J=9.05 Hz, 1H) 9.38 (s, 1H). LC-MS: 678 (M+H).

Example 119

Methyl 3-((R)-1-(R)-2-(1-aminoisoquinolin-ylamino)-2-(5-ethyl-2-fluoro-3-methoxyphenyl)acetyl)pyrrolidin-2-yl)-4-ethylsulfonyl)phenylcarbamate trifluoroacetic acid salt

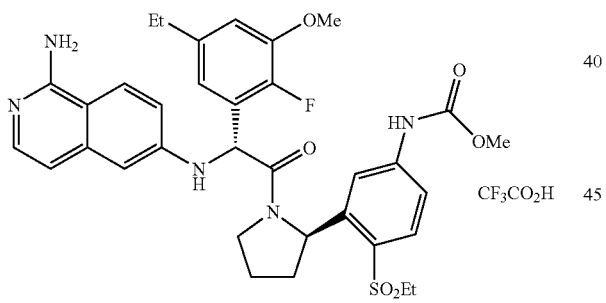

119A: 5-Ethyl-2-fluoro-3-methoxybenzaldehyde

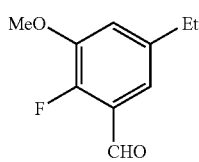

119A was prepared from 118C using a procedure similar to that used in the preparation of 118D. $^1$H NMR (400 MHz, CDCl$_3$) δ ppm 1.23 (t, J=7.47 Hz, 3H) 2.64 (q, J=7.62 Hz, 2H) 3.92 (s, 3H) 7.02 (dd, J=8.13, 1.98 Hz, 1H) 7.23 (dd, J=5.27, 2.20 Hz, 1H) 10.35 (s, 1H).

119B: 2-(5-Ethyl-2-fluoro-3-methoxyphenyl)-2-hydroxyacetonitrile

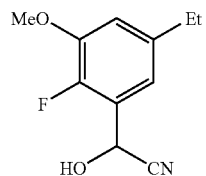

119B was prepared from 119A using a procedure similar to that used in the preparation of 118E. $^1$H NMR (400 MHz, CDCl$_3$) δ ppm 1.23 (t, J=7.47 Hz, 3H) 2.64 (q, J=7.62 Hz, 2H) 3.89 (s, 3H) 5.76 (s, 1H) 6.86 (dd, J=7.91, 2.20 Hz, 1H) 6.98 (dd, J=5.93, 1.98 Hz, 1H).

119C: Methyl 2-(5-ethyl-2-fluoro-3-methoxyphenyl)-2-hydroxyacetate

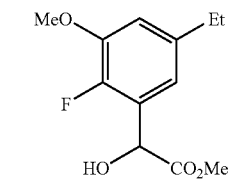

119C was prepared from 119B using a procedure similar to that used in the preparation of 118F. $^1$H NMR (400 MHz, CDCl$_3$) δ ppm 1.21 (t, J=7.69 Hz, 3H) 2.59 (q, J=7.47 Hz, 2H) 3.76 (s, 3H) 3.87 (s, 3H) 5.38 (s, 1H) 6.65-6.85 (m, 2H).

119D: Methyl 2-(1-di-tert-butoxycarbonylaminoisoquinolin-6-ylamino)-2-(5-ethyl-2-fluoro-3-methoxyphenyl)acetic ester

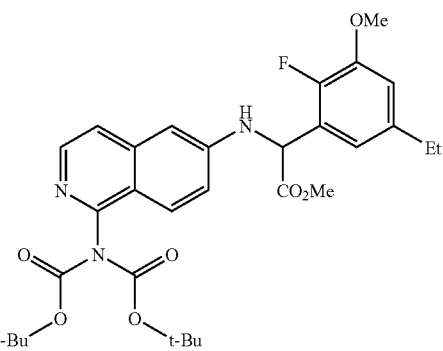

119D was prepared from 119C using a procedure similar to that used in the preparation of 118G. $^1$H NMR (400 MHz, CDCl$_3$) δ ppm 1.17 (t, J=7.47 Hz, 3H) 1.27 (s, 18H) 2.58 (q, J=7.62 Hz, 2H) 3.76 (s, 3H) 3.87 (s, 3H) 5.62 (s, 1H) 6.72 (d, J=2.20 Hz, 1H) 6.85-6.93 (m, 2H) 7.07 (d, J=7.91 Hz, 1H) 7.28 (dd, J=9.23, 2.64 Hz, 1H) 7.46 (d, J=5.71 Hz, 1H) 7.64 (d, J=8.79 Hz, 1H) 8.05 (d, J=5.71 Hz, 1H).

119E: 2-(1-Di-tert-butoxycarbonylaminoisoquinolin-6-ylamino)-2-(5-ethyl-2-fluoro-3-methoxyphenyl)acetic acid

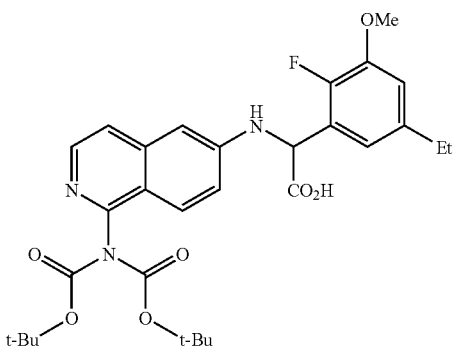

119E was prepared from 119C using a procedure similar to that used in the preparation of 118H. LC-MS: 570 (M+H)+.

119F: Example 119

Example 119 was prepared according to the general coupling-deprotection using 119E and 100G. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.06 (t, J=7.58 Hz, 3H) 1.22-1.36 (m, 3H) 1.73 (dd, J=12.96, 5.62 Hz, 1H) 1.98-2.22 (m, 2H) 2.39-2.65 (m, 3H) 3.41-3.54 (m, 1H) 3.55-3.71 (m, 2H) 3.71-3.80 (m, 3H) 3.83-3.98 (m, 3H) 4.09-4.25 (m, 1H) 5.73 (dd, J=8.07, 5.14 Hz, 1H) 5.82 (s, 1H) 6.54 (dd, J=5.62, 1.71 Hz, 1H) 6.73-6.80 (m, 1H) 6.85-6.97 (m, 2H) 7.05 (s, 1H) 7.14 (dd, J=9.17, 2.32 Hz, 1H) 7.28-7.40 (m, 2H) 7.79 (d, J=8.56 Hz, 1H) 8.00-8.11 (m, 1H) 9.37 (s, 1H). LC-MS: 664 (M+H)+.

Example 120

Diastereomer of Example 119

Methyl 3-((R)-1-((S)-2-(1-aminoisoquinolin-6-ylamino)-2-(5-ethyl-2-fluoro-3-methoxyphenyl)acetyl)pyrrolidin-2-yl)-4-(ethylsulfonyl)phenylcarbamate trifluoroacetic acid salt

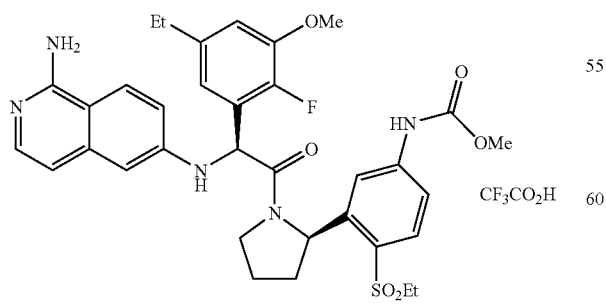

Example 120 was obtained as a diastereomer of Example 119 during its HPLC purification. $^1$H NMR (400 MHz, Methanol-$d_4$) δ ppm 1.07-1.35 (m, 6H) 1.64-2.49 (m, 4H) 2.61 (q, J=7.58 Hz, 2H) 3.34-3.51 (m, 3H) 3.68-3.97 (m, 6H) 4.07-4.22 (m, 1H) 5.60-5.76 (m, 1H) 5.81 (s, 1H) 6.69 (d, J=2.45 Hz, 1H) 6.75-7.03 (m, 3H) 7.09-7.21 (m, 1H) 7.21-7.47 (m, 2H) 7.72-7.86 (m, 2H) 8.02 (t, J=8.31 Hz, 1H). LC-MS: 664 (M+H)+.

Example 121

Methyl 3-((R)-1-((R)-2-(1-aminoisoquinolin-6-ylamino)-2-(5-chloro-2-fluorophenyl)acetyl)pyrrolidin-2-yl)-4-(ethylsulfonyl)phenylcarbamate trifluoroacetic acid salt

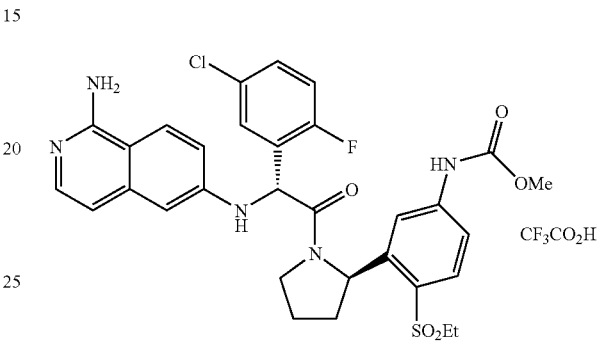

121A: 2-(2-Fluoro-5-chlorophenyl)-2-hydroxyacetonitrile

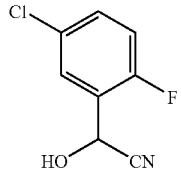

To 2-fluoro-5-chloro-benzaldehyde (12.7 g, 17 mmol) in ethyl acetate (50 mL) was added a solution of KCN (3.3 g) and NaHSO$_3$ (5.3 g) dissolved in H$_2$O (25 mL). It was left stirring overnight before extracted with ethyl acetate (3×50 mL). The combined organic extracts were dried and concentrated. The crude product was purified by silica gel chromatography to give 121A (3.1 g, 99% yield) as an oil.

121B: Methyl 2-(5-chloro-2-fluorophenyl)-2-hydroxyacetate

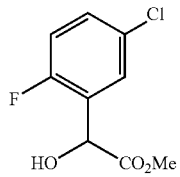

To 121A (640 mg, 3.48 mmol) in anhydrous diethyl ether (115 mL) at 0° C. was added MeOH (1.4 mL) and 4.0 N HCl in dioxane (3.5 mL). The mixture was stirred at 0° C. for 30 min and then at rt for 4 h. The solvent was removed to give methyl 2-(5-chloro-2-fluorophenyl)-2-hydroxyacetimidate HCl salt. To this salt in CH$_2$Cl$_2$ (10 mL) was added H$_2$O (10 mL). The mixture was stirred at rt for 30 min, then extracted with CH$_2$Cl$_2$ (2×50 mL). The combined organic extracts were dried and concentrated. The crude product was purified by silica gel chromatography to give 121B (610 mg, 80% yield) as a viscous oil. $^1$H NMR (400 MHz, CDCl$_3$) δ ppm 3.55 (d, J=4.83 Hz, 1H) 3.80 (s, 3H) 5.38 (d, J=4.83 Hz, 1H) 7.03 (t, J=9.23 Hz, 1H) 7.27-7.31 (m, 1H) 7.39 (dd, J=6.15, 2.64 Hz, 1H).

121C: Methyl 2-(1-di-tert-butoxycarbonylaminoisoquinolin-6-ylamino)-2-(5-chloro-2-fluorophenyl) acetic ester

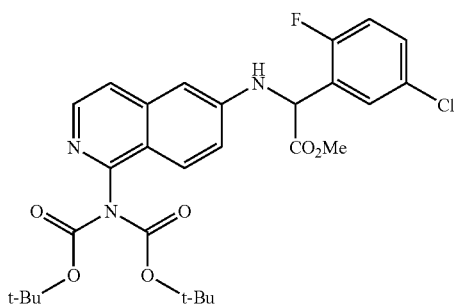

To 121B (320 mg, 1.47 mmol) in CH$_2$Cl$_2$ (5.0 mL) at 0° C. was added trifluoromethanesulfonic anhydride (0.27 mL) and 2,6-lutidine (0.26 mL). The mixture was stirred for 15 min before 1B (475 mg, 1.32 mmol) and 2,6-lutidine (0.51 mL) in CH$_2$Cl$_2$ (2.0 mL) were added. The reaction was left stirring from 0° C. to rt for 3.0 h. It was diluted with ethyl acetate, washed with 0.5 N HCl (3×20 mL). The organic extract was dried and concentrated. A silica gel chromatography purification gave product 121C (447 mg, 60% yield). $^1$H NMR (400 MHz, CDCl$_3$) δ ppm 1.16 (s, 18H) 3.67 (s, 3H) 5.58 (s, 1H) 6.63 (d, J=2.20 Hz, 1H) 7.10 (t, J=9.23 Hz, 1H) 7.19 (dd, J=9.01, 2.42 Hz, 1H) 7.22-7.30 (m, 1H) 7.37 (d, J=5.71 Hz, 1H) 7.44 (d, J=2.64 Hz, 1H) 7.56 (d, J=9.23 Hz, 1H) 7.95 (d, J=5.71 Hz, 1H).

121D: 2-(1-Di-tert-butoxycarbonylaminoisoquinolin-6-ylamino)-2-(5-chloro-2-fluorophenyl)acetic acid

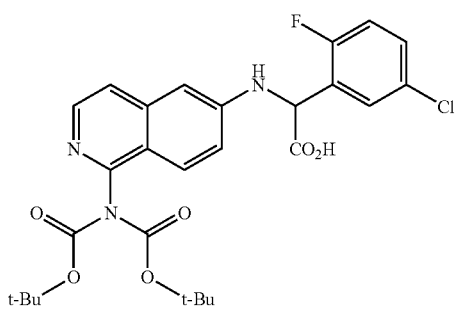

121C (440 mg, 0.79 mmol) was hydrolyzed with NaOH (1.0 N, 0.95 mL, 0.95 mmol) in THF (4 mL) and MeOH (0.5 mL) at rt for 2 h. After acidification with 5% KHSO$_4$, it was extracted with ethyl acetate (2×30 mL). The organic extract was dried and concentrated to give a solid product 121D (400 mg, 93% yield). $^1$H NMR (400 MHz, Methanol-d$_4$) δ ppm 1.29 (s, 18H) 5.62 (s, 1H) 6.77 (d, J=1.76 Hz, 1H) 7.22 (t, J=9.23 Hz, 1H) 7.33-7.40 (m, 2H) 7.54-7.59 (m, 2H) 7.73 (d, J=9.23 Hz, 1H) 8.07 (d, J=6.15 Hz, 1H). LC-MS: 546 (M+H)$^+$.

121E: Example 121

Example 121 was prepared according to the general coupling-deprotection using 121D and 10G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.27 (t, J=7.34 Hz, 3H) 1.64-1.80 (m, 1H) 1.97-2.25 (m, 2H) 2.43-2.59 (m, 1H) 3.39-3.67 (m, 3H) 3.69-3.77 (m, 3H) 4.08-4.26 (m, 1H) 5.71 (dd, J=8.07, 5.38 Hz, 1H) 5.86 (s, 1H) 6.79 (d, J=2.20 Hz, 1H) 6.90 (d, J=7.09 Hz, 1H) 7.08-7.43 (m, 7H) 7.78 (d, J=8.80 Hz, 1H) 8.01-8.10 (m, 1H) 9.47 (s, 1H). LC-MS: 640 (M+H)$^+$.

Example 122

Methyl 3-((R)-1-((R)-2-(1-aminoisoquinolin-6-ylamino)-2-(2-fluoro-5-methoxy-4-methylphenyl) acetyl)pyrrolidin-2-yl)-4-(ethylsulfonyl)phenylcarbamate trifluoroacetic acid salt

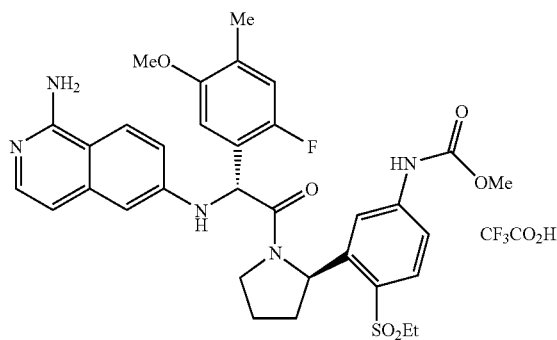

122A: Bis(4-fluoro-2-methylphenyl)carbonate

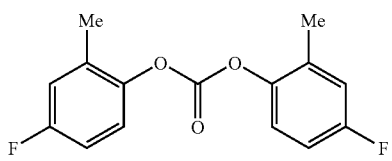

To a solution of 4-fluoro-2-methylphenol (3.8 g, 30.2 mmol) in toluene (8.0 mL) was added pyridine (5.3 mL) and phosgene (1.9M in toluene, 8.0 mL) at 0° C. The mixture was stirred for 2 h at rt before it was quenched by water and extracted with EtOAc. The combined organic layer was washed with brine, dried over MgSO$_4$ and concentrated to give a white solid product 122A. ¹H NMR (400 MHz, CDCl₃) δ ppm 2.30 (s, 6H) 6.87-7.05 (m, 4H) 7.15 (dd, J=8.79, 4.83 Hz, 2H).

122B:
Bis(4-fluoro-5-iodo-2-methylphenyl)carbonate

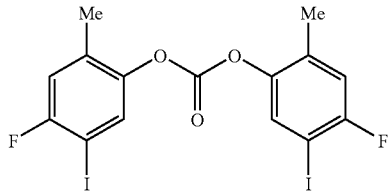

To 122A (2.3 g, 8.3 mmol) in trifluoroacetic acid (25 mL) was added N-succinimide (7.4 g). The mixture was stirred at rt for a week before it was poured into ice and extracted with EtOAc/hexanes (1:1). The organic layer was washed with saturated Na₂S₂O₃, NaHCO₃, brine and dried over MgSO₄. Evaporation of the solvent gave 122B (4.2 g, 95% yield) as a solid. ¹H NMR (400 MHz, CDCl₃) δ ppm 2.27 (s, 6H) 6.99 (d, J=8.35 Hz, 2H) 7.56 (d, J=5.27 Hz, 2H).

122C: 4-Fluoro-5-iodo-2-methylphenol

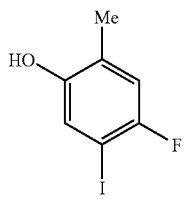

To 122B (4.2 g, 7.9 mmol) in methanol (20 mL) was added NaOH (0.63 g as a 50% aqueous solution) at 0° C. After TLC (10% EtOAc/Hexane) indicated the reaction was complete (2 h at 0° C.), the mixture was diluted with EtOAc, and washed with water and brine. The organic layer was dried over MgSO₄ and concentrated. The crude product was purified by silica gel chromatography to give 122C (3.36 g, 84% yield) as a solid. ¹H NMR (400 MHz, CDCl₃) δ ppm 2.19 (s, 3H) 4.87 (s, 1H) 6.83 (d, J=8.35 Hz, 1H) 7.10 (d, J=5.27 Hz, 1H).

122D: 1-Methoxy-4-fluoro-5-iodo-2-methylbenzene

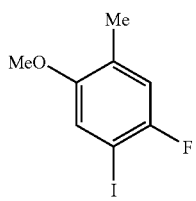

To 122C (1 g, 4 mmol) in acetone (20 mL) was added K₂CO₃ (1.64 g) and iodomethane (0.75 mL). The mixture was stirred at rt for 3 h. After TLC (10% EtOAc/Hexane) indicated the reaction was complete, the mixture was diluted with diethyl ether, washed with water and brine. The organic layer was dried over MgSO₄ and concentrated. The crude product was purified by silica gel chromatography to give 122D (0.75 g, 70% yield). ¹H NMR (400 MHz, CDCl₃) δ ppm 2.16 (s, 3H) 3.78 (s, 3H) 6.85 (d, J=8.79 Hz, 1H) 7.05 (d, J=5.27 Hz, 1H).

122E: 5-Methoxy-2-fluoro-4-methylphenylboronic acid

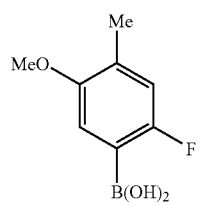

To 122D (750 mg, 2.8 mmol) in THF (10 mL) was added n-BuLi (1.6M in hexane, 2.3 mL) at −78° C. After stirring for 10 min, trimethyl borate (0.63 mL) was introduced. The mixture was stirred from −78° C. to rt for 3 h before it was quenched by 1N HCl and extracted with ethyl acetate. The organic extracts were washed with saturated Na₂S₂O₃, brine and dried over MgSO₄. Evaporation of the solvent gave product 122E (356 mg, 69% yield) as a solid. ¹H NMR (400 MHz, CDCl₃) δ ppm 2.18 (s, 3H) 3.80 (s, 3H) 6.80-6.86 (m, 2H).

122F: 2-(1-Di-tert-butoxycarbonylaminoisoquinolin-6-ylamino)-2-(2-fluoro-5-methoxy-4-methylphenyl)acetic acid

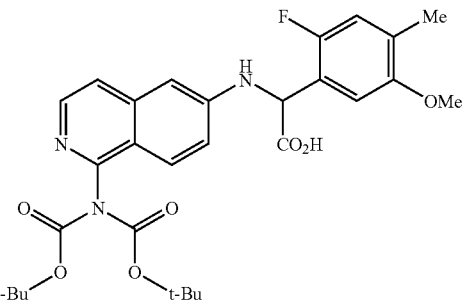

A mixture of 122E (88 mg, 0.48 mmol), 1B (144 mg, 0.4 mmol) and glyoxylic acid monohydrate (44 mg, 0.48 mmol) in acetonitrile (0.7 mL) and DMF (0.07 mL) was heated at 85° C. for 30 min in a Microwave Reactor. The crude product was purified by silica gel chromatography (CH₂Cl₂:MeOH=100:15) to give 122F (160 mg, 72% yield) as a solid. ¹H NMR (400 MHz, Methanol-d₄) δ ppm 1.27 (s, 18H) 2.16 (s, 3H) 3.76 (s, 3H) 5.51 (s, 1H) 6.74 (d, J=2.20 Hz, 1H) 6.94-7.03 (m, 2H) 7.29 (dd, J=9.23, 2.20 Hz, 1H) 7.46 (d, J=6.15 Hz, 1H) 7.64 (d, J=9.23 Hz, 1H) 7.97 (s, 1H) 8.04 (d, J=5.71 Hz, 1H). LC-MS: 556 (M+H)⁺.

122G: Example 122

Example 122 was prepared according to the general coupling-deprotection using 122F and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. ¹H NMR (400 MHz, Methanol-d₄)

δ ppm 1.27 (t, J=7.34 Hz, 3H) 1.73 (dd, J=12.72, 5.62 Hz, 1H) 2.01-2.18 (m, 2H) 2.20 (s, 3H) 2.52 (dd, J=13.08, 7.95 Hz, 1H) 3.40-3.53 (m, 4H) 3.55-3.71 (m, 2H) 3.70-3.76 (m, 3H) 4.09-4.23 (m, 1H) 5.73 (dd, J=8.07, 5.38 Hz, 1H) 5.80 (s, 1H) 6.49 (d, J=5.87 Hz, 1H) 6.79 (d, J=2.20 Hz, 1H) 6.90 (d, J=7.09 Hz, 1H) 6.96 (s, 1H) 7.05 (d, J=10.03 Hz, 1H) 7.15 (dd, J=9.17, 2.32 Hz, 1H) 7.28-7.39 (m, 2H) 7.79 (d, J=8.80 Hz, 1H) 8.05 (d, J=9.29 Hz, 1H) 9.35 (s, 1H). LC-MS: 650 (M+H)$^+$.

Example 123

Diastereomer of Example 122

Methyl 3-((R)-1-((S)-2-(1-aminoisoquinolin-6-ylamino)-2-(2-fluoro-5-methoxy-4-methylphenyl)acetyl)pyrrolidin-2-yl)-4-(ethylsulfonyl)phenylcarbamate trifluoroacetic acid salt

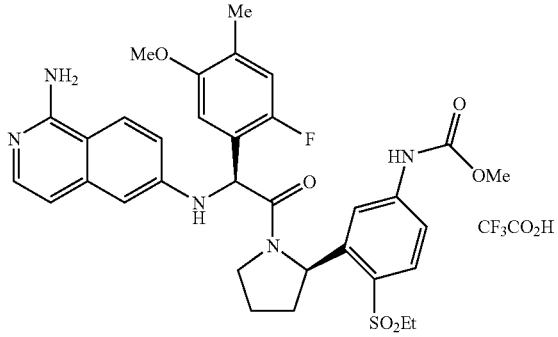

Example 123 was obtained as a diastereomer of Example 122 during its HPLC purification. $^1$H NMR (400 MHz, Methanol-d$_4$) δ ppm 1.18-1.36 (m, 3H) 1.70-1.82 (m, 1H) 1.85-2.02 (m, 2H) 2.14-2.24 (m, 3H) 2.28-2.43 (m, 1H) 3.33-3.58 (m, 3H) 3.68-3.87 (m, 6H) 4.09-4.23 (m, 1H) 5.63-5.72 (m, 1H) 5.80 (s, 1H) 6.69 (d, J=2.45 Hz, 1H) 6.75-6.93 (m, 2H) 6.97-7.24 (m, 2H) 7.24-7.36 (m, 1H) 7.41 (dd, J=8.56, 2.20 Hz, 1H) 7.71-7.85 (m, 2H) 7.95-8.10 (m, 1H). LC-MS: 650 (M+H)$^+$.

Example 124

(2R,3S)-Ethyl 1-((S)-2-(1-aminoisoquinolin-6-ylamino)-2-(5-chloro-2-fluorophenyl)acetyl)-2-(2-(ethylsulfonyl)phenyl)pyrrolidine-3-carboxylate trifluoroacetic acid salt

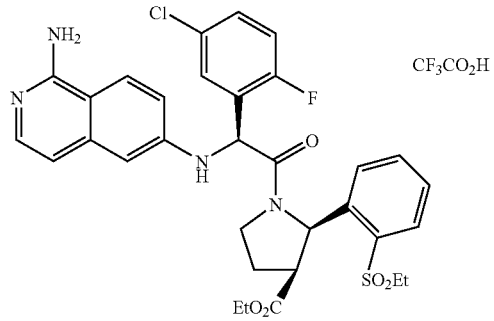

Example 124 was prepared according to the general coupling-deprotection using 121D and 114G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.07-1.38 (m, 6H) 2.15 (dd, J=13.45, 6.85 Hz, 1H) 2.45-2.59 (m, 1H) 2.83-2.93 (m, 1H) 3.32-3.54 (m, 3H) 3.99-4.17 (m, 2H) 4.30-4.49 (m, 1H) 5.93 (s, 1H) 6.03 (s, 1H) 6.81 (d, J=2.45 Hz, 1H) 6.91-7.00 (m, 1H) 7.09-7.32 (m, 2H) 7.35-7.57 (m, 4H) 7.60-7.76 (m, 2H) 7.87-7.98 (m, 1H) 8.01-8.14 (m, 1H). LC-MS: 939 (M+H)$^+$.

Example 125

Diastereomer of Example 124

(2R,3S)-Ethyl 1-((R)-2-(1-aminoisoquinolin-6-ylamino)-2-(5-chloro-2-fluorophenyl)acetyl)-2-(2-(ethylsulfonyl)phenyl)pyrrolidine-3-carboxylate trifluoroacetic acid salt

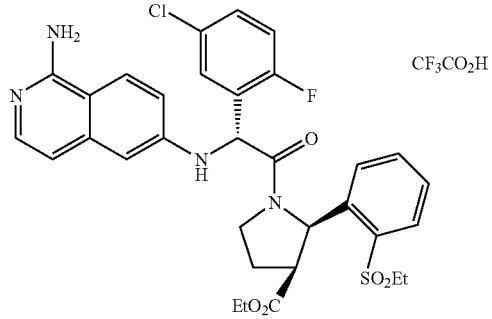

Example 125 was obtained as a diastereomer of Example 124 during its HPLC purification. $^1$H NMR (400 MHz, Methanol-d$_4$) δ ppm 1.11-1.36 (m, 6H) 2.15-2.50 (m, 2H) 2.86-3.00 (m, 1H) 3.33-3.56 (m, 2H) 3.66-3.83 (m, 1H) 4.01-4.29 (m, 3H) 5.84 (s, 1H) 6.03 (d, J=2.69 Hz, 1H) 6.79 (d, J=2.20 Hz, 1H) 6.86-6.94 (m, 1H) 7.01 (d, J=7.09 Hz, 1H) 7.10-7.25 (m, 2H) 7.26-7.41 (m, 2H) 7.42-7.66 (m, 3H) 7.88-8.01 (m, 1H) 8.09 (d, J=9.05 Hz, 1H). LC-MS: 939 (M+H)$^+$.

Example 126

(2R,3S)-Ethyl 1-((S)-2-(1-aminoisoquinolin-6-ylamino)-2-(5-ethyl-2-fluoro-3-methoxyphenyl)acetyl)-2-(2-(ethylsulfonyl)phenyl)pyrrolidine-3-carboxylate trifluoroacetic acid salt

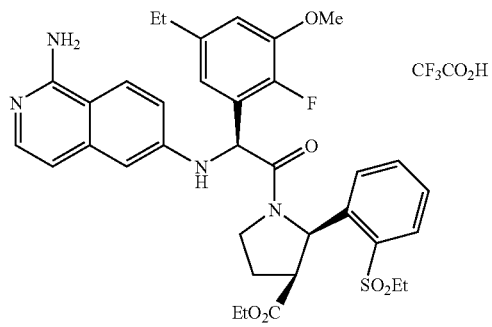

Example 126 was prepared according to the general coupling-deprotection using 119E and 114G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.01-1.44 (m, 9H) 2.01-2.23 (m, 1H) 2.38-2.72 (m, 3H) 2.85 (s, 1H) 3.16-3.26 (m, 1H) 3.34-3.55 (m, 2H) 3.82-4.14 (m, 5H) 4.33 (t, J=11.98 Hz, 1H) 5.87 (s, 1H) 6.02 (s, 1H) 6.76 (s, 1H) 6.87 (s, 1H) 6.90-7.04 (m, 2H) 7.04-7.23 (m, 1H) 7.28-7.41 (m, 1H) 7.43-7.59 (m, 1H) 7.62-7.81 (m, 2H) 7.81-8.14 (m, 2H). LC-MS: 663 (M+H)$^+$.

Example 127

Diastereomer of Example 126

(2R,3S)-Ethyl 1-((R)-2-(1-aminoisoquinolin-6-ylamino)-2-(5-ethyl-2-fluoro-3-methoxyphenyl)acetyl)-2-(2-(ethylsulfonyl)phenyl)pyrrolidine-3-carboxylate trifluoroacetic acid salt

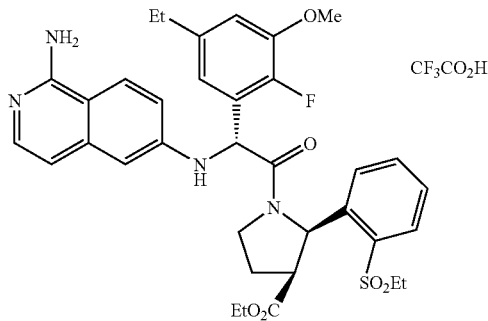

Example 127 was obtained as a diastereomer of Example 126 during its HPLC purification. $^1$H NMR (400 MHz, Methanol-$d_4$) δ ppm 1.09-1.33 (m, 9H) 2.15-2.40 (m, 2H) 2.46-2.63 (m, 2H) 2.83-2.96 (m, 1H) 3.33-3.54 (m, 2H) 3.63-3.75 (m, 1H) 3.82-3.96 (m, 3H) 4.03-4.29 (m, 3H) 5.76 (s, 1H) 6.04 (d, J=2.20 Hz, 1H) 6.60 (dd, J=5.50, 1.83 Hz, 1H) 6.75 (d, J=2.45 Hz, 1H) 6.79-6.87 (m, 1H) 6.99-7.06 (m, 2H) 7.14 (dd, J=9.17, 2.32 Hz, 1H) 7.34 (d, J=6.85 Hz, 1H) 7.42-7.56 (m, 2H) 7.95 (dd, J=7.70, 1.59 Hz, 1H) 8.06 (d, J=9.29 Hz, 1H). LC-MS: 663 (M+H)$^+$.

Example 128

(2R,3S)-1-((R)-2-(1-aminoisoquinolin-6-ylamino)-2-(5-chloro-2-fluorophenyl)acetyl)-2-(2-(ethylsulfonyl)phenyl)pyrrolidine-3-carboxylic acid trifluoroacetic acid salt

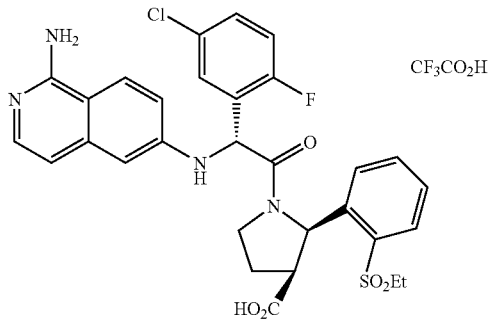

Example 128 was prepared by hydrolysis of the ethyl ester Example 125 using a procedure similar to that used in the preparation of Example 12. $^1$H NMR (400 MHz, Methanol-$d_4$) δ ppm 1.16-1.35 (m, 3H) 2.20-2.53 (m, 2H) 2.94 (d, J=7.58 Hz, 1H) 3.37-3.58 (m, 2H) 3.72-3.87 (m, 1H) 4.00-4.20 (m, 1H) 5.81 (s, 1H) 6.09 (s, 1H) 6.77 (d, J=2.20 Hz, 1H) 6.85-6.95 (m, 1H) 7.04 (d, J=7.34 Hz, 1H) 7.11-7.21 (m, 1H) 7.24 (dd, J=6.11, 2.69 Hz, 1H) 7.27-7.40 (m, 2H) 7.42-7.68 (m, 3H) 7.92-8.04 (m, 1H) 8.09 (d, J=9.29 Hz, 1H). LC-MS: 611 (M+H)$^+$.

Example 129

(2R,3S)-1-((R)-2-(1-Aminoisoquinolin-6-ylamino)-2-(5-ethyl-2-fluoro-3-methoxyphenyl)acetyl)-2-(2-(ethylsulfonyl)phenyl)pyrrolidine-3-carboxylic acid trifluoroacetic acid salt

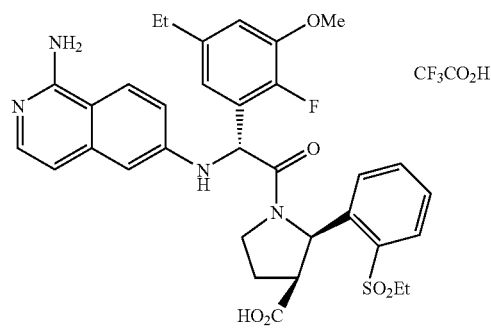

Example 129 was prepared by hydrolysis of the ethyl ester Example 127 using a procedure similar to that used in the preparation of Example 12. $^1$H NMR (400 MHz, Methanol-$d_4$) δ ppm 1.11-1.25 (m, 6H) 2.19-2.43 (m, 2H) 2.49-2.63 (m, 2H) 2.90 (d, J=7.34 Hz, 1H) 3.32-3.54 (m, 2H) 3.65-3.78 (m, 1H) 3.91 (s, 3H) 4.03-4.17 (m, 1H) 5.73 (s, 1H) 6.08 (s, 1H) 6.62 (dd, J=5.38, 1.71 Hz, 1H) 6.73 (d, J=2.20 Hz, 1H) 6.82 (d, J=7.58 Hz, 1H) 6.98-7.07 (m, 2H) 7.14 (dd, J=9.17, 2.32 Hz, 1H) 7.32 (d, J=7.09 Hz, 1H) 7.42-7.57 (m, 2H) 7.96 (dd, J=7.70, 1.59 Hz, 1H) 8.05 (d, J=9.05 Hz, 1H). LC-MS: 635 (M+H)$^+$.

Example 130

Methyl 3-(R)-1-((R)-2-(1-aminoisoquinolin-6-ylamino)-2-(3-(1,1,2,2-tetrafluoroethoxy)phenyl)acetyl)pyrrolidin-2-yl)-4-(ethylsulfonyl)phenylcarbamate trifluoroacetic acid salt

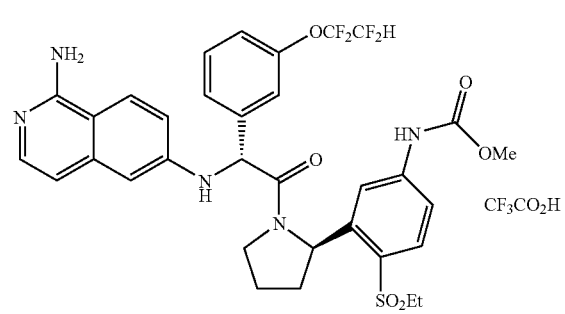

130A: 2-Hydroxy-2-(3-(1,1,2,2-tetrafluoroethoxy) phenyl)acetonitrile

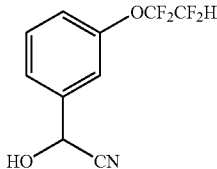

To 3-(1,1,2,2-tetrafluoroethoxy)benzaldehyde (222 mg, 1.0 mmol) in ethyl acetate (5 mL) was added a solution of KCN (195 mg, 3.0 mmol) and NaHSO$_3$ (312 mg, 3.0 mmol) dissolved in H$_2$O (10 mL). The reaction was stirred at rt for 8 h. Another portion of KCN (195 mg, 3.0 mmol) and NaHSO$_3$ (312 mg, 3.0 mmol) dissolved in H$_2$O (10 mL) was added. It was left stirring overnight before it was extracted with ethyl acetate (2×50 mL). The combined organic extracts were dried and concentrated to give 130A as an oil. It was used for next step without purification. $^1$H NMR (400 MHz, CDCl$_3$) δ ppm 5.57 (s, 1H) 5.78-6.04 (m, 1H) 7.28 (d, J=6.15 Hz, 1H) 7.39 (s, 1H) 7.43-7.52 (m, 2H). $^{19}$F NMR (376 MHz, CDCl$_3$) δ ppm −136.72, −88.04.

130B: Methyl 2-hydroxy-2-(3-(1,1,2,2-tetrafluoroethoxy)phenyl)acetate

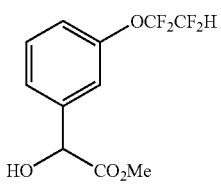

To 130A (249 mg, 1.0 mmol) in anhydrous diethyl ether (4 mL) at 0° C. was added MeOH (0.4 mL, 10 mmol) and 4.0 N HCl in dioxane (2.0 mL, 8 mmol). The mixture was stirred at 0° C. for 30 min and then at rt for 4.0 h. The solvent was removed to give methyl 2-hydroxy-2-(3-(1,1,2,2-tetrafluoroethoxy)phenyl)acetimidate HCl salt. To this salt in CH$_2$Cl$_2$ (4.0 mL) was added H$_2$O (8.0 mL). The mixture was stirred at rt for 30 min, then extracted with CH$_2$Cl$_2$ (2×50 mL). The combined organic extracts were dried and concentrated. The crude product was purified by silica gel chromatography to give 130B (170 mg, 60% yield) as a viscous oil. $^1$H NMR (400 MHz, CDCl$_3$) δ ppm 3.73 (s, 3H) 5.14 (s, 1H) 5.71-6.08 (m, 1H) 7.17 (d, J=7.03 Hz, 1H) 7.28 (s, 1H) 7.31-7.43 (m, 2H).

130C: Methyl 2-(1-di-tert-butoxycarbonylaminoisoquinolin-6-ylamino)-2-(1,1,2,2-tetrafluoroethoxyphenyl)acetic ester

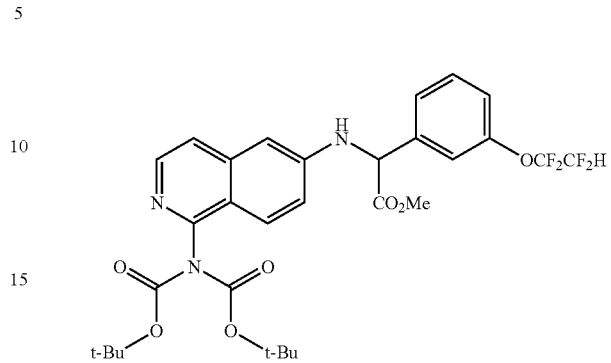

To 130B (160 mg, 0.56 mmol) in CH$_2$Cl$_2$ (2.0 mL) at 0° C. was added trifluoromethanesulfonic anhydride (0.1 mL, 0.56 mmol) and 2,6-lutidine (0.1 mL, 0.9 mmol). The mixture was stirred for 15 min before 1B (203 mg, 0.57 mmol) and 2,6-lutidine (0.2 mL, 0.17 mmol) in CH$_2$Cl$_2$ (2.0 mL) were added. The reaction was left stirring from 0° C. to rt for 3.0 h. It was diluted with ethyl acetate, and washed with 0.5 N HCl (3×20 mL). The organic extract was dried and concentrated. A silica gel chromatography purification (ethyl acetate/hexanes=1/2) gave product 130C (99 mg, 30% yield). $^1$H NMR (400 MHz, CDCl$_3$) δ ppm 1.30 (s, 18H) 3.72 (s, 3H) 5.40 (d, J=6.59 Hz, 1H) 6.07-6.28 (m, 2H) 6.67 (d, J=2.20 Hz, 1H) 7.23 (dd, J=9.23, 2.20 Hz, 2H) 7.35 (d, J=5.27 Hz, 1H) 7.43-7.50 (m, 2H) 7.52-7.57 (m, 1H) 7.67 (d, J=8.79 Hz, 1H) 8.10 (d, J=6.15 Hz, 1H). $^{19}$F NMR (376 MHz, CDCl$_3$) δ ppm −138.29, −88.79.

130D: 2-(1-Di-tert-butoxycarbonylaminoisoquinolin-6-ylamino)-2-(1,1,2,2-tetrafluoroethoxyphenyl)acetic acid

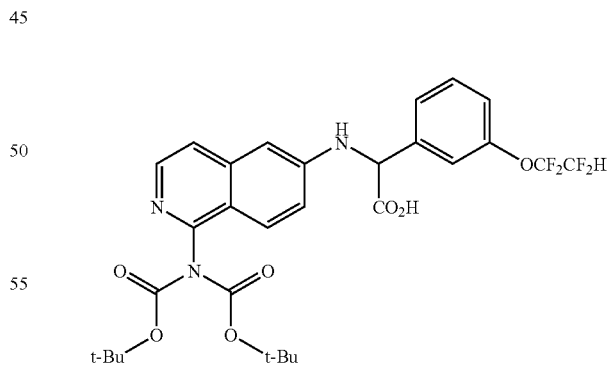

130C (99 mg, 0.16 mmol) was hydrolyzed with NaOH (1.0 N, 0.28 mL, 0.28 mmol) in THF (0.6 mL) and MeOH (0.3 mL) at rt for 1 h. After acidification with 5% KHSO$_4$, it was extracted with ethyl acetate (2×30 mL). The organic extract was dried and concentrated to give a solid product 130D. $^1$H NMR (400 MHz, Methanol-d$_4$) δ ppm 5.38 (s, 1H) 6.10-6.46 (m, 1H) 6.69 (d, J=2.20 Hz, 1H) 7.20 (d, J=9.67 Hz, 1H) 7.33

(dd, J=9.23, 2.20 Hz, 1H) 7.41-7.50 (m, 3H) 7.58 (d, J=7.91 Hz, 1H) 7.67 (d, J=9.23 Hz, 1H) 8.03 (d, J=5.71 Hz, 1H). LC-MS: 610 (M+H)+.

130E: Example 130

Example 130 was prepared according to the general coupling-deprotection using 130D and 100G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.18-1.36 (m, 3H) 1.72 (dd, J=12.96, 5.93 Hz, 1H) 1.98-2.23 (m, 2H) 2.51 (dd, J=12.74, 7.91 Hz, 1H) 3.36-3.51 (m, 2H) 3.54-3.66 (m, 1H) 3.65-3.77 (m, 4H) 4.10-4.27 (m, 1H) 5.65 (s, 1H) 5.70 (dd, J=8.13, 5.49 Hz, 1H) 6.79 (d, J=2.20 Hz, 1H) 6.89 (d, J=7.03 Hz, 1H) 7.08-7.28 (m, 4H) 7.28-7.36 (m, 2H) 7.36-7.50 (m, 2H) 7.76 (d, J=8.79 Hz, 1H) 8.05 (d, J=9.23 Hz, 1H) 9.39 (s, 1H). LC-MS: 704 (M+H)+.

Example 131

Methyl 3-((R)-1-((R)-2-(1-aminoisoquinolin-6-ylamino)-2-(3-(difluoromethoxy)phenyl)acetyl)pyrrolidin-2-yl)-4-(isopropylsulfonyl)phenyl-carbamate trifluoroacetic acid salt

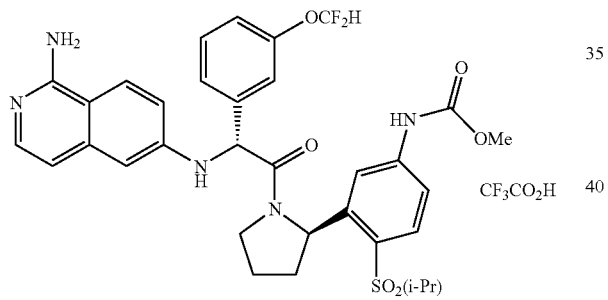

131A: 2-(3-Difluoromethoxyphenyl)-2-hydroxyacetonitrile

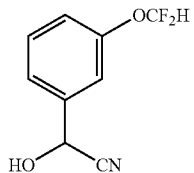

To 3-difluoromethoxybenzaldehyde (1.77 g, 10 mmol) in ethyl acetate (25 mL) was added a solution of KCN (2.0 g) and NaHSO$_3$ (3.2 g) dissolved in H$_2$O (25 mL). It was left stirring overnight before it was extracted with ethyl acetate (2×50 mL). The combined organic extracts were dried and concentrated. The crude product was purified by silica gel chromatography to give 131A (1.85 g, 92% yield) as an oil. $^1$H NMR (400 MHz, CDCl$_3$) δ ppm 5.66 (s, 1H) 6.86 (t, J=73.82 Hz, 1H) 7.18 (dd, J=7.91, 2.20 Hz, 1H) 7.31 (s, 1H) 7.36-7.42 (m, 1H) 7.47 (t, J=7.91 Hz, 1H).

131B: Methyl 2-(3-difluoromethoxyphenyl)-2-hydroxyacetate

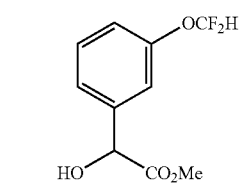

To 131A (1.83 g, 9.2 mmol) in anhydrous CH$_2$Cl$_2$ (30 mL) at 0° C. was added MeOH (2.24 mL) and 4.0 N HCl in dioxane (9.2 mL). The mixture was stirred at 0° C. for 30 min and then at rt for 4.0 h. Solvent was removed to give methyl 2-(3-(difluoromethoxy)-phenyl)-2-hydroxyacetimidate HCl salt. To this salt in CH$_2$Cl$_2$ (10 mL) was added H$_2$O (10 mL). The mixture was stirred at rt for 30 min, then extracted with CH$_2$Cl$_2$ (2×50 mL). The combined organic extracts were dried and concentrated. The crude prouduct was purified by silica gel chromatography to give 131B (700 mg, 33% yield) as a viscous oil. $^1$H NMR (400 MHz, CDCl$_3$) δ ppm 3.70 (s, 3H) 5.22 (s, 1H) 6.82 (t, J=74.04 Hz, 1H) 7.09 (dd, J=7.91, 2.20 Hz, 1H) 7.23 (s, 1H) 7.28-7.34 (m, 1H) 7.38 (t, J=7.91 Hz, 1H).

131C: Methyl 2-(1-di-tert-butoxycarbonylaminoisoquinolin-6-ylamino)-2-(3-difluoromethoxyphenyl) acetic ester

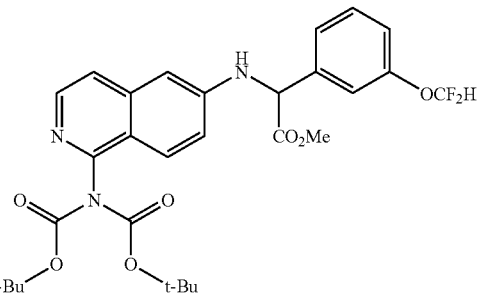

To 131B (650 mg, 2.8 mmol) in CH$_2$Cl$_2$ (10 mL) at 0° C. was added trifluoromethanesulfonic anhydride (0.52 mL) and 2,6-lutidine (0.49 mL). The mixture was stirred for 15 min before 1B (1.0 g, 2.8 mmol) and 2,6-lutidine (0.97 mL) in CH$_2$Cl$_2$ (5.0 mL) were added. The reaction was left stirring from 0° C. to rt for 3.0 h. It was diluted with ethyl acetate, and washed with 0.5 N HCl (3×20 mL). The organic extract was dried and concentrated. A silica gel chromatography purification gave 131C (680 mg, 42% yield). $^1$H NMR (400 MHz, CDCl$_3$) δ ppm 1.27 (s, 18H) 3.76 (s, 3H) 5.44 (s, 1H) 6.56-7.03 (m, 2H) 7.10-7.14 (m, 1H) 7.31 (dd, J=9.23, 2.20 Hz, 1H) 7.35 (s, 1H) 7.41-7.47 (m, 3H) 7.65 (d, J=9.23 Hz, 1H) 8.04 (d, J=6.15 Hz, 1H).

131D: 2-(1-Di-tert-butoxycarbonylaminoisoquinolin-6-ylamino)-2-(3-difluoromethoxyphenyl)acetic acid

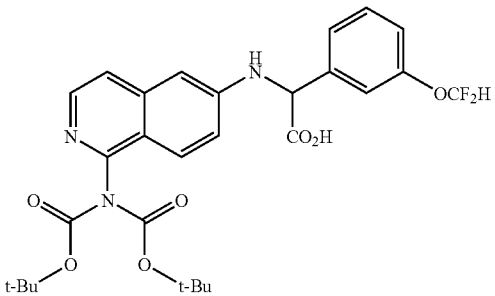

131C (680 mg, 1.2 mmol) was hydrolyzed with NaOH (1.0 N, 1.42 mL, 1.42 mmol) in THF (6 mL) and MeOH (0.5 mL) at rt for 3 h. After acidification with 5% $KHSO_4$, it was extracted with ethyl acetate (2×30 mL). The organic extract was dried and concentrated to give a solid product 131D (650 mg, 96% yield). $^1H$ NMR (400 MHz, Methanol-$d_4$) δ ppm 1.26 (s, 18H) 4.99 (s, 1H) 6.58 (d, J=2.20 Hz, 1H) 6.79 (t, J=74.26 Hz, 1H) 7.01 (dd, J=8.13, 2.42 Hz, 1H) 7.25 (dd, J=8.79, 2.20 Hz, 1H) 7.31-7.40 (m, 3H) 7.47 (d, J=7.91 Hz, 1H) 7.61 (d, J=9.23 Hz, 1H) 7.99 (d, J=5.71 Hz, 1H). LC-MS: 560(M+H)$^+$.

131E: Example 131

Example 131 was prepared according to the general coupling-deprotection using 131D and 44A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1H$ NMR (400 MHz, Methanol-$d_4$) δ ppm 1.17 (d, J=6.57 Hz, 3H) 1.42 (d, J=7.07 Hz, 3H) 1.73 (dd, J=12.76, 5.68 Hz, 1H) 1.96-2.22 (m, 2H) 2.53 (dd, J=13.01, 7.71 Hz, 1H) 3.68-3.83 (m, 4H) 3.87-4.02 (m, 1H) 4.19 (dd, J=6.44, 3.41 Hz, 1H) 5.63 (s, 1H) 5.69 (dd, J=7.96, 5.43 Hz, 1H) 6.71-6.81 (m, 1H) 6.86-6.95 (m, 1H) 7.05-7.25 (m, 5H) 7.27-7.47 (m, 4H) 7.74 (d, J=8.59 Hz, 1H) 8.05 (d, J=9.35 Hz, 1H) 9.35 (s, 1H). LC-MS: 668 (M+H)$^+$.

Example 132

Methyl 3-((R)-1-((R)-2-(3,4-bis(difluoromethoxy)phenyl)-2-(1-aminoisoquinolin-6-ylamino)acetyl)pyrrolidin-2-yl)-4-(isopropylsulfonyl)phenyl-carbamate trifluoroacetic acid salt

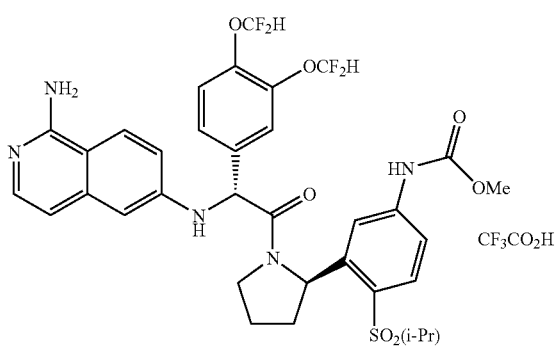

132A: 3,4-Bis(difluoromethoxy)benzaldehyde

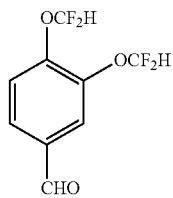

To a solution of 3,4-dihydroxybenzaldehyde (300 mg, 2.2 mmol) in DMF (9.0 mL) and $H_2O$ (1.0 mL) was added sodium chlorodifluoroacetate (1.33 g) and $K_2CO_3$ (729 mg). The mixture was heated up to 100 1C for 2 h before cooling down to rt. Concentrated HCl (1.54 mL) and $H_2O$ (2.0 mL) were added and the reaction was stirred overnight. The mixture was neutralized with 1N NaOH to pH>9, extracted with EtOAc, washed with brine, dried over $MgSO_4$ and concentrated. The crude product was purified by silica gel chromatography to give 132A (470 mg, 90% yield). $^1H$ NMR (400 MHz, $CDCl_3$) δ ppm 6.29-6.89 (m, 2H) 7.42 (d, J=8.35 Hz, 1H) 7.66-7.90 (m, 2H) 9.95 (s, 1H).

132B: 2-(3,4-Bis(difluoromethoxy)phenyl)-2-hydroxyacetonitrile

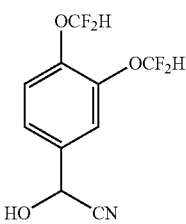

To 132A (470 mg, 2.0 mmol) in ethyl acetate (5 mL) was added a solution of KCN (676 mg) and $NaHSO_3$ (1.08 g) dissolved in $H_2O$ (5 mL). It was left stirring overnight before it was extracted with ethyl acetate (2×50 mL). The combined organic extracts were dried and concentrated. The crude product was purified by silica gel chromatography to give 132B (383 mg, 72% yield) as an oil. $^1H$ NMR (400 MHz, $CDCl_3$) δ ppm 5.56 (d, J=5.27 Hz, 1H) 6.32-6.77 (m, 2H) 7.32-7.36 (m, 1H) 7.40-7.44 (m, 1H) 7.45 (s, 1H).

132C: Methyl 2-(3,4-bis(difluoromethoxy)phenyl)-2-hydroxyacetate

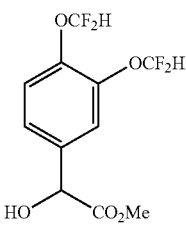

To 132B (308 mg, 1.16 mmol) in anhydrous $CH_2Cl_2$ (5 mL) at 0° C. was added MeOH (0.3 mL) and 4.0 N HCl in dioxane (1.2 mL). The mixture was stirred at 0° C. for 30 min and then at rt for 4.0 h. The solvent was removed to give methyl 2-(3,4-bis(difluoromethoxy)-phenyl)-2-hydroxyacetimidate HCl salt. To this salt in CH$_2$Cl$_2$ (5.0 mL) was added H$_2$O (5.0 mL). The mixture was stirred at rt for 30 min, then extracted with CH$_2$Cl$_2$ (2×50 mL). The combined organic extracts were dried and concentrated. The crude product was purified by silica gel chromatography to give 132C (160 mg, 46% yield) as a viscous oil. $^1$H NMR (400 MHz, CDCl$_3$) δ ppm 3.70 (s, 3H) 5.23 (s, 1H) 6.81 (t, J=73.60 Hz, 2H) 7.26-7.38 (m, 2H) 7.40 (s, 1H).

132D: Methyl 2-(1-di-tert-butoxycarbonylaminoisoquinolin-6-ylamino)-2-(3,4-bis(difluoromethoxy) phenyl)acetic ester

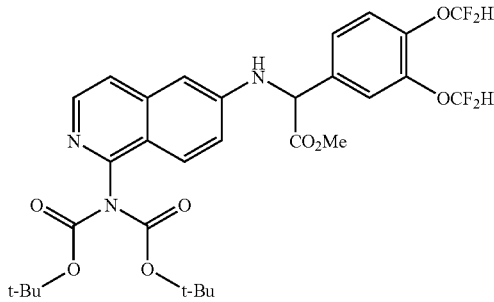

To 132C (120 mg, 0.4 mmol) in CH$_2$Cl$_2$ (2.0 mL) at 0° C. was added trifluoromethanesulfonic anhydride (0.075 mL) and 2,6-lutidine (0.07 mL). The mixture was stirred for 15 min before 1B (144 mg, 0.4 mmol) and 2,6-lutidine (0.14 mL) in CH$_2$Cl$_2$ (1.0 mL) were added. The reaction was left stirring from 0° C. to rt for 3.0 h. It was diluted with ethyl acetate, and washed with 0.5 N HCl (3×20 mL). The organic extract was dried and concentrated. A silica gel chromatography purification gave 132D (120 mg, 47% yield). $^1$H NMR (400 MHz, CDCl$_3$) δ ppm 1.27 (s, 18H) 3.76 (s, 3H) 5.47 (s, 1H) 6.60-7.04 (m, 3H) 7.28-7.35 (m, 2H) 7.45 (d, J=5.71 Hz, 1H) 7.48-7.56 (m, 2H) 7.66 (d, J=9.23 Hz, 1H) 8.05 (d, J=5.71 Hz, 1H).

132E: 2-(1-Di-tert-butoxycarbonylaminoisoquinolin-6-ylamino)-2-(3,4-bis(difluoromethoxy)phenyl)acetic acid

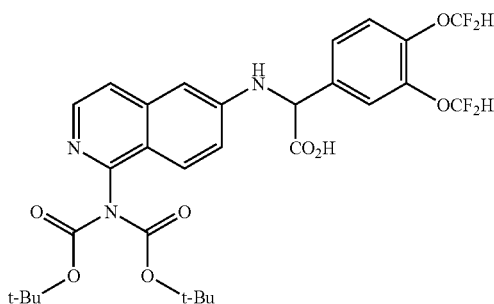

132D (120 mg, 0.19 mmol) was hydrolyzed with NaOH (1.0 N, 0.23 mL, 0.23 mmol) in THF (1 mL) and MeOH (0.3 mL) at rt for 2 h. After acidification with 5% KHSO$_4$, it was extracted with ethyl acetate (2×30 mL). The organic extract was dried and concentrated to give a solid product 132E (102 mg, 87% yield). LC-MS: 626 (M+H)$^+$.

132F: Example 132

Example 132 was prepared according to the general coupling-deprotection using 132E and 44A. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.16 (d, J=6.82 Hz, 3H) 1.41 (d, J=6.82 Hz, 3H) 1.72 (dd, J=12.88, 5.81 Hz, 1H) 1.97-2.22 (m, 2H) 2.52 (dd, J=13.01, 7.71 Hz, 1H) 3.66-3.82 (m, 4H) 3.88-4.01 (m, 1H) 4.11-4.28 (m, 1H) 5.63 (s, 1H) 5.68 (dd, J=7.96, 5.43 Hz, 1H) 6.49-6.84 (m, 3H) 6.86-6.94 (m, 1H) 7.11-7.20 (m, 2H) 7.22 (d, J=1.77 Hz, 1H) 7.24-7.34 (m, 2H) 7.35-7.42 (m, 2H) 7.73 (d, J=8.59 Hz, 1H) 8.05 (d, J=9.09 Hz, 1H) 9.43 (s, 1H). LC-MS: 734 (M+H)$^+$.

Example 133

(2R,3S)-Ethyl 1-(S)-2-(1-aminoisoquinolin-6-ylamino)-2-(5-ethoxy-2-fluoro-4-methoxyphenyl) acetyl)-2-(2-(ethylsulfonyl)phenyl)pyrrolidine-3-carboxylate trifluoroacetic acid salt

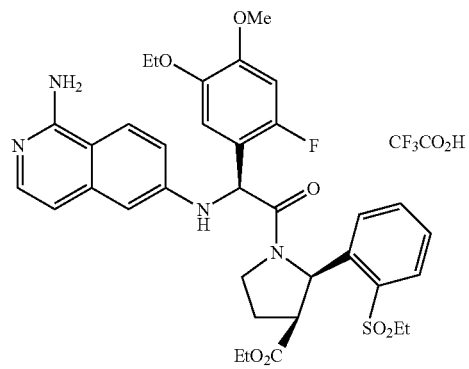

Example 133 was prepared according to the general coupling-deprotection using 64F and 114G. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-d$_4$) δ ppm 1.12 (t, J=7.20 Hz, 3H) 1.24 (t, J=7.33 Hz, 3H) 1.31-1.43 (m, 3H) 2.11 (dd, J=513.52, 6.95 Hz, 1H) 2.41-2.58 (m, 1H) 2.87 (d, J=7.83 Hz, 1H) 3.32-3.39 (m, 1H) 3.39-3.52 (m, 2H) 3.81-3.88 (m, 3H) 3.97-4.19 (m, 4H) 4.25-4.44 (m, 1H) 5.81 (s, 1H) 6.01 (s, 1H) 6.76 (d, J=2.27 Hz, 1H) 6.86-7.01 (m, 3H) 7.06-7.18 (m, 1H) 7.32-7.41 (m, 1H) 7.45-7.56 (m, 1H) 7.63-7.76 (m, 2H) 7.87-7.98 (m, 1H) 7.99-8.10 (m, 1H). LC-MS: 679 (M+H)$^+$.

Example 134

Diastereomer of Example 133

(2R,3S)-Ethyl 1-((R)-2-(1-aminoisoquinolin-6-ylamino)-2-(5-ethoxy-2-fluoro-4-methoxyphenyl)acetyl)-2-(2-(ethylsulfonyl)phenyl)pyrrolidine-3-carboxylate trifluoroacetic acid salt

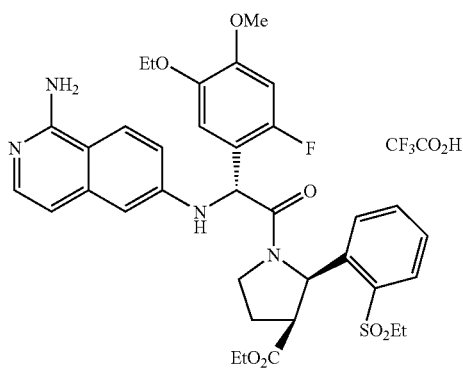

Example 134 was obtained as a diastereomer of Example 133 during its HPLC purification. $^1$H NMR (400 MHz, Methanol-$d_4$) δ ppm 1.16-1.34 (m, 9H) 2.19-2.43 (m, 2H) 2.87-2.98 (m, 1H) 3.36-3.55 (m, 2H) 3.65-3.87 (m, 3H) 3.86-3.91 (m, 3H) 4.05-4.31 (m, 3H) 5.70 (s, 1H) 6.04 (d, J=2.27 Hz, 1H) 6.70 (d, J=7.07 Hz, 1H) 6.75 (d, J=2.27 Hz, 1H) 6.78-6.83 (m, 1H) 6.96 (d, J=11.37 Hz, 1H) 7.03 (d, J=7.07 Hz, 1H) 7.15 (dd, J=9.09, 2.27 Hz, 1H) 7.36 (d, J=7.07 Hz, 1H) 7.41-7.56 (m, 2H) 7.96 (dd, J=7.71, 1.39 Hz, 1H) 8.07 (d, J=9.09 Hz, 1H). LC-MS: 679 (M+H)$^+$.

Example 135

(2R,3S)-1-((R)-2-(1-Aminoisoquinolin-6-ylamino)-2-(5-ethoxy-2-fluorophenyl)acetyl)-2-(2-(ethylsulfonyl)phenyl)pyrrolidine-3-carboxylic acid trifluoroacetic acid salt

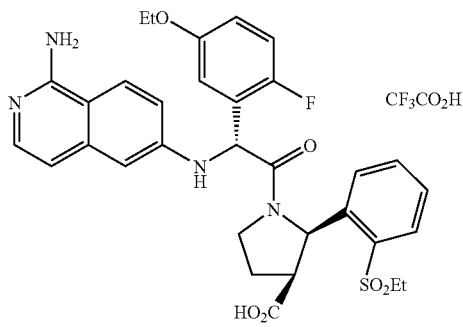

Example 135 was prepared by hydrolysis of the ethyl ester which was prepared according to the general coupling-deprotection using 30A and 114G. The diastereomers were separated by prep HPLC equipped with a C18 Luna column (21× 100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.22 (t, J=7.45 Hz, 3H) 1.26-1.35 (m, 3H) 2.17-2.48 (m, 2H) 2.92 (d, J=7.58 Hz, 1H) 3.36-3.56 (m, 2H) 3.72-3.98 (m, 3H) 4.03-4.20 (m, 1H) 5.75 (s, 1H) 6.10 (s, 1H) 6.72-6.80 (m, 2H) 6.83 (dd, J=7.71, 1.14 Hz, 1H) 6.96-7.07 (m, 2H) 7.11-7.25 (m, 2H) 7.33 (d, J=7.07 Hz, 1H) 7.41-7.59 (m, 2H) 7.97 (dd, J=7.71, 1.39 Hz, 1H) 8.07 (d, J=9.35 Hz, 1H). LC-MS: 621 (M+H)$^+$.

Example 136

(2R,3S)-1-((R)-2-(1-Aminoisoquinolin-6-ylamino)-2-(5-ethoxy-2-fluoro-4-methoxyphenyl)acetyl)-2-(2-(ethylsulfonyl)phenyl)pyrrolidine-3-carboxylic acid trifluoroacetic acid salt

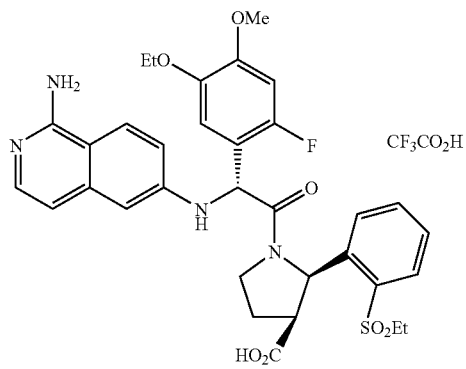

Example 136 was prepared by hydrolysis of the ethyl ester Example 134 using a procedure similar to that used in the preparation of Example 12. $^1$H NMR (400 MHz, Methanol-$d_4$) δ ppm 1.14-1.33 (m, 6H) 2.22-2.48 (m, 2H) 2.91 (d, J=7.58 Hz, 1H) 3.34-3.55 (m, 2H) 3.62-3.87 (m, 3H) 3.86-3.93 (m, 3H) 4.03-4.21 (m, 1H) 5.67 (s, 1H) 6.09 (s, 1H) 6.72 (dd, J=4.67, 2.15 Hz, 2H) 6.76-6.83 (m, 1H) 6.97 (d, J=11.37 Hz, 1H) 7.05 (d, J=7.07 Hz, 1H) 7.14 (dd, J=9.22, 2.40 Hz, 1H) 7.33 (d, J=7.07 Hz, 1H) 7.41-7.58 (m, 2H) 7.97 (dd, J=7.71, 1.39 Hz, 1H) 8.06 (d, J=9.09 Hz, 1H). LC-MS: 651 (M+H)$^+$.

Example 137

Methyl 3-((R)-1-((R)-2-(1-aminoisoquinolin-6-yloxy)-2-(3,4-dimethoxyphenyl)acetyl)pyrrolidin-2-yl)-4-(isopropylsulfonyl)phenylcarbamate-trifluoroacetic acid salt

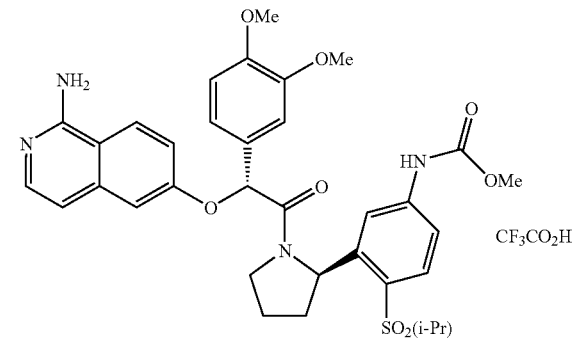

137A: 2-(3,4-Dimethoxyphenyl)-2-hydroxyacetonitrile

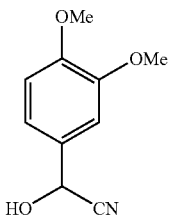

To 3,4-dimethoxybenzaldehyde (1.66 g, 10 mmol) in ethyl acetate (20 mL) was added NaHSO$_3$ (5.2 g, 50 mmol) in water (20 mL), followed by potassium cyanide (3.26 g, 50 mmol) in water (20 mL). The mixture was stirred overnight at rt, then warmed to 50° C. for 6 h. The reaction was cooled to rt, diluted with ethyl acetate, and the layers were separated. The organic layer was washed with brine, dried (Na$_2$SO$_4$), filtered and concentrated. The resulting residue was purified via silica gel chromatography (0-50% ethyl acetate/hexanes) to provide 137A (1.25 g, 65%) and starting material (0.52 mg). LC-MS: 176.22 (M−H$_2$O)$^+$.

137B: Methyl 2-(3,4-dimethoxyphenyl)-2-hydroxyacetate

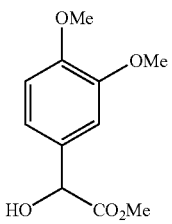

To 137A (1.25 g, 6.48 mmol) in ether (20 mL) and MeOH (1.5 mL) at −10° C. was added 4N HCl in dioxane (6 mL, 24 mmol). The reaction was stirred at −10C for 1 h, then stored at 4° C. for 2 days. The reaction was filtered, and washed with ether. The solid was dissolved in water (15 mL) and CH$_2$Cl$_2$ (15 mL) and stirred for 1 h. The layers were separated, and the aqueous layer was extracted with CH$_2$Cl$_2$ (3×20 mL), dried (Na$_2$SO$_4$), filtered and concentrated. The resulting residue was purified via silica gel chromatography (0-60% ethyl acetate/hexanes) to provide 137B (1.35 g, 92%). LC-MS: 249.16 (M+Na)$^+$.

137C: 2-(3,4-Dimethoxyphenyl)-2-hydroxyacetic acid

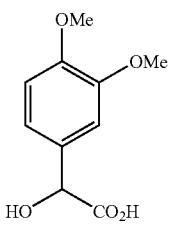

137B (890 mg, 3.9 mmol) was dissolved in THF (6 mL). 1M LiOH (6 mL) was added, and the reaction was stirred at rt for 1 h. The solvent was removed under reduced pressure, and water (10 mL) was added. The solution was acidified with 1 N HCl, then extracted with ethyl acetate (3×20 mL). The organic layer was concentrated to provide 137C (830 mg, 100%). LC-MS: 235.11 (M+Na)$^+$.

137D: Benzyl 2-(3,4-dimethoxyphenyl)-2-hydroxyacetate

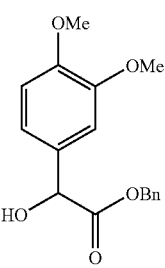

To 137C (830 mg, 3.9 mmol) in DMF (15 mL) was added cesium carbonate (2.6 g, 8.0 mmol) followed by benzyl bromide (0.6 mL, 5 mmol). After stirring at rt overnight, the reaction was diluted with water, and was extracted with ethyl acetate (2×30 mL). The organic layer was washed with brine, dried (Na$_2$SO$_4$), filtered and concentrated. The resulting residue was purified via silica gel chromatography (0-40% ethyl acetate/hexanes) to provide 137D (520 mg, 44%). LC-MS: 445.31 (M+H)$^+$.

137E: Benzyl 2-chloro-2-(3,4-dimethoxyphenyl)acetate

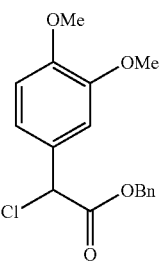

To 137D (450 mg, 1.5 mmol) in CH$_2$Cl$_2$ (5 mL) at 0° C. was added triethylamine (0.42 mL, 3.0 mmol) followed by mesyl chloride (0.14 mL, 1.8 mmol). After stirring at rt overnight, the reaction was concentrated and purified via silica gel chromatography (0-25% ethyl acetate/hexanes) to provide 137E (268 mg, 56%). $^1$H NMR (400 MHz, Methanol-d$_4$) δ ppm 3.81 (s, 3H) 3.87 (s, 3H) 5.19 (m, 2H) 5.36 (s, 1H) 6.81 (d, J=8.35 Hz, 1H) 6.93-7.07 (m, 2H) 7.20-7.42 (m, 5H).

137F: Benzyl 2-(1-aminoisoquinolin-6-yloxy)-2-(3,4-dimethoxyphenyl)acetate trifluoroacetic acid salt

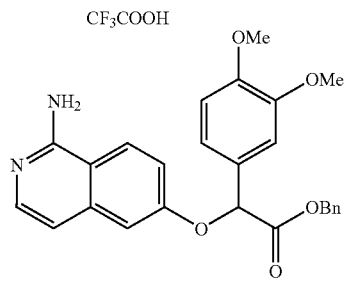

A mixture of 83G (30 mg, 0.19 mmol) in DMF (1 mL) and 60% NaH (10 mg, 0.25 mmol) was stirred for 10 min. To this mixture was added 137E (80 mg, 0.25 mmol) in DMF (1 mL). After stirring for 1 h, the reaction was diluted with ethyl acetate, washed with water and brine then dried ($Na_2SO_4$), filtered and concentrated. The resulting residue was purified via preparative HPLC (MeOH/water/TFA) to provide 137F (60 mg, 69%). LC-MS: 445.31 $(M+H)^+$.

137G: 2-(1-Aminoisoquinolin-6-yloxy)-2-(3,4-dimethoxyphenyl)acetic acid

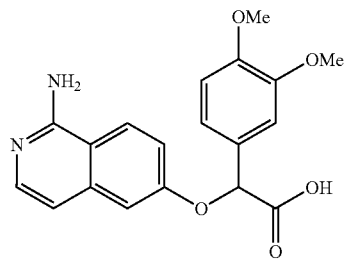

137F (130 mg, 0.29 mmol) was dissolved in THF (8 mL). To this solution was added 10% Pd/C (cat.), and the mixture was hydrogenated at 50 psi for 16 h. The reaction was filtered and concentrated to provide 2-(1-aminoisoquinolin-6-yloxy)-2-(3,4-dimethoxyphenyl)acetic acid (113 mg, 10%). LC-MS: 355.19 $(M+H)^+$

137H: Example 137

Example 137 was prepared from 137G (35 mg, 0.10 mmol) and 44A (36 mg, 1.0 mmol) following a procedure analogous to that used in the preparation of Example 83 (Example 137 was the first compound to elute, 11.3 mg, 15%); $^1$H NMR (400 MHz, $CD_3OD$) δ ppm 1.13 (d, J=6.59 Hz, 3H) 1.37 (d, J=6.59 Hz, 3H) 1.71 (m, 1H) 1.97-2.21 (m, 2H) 2.51 (m, 1H) 3.68 (s, 3H) 3.70 (s, 3H) 3.79-3.87 (m, 2H) 3.87 (s, 3H) 4.11-4.25 (m, 1H) 5.71 (dd, J=7.91, 4.83 Hz, 1H) 6.21 (s, 1H) 6.98 (dd, J=5.05, 3.30 Hz, 2H) 7.06-7.15 (m, 3H) 7.19 (dd, J=8.79, 2.20 Hz, 1H) 7.27 (d, J=2.20 Hz, 1H) 7.39 (dd, J=9.23, 2.64 Hz, 1H) 7.49 (d, J=7.47 Hz, 1H) 7.73 (d, J=8.79 Hz, 1H) 8.32 (d, J=9.23 Hz, 1H) 9.39 (s, 1H); LC-MS: 663.42 $(M+H)^+$.

Example 138

Diastereomer of Example 137

Methyl 3-((R)-1-((S)-2-(1-aminoisoquinolin-6-yloxy)-2-(3,4-dimethoxyphenyl)acetyl)-pyrrolidin-2-yl)-4-(isopropylsulfonyl)phenylcarbamate trifluoroacetic acid salt

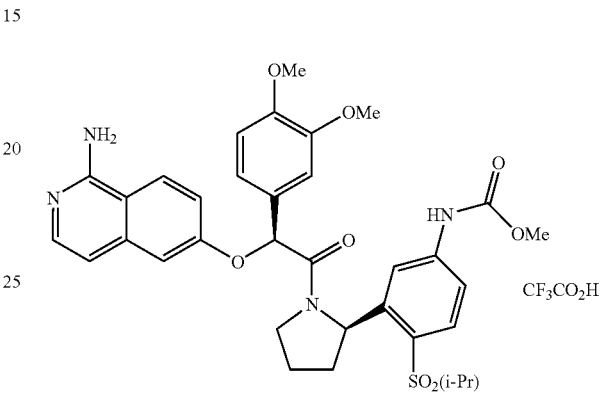

Example 138 was obtained as a diastereomer of Example 137 during its HPLC purification (Example 138 was the second compound to elute, 11.8 mg, 16%); $^1$H NMR (400 MHz, $CD_3OD$) δ ppm 1.08 (d, J=6.59 Hz, 3H) 1.40 (d, J=7.03 Hz, 3H) 1.67-1.80 (m, 1H) 1.82-1.94 (m, 2H) 2.06-2.23 (m, 1H) 2.25-2.39 (m, 1H) 3.47-3.62 (m, 1H) 3.83 (s, 3H) 3.84 (s, 3H) 3.86 (s, 3H) 4.10-4.21 (m, 1H) 5.65 (dd, J=8.35, 3.52 Hz, 1H) 6.27 (s, 1H) 7.01-7.05 (m, 2H) 7.13-7.21 (m, 3H) 7.29-7.35 (m, 1H) 7.39 (dd, J=9.23, 2.64 Hz, 1H) 7.43 (d, J=7.03 Hz, 1H) 7.70-7.78 (m, 1H) 7.88 (s, 1H) 8.26 (d, J=9.23 Hz, 1H); LC-MS: 663.42 $(M+H)^+$.

Example 139

Methyl 3-((R)-1-((R)-2-(1-aminoisoquinolin-6-yloxy)-2-(2-fluoro-4,5-dimethoxyphenyl)acetyl)pyrrolidin-2-yl)-4-(isopropylsulfonyl)phenylcarbamate trifluoroacetic acid salt

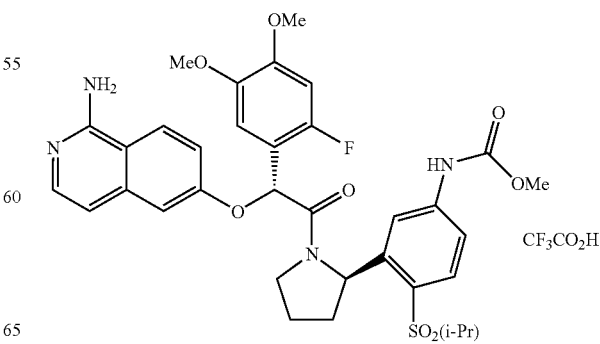

139A: Methyl 2-(2-fluoro-4,5-dimethoxyphenyl)-2-hydroxyacetate

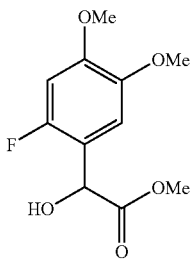

139A (1.05 g, 44%) was prepared in 2 steps from 2-fluoro-4,5-dimethoxybenzaldehyde following procedures analogous to those used in the preparation of 137B. LC-MS: 267.11 (M+Na)⁺.

139B: Methyl 2-chloro-2-(2-fluoro-4,5-dimethoxyphenyl)acetate

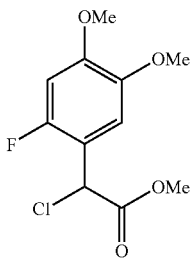

To 139A (280 mg, 1.2 mmol) in CH₂Cl₂ (5 mL) at 0° C. was added triethylamine (0.42 mL, 3.0 mmol) followed by mesyl chloride (0.12 mL, 1.5 mmol). After stirring at rt overnight, the reaction was filtered, concentrated and purified via silica gel chromatography (0-30% ethyl acetate/hexanes) to provide 139B (268 mg, 89%).

139C: Methyl 2-(1-aminoisoquinolin-6-yloxy)-2-(2-fluoro-4,5-dimethoxyphenyl)-acetate trifluoroacetic acid salt

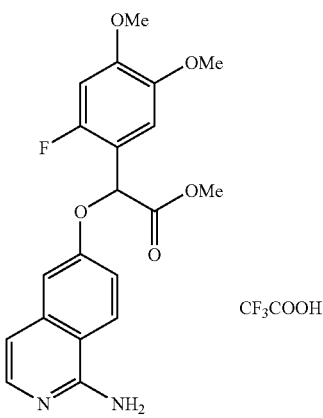

A mixture of 83G (32 mg, 0.20 mmol) in DMF (1 mL) and 60% NaH (10 mg, 0.25 mmol) was stirred for 10 min. To this mixture was added 139B (58 mg, 0.22 mmol) in DMF (0.7 mL). After stirring for 1 h, the reaction was filtered, concentrated and purified via preparative HPLC (MeOH/water/TFA) to provide 139C (80 mg, 80%). LC-MS: 387.21 (M+H)⁺.

139D: 2-(1-Aminoisoquinolin-6-yloxy)-2-(2-fluoro-4,5-dimethoxyphenyl)acetic acid trifluoroacetic acid salt

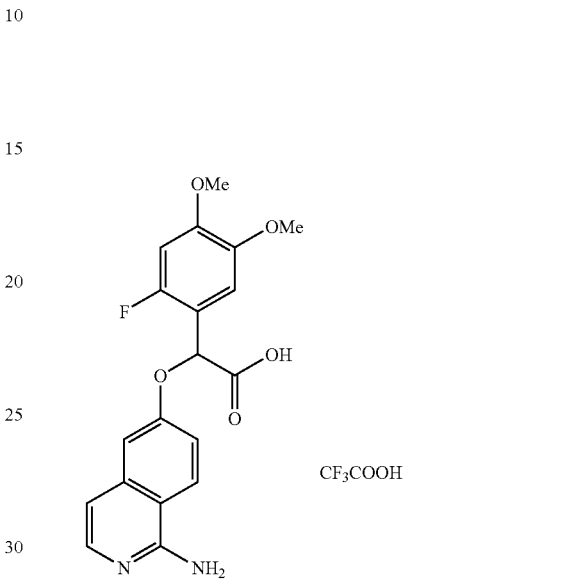

139C (80 mg, 0.21 mmol) was dissolved in THF (2 mL). 1M LiOH (0.4 mL) was added, and the reaction was stirred at rt for 0.5 h. Additional 1M LiOH was added (0.4 mL) and the reaction was stirred for 3 h. The solvent was removed under reduced pressure, and water (10 mL) was added. The solution was acidified with 1 N HCl, then purified via preparative HPLC (MeOH/water/TFA) to provide 139D (65 mg, 64%). LC-MS: 373.18 (M+H)⁺

139E: Example 139

Example 139 was prepared from 139D (50 mg, 0.10 mmol) and 44A (36 mg, 1.0 mmol) following a procedure analogous to that used in the preparation of Example 83 (Example 139 was the first compound to elute, 20.6 mg, 26%); ¹H NMR (400 MHz, CD₃OD) δ ppm 1.13 (d, J=6.59 Hz, 3H) 1.37 (d, J=7.03 Hz, 3H) 1.73 (dd, J=12.74, 5.71 Hz, 1H) 1.96-2.21 (m, 2H) 2.40-2.61 (m, 1H) 3.52 (s, 3H) 3.70 (s, 3H) 3.73-3.86 (m, 2H) 3.88 (s, 3H) 4.17-4.31 (m, 1H) 5.72 (dd, J=8.13, 5.05 Hz, 1H) 6.50 (s, 1H) 6.65 (d, J=6.59 Hz, 1H) 6.93 (d, J=11.42 Hz, 1H) 7.11-7.22 (m, 2H) 7.25 (s, 1H) 7.33 (d, J=2.20 Hz, 1H) 7.39 (dd, J=9.23, 2.64 Hz, 1H) 7.50 (d, J=7.03 Hz, 1H) 7.75 (d, J=8.79 Hz, 1H) 8.32 (d, J=9.23 Hz, 1H) 9.52 (s, 1H); LC-MS: 681.45 (M+H)⁺.

Example 140

Diastereomer of Example 139

Methyl 3-((R)-1-((S)-2-(1-aminoisoquinolin-6-yloxy)-2-(2-fluoro-4,5-dimethoxyphenyl)acetyl)pyrrolidin-2-yl)-4-(isopropylsulfonyl)phenylcarbamate trifluoroacetic acid salt

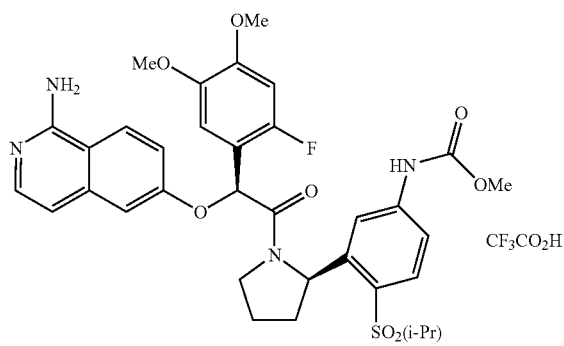

Example 140 was obtained as a diastereomer of Example 139 during its HPLC purification (Example 140 was the second compound to elute). (11.6 mg, 15%); $^1$H NMR (400 MHz, CD$_3$OD) δ ppm 1.09 (t, J=6.81 Hz, 3H) 1.39 (d, J=6.59 Hz, 3H) 1.70-1.83 (m, 1H) 1.85-2.00 (m, 2H) 2.12-2.25 (m, 1H) 2.29-2.45 (m, 1H) 3.42-3.52 (m, 1H) 3.78 (s, 3H) 3.84 (s, 3H) 3.86 (s, 3H) 4.11-4.25 (m, 1H) 5.67 (dd, J=8.35, 3.52 Hz, 1H) 6.50 (s, 1H) 6.93 (d, J=11.42 Hz, 1H) 7.01 (dd, J=13.18, 7.03 Hz, 2H) 7.19 (d, J=2.20 Hz, 1H) 7.33-7.42 (m, 2H) 7.44 (d, J=7.47 Hz, 1H) 7.76 (d, J=8.79 Hz, 1H) 7.91 (s, 1H) 8.27 (d, J=9.23 Hz, 1H); LC-MS: 681.42 (M+H)$^+$.

Example 141

Methyl 3-((R)-1-((R)-2-(4-carbamimidoylphenylamino)-2-(3-ethoxy-4-isopropoxyphenyl)acetyl)pyrrolidin-2-yl)-4-(isopropylsulfonyl)phenylcarbamate

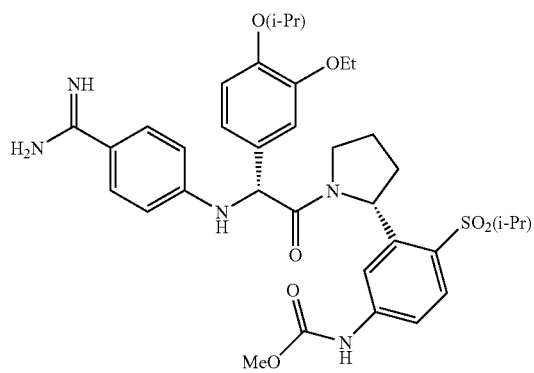

141A: 3-Ethoxy-4-isopropoxybenzaldehyde

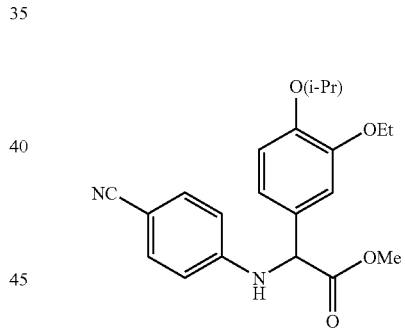

To 3-ethoxy-4-hydroxybenzaldehyde (20.0 g, 120 mmol) in dimethylformamide (250 mL) was added potassium carbonate (33.1 g, 240 mmol) then 2-iodopropane (18 mL, 180 mmol). The reaction mixture was heated to 45° C. and stirred for 3 h. After cooling to rt, the crude reaction mixture was extracted with ethyl acetate (3×). The combined extracts were then washed with water (3×) then brine and dried over sodium sulfate. The solvent was removed to give 24 g of 141A as a yellow oil. LC-MS: 231.17 (M+Na)$^+$.

141B: Methyl 2-(4-cyanophenylamino)-2-(3-ethoxy-4-isopropoxyphenyl)acetate

A solution of 141A (7.42 g, 35:6 mmol) and 4-cyanoaniline (4.21 g, 35.6 mmol) in methanol (120 mL) was stirred at 60° C. for 2 h. The reaction was cooled to 0° C. and p-toluenesulfonylmethyl isocyanide (6.95 g, 35.6 mmol) was added followed by dropwise addition of boron trifluoride etherate (13.5 mL, 107 mmol). After stirring for 30 min at 0° C., the reaction was allowed to warm to rt and stirring was continued for 2 h. Water (4 mL) was added and bright yellow precipitate was observed after stirring for 2 days. The solvent was removed and the residue was redissolved in ethyl acetate. The precipitate was filtered and dried to give 7.89 g of 141B as a white solid. $^1$H NMR (400 MHz, Methanol-d$_4$) δ ppm 1.18-1.20 (m, 6H) 1.28 (t, J=6.98, 3H) 3.62 (s, 3H) 3.90-3.98 (m, 2H) 4.40-4.50 (m, 1H) 5.06 (s, 1H) 6.59 (d, J=8.90 Hz, 2H) 6.80-7.00 (m, 3H) 7.29 (d, J=8.90 Hz, 2H).

141C: Methyl 2-(4-(N-(hydroxycarbamimidoyl)phenylamino)-2-(3-ethoxy-4-isopropoxyphenyl)acetate

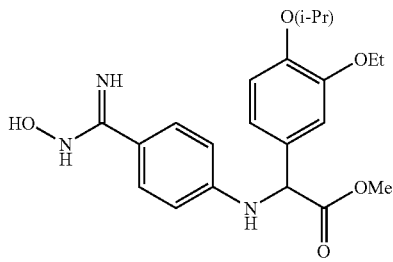

To hydroxylamine hydrogen chloride salt (5.16 g, 74.3 mmol) in dimethylsulfoxide was added triethylamine (10.3 mL, 74.3 mmol) and the reaction was stirred for 10 min at rt under nitrogen. The salt was filtered and the filtrate was added directly to 141B (7.8 g, 21.2 mmol) in dimethylsulfoxide. After heating to 70° C. overnight with stirring, the solvent was distilled. The resulting residue was diluted with ethyl acetate and washed with sodium bicarbonate, brine and dried over sodium sulfate. The solvent was removed to give 6.0 g of 141C as a white foamy solid. LC-MS: 402.08 (M+H)$^+$.

141D: Methyl 2-(4-carbamimidoylphenylamino)-2-(3-ethoxy-4-isopropoxyphenyl)-acetate

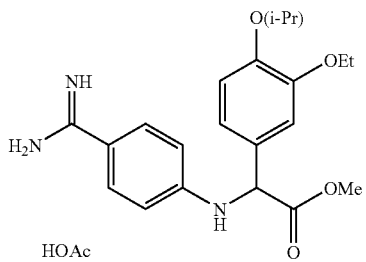

To 141C (6.0 g, 14.9 mmol) in acetic acid (100 mL) was added acetic anhydride (1.6 mL, 17.2 mmol) followed by palladium on carbon (0.6 g) under nitrogen. Hydrogen gas was introduced using a balloon and the reaction was stirred at rt for 4 h. The catalyst was filtered carefully over celite and washed with methanol. The filtrate and washings were combined and concentrated, and the residue was dried under vacuum to give 6.7 g of 141D as a brown solid. LC-MS: 386.09 (M+H)$^+$.

141E: Methyl 2-(4-(N-(benzyloxycarbonyl)carbamimidoyl)phenylamino)-2-(3-ethoxy-4-isopropoxyphenyl)acetate

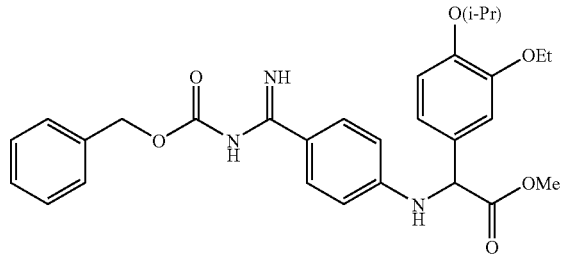

To 141D (6.7 g; 13.25 mmol) in dichloromethane (80 mL) was added sodium bicarbonate (132 mL, 1 M). Benzyl chloroformate (1.89 mL, 13.25 mmol) in dichloromethane (20 mL) was then added dropwise using an addition funnel over a period of 1 h. After the addition was complete, the suspension turned to a clear orange solution. The layers were separated and the organic layer was washed with brine and dried over sodium sulfate. The solvent was removed and the crude residue was purified by flash column chromatography to give 4.6 g of 141E as a yellow solid (69% yield). LC-MS: 520.10 (M+H)$^+$.

141F: (R)-2-(4-(N-(Benzyloxycarbonyl)carbamimidoyl)phenylamino)-2-(3-ethoxy-4-isopropoxyphenyl)acetic acid

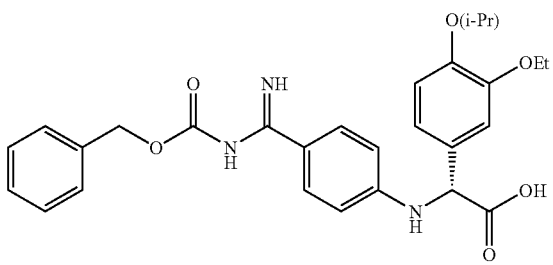

To 141E (4.64 g, 8.9 mmol) in THF (20 mL) was added lithium hydroxide (17.8 mL, 1M, 17.8 mmol) then methanol (5 mL). After stirring for 2 h at rt, the reaction was concentrated and redissolved in ethyl acetate. The aqueous layer was neutralized and acidified to pH 3-4 using 10% citric acid. The product was extracted with ethyl acetate (3×) and washed with brine and dried over sodium sulfate. The solvent was removed to give 3.6 g of 2-(4-(N-(benzyloxycarbonyl)carbamimidoyl)phenylamino)-2-(3-ethoxy-4-isopropoxyphenyl)acetic acid as a yellow solid (80% yield). LC-MS: 506.11 (M+H)$^+$. The enantiomers were separated using a semi-preparative HPLC equipped with an Astex Chirobiotic T column (20 mm×500 mm). The separation was performed using an isocratic method of methanol with 0.1% triethylamine plus 0.2% acetic acid to provide 141F.

141G: [3-{(R)-1-[(R)-2-[4-(Benzyloxycarbonylamino-imino-methyl)-phenylamino]-2-(3-ethoxy-4-isopropoxy-phenyl)-acetyl]-pyrrolidin-2-yl}-4-(propane-2-sulfonyl)-phenyl]-carbamic acid methyl ester

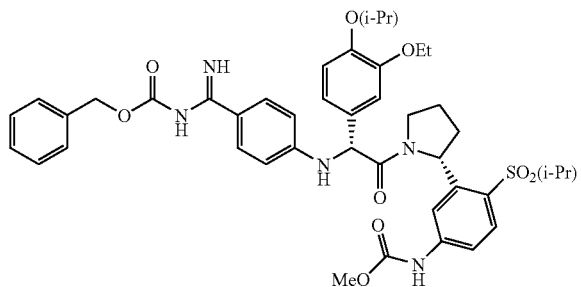

141G was prepared according to the general coupling-deprotection using 141F and 44A. LC-MS: 814.39 (M+H)$^+$.

141H: Example 141

To palladium on carbon (0.05 g) was added 141G (0.08 g, 0.099 mmol) in methanol (5 mL) under nitrogen. Hydrogen gas was introduced using a balloon and the reaction was stirred at rt for 2 h. The catalyst was filtered carefully over celite and washed with methanol. The filtrate and washings were combined and the residue was dried under vacuum and purified to give 22 mg of Example 141 as a white amorphous solid. The final product was purified using a preparative HPLC equipped with C18 Luna column (30×100 mm, 5μ). The separations were performed using a linear gradient (mobile phase A: 10% MeOH-90% water-0.1% TFA; mobile phase B: 90% MeOH-10% water-0.1% TFA; 30 to 90% B in 10 min, then 90% B for 2 min) with a flow rate of 40 mL/min. $^1$H NMR (400 MHz, Methanol-$d_4$) δ ppm 1.10-1.22 (m, 3H) 1.25-1.36 (m, 9H) 1.36-1.49 (m, 3H) 1.62-1.82 (m, 1H) 1.89-2.20 (m, 2H) 2.37-2.58 (m, 1H) 3.61-3.98 (m, 7H) 3.99-4.22 (m, 1H) 4.43-4.61 (m, 1H) 5.39 (s, 1H) 5.67 (dd, J=8.19, 4.77 Hz, 1H) 6.70-6.81 (m, 2H) 6.83 (d, J=1.96 Hz, 1H) 6.87-7.02 (m, 2H) 7.17 (d, J=1.96 Hz, 1H) 7.23 (dd, J=8.56, 2.20 Hz, 1H) 7.52-7.64 (m, 2H) 7.75 (d, J=8.56 Hz, 1H) 9.37 (s, 1H). LC-MS: 680.38 (M+H)$^+$.

Example 142

(2R,3S)-Ethyl 1-((S)-2-(1-aminoisoquinolin-6-ylamino)-2-(4-chloro-3-ethoxyphenyl)acetyl)-2-(2-(ethylsulfonyl)phenyl)pyrrolidine-3-carboxylate trifluoroacetic acid salt

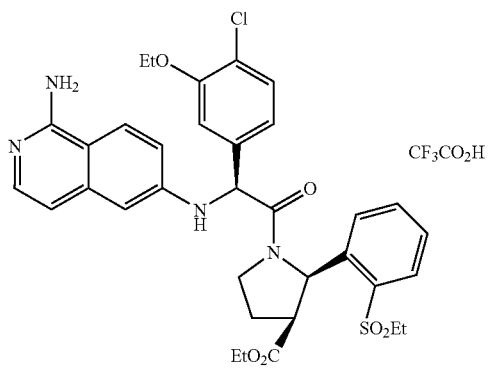

Example 142 was prepared according to the general coupling-deprotection using 31C and 114G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.04-1.52 (m, 9H) 2.15 (dd, J=13.52, 6.69 Hz, 1H) 2.45-2.63 (m, 1H) 2.88 (d, J=8.08 Hz, 1H) 3.34-3.53 (m, 3H) 4.02-4.12 (m, 2H) 4.14-4.28 (m, 2H) 4.38 (d, J=10.36 Hz, 1H) 5.65 (s, 1H) 6.03 (s, 1H) 6.76 (d, J=2.27 Hz, 1H) 6.96-7.04 (m, 1H) 7.06-7.17 (m, 2H) 7.22 (d, J=1.77 Hz, 1H) 7.38 (d, J=7.07 Hz, 1H) 7.41-7.56 (m, 2H) 7.63-7.77 (m, 2H) 7.94 (dd, J=7.83, 1.01 Hz, 1H) 8.03 (d, J=9.35 Hz, 1H). LC-MS 665 (M+H).

Example 143

Diastereomer of Example 142

(2R,3S)-Ethyl 1-((R)-2-(1-aminoisoquinolin-6-ylamino)-2-(4-chloro-3-ethoxyphenyl)acetyl)-2-(2-(ethylsulfonyl)phenyl)pyrrolidine-3-carboxylate trifluoroacetic acid salt

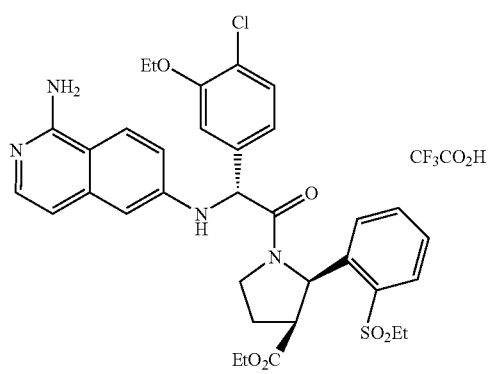

Example 143 was obtained as a diastereomer of Example 142 during its HPLC purification. $^1$H NMR (400 MHz, Methanol-$d_4$) δ ppm 1.11-1.40 (m, 9H) 2.16-2.44 (m, 2H) 2.86-2.95 (m, 1H) 3.32-3.53 (m, 2H) 3.74-3.97 (m, 2H) 3.97-4.09 (m, 1H) 4.09-4.33 (m, 3H) 5.51 (s, 1H) 6.03 (d, J=2.02 Hz, 1H) 6.70-6.78 (m, 2H) 7.01-7.19 (m, 4H) 7.35 (d, J=7.07 Hz, 1H) 7.40-7.55 (m, 3H) 7.94 (dd, J=7.83, 1.26 Hz, 1H) 8.06 (d, J=9.09 Hz, 1H), LC-MS 665 (M+H).

Example 144

(2R,3S)-Ethyl 1-((R)-2-(1-aminoisoquinolin-6-ylamino)-2-(4-fluoro-3-methoxyphenyl)acetyl)-2-(2-(ethylsulfonyl)phenyl)pyrrolidine-3-carboxylate trifluoroacetic acid salt

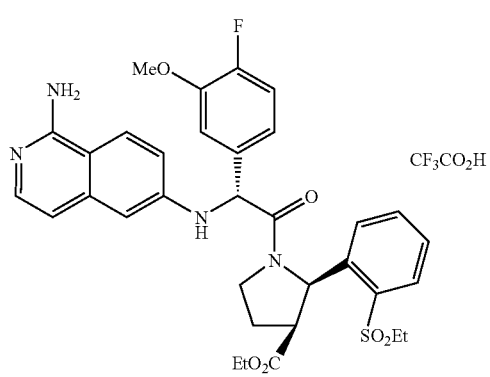

Example 144 was prepared according to the general coupling-deprotection using 23D and 114G. The diastereomers were separated by prep HPLC equipped with a C18 Luna column (21×100 mm, 5μ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$)

δ ppm 1.19 (t, J=7.33 Hz, 3H) 1.27 (t, J=7.20 Hz, 3H) 2.15-2.45 (m, 2H) 2.87-2.96 (m, 1H) 3.32-3.54 (m, 2H) 3.76 (s, 3H) 3.78-3.88 (m, 1H) 4.07-4.32 (m, 3H) 5.51 (s, 1H) 6.04 (d, J=1.77 Hz, 1H) 6.70-6.79 (m, 2H) 7.01-7.24 (m, 5H) 7.35 (d, J=7.07 Hz, 1H) 7.41-7.57 (m, 2H) 7.94 (dd, J=7.58, 1.52 Hz, 1H) 8.06 (d, J=9.09 Hz, 1H), LC-MS 635 (M+H).

Example 145

Diastereomer of Example 144

(2R,3S)-Ethyl 1-((S)-2-(1-aminoisoquinolin-6-ylamino)-2-(4-fluoro-3-methoxyphenyl)acetyl)-2-(2-(ethylsulfonyl)phenyl)pyrrolidine-3-carboxylate trifluoroacetic acid salt

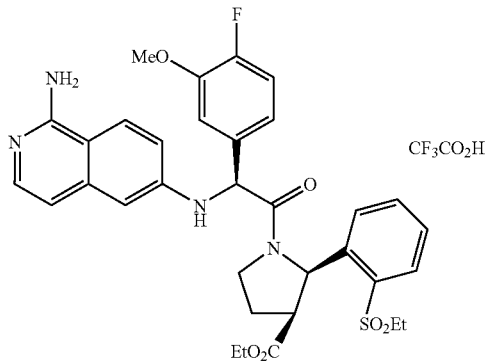

Example 145 was obtained as a diastereomer of Example 144 during its HPLC purification. $^1$H NMR (400 MHz, Methanol-$d_4$) δ ppm 1.02-1.39 (m, 6H) 2.04-2.19 (m, 1H) 2.44-2.60 (m, 1H) 2.88 (d, J=7.83 Hz, 1H) 3.33-3.51 (m, 3H) 3.94 (s, 3H) 4.07 (dd, J=7.07, 2.02 Hz, 2H) 4.29-4.44 (m, 1H) 5.64 (s, 1H) 6.03 (s, 1H) 6.74 (d, J=2.27 Hz, 1H) 7.00 (d, J=7.07 Hz, 1H) 7.04-7.30 (m, 4H) 7.37 (d, J=7.07 Hz, 1H) 7.50 (d, J=8.08 Hz, 1H) 7.63-7.76 (m, 2H) 7.93 (d, J=7.58 Hz, 1H) 8.01 (d, J=9.09 Hz, 1H), LC-MS 635 (M+H).

Example 146

(2R,3S)-Ethyl 1-((S)-2-(1-aminoisoquinolin-6-ylamino)-2-(3-ethoxy-4-fluorophenyl)acetyl)-2-(2-(ethylsulfonyl)phenyl)pyrrolidine-3-carboxylate trifluoroacetic acid salt

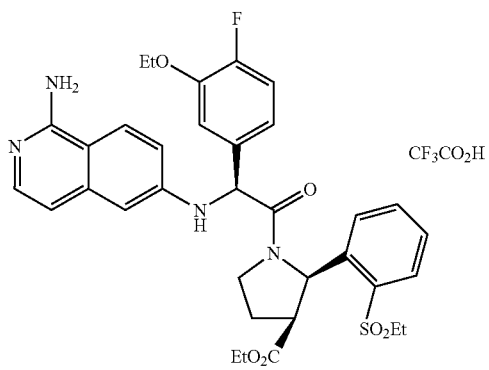

Example 146 was prepared according to the general coupling-deprotection using 32C and 114G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.07-1.51 (m, 9H) 2.05-2.66 (m, 2H) 2.83-2.94 (m, 1H) 3.33-3.55 (m, 3H) 3.87-4.45 (m, 5H) 5.62 (s, 1H) 6.02 (s, 1H) 6.74 (d, J=2.27 Hz, 1H) 6.99 (d, J=7.07 Hz, 1H) 7.06-7.30 (m, 4H) 7.37 (d, J=7.07 Hz, 1H) 7.37 (d, J=7.07 Hz, 1H) 7.44-7.55 (m, 1H) 7.61-7.78 (m, 2H) 7.89-7.96 (m, 1H) 8.01 (d, J=9.09 Hz, 1H), LC-MS 649 (M+H).

Example 147

Diastereomer of Example 146

(2R,3S)-Ethyl 1-((R)-2-(1-aminoisoquinolin-6-ylamino)-2-(3-ethoxy-4-fluorophenyl)acetyl)-2-(2-(ethylsulfonyl)phenyl)pyrrolidine-3-carboxylate trifluoroacetic acid salt

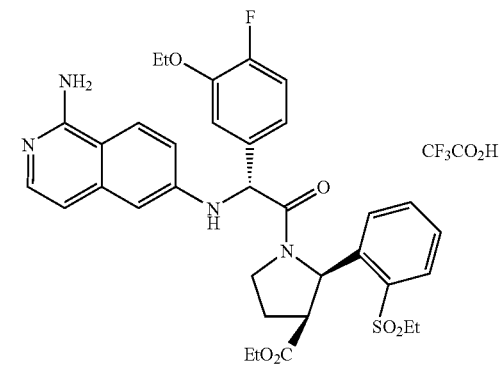

Example 147 was obtained as a diastereomer of Example 146 during its HPLC purification. $^1$H NMR (400 MHz, Methanol-$d_4$) δ ppm 1.20 (t, J=7.33 Hz, 3H) 1.28 (t, J=7.07 Hz, 3H) 1.35 (t, J=7.07 Hz, 3H) 2.13-2.45 (m, 2H) 2.85-2.96 (m, 1H) 3.32-3.56 (m, 2H) 3.75-4.33 (m, 6H) 5.50 (s, 1H) 6.04 (s, 1H) 6.68-6.78 (m, 2H) 7.00-7.25 (m, 5H) 7.36 (d, J=7.07 Hz, 1H) 7.40-7.59 (m, 2H) 7.95 (d, J=7.83 Hz, 1H) 8.07 (d, J=9.35 Hz, 1H), LC-MS 649 (M+H).

Example 148

(2R,3S)-1-((R)-2-(1-Aminoisoquinolin-6-ylamino)-2-(4-chloro-3-ethoxyphenyl)acetyl)-2-(2-(ethylsulfonyl)phenyl)pyrrolidine-3-carboxylic acid trifluoroacetic acid salt

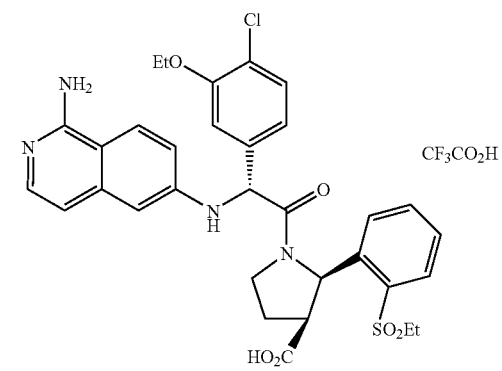

Example 148 was prepared by hydrolysis of the ethyl ester Example 143 using a procedure similar to that used in the preparation of Example 12. ¹H NMR (400 MHz, Methanol-d₄) δ ppm 1.20 (t, J=7.45 Hz, 3H) 1.36 (q, J=6.57 Hz, 3H) 2.17-2.49 (m, 2H) 2.91 (d, J=7.58 Hz, 1H) 3.33-3.55 (m, 2H) 3.78-4.26 (m, 4H) 5.50 (s, 1H) 6.09 (s, 1H) 6.68-6.77 (m, 2H) 7.03-7.20 (m, 4H) 7.31 (t, J=7.83 Hz, 1H) 7.39-7.60 (m, 3H) 7.96 (dd, J=7.71, 1.39 Hz, 1H) 8.06 (d, J=9.09 Hz, 1H), LC-MS 637 (M+H)

Example 149

(2R,3S)-1-((R)-2-(1-Aminoisoquinolin-6-ylamino)-2-(4-fluoro-3-methoxyphenyl)acetyl)-2-(2-(ethylsulfonyl)phenyl)pyrrolidine-3-carboxylic acid trifluoroacetic acid salt

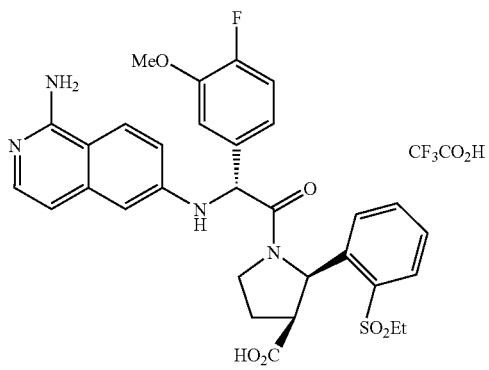

Example 149 was prepared by hydrolysis of the ethyl ester Example 144 using a procedure similar to that used in the preparation of Example 12. ¹H NMR (400 MHz, Methanol-d₄) δ ppm 1.20 (t, J=7.33 Hz, 3H) 2.22-2.46 (m, 2H) 2.91 (d, J=7.33 Hz, 1H) 3.32-3.56 (m, 2H) 3.78 (s, 3H) 3.81-3.92 (m, 1H) 4.06-4.24 (m, 1H) 5.49 (s, 1H) 6.09 (s, 1H) 6.72 (d, J=2.27 Hz, 1H) 6.76 (d, J=7.58 Hz, 1H) 7.04-7.25 (m, 5H) 7.32 (d, J=7.33 Hz, 1H) 7.43-7.58 (m, 2H) 7.96 (dd, J=7.58, 1.52 Hz, 1H) 8.06 (d, J=9.09 Hz, 1H), LC-MS 607 (M+H).

Example 150

(2R,3S)-1-((R)-2-(1-Aminoisoquinolin-6-ylamino)-2-(3-ethoxy-4-fluorophenyl)acetyl)-2-(2-(ethylsulfonyl)phenyl)pyrrolidine-3-carboxylic acid trifluoroacetic acid salt

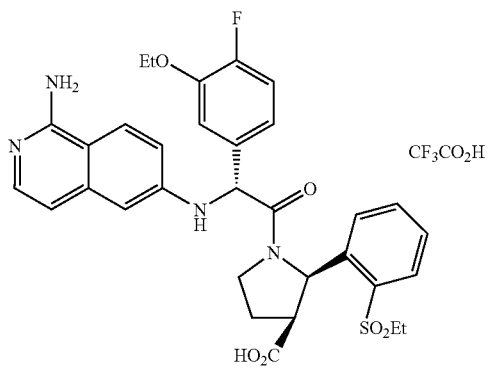

Example 150 was prepared by hydrolysis of the ethyl ester Example 147 using a procedure similar to that used in the preparation of Example 12. ¹H NMR (400 MHz, Methanol-d₄) δ ppm 1.20 (t, J=7.33 Hz, 3H) 1.30-1.40 (m, 3H) 2.17-2.46 (m, 2H) 2.91 (d, J=7.33 Hz, 1H) 3.32-3.55 (m, 2H) 3.78-4.24 (m, 4H) 5.47 (s, 1H) 6.09 (s, 1H) 6.67-6.80 (m, 2H) 7.05-7.24 (m, 5H) 7.32 (d, J=7.07 Hz, 1H) 7.42-7.58 (m, 2H) 7.96 (dd, J=7.71, 1.39 Hz, 1H) 8.06 (d, J=9.35 Hz, 1H), LC-MS 621 (M+H).

Example 151

(2R,3S)-Ethyl 1-((R)-2-(1-aminoisoquinolin-6-ylamino)-2-(4-chloro-3-methoxyphenyl)acetyl)-2-(2-(ethylsulfonyl)phenyl)pyrrolidine-3-carboxylate trifluoroacetic acid salt

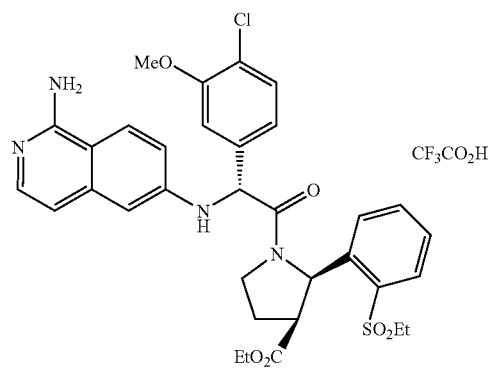

Example 151 was prepared according to the general coupling-deprotection using 50B and 114G. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. ¹H NMR (400 MHz, Methanol-d₄) δ ppm 1.15-1.22 (m, 3H) 1.23-1.31 (m, 3H) 2.18-2.43 (m, 2H) 2.86-2.96 (m, 1H) 3.33-3.54 (m, 2H) 3.77 (s, 3H) 3.79-3.88 (m, 1H) 4.09-4.29 (m, 3H) 5.54 (s, 1H) 6.04 (d, J=2.02 Hz, 1H) 6.70-6.80 (m, 2H) 7.01-7.19 (m, 4H) 7.35 (t, J=6.57 Hz, 1H) 7.40-7.57 (m, 3H) 7.94 (dd, J=7.58, 1.52 Hz, 1H) 8.07 (d, J=9.09 Hz, 1H), LC-MS 651 (M+H).

Example 152

Diastereomer of Example 151

(2R,3S)-Ethyl 1-((S)-2-(1-aminoisoquinolin-6-ylamino)-2-(4-chloro-3-methoxyphenyl)acetyl)-2-(2-(ethylsulfonyl)phenyl)pyrrolidine-3-carboxylate trifluoroacetic acid salt

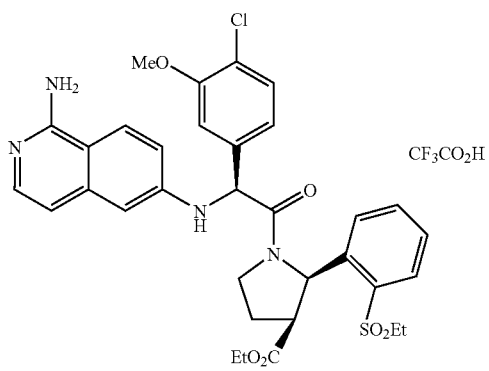

Example 152 was obtained as a diastereomer of Example 151 during its HPLC purification. $^1$H NMR (400 MHz, Methanol-d$_4$) δ ppm 1.05-1.40 (m, 6H) 2.07-2.21 (m, 1H) 2.48-2.62 (m, 1H) 2.84-2.94 (m, 1H) 3.33-3.54 (m, 3H) 3.71-4.00 (m, 3H) 4.00-4.16 (m, 2H) 4.38 (d, J=10.36 Hz, 1H) 5.67 (s, 1H) 5.98-6.08 (m, 1H) 6.76 (d, J=2.02 Hz, 1H) 6.95-7.04 (m, 1H) 7.04-7.26 (m, 4H) 7.37 (t, J=6.44 Hz, 1H) 7.41-7.55 (m, 2H) 7.63-7.78 (m, 1H) 7.86-7.99 (m, 1H) 8.00-8.12 (m, 1H), LC-MS 651 (M+H).

Example 153

(2R,3S)-1-((R)-2-(1-Aminoisoquinolin-6-ylamino)-2-(4-chloro-3-methoxyphenyl)acetyl)-2-(2-(ethylsulfonyl)phenyl)pyrrolidine-3-carboxylic acid trifluoroacetic acid salt

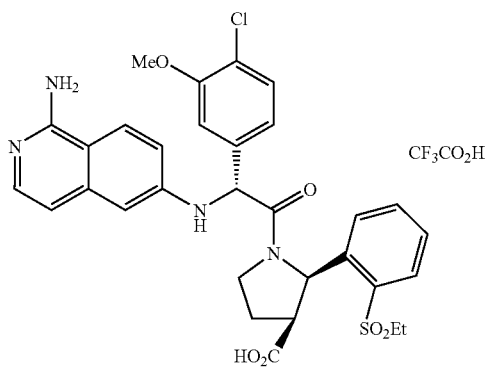

Example 153 was prepared by hydrolysis of the ethyl ester Example 151 using a procedure similar to that used in the preparation of Example 12. $^1$H NMR (400 MHz, Methanol-d$_4$) δ ppm 1.21 (t, J=7.45 Hz, 3H) 2.24-2.50 (m, 2H) 2.92 (d, J=7.58 Hz, 1H) 3.34-3.54 (m, 2H) 3.79 (s, 3H) 3.84-3.94 (m, 1H) 4.08-4.24 (m, 1H) 5.52 (s, 1H) 6.10 (s, 1H) 6.71-6.81 (m, 2H) 7.04-7.21 (m, 4H) 7.33 (d, J=7.07 Hz, 1H) 7.41-7.58 (m, 3H) 7.97 (dd, J=7.71, 1.39 Hz, 1H) 8.07 (d, J=9.35 Hz, 1H), LC-MS 623 (M+H).

Example 154

(2R,3S)-Ethyl 1-((S)-2-(1-aminoisoquinolin-6-ylamino)-2-(4-fluoro-3-methoxyphenyl)acetyl)-2-(2-(isopropylsulfonyl)phenyl)pyrrolidine-3-carboxylate trifluoroacetic acid salt

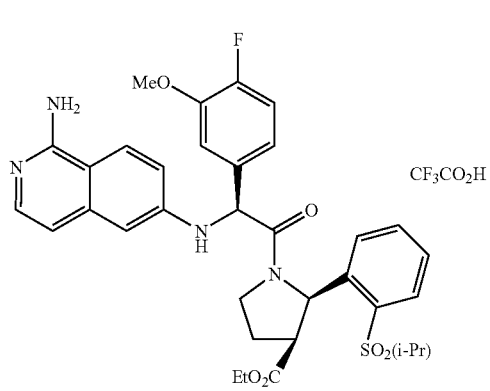

154A: (cis)-Ethyl 2-(2-(isopropylsulfonyl)phenyl)pyrrolidine-3-carboxylate hydrochloride

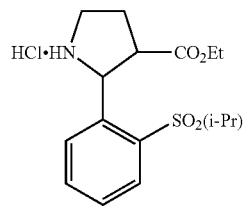

Similar to 13C, 154A was prepared according to the procedure of 11A-C and 13A-C using ethyl aminobutyric ester HCl salt instead of methyl aminobutyric ester HCl salt.

154B: (2R,3S)-Ethyl 2-(2-(isopropylsulfonyl)phenyl)pyrrolidine-3-carboxylate and 154C: (2S,3R)-Ethyl 2-(2-(isopropylsulfonyl)phenyl)pyrrolidine-3-carboxylate

154B

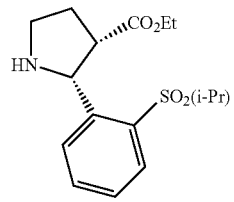

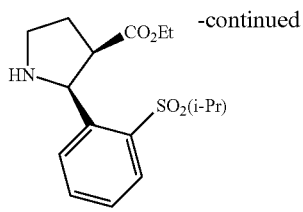

-continued

154C

The enantiomers of 154A were separated using a preparative HPLC equipped with a Chiralpak®AS column (5 cm×50 cm, 20μ). The separation was performed using an isocratic method of 10% isopropanol/heptane with 0.1% diethylamine with a flow rate of 50 mL/min. The first peak is 154B: $^1$H NMR (400 MHz, Methanol-$d_4$) δ ppm 1.13 (t, J=7.07 Hz, 3H) 1.25 (dd, J=6.82, 4.04 Hz, 6H) 2.11-2.39 (m, 2H) 3.05-3.28 (m, 3H) 3.48-3.63 (m, 1H) 3.98-4.15 (m, 2H) 5.12 (d, J=7.83 Hz, 1H) 7.47-7.58 (m, 1H) 7.71-7.77 (m, 1H) 7.77-7.84 (m, 1H) 7.95 (dd, J=8.08, 1.26 Hz, 1H). The second peak corresponds to 154C: $^1$H NMR (400 MHz, Methanol-$d_4$) δ ppm 1.08-1.17 (m, 3H) 1.20-1.30 (m, 6H) 2.10-2.39 (m, 2H) 3.01-3.27 (m, 3H) 3.46-3.66 (m, 1H) 3.97-4.14 (m, 2H) 5.13 (d, J=7.83 Hz, 1H) 7.45-7.61 (m, 1H) 7.69-7.79 (m, 1H) 7.76-7.83 (m, 1H) 7.95 (dd, J=8.08, 1.26 Hz, 1H).

154D: Example 154

Example 154 was prepared according to the general coupling-deprotection using 23D and 154B. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.07-1.46 (m, 9H) 2.05-2.20 (m, 1H) 2.42-2.58 (m, 1H) 2.82-2.94 (m, 1H) 3.31-3.40 (m, 1H) 3.69-3.80 (m, 1H) 3.89-3.97 (m, 3H) 4.06 (q, J=7.07 Hz, 2H) 4.28-4.42 (m, 1H) 5.63 (s, 1H) 6.01 (s, 1H) 6.75 (d, J=2.27 Hz, 1H) 6.99 (d, J=7.07 Hz, 1H) 7.06-7.29 (m, 4H) 7.37 (d, J=7.07 Hz, 1H) 7.44-7.54 (m, 1H) 7.62-7.75 (m, 2H) 7.85-7.95 (m, 1H) 8.01 (d, J=9.09 Hz, 1H), LC-MS 649 (M+H).

Example 155

Diastereomer of Example 154

(2R,3S)-ethyl 1-((R)-2-(1-aminoisoquinolin-6-ylamino)-2-(4-fluoro-3-methoxyphenyl)acetyl)-2-(24 isopropylsulfonyl)phenyl)pyrrolidine-3-carboxylate trifluoroacetic acid salt

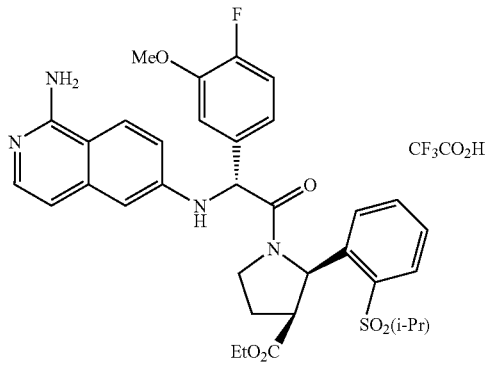

Example 155 was obtained as a diastereomer of Example 154 during its HPLC purification. $^1$H NMR (400 MHz, Methanol-$d_4$) δ ppm 1.12 (d, J=6.57 Hz, 3H) 1.29 (t, J=7.20 Hz, 3H) 1.35 (d, J=6.82 Hz, 3H) 2.15-2.43 (m, 2H) 2.92 (d, J=7.58 Hz, 1H) 3.70-3.89 (m, 5H) 4.07-4.19 (m, 1H) 4.19-4.32 (m, 2H) 5.51 (s, 1H) 6.04 (d, J=1.26 Hz, 1H) 6.70-6.80 (m, 2H) 7.01-7.25 (m, 5H) 7.36 (d, J=7.07 Hz, 1H) 7.41-7.57 (m, 2H) 7.93 (dd, J=7.58, 1.52 Hz, 1H) 8.07 (d, J=9.35 Hz, 1H), LC-MS 649 (M+H).

Example 156

(2S,3R)-Ethyl 1-((S)-2-(1-aminoisoquinolin-6-ylamino)-2-(4-fluoro-3-methoxyphenyl)acetyl)-2-(2-(isopropylsulfonyl)phenyl)pyrrolidine-3-carboxylate trifluoroacetic acid salt Example 156 was prepared according to the general coupling-deprotection using 23D and 154C. The diastereomers were separated by prep HPLC equipped with a C18 Luna column (21×100 mm, 5μ). The separation was performed using a linear gradient (mobile phase A:10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 1.07-1.18 (m, 3H) 1.23-1.37 (m, 3H) 1.41 (t, J=6.95 Hz, 3H) 2.13 (dd, J=513.77, 6.69 Hz, 1H) 2.46-2.61 (m, 1H) 2.82-2.95 (m, 1H) 3.32-3.41 (m, 1H) 3.71-3.96 (m, 4H) 4.07 (q, J=7.07 Hz, 2H) 4.38 (t, J=9.47 Hz, 1H) 5.64 (s, 1H) 6.02 (s, 1H) 6.76 (d, J=2.27 Hz, 1H) 7.00 (d, J=7.33 Hz, 1H) 7.07-7.30 (m, 4H) 7.37 (d, J=7.07 Hz, 1H) 7.44-7.54 (m, 1H) 7.63-7.76 (m, 2H) 7.88-7.95 (m, 1H) 8.02 (d, J=9.09 Hz, 1H), LC-MS 649 (M+H).

Example 157

Diastereomer of Example 156

(2S,3R)-Ethyl 1-((R)-2-(1-aminoisoquinolin-6-ylamino)-2-(4-fluoro-3-methoxyphenyl)acetyl)-2-(2-(isopropylsulfonyl)phenyl)pyrrolidine-3-carboxylate trifluoroacetic acid salt

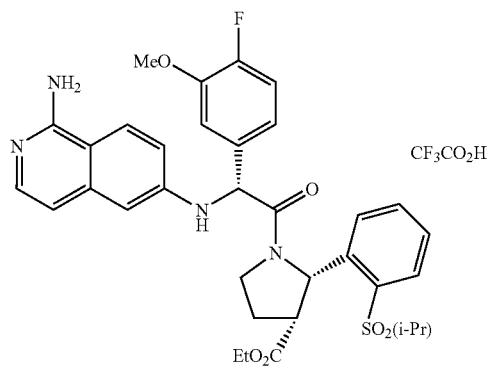

Example 157 was obtained as a diastereomer of Example 156 during its HPLC purification. $^1$H NMR (400 MHz, Methanol-$d_4$) δ ppm 1.12 (d, J=6.57 Hz, 3H) 1.29 (t, J=7.20 Hz, 3H) 1.35 (d, J=6.82 Hz, 3H) 2.17-2.41 (m, 2H) 2.88-2.98 (m, 1H) 3.71-3.93 (m, 5H) 4.14 (d, J=7.07 Hz, 1H) 4.19-4.33 (m, 2H) 5.51 (s, 1H) 6.04 (d, J=1.52 Hz, 1H) 6.71-6.80 (m, 2H) 7.02-7.26 (m, 5H) 7.36 (d, J=7.07 Hz, 1H) 7.41-7.59 (m, 2H) 7.93 (dd, J=7.58, 1.52 Hz, 1H) 8.07 (d, J=9.09 Hz, 1H), LC-MS 649 (M+H).

Example 158

(2R,3S)-Ethyl 1-((S)-2-(1-aminoisoquinolin-6-ylamino)-2-(4-chloro-3-methoxyphenyl)acetyl)-2-(2-(isopropylsulfonyl)phenyl)pyrrolidine-3-carboxylate trifluoroacetic acid salt

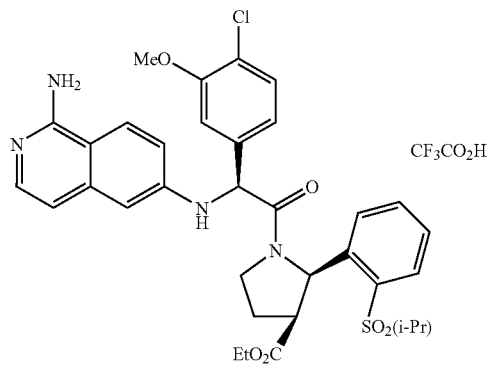

Example 158 was prepared according to the general coupling-deprotection using 50B and 154B. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow-rate of 20 mL/min. $^1$H NMR (400 MHz, Methanol-$d_4$) δ ppm 1.06-1.50 (m, 9H) 2.13 (dd, J=13.39, 6.57 Hz, 1H) 2.44-2.59 (m, 1H) 2.82-2.94 (m, 1H) 3.32-3.40 (m, 1H) 3.69-3.82 (m, 1H) 3.95 (s, 3H) 4.07 (q, J=7.07 Hz, 2H) 4.31-4.45 (m, 1H) 5.67 (s, 1H) 6.02 (s, 1H) 6.77 (d, J=2.27 Hz, 1H) 6.95-7.03 (m, 1H) 7.05-7.18 (m, 2H) 7.18-7.27 (m, 1H) 7.33-7.55 (m, 3H) 7.62-7.76 (m, 2H) 7.84-7.95 (m, 1H) 8.02 (d, J=9.09 Hz, 1H), LC-MS 665 (M+H).

Example 159

Diastereomer of Example 158

(2R,3S)-Ethyl 1-((R)-2-(1-aminoisoquinolin-6-ylamino)-2-(4-chloro-3-methoxyphenyl)acetyl)-2-(2-(isopropylsulfonyl)phenyl)pyrrolidine-3-carboxylate trifluoroacetic acid salt

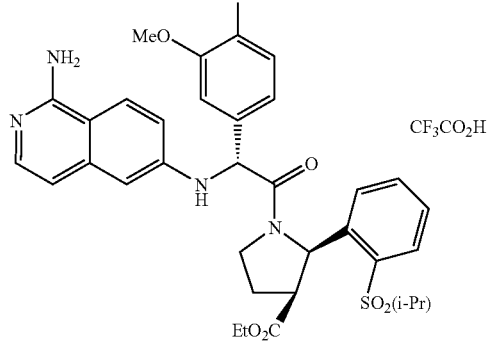

Example 159 was obtained as a diastereomer of Example 158 during its HPLC purification. $^1$H NMR (400 MHz, Methanol-$d_4$) δ ppm 1.12 (d, J=6.57 Hz, 3H) 1.28 (t, J=7.07 Hz, 3H) 1.35 (d, J=6.82 Hz, 3H) 2.16-2.43 (m, 2H) 2.89-2.97 (m, 1H) 3.69-3.91 (m, 5H) 4.14 (d, J=7.33 Hz, 1H) 4.19-4.34 (m, 2H) 5.53 (s, 1H) 6.04 (d, J=1.52 Hz, 1H) 6.70-6.81 (m, 2H) 7.00-7.22 (m, 4H) 7.36 (d, J=7.07 Hz, 1H) 7.40-7.57 (m, 3H) 7.92 (dd, J=7.71, 1.39 Hz, 1H) 8.08 (d, J=9.09 Hz, 1H), LC-MS 665 (M+H).

Example 160

(2R,3R)-Ethyl 1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylate trifluoroacetic acid salt

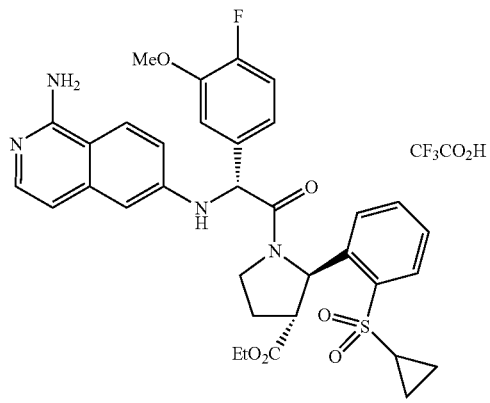

160A: 2-(Cyclopropylthio)benzonitrile

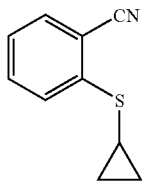

To a solution of 0.5 M cyclopropyl magnesium bromide in THF (150 mL, 75 mmol) at −78° C. was added 2,2'-dithiobis(benzonitrile) (Sumitomo Seika Chemical Co., 6.4 g, 23.4 mmol). The mixture was stirred between −70 to −65° C. for 15 min before it was quenched with sat. $NH_4Cl$ (200 mL) and extracted with ethyl acetate. The organic layer was washed with brine, dried ($Na_2SO_4$), filtered and concentrated. The resulting residue was purified via silica gel chromatography (0-30% ethyl acetate/hexanes) to provide 160A (4.0 g, 100%) as an oil. $^1$H NMR (400 MHz, $CDCl_3$) δ ppm 0.74 (ddd, J=6.70, 4.83, 4.72 Hz, 2H) 1.10-1.16 (m, 2H) 2.20-2.26 (m, 1H) 7.16-7.21 (m, 1H) 7.48-7.52 (m, 1H) 7.55 (d, J=7.91 Hz, 1H) 7.62 (d, J=7.91 Hz, 1H).

160B: 2-(Cyclopropylthio)benzaldehyde

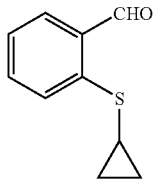

To 160A (3.4 g, 19.4 mmol) in toluene (30 mL) at −78° C. was added 1.5 M DIBAL in toluene (18.1 mL, 27.2 mmol) slowly. After stirring for 1.5 h, another portion of DIBAL (3.8 mL, 5.7 mmol) was added and stirred for additional 50 min. TLC indicated a clean conversion of 160A. The reaction was quenched at −78° C. with acetic acid (28 mL) and water (15 mL). After stirring at rt for 1.0 h, it was extracted with diethyl ether. The organic layer was washed with sat. $NaHCO_3$, brine, dried ($Na_2SO_4$), filtered and concentrated. The resulting residue was purified via silica gel chromatography (0-30% ethyl acetate/hexanes) to provide 160B (3.4 g, 95%) as an oil. $^1$H NMR (400 MHz, $CDCl_3$) δ ppm 0.69-0.76 (m, 2H) 1.10-1.17 (m, 2H) 2.07-2.15 (m, 1H) 7.27 (t, J=7.47 Hz, 1H) 7.49-7.56 (m, 1H) 7.77 (d, J=7.47 Hz, 2H) 10.14 (s, 1H).

160C: (E)-Ethyl 4-(2-(cyclopropylthio)benzylideneamino)butanoate

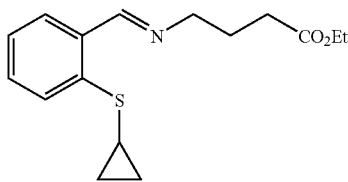

To ethyl aminobutyric ester HCl salt (2.56 g, 15.3 mmol) in $CH_2Cl_2$ (50 mL) was added 4 Å molecular sieve (1.3 g), $Et_3N$ (3.2 mL, 23 mmol) and 160B (2.72 g, 15.3 mmol). The mixture was stirred at rt over night. After removal of the solid by filtration, the filtrate was concentrated to give a white solid containing imine 160C and triethylamine HCl salt. The triethylamine HCl salt could be completely removed by trituration with dry diethyl ether and filtration. However, presence of the salt did not affect the next step conversion. $^1$H NMR (400 MHz, $CDCl_3$) δ ppm 0.65 (ddd, J=6.37, 4.83, 4.61 Hz, 2H) 0.99-1.06 (m, 2H) 1.18 (t, J=7.25 Hz, 3H) 1.94-2.02 (m, J=7.14, 7.14, 7.03, 6.81 Hz, 2H) 2.02-2.10 (m, 1H) 2.36 (t, J=7.47 Hz, 2H) 3.60 (t, J=6.15 Hz, 2H) 4.06 (q, J=7.18 Hz, 2H) 7.13 (t, J=7.47 Hz, 1H) 7.27-7.34 (m, 1H) 7.59 (d, J=8.35 Hz, 1H) 7.73 (d, J=7.47 Hz, 1H) 8.53 (s, 1H).

160D: 1-tert-Butyl 3-ethyl 2-(2-(cyclopropylthio)phenyl)pyrrolidine-1,3-dicarboxylate

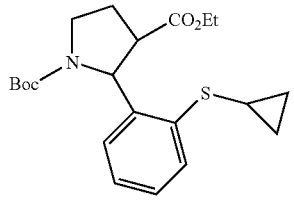

To 160C (15 mmol) in $CH_2Cl_2$ (100 mL) at −15° C. was added $Et_3N$ (2.1 mL, 15 mmol) followed by $TiCl_4$ (1.0 M in $CH_2Cl_2$, 30 mL, 30 mmol). The mixture was stirred from −15° C. to rt over 3.0 h before it was quenched with sat. $K_2CO_3$ (100 mL) at 0° C. and stirred at rt for 1.0 h. The mixture was filtered through a pad of wet celite, extracted with $CH_2Cl_2$ (3×40 mL). The organic layer was washed with water, dried over $Na_2SO_4$. A small portion of the dried organic layer was concentrated to give crude ethyl 2-(2-(cyclopropylthio)phenyl)pyrrolidine-3-carboxylate: $^1$H NMR indicated a mixture of cis and trans isomer in ca. 1:1 ratio. LC-MS 292 (M+H). To the above ethyl 2-(2-(cyclopropylthio)phenyl)pyrrolidine-3-carboxylate in $CH_2Cl_2$ was added $Et_3N$ (2.1 mL, 15 mmol) and di-tert-butyl dicarbonate (1.0 M in THF, 15 mL, 15 mmol). The mixture was stirred at rt over night before it was quenched with 0.5 N HCl (50 mL). The organic layer was washed with brine, dried ($Na_2SO_4$), filtered and concentrated. The resulting residue was purified via silica gel chromatography (0-30% ethyl acetate/hexanes) to provide 160D (3.3 g, 56%) as an oil. $^1$H NMR (400 MHz, $CDCl_3$) δ ppm: a mixture of cis and trans isomer in 1:1 ratio: 0.66-0.75 (m, 2H) 0.87 (t, J=7.03 Hz, 3H) 1.05-1.08 (m, 2H) 1.14-1.16 (s, 9H) 2.02-2.18 (m, 3H) 3.43-4.19 (m, 5H) 7.06-7.13 (m, 2H) 7.16-7.25 (m, 1H) 7.51-7.60 (m, 1H); LC-MS 292 (M+H).

160E: 1-tert-Butyl 3-ethyl 2-(2-(cyclopropylsulfonyl)phenyl)pyrrolidine-1,3-dicarboxylate

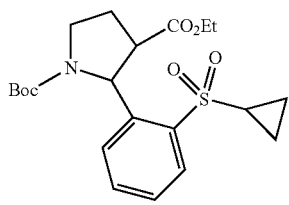

To 160D (3.3 g, 8.43 mmol) in EtOH (25 mL) at 0° C. was added a solution of Oxone (11.4 g, 18.6 mmol) in water (60 mL). The mixture was stirred at rt over night. The precipitate was filtered. The filtrate was neutralized with sat. $NaHCO_3$ and EtOH was removed under reduced pressure. The residue was extracted with EtOAc. The organic layer was washed with brine, dried ($Na_2SO_4$), filtered and concentrated to give crude 160E with >90% purity. $^1$H NMR of the crude 160E indicated a mixture of cis and trans isomer in ca 1:1 ratio and complicated by the presence of rotamers. LC-MS 424 (M+H).

160F: cis-Ethyl 2-(2-(cyclopropylsulfonyl)phenyl)pyrrolidine-3-carboxylate and

160G: trans-Ethyl 2-(2-(cyclopropylsulfonyl)phenyl)pyrrolidine-1,3-dicarboxylate

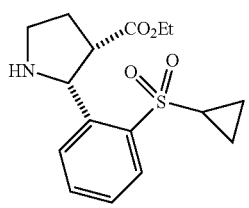

160F

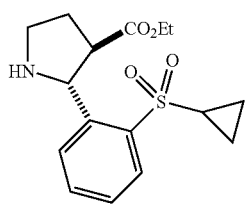

160G

The cis and trans diastereomers of 160E were separated by the preparative HPLC equipped with a C18 Luna column (30×100 mm, 5µ). The separations were performed using a linear gradient (mobile phase A: 10% Acetonitrile-90% water-0.1% TFA; mobile phase B: 90% Acetonitrile-10% water-0.1% TFA; 40 to 65% B in 10 min, then 65% B for 2 min) with a flow rate of 40 mL/min. 160F was obtained as HCl salt after treatment of the cis isomer with 4.0N HCl in dioxane (50 eq), LC-MS 324 (M+H); 160G was obtained as HCl salt after treatment of the trans isomer with 4.0N HCl in dioxane (50 eq), LC-MS 324 (M+H).

160H: (2R,3S)-Ethyl 2-(2-(cyclopropylsulfonyl)phenyl)pyrrolidine-3-carboxylate and

160I: (2S,3R)-Ethyl 2-(2-(cyclopropylsulfonyl)phenyl)pyrrolidine-3-carboxylate

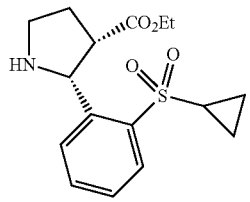

160H

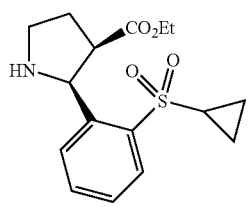

160I

The enantiomers of racemic cis 160F were separated using a semi-preparative HPLC equipped with a Chiralpak® AS-H column (250 mm×20 mm, 5µ). The separation was performed using an isocratic method of 10% isopropanol/heptane with 0.1% diethylamine with a flow rate of 15 mL/min. The first peak is 160H: $^1$H NMR (400 MHz, Methanol-$d_4$) δ ppm 0.73 (t, J=7.20 Hz, 3H) 0.99-1.37 (m, 4H) 2.09-2.23 (m, 1H) 2.28-2.44 (m, 1H) 2.80-2.94 (m, 1H) 2.95-3.09 (m, 1H) 3.37-3.75 (m, 4H) 5.32 (d, J=8.34 Hz, 1H) 7.46-7.56 (m, 1H) 7.59-7.72 (m, 2H) 7.90-7.98 (m, 1H). The second peak is 160I: $^1$H NMR (400 MHz, Methanol-$d_4$) δ ppm 0.73 (t, J=7.07 Hz, 3H) 0.99-1.37 (m, 4H) 2.11-2.25 (m, 1H) 2.30-2.45 (m, 1H) 2.81-2.93 (m, 1H) 2.97-3.15 (m, 1H) 3.39-3.75 (m, 4H) 5.38 (d, J=8.34 Hz, 1H) 7.44-7.58 (m, 1H) 7.64 (d, J=3.79 Hz, 2H) 7.96 (t, 1H).

160J: (2R,3R)-Ethyl 2-(2-(cyclopropylsulfonyl)phenyl)pyrrolidine-3-carboxylate and

160K: (2S,3S)-Ethyl 2-(2-(cyclopropylsulfonyl)phenyl)pyrrolidine-3-carboxylate

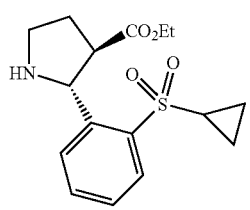

160J

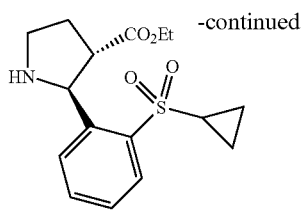

160K

The enantiomers of racemic trans 160G were separated using a preparative HPLC equipped with a Chiralpak® AS column (5 cm×50 cm, 20µ). The separation was performed using an isocratic method of 10% isopropanol/heptane with 0.1% diethylamine with a flow rate of 50 mL/min. The first peak is 160J: $^1$H NMR (400 MHz, Methanol-$d_4$) δ ppm 1.02-1.37 (m, 7H) 2.18-2.31 (m, 1H) 2.31-2.50 (m, 1H) 2.89-3.09 (m, 2H) 3.15-3.29 (m, 2H) 3.98-4.16 (m, 2H) 5.38 (d, J=7.83 Hz, 1H) 7.48-7.60 (m, 1H) 7.68-7.78 (m, 1H) 7.78-7.86 (m, 1H) 7.93 (dd, J=7.83, 1.26 Hz, 1H). The second peak is 160K: $^1$H NMR (400 MHz, Methanol-$d_4$) δ ppm 1.01-1.33 (m, 7H) 2.15-2.29 (m, 1H) 2.30-2.43 (m, 1H) 2.88-3.27 (m, 4H) 4.00-4.14 (m, 2H) 5.35 (d, J=7.83 Hz, 1H) 7.50-7.58 (m, 1H) 7.70-7.78 (m, 1H) 7.79-7.85 (m, 1H) 7.92 (dd, J=7.96, 1.39 Hz, 1H).

160L: Example 160

Example 160 was prepared according to the general coupling-deprotection using 23D and 160J. The diastereomers were separated by prep HPLC equipped with a C18 Luna column (21×100 mm, 5µ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. $^1$H NMR (400 MHz, Methanol-$d_4$) δ ppm 0.91-1.49 (m, 7H) 2.15-2.46 (m, 2H) 2.90-2.98 (m, 1H) 2.98-3.09 (m, 1H) 3.75-3.96 (m, 4H) 4.01-4.35 (m, 3H) 5.52 (s, 1H) 6.24 (d, J=1.52 Hz, 1H) 6.70-6.83 (m, 2H) 7.00-7.26 (m, 5H) 7.37 (d, J=7.07 Hz, 1H) 7.40-7.56 (m, 2H) 7.89 (dd, J=7.58, 1.52 Hz, 1H) 8.08 (d, J=9.09 Hz, 1H), LC-MS 647 (M+H).

Example 161

(2R,3S)-1-((R)-2-(1-aminoisoquinolin-6-ylamino)-2-(4-fluoro-3-methoxyphenyl)acetyl)-2-(2-(isopropyl-sulfonyl)phenyl)pyrrolidine-3-carboxylic acid trifluoroacetic acid salt

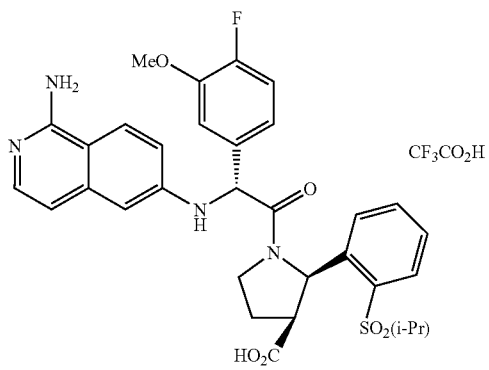

Example 161 was prepared by hydrolysis of the ethyl ester Example 155 using a procedure similar to that used in the preparation of Example 12. $^1$H NMR (400 MHz, Methanol-$d_4$) δ ppm 1.11 (d, J=6.82 Hz, 3H) 1.35 (d, J=7.07 Hz, 3H) 2.20-2.47 (m, 2H) 2.92 (d, J=7.33 Hz, 1H) 3.69-3.81 (m, 4H) 3.82-3.92 (m, 1H) 4.06-4.22 (m, 1H) 5.48 (s, 1H) 6.03-6.14 (m, 1H) 6.69-6.78 (m, 2H) 7.04-7.24 (m, 5H) 7.32 (d, J=7.07 Hz, 1H) 7.40-7.58 (m, 2H) 7.93 (dd, J=7.83, 1.52 Hz, 1H) 8.06 (d, J=9.35 Hz, 1H), LC-MS 621 (M+H).

Example 162

(2S,3R)-1-((R)-2-(1-aminoisoquinolin-6-ylamino)-2-(4-fluoro-3-methoxyphenyl)acetyl)-2-(2-(isopropyl-sulfonyl)phenyl)pyrrolidine-3-carboxylic acid trifluoroacetic acid salt

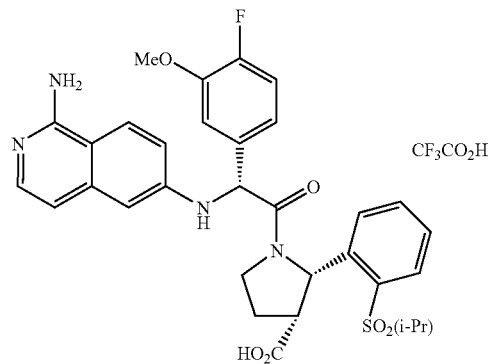

Example 162 was prepared by hydrolysis of the ethyl ester Example 157 using a procedure similar to that used in the preparation of Example 12. $^1$H NMR (400 MHz, Methanol-$d_4$) δ ppm 1.11 (d, J=6.57 Hz, 3H) 1.34 (t, J=7.83 Hz, 3H) 2.17-2.44 (m, 2H) 2.92 (d, J=57.33 Hz, 1H) 3.67-3.81 (m, 4H) 3.83-3.93 (m, 1H) 4.14 (d, J=7.33 Hz, 1H) 5.49 (s, 1H) 6.04-6.13 (m, 1H) 6.65-6.79 (m, 2H) 7.03-7.24 (m, 5H) 7.32 (d, J=7.07 Hz, 1H) 7.40-7.59 (m, 2H) 7.93 (dd, J=7.58, 1.52 Hz, 1H) 8.05 (d, J=9.35 Hz, 1H); LC-MS 621 (M+H).

Example 163

(2R,3S)-1-((R)-2-(1-aminoisoquinolin-6-ylamino)-2-(4-chloro-3-methoxyphenyl)acetyl)-2-(2-(isopropyl-sulfonyl)phenyl)pyrrolidine-3-carboxylic acid trifluoroacetic acid salt

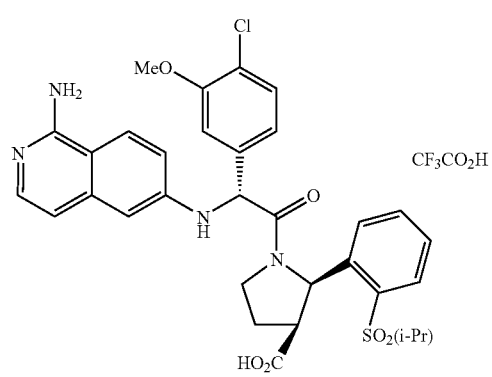

Example 163 was prepared by hydrolysis of the ethyl ester Example 159 using a procedure similar to that used in the preparation of Example 12. ¹H NMR (400 MHz, Methanol-d₄) δ ppm 1.12 (d, J=6.57 Hz, 3H) 1.32-1.40 (m, 3H) 2.20-2.45 (m, 2H) 2.92 (d, J=7.58 Hz, 1H) 3.71-3.83 (m, 4H) 3.82-3.93 (m, 1H) 4.05-4.21 (m, 1H) 5.51 (s, 1H) 6.08 (s, 1H) 6.70-6.79 (m, 2H) 7.04-7.19 (m, 4 H) 7.28-7.36 (m, 1H) 7.40-7.58 (m, 3H) 7.93 (dd, J=7.58, 1.52 Hz, 1H) 8.06 (d, J=9.09 Hz, 1H); LC-MS 637 (M+H).

Example 164

(2R,3S)-1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid trifluoroacetic acid salt

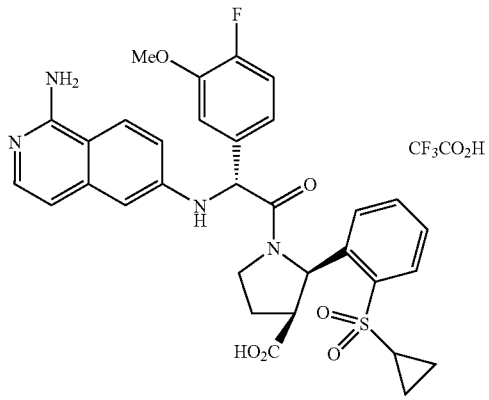

164A: (2R,3S)-Ethyl 1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylate trifluoroacetic acid salt

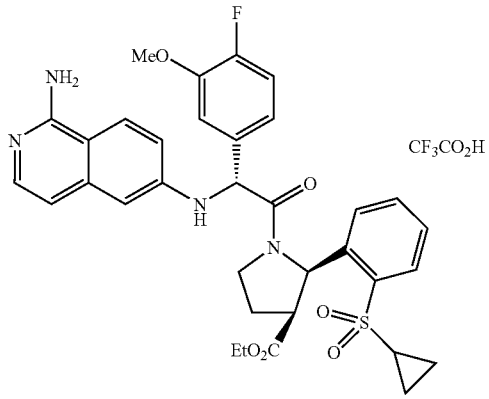

164A was prepared according to the general coupling-deprotection using 23D and 160H. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. LC-MS 647 (M+H).

164B: Example 164

Example 164 was prepared by hydrolysis of 164A using a procedure similar to that used in the preparation of Example 12. ¹H NMR (400 MHz, Methanol-d₄) δ ppm 0.94-1.11 (m, 2H) 1.18-1.51 (m, 2H) 2.22-2.47 (m, 2H) 2.96 (d, J=7.33 Hz, 1H) 2.99-3.09 (m, J=4.80 Hz, 1H) 3.76-3.98 (m, 4H) 4.07-4.24 (m, 1H) 5.50 (s, 1H) 6.28 (s, 1H) 6.71-6.80 (m, 2H) 7.08-7.26 (m, 5H) 7.33 (d, J=7.07 Hz, 1H) 7.41-7.56 (m, 2H) 7.91 (dd, J=7.58, 1.52 Hz, 1H) 8.06 (d, J=9.35 Hz, 1H); LC-MS 619 (M+H).

Example 165

(2R,3R)-1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid trifluoroacetic acid salt

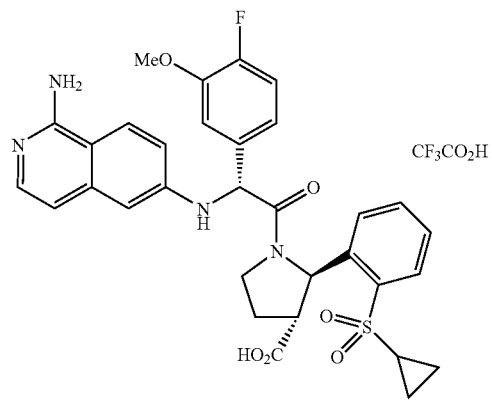

Example 165 was prepared by hydrolysis of the ethyl ester Example 160 using a procedure similar to that used in the preparation of Example 12. ¹H NMR (400 MHz, Methanol-d₄) δ ppm 0.90-1.10 (m, 2H) 1.18-1.35 (m, 1H) 1.35-1.52 (m, 1H) 2.21-2.47 (m, 2H) 2.95 (d, J=7.33 Hz, 1H) 3.00-3.09 (m, 1H) 3.77-3.82 (m, 3H) 3.86 (t, J=8.72 Hz, 1H) 4.08-4.25 (m, 1H) 5.49 (s, 1H) 6.27 (s, 1H) 6.72 (d, J=2.27 Hz, 1H) 6.76 (dd, J=7.45, 1.39 Hz, 1H) 7.07-7.25 (m, 5H) 7.32 (d, J=7.07 Hz, 1H) 7.39-7.54 (m, 2H) 7.90 (dd, J=7.71, 1.64 Hz, 1H) 8.05 (d, J=9.09 Hz, 1H), LC-MS 619 (M+H).

Example 166

(2S,3S)-1-(R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid trifluoroacetic acid salt

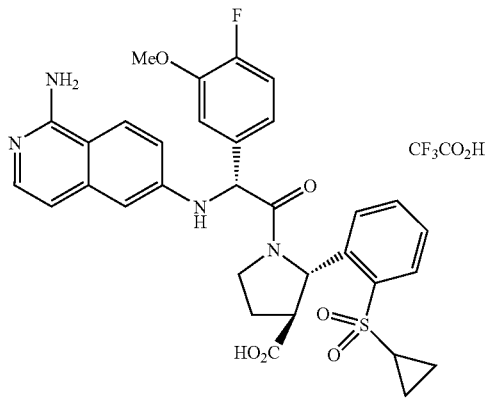

166A: (2S,3S)-Ethyl 1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylate trifluoroacetic acid salt

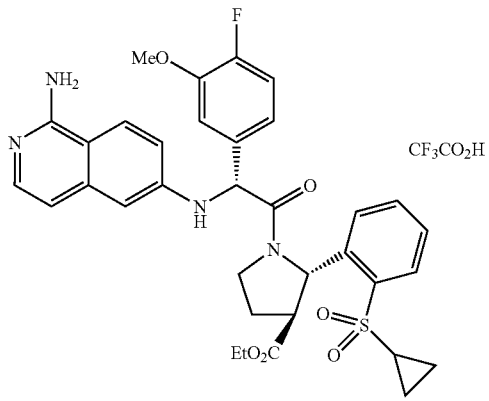

166A was prepared according to the general coupling-deprotection using 23D and 160K. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. LC-MS 647 (M+H).

166B: Example 166

Example 166 was prepared by hydrolysis of 166A using a procedure similar to that used in the preparation of Example 12. $^1$H NMR (400 MHz, Methanol-$d_4$) δ ppm 0.87-1.11 (m, 2H) 1.15-1.49 (m, 2H) 2.21-2.46 (m, 2H) 2.95 (d, J=7.33 Hz, 1H) 2.98-3.07 (m, 1H) 3.80 (s, 3H) 3.82-3.91 (m, 1H) 4.09-4.24 (m, 1H) 5.49 (s, 1H) 6.27 (s, 1H) 6.72 (d, J=2.27 Hz, 1H) 6.74-6.80 (m, 1H) 7.06-7.24 (m, 5H) 7.33 (d, J=7.07 Hz, 1H) 7.41-7.55 (m, 2H) 7.90 (dd, J=7.58, 1.52 Hz, 1H) 8.06 (d, J=9.09 Hz, 1H); LC-MS 619 (M+H).

Example 167

(2S,3R)-1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid trifluoroacetic acid salt

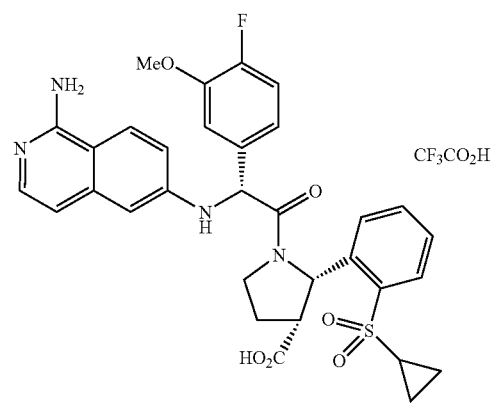

167A: (2S,3R)-Ethyl 1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylate trifluoroacetic acid salt

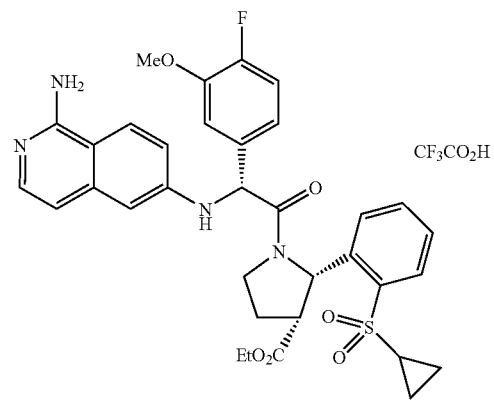

167A was prepared according to the general coupling-deprotection using 23D and 160I. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water-0.1% TFA; 5 to 50% B in 10 min, then 50% B for 2 min) with a flow rate of 20 mL/min. LC-MS 647 (M+H).

167B: Example 167

Example 167 was prepared by hydrolysis of 167A using a procedure similar to that used in the preparation of Example 12. $^1$H NMR (400 MHz, Methanol-$d_4$) δ ppm 0.90-1.10 (m, 2H) 1.25-1.37 (m, 1H) 1.36-1.49 (m, 1H) 2.23-2.42 (m, 2H) 2.95 (d, J=7.33 Hz, 1H) 2.99-3.09 (m, 1H) 3.80 (s, 3H) 3.82-3.90 (m, 1H) 4.07-4.23 (m, 1H) 5.49 (s, 1H) 6.27 (s, 1H) 6.72 (d, J=2.53 Hz, 1H) 6.76 (dd, J=7.33, 1.26 Hz, 1H) 7.06-7.25 (m, 5H) 7.33 (d, J=7.07 Hz, 1H) 7.40-7.55 (m, 2H) 7.90 (dd, J=7.45, 1.64 Hz, 1H) 8.06 (d, J=9.09 Hz, 1H); LC-MS 619 (M+H).

Example 168

(2R,3S)-1-((R)-2-(1-aminoisoquinolin-6-ylamino)-2-(3-ethoxy-4-fluorophenyl)acetyl)-2-(2-(ethylsulfonyl)phenyl)-N,N-dimethylpyrrolidine-3-carboxamide trifluoroacetic acid salt Example 169

3-(3-((R)-1-(R)-2-(1-aminoisoquinolin-6-ylamino)-2-(4-fluoro-3-methoxyphenyl)acetyl)pyrrolidin-2-yl)-4-(isopropylsulfonyl)phenyl)-1,1-dimethylurea trifluoroacetic acid salt

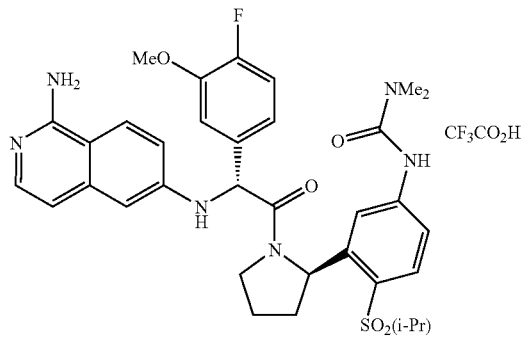

169A: (R)-3-(4-(isopropylsulfonyl)-3-(pyrrolidin-2-yl)phenyl)-1,1-dimethylurea hydrochloride

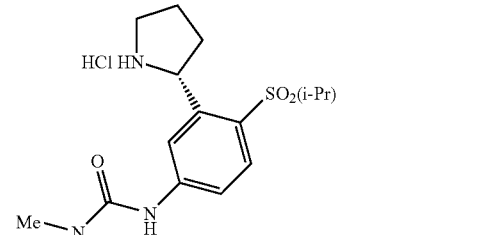

To 40A (0.25 g, 0.68 mmol) in dichloromethane (5 mL) at 0° C. was added sodium bicarbonate (0.57 g, 6.8 mmol), then phosgene (0.71 mL, 1.36 mmol, 20% in tolouene). The reaction was stirred at 0° C. for 30 min. The crude mixture was filtered and washed with dichloromethane. To the filtrate was added triethylamine (0.27 mL, 2.04 mmol), then dimethylamine hydrochloride (0.083 g, 1.02 mmol) and the reaction was stirred for 2 h at rt. The solution was washed with water and brine and dried over sodium sulfate. The solvent was removed and the residue was redissolved in ethyl acetate (2 mL). HCl (4 mL, 4M in dioxane) was added and the reaction was stirred at rt for 4 h. The solvent was removed and dried under high vacuo. $^1$H NMR (400 MHz, Methanol-$d_4$) δ ppm 1.23 (d, J=6.59 Hz, 3H) 1.31-1.40 (m, 3H) 2.14-2.27 (m, 1H) 2.29-2.43 (m, 2H) 2.44-2.60 (m, 1H) 3.02-3.11 (m, 6H) 3.37-3.53 (m, 3H) 5.42 (t, J=7.69 Hz, 1H) 7.64 (dd, J=8.79, 1.76 Hz, 1H) 7.91 (d, J=8.79 Hz, 1H) 8.08 (d, J=2.20 Hz, 1H).

169B: Example 169

Example 169 was prepared according to the general coupling-deprotection using 23D and 169A. The diastereomers were separated by prep HPLC equipped with a C18 Luna column (21×100 mm, 5μ). The separation was performed using a linear gradient (mobile phase A: 10% MeOH-90% water-0.1% TFA; mobile phase B: 90% MeOH-10% water- To Example 150 (0.01 g, 0.013 mmol) in DMF (0.6 mL) was added triethylamine (0.018 mL, 0.13 mmol), dimethylamine hydrochloride (0.003 g, 0.04 mmol) and then BOP (0.009 g, 0.02 mmol). The resulting heterogenous reaction was stirred for 3 h at room temperature. The crude material was purified by preparative HPLC equipped with a YMC ODS column (20×100 mm). The purification was performed using a linear gradient (mobile phase A: 10% Acetonitrile-90% water-0.1% TFA; mobile phase B: 90% Acetonitrile-10% water-0.1% TFA; 20 to 100% B in 10 min, then 100% B for 2 min) with a flow rate of 20 mL/min. $^1$H NMR (400 MHz, Methanol-$d_4$) δ ppm 1.21 (t, J=7.25 Hz, 3H) 1.31 (t, J=7.03 Hz, 3H) 2.11 (dd, J=13.62, 7.03 Hz, 1H) 2.27-2.45 (m, 1H) 2.94 (s, 3H) 2.99-3.03 (m, 3H) 3.33-3.58 (m, 2H) 3.71-3.98 (m, 3H) 4.03-4.17 (m, 1H) 5.74 (s, 1H) 5.97 (s, 1H) 6.75 (dd, J=5.71, 3.08 Hz, 1H) 6.82 (d, J=2.20 Hz, 1H) 6.87 (d, J=7.47 Hz, 1H) 6.94-7.05 (m, 1H) 7.08 (d, J=7.03 Hz, 1H) 7.13-7.25 (m, 2H) 7.34 (d, J=7.03 Hz, 1H) 7.42-7.58 (m, 2H) 7.96 (dd, J=7.47, 1.76 Hz, 1H) 8.07 (d, J=9.23 Hz, 1H); LC-MS 648 (M+H).

0.1% TFA; 5 to 50% B in 10 min, then 50% B for 2 min) with a flow rate of 20 mL/min. $^1$H NMR (400 MHz, Methanol-$d_4$) δ ppm 1.17 (t, J=6.44 Hz, 3H) 1.41 (t, J=7.71 Hz, 3H) 1.75 (dd, J=12.51, 5.94 Hz, 1H) 1.93-2.23 (m, 2H) 2.40-2.59 (m, 1H) 2.96-3.04 (m, 6H) 3.64-3.96 (m, 5H) 4.08-4.25 (m, 1H) 5.54 (s, 1H) 5.67 (dd, J=8.08, 5.05 Hz, 1H) 6.74-6.82 (m, 1H) 6.85-6.95 (m, 2H) 6.97-7.05 (m, 1H) 7.05-7.17 (m, 3H) 7.21-7.37 (m, 2H) 7.70 (t, J=8.84 Hz, 1H) 8.04 (d, J=9.09 Hz, 1H) 8.23 (s, 1H); LC-MS 663 (M+H).

Example 170

Diastereomer of Example 169

3-(3-((R)-1-((S)-2-(1-aminoisoquinolin-6-ylamino)-2-(4-fluoro-3-methoxyphenyl)acetyl)pyrrolidin-2-yl)-4-(isopropylsulfonyl)phenyl)-1,1-dimethylurea trifluoroacetic acid salt

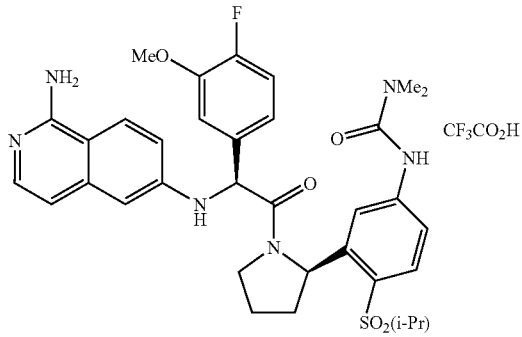

Example 170 was obtained as a diastereomer of Example 169 during its HPLC purification. $^1$H NMR (400 MHz, Methanol-$d_4$) δ ppm 0.89-1.22 (m, 3H) 1.23-1.55 (m, 3H) 1.93 (s, 2H) 2.13-2.46 (m, 2H) 2.91-3.16 (m, 6H) 3.52-3.92 (m, 5H) 4.16-4.32 (m, 1H) 5.53-5.72 (m, 2H) 6.65-6.81 (m, 1H) 6.80-6.94 (m, 1H) 7.03-7.43 (m, 6H) 7.61-7.80 (m, 2H) 7.79-7.90 (m, 1H); LC-MS 663 (M+H).

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders" as used herein includes arterial or venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but not limited to: prosthetic valves, indwelling catheters, stents, and vessel grafts. The procedures include, but not limited to: cardiopulmonary bypass and hemodialysis. It is noted that thrombosis includes occlusion (e.g. after a bypass) and reocclusion (e.g., during or after percutaneous transluminal coronary angioplasty). The term "stroke", as used herein, refers to embolic stroke or atherothrombotic stroke arising from occlusive thrombosis in the carotid communis, carotid interna, or intracerebral arteries. The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade, more specifically, inhibition of the coagulation factors: factor VIIa, factor IXa, factor Xa, factor XIa or thrombin.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, preferred compounds of the present invention, such as the particular compounds disclosed in the above examples, have been identified to be active and exhibit $K_i$'s of equal to or less than 15 μM in the Factor VIIa assay, thereby demonstrating the utility of the compounds of the present invention as especially effective inhibitors of coagulation Factor VIIa. More preferred compounds have $K_i$'s of equal to or less than 5 μM, preferably equal to or less than 1 μM, more preferably equal to or less than 0.5 μM, even more preferably equal to or less than 0.1 μM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, compounds tested in the Factor XIa assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and useful as anticoagulants for the prevention or treatment of thromboembolic disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and $K_i=IC_{50}/(1+S/K_m)$ for a competitive inhibitor where:

$v_o$ is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention can be administered alone or in combination with one or more additional therapeutic agents. These other agents include, but are not limited to, other anti-coagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa, VIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P2Y_1$ and $P2Y_{12}$, with $P2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of plasma kallikrein, thrombin, factor VIIa, IXa, Xa and/or XIa. Such compounds may be provided in a commercial kit, for example, for use in pharmaceutical research involving plasma kallikrein, thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma kallikrein, thrombin, factor VIIa, IXa, Xa, and/or XIa. For example, the presence of plasma kallikrein, thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages.

The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

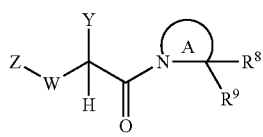

or a stereoisomer, a tautomer or a pharmaceutically acceptable salt thereof, wherein:

Y is selected from:

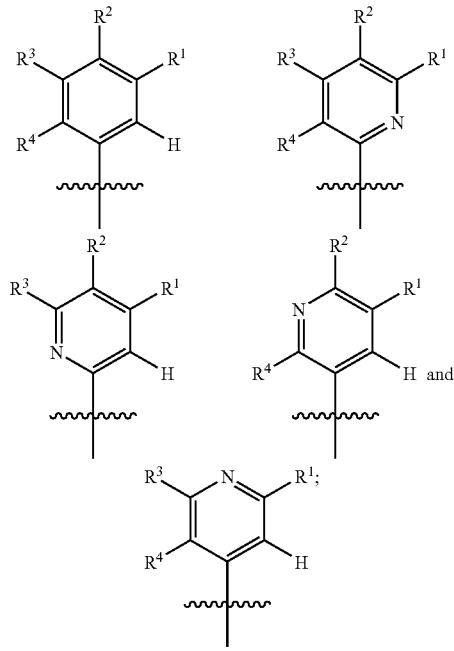

$R^1$ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

$R^2$ and $R^3$ are, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle is substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

W is NH or O;

Z is

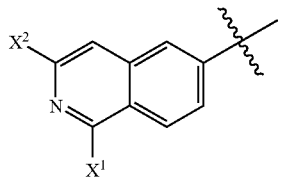

substituted with 0-2 $R^6$;

$R^6$ is, independently at each occurrence, F, Cl, Br, I, CN, OH, $CF_3$, $C_{1-4}$ alkyl, $C_{1-4}$ haloalkyl, or $C_{1-4}$ alkoxy;

$X^1$ and $X^2$ are, independently at each occurrence, H or $NH_2$;

ring A is a 4- to 8-membered heterocycle comprising: the nitrogen atom shown in the ring, carbon atoms and 0-1 additional heteroatom selected from N, $NR^c$, O, and $S(O)_p$, 0-1 carbonyl, and 0-2 double bonds, wherein said heterocycle is substituted with 0-2 $R^7$;

$R^7$ is, independently at each occurrence, $OR^a$, F, Cl, Br, I, CN, $NO_2$, —$OCF_3$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^8$ is H, CN, —$CO_2R^a$, —$C(O)NR^cR^d$, tetrazolyl, or $C_{1-4}$ alkyl substituted with 0-2 $R^{8a}$;

$R^{8a}$ is, independently at each occurrence, =O, $OR^a$, F, Cl, Br, I, CN, $NO_2$, —$OCF_3$, —$NR^bR^c$, —$C(O)R^a$, —$CO_2R^a$, —$OC(O)R^a$, —$OC(O)NR^cR^d$, —$NR^dC(O)R^a$, —$C(O)NR^cR^d$, —$NR^cC(O)NR^cR^d$, $NR^cC(O)OR^a$, —$SO_2NR^cR^d$, —$NR^cSO_2R^i$, —$NR^cSO_2NR^cR^d$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, $C_{3-6}$ cycloalkyl substituted with 0-3 $R^f$, phenyl substituted with 0-3 $R^f$, or 5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is phenyl substituted with 0-3 $R^{10}$, naphthyl substituted with 0-3 $R^{10}$, or a 5- to 10-membered heterocycle comprising: carbon atoms and 1-4 heteroatoms selected from N, $NR^c$, O, and $S(O)_p$, wherein said heterocycle is substituted with 0-3 $R^{11}$;

$R^{10}$ is, independently at each occurrence, F, Cl, Br, I, —$(CH_2)_r$—$OR^a$, $SR^a$, $OCF_3$, $SCF_3$, CN, $NO_2$, —$B(OH)_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^{11}$ is, independently at each occurrence, =O, F, Cl, Br, I, —$(CH_2)_r$—$OR^a$, $SR^a$, $OCF_3$, $SCF_3$, CN, $NO_2$, —$B(OH)_2$, —$(CH_2)_r$$NR^bR^c$, —$C(O)R^a$, —$(CH_2)_r$$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$, —$(CH_2)_r$—$C_{3-10}$ carbocycle substituted with 0-3 $R^f$, —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heteroaryl is substituted with 0-4 $R^f$;

$R^b$ is, independently at each occurrence, H, $C_{1-6}$ alkyl, —$(CH_2)_n$-phenyl, $(C_{1-6}$ alkyl$)C(O)$—, $(C_{3-6}$ cycloalkyl$)$-$C_{0-4}$ alkyl-$C(O)$—, $(C_{6-10}$ aryl$)$-$(C_{0-4}$ alkyl$)$-$C(O)$—, (5- to 10-membered heteroaryl)-$C_{0-4}$ alkyl-$C(O)$—, $(C_{1-6}$ alkyl$)$-NHC(O)—, $(C_{1-6}$ alkyl$)_2$—NHC(O)—, $(C_{6-10}$ aryl$)$-$C_{0-4}$ alkyl-NHC(O)—, (5- to 10-membered heteroaryl)-$C_{0-4}$ alkyl-NHC(O)—, $(C_{1-6}$ alkyl$)$-$SO_2$—, $(C_{6-10}$ aryl$)$-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each occurrence, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each occurrence, =O, $OR^a$, F, Cl, Br, I, CN, $NO_2$, —$SR^a$, —$OCF_3$, —$NR^bR^c$, —$C(O)R^a$, —$CO_2R^a$, —$NR^dC(O)R^a$, —$C(O)NR^cR^d$, —$OC(O)R^a$, —$NR^dC(O)OR^a$, —$NR^dC(O)NR^cR^d$, —$OC(O)NR^cR^d$, —$SO_2NR^cR^d$, —$NC(O)OR^a$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, —$SR^g$, —$OCF_3$, —$NR^cR^c$, —$C(O)R^g$, —$CO_2R^g$, —$NR^cC(O)R^g$, —$C(O)NR^cR^c$, —$OC(O)R^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$ —NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$ C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10 -membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;
p, at each occurrence, is selected from 0, 1, and 2; and
r, at each occurrence, is selected from 0, 1, 2, 3, and 4.

2. A compound according to claim 1, wherein:
R$^1$ is, independently at each occurrence, H, F, Cl, Br, C$_{1-3}$ alkyl substituted with 0-1 OH, C$_{1-3}$ haloalkyl, C$_{2-3}$ alkenyl, C$_{2-3}$ alkynyl, —O—C$_{1-3}$ alkyl, or C$_{3-6}$ cycloalkyl;
W is NH or O;
Z is

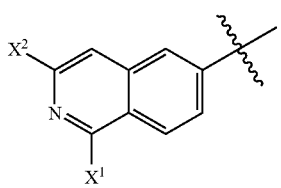

substituted with 0-2 R$^6$;
ring A is a 4- to 7-membered heterocycle comprising: the nitrogen atom shown in the ring, carbon atoms and 0-1 additional heteroatom selected from N, NR$^c$, O, and S(O)$_p$, wherein said heterocycle is substituted with 0-2 R$^7$; and
R$^9$ is phenyl substituted with 0-3 R$^{10}$, naphthyl, or a heterocycle substituted with 0-3 R$^{11}$ and selected from: furyl, thienyl, thiazolyl, imidazolyl, pyrazolyl, pyridyl, dihydroindolyl, indolyl, or 2,3-dihydro-1,4-benzodioxinyl.

3. A compound according to claim 1, wherein the compound is of Formula (Ia):

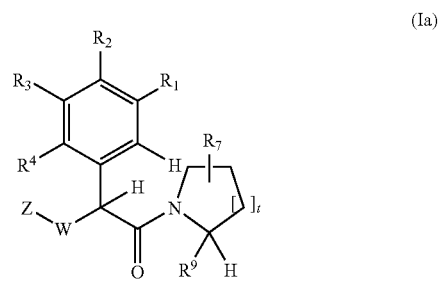

or a stereoisomer, a tautomer, or a pharmaceutically acceptable salt, thereof, wherein:
R$^1$ is H, F, Cl, Br, C$_{1-3}$ alkyl substituted with 0-1 OH, C$_{1-3}$ haloalkyl, C$_{2-3}$ alkenyl, C$_{2-3}$ alkynyl, —O—C$_{1-3}$ alkyl, or C$_{3-6}$ cycloalkyl;
R$^2$ and R$^3$ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —NR$^c$C(O)OR$^a$, —NR$^c$C(O)NR$^c$R$^d$, —SO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-10}$ carbocycle substituted with 0-3 R$^f$, or a 5- to 10-membered heterocycle comprising: carbon atoms and 1-4 heteroatoms selected from N, NR$^c$, O, and S(O)$_p$, wherein said heterocycle are substituted with 0-3 R$^f$;
R$^4$ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —NR$^c$C(O)OR$^a$, —NR$^c$C(O)NR$^c$R$^d$, —SO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-10}$ carbocycle substituted with 0-3 R$^f$, or a 5- to 10-membered heterocycle comprising: carbon atoms and 1-4 heteroatoms selected from N, NR$^c$, O, and S(O)$_p$, wherein said heterocycle are substituted with 0-3 R$^f$;
alternatively, R$^2$ and R$^3$ may combine to form a 5- to 7-membered carbocycle or heterocycle comprising: carbon atoms and 04 heteroatoms selected from N, NR$^c$, O, and S(O)$_p$, wherein said carbocycle and heterocycle are substituted with 0-3 R$^f$;
alternatively, R$^3$ and R$^4$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;
Z is

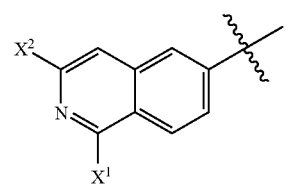

substituted with 0-2 R$^6$ ;

W is NH or O;

$R^6$ is, independently at each occurrence, F, Cl, $CH_3$, OH or $CF_3$;

$X^1$ and $X^2$ are, independently at each occurrence, H or $NH_2$;

$R^7$ is, independently at each occurrence, $OR^a$, F, Cl, Br, I, CN, $NO_2$, —$OCF_3$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is selected from:

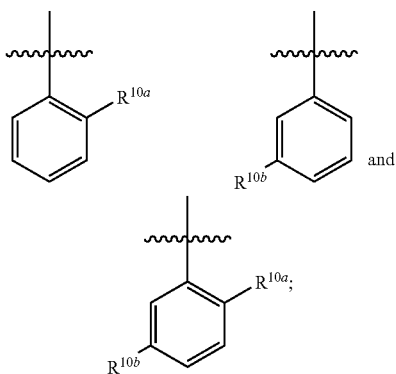

and $R^{10a}$ and $R^{10b}$ are, independently at each occurrence, H, F, Cl, Br, I, —$(CH_2)_r$—$OR^a$, $SR^a$, $OCF_3$, $SCF_3$, CN, $NO_2$, —$B(OH)_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heteroaryl is substituted with 0-4 $R^f$;

$R^b$ is, independently at each occurrence, H, $C_{1-6}$ alkyl, —$(CH_2)_n$-phenyl, $(C_{1-6}$ alkyl$)C(O)$—, $(C_{3-6}$ cycloalkyl$)$-$C_{0-4}$alkyl-$C(O)$—, $(C_{6-10}$ aryl$)$-$(C_{0-4}$alkyl$)$-$C(O)$—, (5- to 10-membered heteroaryl)-$C_{0-4}$ alkyl-$C(O)$—, $(C_{1-6}$ alkyl$)$-$NHC(O)$—, $(C_{1-6}$ alkyl$)_2$—$NHC(O)$—, $(C_{6-10}$ aryl$)$-$C_{0-4}$ alkyl-$NHC(O)$—, (5- to 10-membered heteroaryl)-$C_{0-4}$ alkyl-$NHC(O)$—, $(C_{1-6}$ alkyl$)$-$SO_2$—, $(C_{6-10}$ aryl$)$-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each occurrence, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each occurrence, =O, $OR^a$, F, Cl, Br, I, CN, $NO_2$, —$SR^a$, —$OCF_3$, —$NR^bR^c$, —$C(O)R^a$, —$CO_2R^a$, —$NR^dC(O)R^a$, —$C(O)NR^cR^d$, —$OC(O)R^a$, —$NR^dC(O)OR^a$, —$NR^dC(O)NR^cR^d$, —$OC(O)NR^cR^d$, —$SO_2NR^cR^d$, —$NC(O)OR^a$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, —$SR^g$, —$OCF_3$, —$NR^cR^c$, —$C(O)R^g$, —$CO_2R^g$, —$NR^cC(O)R^g$, —$C(O)NR^cR^c$, —$OC(O)R^g$, —$NR^cC(O)OR^g$, —$NR^cC(O)NR^cR^c$, $OC(O)NR^cR^c$, —$SO_2NR^cR^c$, —$NR^cSO_2NR^cR^c$, —$NR^cSO_2R^i$, —$NR^cSO_2CF_3$, —$SO_2CF_3$, —$S(O)_pR^i$, —$(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each occurrence, H, $C_{1-6}$ alkyl, or —$(CH_2)_n$-phenyl;

$R^h$ is, independently at each occurrence, =O, —$(CH_2)_r$ $OR^g$, F, Cl, Br, I, CN, $NO_2$, —$OCF_3$, —$NR^gR^g$, —$C(O)$ $R^g$, —$CO_2R^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$SO_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, $(C_{1-6}$ alkyl$)C$ $(O)$—, $(C_{3-6}$ cycloalkyl$)$-$C_{0-4}$ alkyl-$C(O)$—, $(C_{6-10}$ aryl$)$-$(C_{0-4}$ alkyl$)$-$C(O)$—, (5-10 membered heteroaryl)-$C_{0-4}$ alkyl-$C(O)$—, $(C_{1-6}$ alkyl$)$-$NHC(O)$—, $(C_{1-6}$ alkyl$)_2$—$NHC(O)$—, $(C_{6-10}$ aryl$)$-$C_{0-4}$ alkyl-$NHC(O)$—, (5-10 membered heteroaryl)-$C_{0-4}$ alkyl-$NHC(O)$—, $(C_{1-6}$ alkyl$)$-$SO_2$—, $(C_{6-10}$aryl$)$-$C_{0-4}$ alkyl-$SO_2$—, (5-10 membered heteroaryl)-$C_{0-4}$ alkyl-$SO_2$—, —$(CH_2)_r$—$C_{3-10}$ carbocycle, or a —$(CH_2)_r$-5- to 12-membered heterocycle comprising: carbon atoms and 1-4 heteroatoms selected from N, $NR^g$, O, and $S(O)_p$;

$R^i$ is, independently at each occurrence, H, $C_{1-6}$ alkyl substituted with 0-3 $R^h$, $C_{3-6}$ cycloalkyl substituted with 0-3 $R^h$, —$(CH_2)_n$-phenyl substituted with 0-3 $R^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;
p, at each occurrence, is selected from 0, 1, and 2;
r, at each occurrence, is selected from 0, 1, 2, 3, and 4; and
t is selected from 0, 1, 2, and 3.

4. A compound according to claim 3, wherein:

R$^1$ is H, F, Cl, Br, Me, Et, vinyl, 2-propenyl, ethynyl, —CH(OH)Me, OMe, OEt, cyclopropyl, —OCHF$_2$, or —OCF$_2$CHF$_2$;

R$^2$ and R$^3$ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

R$^4$ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

Z is

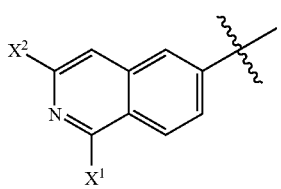

substituted with 0-1 R$^6$;

R$^a$ is, independently at each occurrence, H, C$_{1-6}$ alkyl substituted with 0-2 R$^h$, —(CH$_2$)$_r$—C$_{3-6}$ cycloalkyl substituted with 0-2 R$^f$, —(CH$_2$)$_n$-phenyl substituted with 0-3 R$^f$, or —(CH$_2$)$_r$-5- to 6-membered heterocycle comprising: carbon atoms and 1-4 heteroatoms selected from N, NR$^g$, O, and S(O)$_p$, wherein said heteroaryl is substituted with 0-3 R$^f$;

R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, phenyl-(C$_{0-4}$ alkyl)-C(O)—, (5- to 6-membered heteroaryl)-C$_{0-4}$ alkyl-C(O)—, (C$_{1-6}$ alkyl)-NHC(O)—, (C$_{1-6}$ alkyl)$_2$—NHC(O)—, phenyl-C$_{0-4}$ alkyl-NHC(O)—, (5- to 6-membered heteroaryl)-C$_{0-4}$ alkyl-NHC(O)—, (C$_{1-6}$ alkyl)-SO$_2$—, phenyl-C$_{0-4}$ alkyl-SO$_2$—, or (5- to 6-membered heteroaryl)-C$_{0-4}$ alkyl-SO$_2$—, wherein said phenyl and heteroaryl are substituted with 0-2 R$^f$;

R$^c$ is, independently at each occurrence, H, C$_{1-6}$ alkyl substituted with 0-3 R$^h$, —(CH$_2$)$_n$—C$_{3-6}$ cycloalkyl substituted with 0-2 R$^h$, or —(CH$_2$)$_n$-phenyl substituted with 0-3 R$^h$;

R$^d$ is, independently at each occurrence, H, C$_{1-6}$ alkyl, —(CH$_2$)$_n$—C$_{3-6}$ cycloalkyl substituted with 0-2 R$^f$, —(CH$_2$)$_r$-phenyl substituted with 0-3 R$^f$, or a —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, and substituted with 0-3 R$^h$;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$—NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, C$_{3-6}$ cycloalkyl, phenyl, or a —(CH$_2$)$_r$-5- to 10-membered heterocycle comprising: carbon atoms and 1-4 heteroatoms selected from N, NR$^g$, O, and S(O)$_p$; and R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 R$^h$.

5. A compound according to claim 1, wherein the compound is of Formula (Ib):

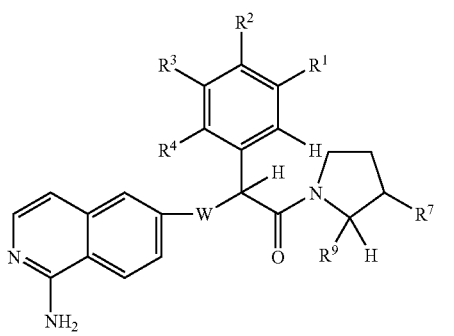

(Ib)

or a stereoisomer, a tautomer, or a pharmaceutically acceptable salt, thereof, wherein:

W is NH or O;

R¹ is H, F, Cl, Br, Me, Et, vinyl, 2-propenyl, ethynyl, —CH(OH)Me, OMe, OEt, cyclopropyl, —OCHF₂, or —OCF₂CHF₂;

R² is H, F, Cl, Me, Et, OMe, O(i-Pr), or —OCHF₂;

R³ is H, OMe, or OEt;

R⁴ is H or F;

R⁷ is H, CO₂H, CO₂Me, CO₂Et, or CONMe₂;

R⁹ is selected from:

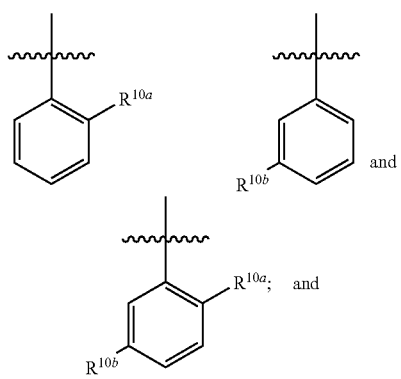

R¹⁰ᵃ and R¹⁰ᵇ are, independently at each occurrence, H, C₁₋₄ alkyl, F, Cl, OH, —O—C₁₋₄ alkyl, —S—C₁₋₄ alkyl, CF₃, OCF₃, SCF₃, CO₂Me, CONH₂, NH₂, NHMe, NHEt, NMe₂, —NHCOH, —NHCOMe, —NHCOEt, —NHCOPr, —NHCO(i-Pr), —NHCO(i-Bu), —NHCO-cyclopropyl, —N(Me)COMe, —NHCO₂Me, —NHCO₂Et, —NHCONH₂, —NHCONHMe, —NHCONMe₂, —NHCON(Me)Et, —NHCO-(1-azetidinyl), —NHCO-(1-pyrrolidinyl), —SO₂Me, —SO₂Et, —SO₂Pr, —SO₂(i-Pr), —SO₂(i-Bu), —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂-(4-morpholinyl), —SO₂-(4-thiamorpholinyl), —SO₂-(4-Me-1-piperazinyl), —SO₂NH₂, —SO₂NHMe, —SO₂NHEt, —SO₂NH(i-Pr), —SO₂NH-cyclopropyl, —SO₂NH-cyclohexyl, —SO₂NH(t-Bu), —SO₂N(Me)Bn, —SO₂NMe₂, —OSO₂NH₂, —NHSO₂NH₂, —NHSO₂Me, Ph, 4-F-Ph, 1-piperidyl, 4-morpholinyl, NO₂, or —B(OH)₂.

6. A compound according to claim 5, wherein:

W is NH;

R¹ is H, F, Cl, Et, OMe, or OEt;

R¹⁰ᵃ is, independently at each occurrence, H, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, or 4-morpholinyl; and R¹⁰ᵇ is, independently at each occurrence, H, OH, NH₂, —NHCOH, —NHCOMe, —NHCOEt, —NHCO₂Me, —NHCO₂Et, —NHCONHMe, —NHCONH₂, —NHCONMe₂, —NHCON(Me)Et, —NHCO-(1-azetidinyl), —NHCO-(1-pyrrolidinyl), —OSO₂NH₂, —NHSO₂NH₂, —NHSO₂Me, —SO₂NH₂, or NO₂.

7. A compound according to claim 5, wherein:

R⁷ is H;

R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, or 4-morpholinyl; and R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCO-(1-pyrrolidinyl), —NHCONH₂, —OSO₂NH₂, —NHSO₂NH₂, —NHSO₂Me, or —SO₂NH₂.

8. A compound according to claim 5, wherein:

R⁷ is CO₂H, CO₂Me, CO₂Et, or CONMe₂;

R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, or 4-morpholinyl; and R¹⁰ᵇ is H.

9. A compound according to claim 5, wherein:

R⁷ is CO₂H, CO₂Me, CO₂Et, or CONMe₂;

R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, or 4-morpholinyl; and R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCO-(1-pyrrolidinyl), —NHCONH₂, —OSO₂NH₂, —NHSO₂NH₂, —NHSO₂Me, or —SO₂NH₂.

10. A compound according to claim 5, wherein:

R⁷ is CO₂H, CO₂Me, or CO₂Et;

R¹⁰ᵃ is H;

R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCO-(1-pyrrolidinyl), —NHCONH₂, —OSO₂NH₂, —NHSO₂NH₂, —NHSO₂Me, or —SO₂NH₂.

11. A compound according to claim 5, wherein the compound is of Formula (1c):

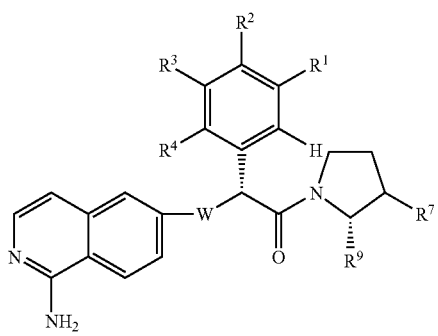

(Ic)

or a stereoisomer, a tautomer, or a pharmaceutically acceptable salt thereof.

12. A compound selected from the group consisting of:
2-(1-aminoisoquinolin-6-ylamino)-2-(3-ethoxy-4-isopropoxyphenyl)-1-(2-phenylpyrrolidin-1-yl)ethanone;
3-(1-(2-(1-aminoisoquinolin-6-ylamino)-2-(3-ethoxy-4-isopropoxyphenyl)acetyl)-pyrrohdin-2-yl)benzenesulfonamide;
N-(3-((R)-1-((R)-2-(1-aminoisoquinolin-6-ylamino)-2-(3-ethoxy-4-isopropoxyphenyl)acetyl)pyrrolidin-2-yl)phenyl)acetamide;
N-(3-((R)-1-((S)-2-(1-aminoisoquinohn-6-ylamino)-2-(3-ethoxy-4-isopropoxyphenyl)acetyl)pyrrolidin-2-yl)phenyl)acetamide;
N-(3-((S)-1-((R)-2-(1-aminoisoquinolin-6-ylaminol)-2-(3-ethoxy-4-isopropoxyphenyl)acetyl)pyrrolidin-2-yl)phenyl)acetamide;
N-(3-((S) 1-((S)-2-(1-aminoisoquinolin-6-ylamino)-2-(3-ethoxy-4-isopropoxyphenyl)acetyl)pyrrolidin-2-yl)phenyl)acetamide;
N-(3-((R)-1-(2-(1-aminoisoquinolin-6-ylamino)-2-(3,4-dimethoxyphenyl)acetyl)pyrrohdin-2-yl)phenyl)acetamide;
methyl 1-(2-(1-aminoisoquinolin-6-ylamino)-2-(3-ethoxy-4-isopropoxyphenyl)acetyl)-2-phenylpyrrolidine-3-carboxylate;
1-(2-(1-aminoisoquinolin-6-ylamino)-2-(3-ethoxy-4-isopropoxyphenyl)acetyl)-2-phenylpyrrolidine-3-carboxylic acid;
methyl 1-(2-(1-aininoisoquinolin-6-ylamino)-2-(3-ethoxy-4-isopropoxyphenyl)acetyl)-2-(2-(isopropylthio)phenyl)pyrrolidine-3-carboxylate;
1-(2-(1-aminoisoquinolin-6-ylamino)-2-(3-ethoxy-4-isopropoxyphenyl)acetyl)-2-(2-(isopropylthio)phenyl)pyrrolidine-3-carboxylic acid;
methyl 1-(2-(1 -aminoisoquinolin-6-ylamino)-2-(3-ethoxy-4-sopropoxyphenyl)acetyl)-2-(2-(isopropylsulfonyl)phenyl)pyrrolidine-3-carboxylate;
1-(2-(1-aminoisoquinolin-6ylamino)-2-(3-ethoxy-4-isopropoxyphenyl)acetyl)-2-(2-(isopropylsufonyl)phenyl)pyrrolidine-3-carboxylic acid;
methyl 1-(2-(1-aminoisoquinolin-6-ylamino)-2-(3-ethoxy-4-isopropoxyphenyl)acetyl)-2-(3-nitrophenyl)pyrrolidine-3-carboxylate;
1-(2-(1-aminoisoquinolin-6-ylamino)-2-(3-ethoxy-4-isopropoxyphenyl)acetyl)-2-(3-nitrophenyl)pyrrolidine-3-carboxylic acid;
methyl 2-(3-acetamidophenyl)-1-(2-(1-aminoisoquinolin-6-ylamino)-2-(3-ethoxy-4-isopropoxyphenyl)acetyl)pyrrolidine-3-carboxylate;
2-(3-acetamidophenyl)-1-(2-(1-aminoisoquinolin-6-ylamino)-2-(3-cthoxy-4-isopropoxyphenyl)acetyl)pyrrolidine-3-carboxylic acid;
1-(2-(5-amino-2(isopropylsulfonyl)phenyl)pyrrolidin-1-yl)-2-(1-aminoisoquinolin-6-ylamino)-2-(3-ethoxy-4-isopropoxyphenyl)ethanone;
methyl 2-(5-amino-2isopropylsulfonyl)phenyl)-1-(2-(1-aminoisoquinolin-6-ylamino)-2-(3-ethoxy-4-isopropoxyphenyl)acetyl)pyrrolidine-3-carboxylate;
2-(1-aminoisoquinolin-6-ylamino)-2-(3-ethoxy-4-isopropoxyphenyl)-1-(2-(2-(isopropylsulfonyl)phenyl)pyrrolidin-1-yl)ethanone;
2-(5 -amino-2-(isopropylsulfonyl)phenyl) 1(2-(1-aminoisoquinolin-6-ylamino)-2-(3-ethoxy-4-isopropoxyphenyl)acetyl)pyrrolidine-3-carboxylic acid;
N-(3-(1-(2-(1-aminoisoquinolin-6-ylamino)-2-(4-fluoro-3-methoxyphenyl)acetyl)pyrrolidin-2-yl)-4-(isopropylsulfoflyl)phenyl)acetamide;
methyl 1-(2-(1-aminoisoquinolin-6-ylamino)-2-(3-ethoxy-4-isopropoxyphenyl)acetyl)-2-(2-(isopropylsulfonyl)-5-nitrophenyl)pyrrolidine-3-carboxylatc;
1-(2-(1-aminoisoquinolin-6-ylarnino)-2-(3-ethoxy-4-isopropoxyphenyl)acetyl)-2-(2-(isopropylsulfonyl)-5-nitrophenyl)pyrrolidine-3-carboxylic acid;
(cis)-methyl 2-(5-acetamido-2isopropylsulfonyl)phenyl) 1-(2-(1-aminoisoquinolin-6-ylamino)-2-(3-ethoxy-4-isopropoxyphenyl)acetyl)pyrrolidine-3-carboxylate;
trans-methyl 2-(5-acetamido-2-(isopropylsulfonyl)phenyl) 1-(2-(1-aminoisoquinolin-6-ylamino)-2-(3-ethoxy-4-isopropoxyphenyl)acetyl)pyrrolidine-3-carboxylate;
cis-methyl 1-(2-(1-aminoisoquinolin-6-ylamino)-2-(3-ethoxy-4-isopropoxyphenyl)acetyl)-2-(2-(isopropylsulfonyl)-5methoxycarbonyl)phenyl)pyrrolidine-3-carboxylate;
trans-methyl 1-(2-(1-aminoisoquinolin-6-ylamino)-2-(3-ethoxy-4-isopropoxyphenyl)acetyl)-2-(2-isopropylsulfonyl)-5-(methoxycarbonyl)phenyl)pyrrolidine-3-carboxylate;
N-(3-(1-(2-(1-aminoisoquinolin-6-ylamino)-2-(5-ethoxy-2-fluorophenyl)acetyl)pyrrolidin-2-yl)-4-(isopropylsulfonyl)phenyl)acetamide;
N-(3-(1-(2-(1-aminoisoquinoliu-6-ylamino)-2-(4-chloro-3-ethoxypheny1)acetyl)pyrrolidin-2-yl)-4-(isopropylsulfonyl)phenyl)acetamide;
N-(3-(1-(2-(1-aminoisoquinolin-6-ylarnino)-2-(3-ethoxy-4-fluorophenyl)acetyl)pyrrolidin-2-yl)-4-(isopropylsulfony)phenyl)acetamide;
cis-2-(5-acetamido-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylic acid;
trans-2-(5-acetamido-2-(isopropylsulfonyl)phenyl)-1-(2-(1-aminoisoquinolin-6-ylamino)-2-(3-ethoxy-4-isopropoxyphenyl)acetyl)pyrrolidine-3-carboxylic acid;
cis-1-(2-(1-aminoisoquinolin-6-ylamino)-2-(3-ethoxy-4-isopropoxyphenyl)acetyl)-2-(2-(isopropylsulfonyl)-5-(metboxycarbonyl)phenyl)pyrrolidine-3-carboxylic acid;
trans-1-(2-(1-aminoisoquinolin-6-ylamino)-2-(3-ethoxy-4-isopropoxyphenyl)acetyl)-2-(2isopropylsulfonyl)-5-(methoxycarbonyl)phenyl)pyrrolidine-3-carboxylic acid;
cis-methyl 1-(2-(1-arninoisoquino-6-ylamino)-2-(3-ethoxy-4-fluoropheny)acetyl)- 2-(2-(isopropylsulfonyl)phenyl)pyrrolidine-3-carboxylate;

cis-methyl 1-(2-(1-aminoisoquinolin-6-ylamino)-2-(4-chloro-3-ethoxyphenyl)acetyl)- 2-(2-(isopropylsulfonyl)phenyl)pyrrolidine-3-carboxylate;

cis-methyl 1-(2-(1-aminoisoquinolin-6-ylamino)-2-(4-fluoro-3- methoxyphenyl)acetyl)-2-(2-(isopropylsulfonyl)pheny)pyrrolidine-3-carboxylate;

N-(3((R)-1-((R)-2-(1-aminoisoquinolin-6-ylamino)-2-(3-ethoxy-4- isopropoxyphenyt)acetyl)pyrrolidin-2-yl)-4-isopropylsulfonyl)phenyl)acetamide;

N-(3-((R)-1-((S)-2-(1-aminoisoquinolin-6-ylamino)-2-(3-ethoxy-4- isopropoxyphenyl)acetyl)pyrrolidin-2-yl)-4-(isopropylsufonyl)phenyl)acetamide;

N-(3-((S)-1((R)-2-(1-aminoisoquinolin-6-ylamino)-2-(3-ethoxy-4- isopropoxyphenyl)acetyl)pyrrolidin-2-yl)-4-(isopropylsulfonyl)phenylacetamide;

N-(3-((S)-1-((5)-2-(1-aminoisoquinolin-6-ylamino)-2-(3-ethoxy-4- isopropoxyphenyl)acetyl)pyrrolidin-2-yl)-4-(isopropylsulfonyl)phenyl)acetamide;

methyl 3-((R)-1-((R)-2-(1-aminoisoquinolin-6-ylamino)-2-(3-ethoxy-4- isopropoxyphenyl)acetyl)pyrrolidin-2-yl)-4-(isopropylsulfonyl)phenylcarbamate;

methyl 3-((R)-1-((S)-2-(1-aminoisoquinolin-6-ylamino)-2-(3-ethoxy-4- isopropoxyphenyi)acetyl)pyrrolidin-2-yl)-4-(isopropylsulfonyl)phenycarbamate;

methyl 3-1-(R)-2-(1aminoisoquinolin-6-ylamino)-2-(3-ethoxy-4- isopropoxyphenyl)acetyl)pyrrolidin-2-yl)-4-(isopropylsulfony)phenylcarbamate;

methyl 3-(R)-1-((S)-2-(1-aminoisoquinolin-6-ylamino)-2-(3-ethoxy-4- isopropoxyphenyl)acetyl)pyrrolidin-2-yI)-4-isopropylsulfonyl)phenylcarbamate;

methyl 3-((R)-1-((R)-2-(1-aminoisoquinolin-6-ylamino)-2-(4-chloro-3- methoxyphenyl)acetyl)pyrrolidin-2-yl)-4-isopropylsulfonyl)phenylearbamate;

methyl 3-((R)-1-((S)-2-(1-aminoisoquinolin-6-ylamino)-2-(4-chloro-3- methoxyphenyl)acetyl)pyrrolidin-2-yl)-4-(isopropylsulfonyl)phenylcarbamate;

methyl 3-((R)-1-((R)-2-(1-aminoisoquinolin-6-ylamino)-2-(5-ethoxy-2- fluorophenyl)acetyl)pyrrolidin-2-yl)-4-isopropylsulfonyl)phenyIcarbamate;

methyl 3-((R)-1-((S)-2-(1-aminoisoquinolin-6-ylamino)-2-(5-ethoxy-2- fluorophenyl)acetyl)pyrrolidin-2-yl)-4-(isopropylsulfonyl)phenylcarbamate;

N-(3-((R)-1-((R)-2(1-aminoisoquinolin-6-ylamino)-2-phenylacetyl)pyrrolidin-2-yl)- 4-(isopropylsuifonyl)phenyl)acetamide;

N-(3((R)-1-((S)-2-(1-aminoisoquinolin-6-ylamino)-2-phenylacetyl)pyrrolidin-2-yl)- 4-(isopropylsulfonyl)phenyl)acetamide;

methyl 3-((R)-1-((R)-2-(1-aminoisoquinohn-6-ylamino)-2-(4-fluoro-3- methoxypheny)acetyl)pyrrolidin-2-yl)-4-(isopropylsulfonyl)phenycarbamate;

methyl 3((R)-1((S)-2-(1-aminoisoquinolin-6-ylamino)-2-(4-fluoro-3- methoxyphenyl)acetyl)pyrrolidin-2-yl)-4-(isopropylsulfonyl)phenylcarbamate;

(2R, 3S)-methyl 1-((S)-2-(1-aminoisoquinolin-6-ylamino)-2-(3-ethoxy-4- isopropoxyphenyl)acetyl)-2-(2-(isopropylsulfonyl)phenyl)pyrrolidine-3-carboxylate;

(2R, 3S)-methyl 1-((R)-2-(1-aminoisoquinolin-6-ylarnino)-2-(3-ethoxy-4- isopropoxyphenyl)acetyl)-2-(2-(isopropylsulfonyl)phenyl)pyrrolidine-3-carboxylate;

(2S, 3R)-methyl 1((R)-2-(1-aminoisoquinolin-6-ylamino)-2-(3 -ethoxy-4- isopropoxyphenyl)acetyl)-2-(2-(isopropylsulfonyl)phenyl)pyrrolidine-3carboxylate;

(2R, 3S)-methyl 2(-acetarnido-2-(isopropylsulfonyl)phenyl)-1-((R)-2-(1- aminoisoquinolin-6-ylamino)-2-(5ethoxy-2-fluorophenyl)acetyl)pyrrolidine-3-carboxylate;

(2R, 3S)-methyl 2-(5-acetamido-2-isopropylsulfonyl)phenyl)-1-((S)-2-(1- arninoisoquinolin-6-ylamino)-2-(5 -ethoxy-2-fluorophenyl)acetyl)pyrrolidine-3-carboxylate;

(2S, 3R)-methyl 1-((R)-2-(1-aminoisoquinolin-6-ylamino)-2-(3-ethoxy-4- isopropoxyphenyl)acetyl)-2-(2isopropylsulfonyl)phenyl)pyrrolidine-3-carboxylate;

methyl 3-((R)-1-((R)-2-(1-aminoisoquinolin-6-ylamino)-2-(5-ethoxy-2-fluoro-4- methoxyphenyl)acetyl)pyrrolidin-2-yl)-4-(isopropylsulfony)phenylcarbamate;

methyl 3-((R)-1-((S)-2-(1-aminoisoquinolin-6-ylamino)-2-(5-ethoxy-2-fluoro-4- methoxyphenyl)acetyl)pyrrolidin-2-yI)-4-(isopropylsulfonyl)phenylcarbamate;

methyl 3-((R)-1-((R)-2-(1-aminoisoquinolin-6ylamino)-2-(2-fluoro-5- methoxyphenyl)acetyl)pyrrolidin-2-yl)-4-(isopropylsulfonyl)phenylcarbamate;

methyl 3-((R)-1-((S)-2-(1-aminoisoquinolin-6-ylamino)-2-(2-fluoro-5- methoxyphenyl)acetyl)pyrrolidin-2-yl)-4-(isopropyisulfonyl)phenylcarbamate;

methyl 3-((R)-1((R)-2-(aminoisoquinolin-6-ylamino)-2-(2-fluoro-5- methylphenyl)acetyl)pyrrolidin-2-yl)-4-(isopropylsulfonyl)phenylcarbamate;

methyl 3((R)-1-((S)-2-(1-aminoisoquinolin-6-ylamino)-2-(2-fluoro-5- methylphenyl)acetyl)pyrrolidin-2-yl)-4-(isopropylsulfonyl)phenylcarbamate;

(2S, 3R)-1((R)-2-(1-aminoisoquinolin-6-ylamino)-2-(3-ethoxy-4- isopropoxyphenyl)acetyl-2-(2-(isopropylsulfonyl)phenyl)pyrrolidine-3-carboxylic acid;

methyl 3((R)-1-((R)-2-(1-aminoisoquinolin-6-ylamino)-2-(2- fluorophenyl)acetyl)pyrrolidin-2-yl)-4-(isopropylsuifonyl)phenylcarbamate;

methyl 3((R)-1-((S)-2-(1-aminoisoquinohn-6-ylamino)-2- fluorophenyl)acetyl)pyrrolidin-2-yl)-4-(isopropylsulfony)phenylcarbamate;

(S)-2-(1aminoisoquinolin-6-ylamino)-2(5-ethoxy-2-fluorophenyl)-1((R)-2-(2- (isopropylsulfonyl)phenyl)pyrrolidin-1-yl)ethanone;

(R)-2-(1-aminoisoquinolin-6-ylamino)-2(5-ethoxy-2-fluorophenyl)-1-((R)-2-(2- (isopropylsulfonyl)phenyl)pyrrolidin-1-yl)ethanone;

(2S, 3R)-methyl 1((R)-2-(1-aminoisoquinolin-6-ylamino)-2-(5-ethoxy-2- fluorophenyl)acetyl)-2-(2-(isopropylsulfonyl)-5-(methoxycarbonyl)phenyl)-pyrrolidine-3- carboxylate;

(2S, 3R)-methyl 1-((S)-2-(1-aminoisoquinolin-6-ylamino)-2-(5-ethoxy-2- fluorophenyl)acetyl)-2-(2-(isopropylsulfonyl)-5-(methoxycarbonyl)phenyl)-pyrrolidine-3- carboxylate;

(R)-1-((R)-2-(5-amino-2-(isopropylsulfonyl)phenyl)pyrrolidin-1-yl)-2-( 1- aminoisoquinolin-6-ylamino)-2(5-ethoxy-2-fluorophenyl)ethanone;

methyl 3-((R)-1-((R)-2-(1-aminoisoquinolin-6-ylamino)-2-phenylacetyl)pyrrolidin-2- yl)-4-(isopropylsulfonyl)phenylcarbamate;

methyl 3((R)-1-((S)-2-(1-aminoisoquinolin-6-ylamino)-2-phenylacetyl)pyrrolidin-2- yl)-4-(isopropylsulfonyl)phenylcarbamate;

(R)-1-((S)-2-amino-2-(isopropylsulfonyl)phenyl)pyrrolidin-1-yl)-2-(1- aminoisoquinolin-6-ylamino)-2-(ethoxy-2-fluorophenyl)ethanone;

methyl 3-((R)-1-((R)-2-(aminoisoquinolin-6-yloxy)-2-(3-ethoxy-4- isopropoxyphenyl)acetyl)pyrrolidin-2-yI)-4-(isopropylsulfonyl)phenylcarbamate;

methyl 3-((R)-1-((R)-2-(1-aminoisoquinolin-6-ylamino)-2-(5-ethyl-2-ftuorophenyl)acetyl)pyrrolidin-2-yl)-4-(isopropylsulfonyl)phenylcarbamate;

methyl 3((R)-1-((R)-2-(1-aminoisoquinolin-6-ylamino)-2-(5-ethyl-2-fluorophenyl)acetyl)pyrrolidin-2-yl)-4-(isopropylsulfonyl)phenylcarbamate;

methyl 3((R)-1((R)-2-(1-aminoisoquinolin-6-ylamino)-2-(2-fluoro-4,5-dimethoxyphenyl)acetyl)pyrrolidin-2-yl)-4-(isopropylsulfonyl)phenylcarbamate;

methyl 3-((R)-1-(S))-2-(1-aminoisoquinolin-6-ylamino)-2-(fluoro-4,5-dimethoxyphenyl)acetyl)pyrrolidin-2-yl)-4-(isopropylsulfonyl)phenylcarbamate;

(2R, 3S)-methyl 1-((S)-2-(1-aminoisoquinolin-6-ylamino)-2-(5-ethoxy-2-fluorophenyl)acetyl)-2-(2-(isopropylsulfonyl)phenyl)pyrrolidine-3carboxylate;

(2R, 3S)-methyl 1-((R)-2-(1-aminoisoquinolin-6-ylainino)-2-(5-ethoxy-2-fluorophenyl)acetyl)-2-(isopropylsulfonyl)phenyl)pyrrolidine-3-carboxylate;

methyl 3-((R)-1-((S)-2-(1-aminoisoquinolin-6-yloxy)-2-(3-ethoxy-4-isopropoxyphenyl)acetyl)pyrrolidin-2-yl)-4-(isopropylsulfony)phenylcarbamate;

(2R, 3S)-methyl 1-((5)-2-(1-aminoisoquinolin-6-ylamino)-2-(2-fluoro-4,5-dimethoxyphenyl)acetyl)-2-(isopropylsulfonyl)phenyl)pyrrolidine-3-carboxylate;

(2R, 3S)-methyl 1-((R)-2-(1-aminoisoquinolin-6-ylamino)-2-(2-fluoro-4,5-dimethoxyphenyl)acetyi)-2-(isopropylsulfonyl)pheny)pyrrolidine-3-carboxylate;

(2R, 3S)-1-((R)-2-(1-aminoisoquinolin-6-ylamino)-2-(2-fluoro-4,5-dimethoxyphenyl)acetyl)-2-(2-(isopropylsulfonyl)phenyl)pyrrolidine-3-carboxylic acid;

methyl 3-((R)-1-((R)-2-(1-aminoisoquinolin-6-ylamino)-2-(2,4-difluoro-5-methylphenyl)acetyl)pyrrolidin-2-yl)-4-(isopropylsulfony)phenylcarbamate;

methyl 3-((R)-1-((R)-2-(1-ammnoisoquinolin-6-ylamino)-2-(2,4-difluoro-5-methylphenyl)acetyl)pyrrolidin-2-yl)-4-(isopropylsulfonyl)phenylcarbamate;

(2R, 3S)-1-((R)-2-(1-aminoisoquinolin-6-ylamino)-2-(5-ethoxy-2-fluoro-4-isopropoxyphenyl)acetyl)-2-(2-(isopropylsulfonyl)phenyl)pyrrolidine-3-carboxylic acid;

methyl 3-((R)-1-((R)-2-(1-aminoisoquinolin-6-ylamino)-2-ethoxy-2,4-difluorophenyl)acetyl)pyrrolidin-2-yI)-4-(isopropylsulfonyt)phenylcarbamate;

methyl 3-((R)-1-((R)-2-(1-aminoisoquinolin-6-ylamino)-2-(2,4-difluoro-5-methoxyphenyl)acetyl)pyrrolidin-2-yl)-4-(isopropylsulfonyl)phenylcarbamate;

(2R, 3S)-1-((R)-2-(1-aminoisoquinolin-6-ylamino)-2-(5-ethoxy-2-fluorophenyl)acetyl)-2-(2-(isopropylsulfonyl)-5-(metboxycarbonyl)phenyl)-pyrrolidine-3-carboxylic acid;

methyl 3-((S)-1-((R)-2-(1-aminoisoquinolin-6-ylamino)-2-(3ethoxy-4-isopropoxyphenyl)acetyl)pyyrrolidin-2-yl)-4-(ethylsulfonyl)phenylcarbamate;

methyl 3-((S)-1-((S)-2-(1-aminoisoquinolin-6-ylamino)-2-(3-ethoxy-4-isopropoxyphenyl)acetyl)pyrrolidin-2-yl)-4-(ethylsulfonyl)phenylcarbamate;

methyl 3-((R)-1-((R)-2-(1-aminoisoquinolin-6-ylamino)-2-(3ethoxy-4-isopropoxyphenyl)acetyl)pyrrolidin-2-yl)-4-(ethylsulfonyl)phenylcarbamate;

methyl 3-((R)-1-((S)-2-(1-aminoisoquinolin-6-ylamino)-2-(3-ethoxy-4-isopropoxyphenyl)acetyl)pyrrolidin-2-yl)-4-(ethylsulfonyl)phenylcarbamate;

methyl 3-((R)-1-((R)-2-(1-aminoisoquinolin-6-ylamino)-2-(5ethoxy-2-fluorophenyl)acetyl)pyrrolidin-2-yI)-4-(ethylsulfonyl)phenylcarbamate;

methyl 3-((R)-1-((S)-2-(1-aminoisoquinolin-6-ylamino)-2-(5-ethoxy-2-fluorophenyl)acetyl)pyrrolidin-2-yl)-4-(ethylsulfonyl)phenylcarbamate;

methyl 3-((R)-1-((R)-2-(1-aminoisoquinolin-6-ylamino)-2-(2,4-difluoro-5-methoxyphenyl)acetyl)pyrrolidin-2-yl)-4-(ethylsulfonyl)phenylcarbamate;

methyl 3-((R)-1-((S)-2-(1-aminoisoquinolin-6-ylamino)-2-(2,4-difluoro-5-methoxyphenyl)acetyl)pyrrolidin-2-yl)-4-(ethylsulfonyl)phenylcarbamate;

ethyl 3-((R)-1((R)-2-(1-aminoisoquinolin-6-ylamino)-2-(5-ethoxy-2-fluorophenyl)acety)pyrrolidin-2-yl)-4-(ethylsulfonyl)phenylcarbamate;

ethyl 3(R)-1-((S)-2(1-aminoisoquinolin-6-ylamino)-2-(5-ethoxy-2-fluorophenyl)acetyl)pyrrolidin-2-yl)-4-(ethylsulfony)phenylcarbamate;

methyl 3-((R)-1-((R)-2-(1-aminoisoquinolin-6-ylamino)-2-(2-fluoro-4,5-dimethoxyphenyl)acetyl)pyrrolidin-2-yl)-4-(ethylsulfonyl)phenylcarbamate;

methyl 3(R)-1-((R)-2-(1-aminoisoquinolin-6-ylamino)-2-(3,4-dimethoxyphenyl)acetyl)pyrrolidin-2-yl)-4-(ethylsulfonyl)phenylcarbamate;

methyl 3-((R)-1-((S)2-(1-aminoisoquinolin-6-ylamino)-2-(3,4-dimethoxyphenyl)acetyl)pyrrolidin-2-yl)-4-(ethylsulfonyl)phenylcarbamate;

(R)-2-(1-aminoisoquinolin-6-ylamino)-2-(3-ethoxy-4-isopropoxyphenyl)-1-((2R, 4R)-4-hydroxy-2-phenylpyrrolidin-1-yl)ethanone;

(2R, 3S)-ethyl 1-((S)-2-(1-aminoisoquinolin-6-ylamino)-2-(2-fluoro-4,5-dimethoxyphenyl)acetyl)-2-(2-(ethylsulfonyl)phenyl)pyrrolidine-3-carboxylate;

(2R, 3S)-ethyl 1-((R)-2-(1-aminoisoquinolin-6-ylamino)-2-(2-fluoro-4,5dimethoxyphenyl)acetyl)-2-(2-(ethylsulfonyl)phenyl)pyrrolidine-3-carboxylate;

(2R, 3S)-1-((R)-2-(1-aminoisoquinolin-6-ylamino)-2-(2-fluoro-4,5-dimethoxyphenyl)acetyl)-2-(2-(ethylsulfonyl)phenyl)pyrrolidine-3-carboxylic acid;

(2R, 3S)-1-((S)-2-(1-aminoisoquinolin-6-ylamino)-2-fluoro-4,5-dimethoxyphenyl)acetyl)-2-(ethylsulfonyl)phenyl)pyrrolidine-3-carboxylic acid;

methyl 3((R)-1-((R)-2-(1-aminoisoquinolin-6-ylamino)-2-(3-ethoxy-5-ethyl-2-fluorophenyl)acetyl)pyrrolidin-2-yl)-4-(ethylsulfonyl)phenylcarbamate;

methyl 3-((R)-1-((R)-2-(1-aminoisoquinolin-6-ylamino)-2(5-ethyl-2-fluoro-3-methoxyphenyl)acetyl)pyrrolidin-2-yl)-4-(ethylsulfonyl)phenylcarbamate;

methyl 3((R)-1((S)-2-(1-aminoisoquinolin-6-ylamino)-2-(5-ethyl-2-fluoro-3-methoxyphenyl)acetyl)pyrrolidin-2-yl)-4-(ethylsulfonyl)phenylcarbamate;

methyl 3-((R)-1-((R)-2-(1-aminoisoquinolin-6-ylamino)-2-(5-chloro-2-fluorophenyl)acetyl)pyrrolidin-2-yI)-4-(ethylsulfonyl)phenylcarbamate;

methyl 3-((R)-1-((R)-2-(1-aminoisoquinolin-6-ylamino)-2-(2-fluoro-5-methoxy-4-methylphenyl)acetyl)pyrrolidin-2-yl)-4-(ethylsulfonyl)phenylcarbamate;

methyl 3-((R)-1-((S)-2-(1-aminoisoquinolin-6-ylamino)-2-(2-fluoro-5-methoxy-4-methylphenyl)acetyl)pyrrolidin-2-yl)-4ethylsulfonyl)phenylcarbamate;

(2R, 3S)-ethyl 1-((S)-2-(1-aminoisoquinolin-6-ylamino)-2-(5-chloro-2-fluorophenyl)acetyl)-2-(2-(ethylsuifonyl)phenyl)pyrrolidine-3-carboxylate;

(2R, 3S)-ethyl 1-((R)-2-(1-aminoisoquinolin-6-ylamino)-2-(5-chloro-2-fluorophenyl)acetyl)-2-(2ethylsulfonyl)phenyl)pyrrolidine-3carboxylate;

(2R, 3S)-ethyl 1-((S)-2-(1-aminoisoquinolin-6-ylamino)-2-ethyl-2-fluoro-3-methoxyphenyl)acetyl)-2-(2ethylsulfonyl)phenyl)pyrrolidine-3carboxylate;

(2R, 3S)-ethyl 1-((R)-2-(1-aminoisoquinolin-6-ylamino)-2-(5-ethyl-2-fluoro-3-methoxyphenyl)acetyl)-2-(2-(ethylsulfonyl)phenyl)pyrrolidine-3-carboxylate;

(2R, 3S)-1-((R)-2-(1-aminoisoquinolin-6-ylamino)-2-(5-chloro-2-fluorophenyl)acetyl)-2-(2-(ethylsulfonyl)phenyl)pyrrolidine-3-carboxylic acid;

(2R, 3)-1-((R)-2-(1-aminoisoquinolin-6-ylamino)-2-(5-ethyl-2-fluoro-3-methoxyphenyl)acetyl)-2-(2-)ethylsulfonyl)phenyl)pyrrolidine-3-carboxylic acid; methyl 3-((R)-1-((R)-2-(1-aminoisoquinolin-6-ylamino)-2-(3-(1,1,2,2-tetrafluoroethoxy)phenyl)acetyl)pyrrolidin-2-yl)-4-(ethylsulfonyl)phenylcarbamate;

methyl 3-((R)-1-((R)-2-(1-aminoisoquinolin-6-ylamino)-2-(3-(difluoromethoxy)phenyl)acetyl)pyrrolidin-2-yl)-4-(isopropylsulfonyl)phenyl-carbamate;

methyl 3-((R)-1-((R)-2-(3,4-bis(difluoromethoxy)phenyl)-2-(1-aminoisoquinolin-6-ylamino)acetyl)pyrrolidin-2-yl)-4-(isopropylsulfonyl)phenyl-carbamate;

(2R, 3S)ethyl 1((S)-2-(1-aminoisoquinolin-6-ylamino)-2-(5-ethoxy-2-fluoro-4-methoxyphenyl)acetyl)-2-(2-(ethylsulfonyl)phenyl)pyrrolidine-3-carboxylate;

(2R, 3S)-ethyl 1-((R)-2-(1-aminoisoquinolin-6-ylamino)-2-(5-ethoxy-2-fluoro-4-methoxyphenyl)acetyl)-2-(2-(ethylsulfonyl)phenyl)pyrrolidine-3-carboxylate;

(2R, 3S)-1-((R)-2-(1-aminoisoquinolin-6-ylamino)-2-(5-ethoxy-2-fluorophenyl)acetyl)-2-(2-(ethylsulfonyl)phenyl)pyrrolidine-3-carboxylic acid;

(2R, 3S)-1-((R)-2-(1-aminoisoquinolin-6-ylamino)-2-(5-ethoxy-2-fluoro-4-methoxyphenyl)acetyl)-2-(2-(ethylsulfonyl)phenyl)pyrrolidine-3-carboxylic acid;

methyl 3-((R)-1-((R)-2-(1-aminoisoquinolin-6-yloxy)-2-(3 4-dimethoxyphenyl)acetyl)pyrrolidin-2-yl)-4-(isopropylsulfonyl)phenylcarbamate;

methyl 3-((R)-1-((S)-2-(1-aminoisoquinolin-6-yloxy)-2-(3, 4-dimethoxyphenyl)acetyl)-pyrrolidin-2-yl)-4-(isopropylsulfonyl)phenylcarbamate;

methyl 3-((R)-1-((R)-2-(1-aminoisoquiuolin-6-yloxy)2-(2-fluoro-4,5-dimethoxyphenyl)acetyl)pyrrolidin-2-yl)-4-(isopropylsulfonyl)phenylcarbamate;

methyl 3-((R)-1-((S)-2-(1-aminoisoquino-6-yloxy)-2-(2-fluoro-4,5-dimethoxyphenyl)acetyl)pyrrolidin-2-yl)-4-(isopropylsalfonyl)phenylcarbamate;

(2R, 3S)-ethyl 1-((S)-2-(1-aminoisoquinolin-6-ylamino)-2-(4-chloro-3-ethoxyphenyl)acetyl)-2-(2-(ethylsulfonyl)phenyl)pyrrolidine-3-carboxylate;

(2R, 3S)-ethyl 1-((R)-2-(1-aminoisoquinolin-6-ylamino)-2-(4-chloro-3-ethoxyphenyl)acetyl)-2-(2-(ethylsulfonyl)phenyl)pyrrolidine-3-carboxylate;

(2R, 3S)-ethyl 1-((R)-2-(1-aminoisoquinolin-6-ylamino)-2-(4-fluoro-3-methoxyphenyl)acetyl)-2-(2-(ethylsulfonyl)phenyl)pyrrolidine-3-carboxylate;

(2R, 3S)-ethyl 1-((S)-2-(1-aminoisoquinolin-6-ylamino)-2-(4-fluoro-3-methoxyphenyl)acetyl)-2-(2-(ethylsulfonyl)phenyl)pyrrolidine-3-carboxylate;

(2R, 3S)-ethyl 1-((S)-2-(1-aminoisoquinolin-6-ylarnino)-2-(3-ethoxy-4-fluorophenyl)acetyl)-2-(ethylsulfonyl)phenyl)pyrrolidine-3-carboxylate;

(2R, 3S)-ethyl 1-((R)-2-(1-arninoisoquinolin-6-ylamino)-2-(3-ethoxy-4-fluorophenyl)acetyl)-2-(2-(ethylsulfonyl)phenyl)pyrrolidine-3-carboxylate;

(2R, 3S)-2-((R)-2-(1-aminoisoquinolim6-ylamino)-2-(4-chloro-3-ethoxyphenyl)acetyl)-2-(ethysulfonyl)phenyl)pyrrolidine-3-carboxylic acid;

(2R, 3S)-1-((R)-2-(1-aminoisoquinolin-6-ylamino)-2-fluoro-3-methoxyphenyl)acetyl)-2-(2-(ethylsulfonyl)phenyl)pyrrolidine-3-carboxylic acid;

(2R, 3S)-1-((R)-2-(1-aminoisoquinolin-6-ylamino)-2-(3-ethoxy-4-fluorophenyl)acetyl)-2-(2-(ethylsulfonyl)phenyl)pyrrolidine-3-carboxylic acid;

(2R, 3S)-ethyl 1-((R)-2-(1-aminoisoquinolin-6-ylamino)-2-(4-chloro-3-methoxyphenyl)acetyl)-2-(2-(ethylsulfonyl)phenyl)pyrrolidine-3-carboxylate;

(2R, 3S)-ethyl 1-((S)-2-(1-aminoisoquinolin-6-ylamino)-2-(4-chloro-3-rnethoxyphenyl)acetyl)-2-(2-(ethylsulfonyl)phenyl)pyrrolidine-3-carboxylate;

(2R, 3S)-1-((R)-2-(1-aminoisoquinolin-6-ylamino)-2-(4-chloro-3-methoxyphenyl)acetyl)-2-(2-(ethylsulfonyl)phenyl)pyrrolidine-3-carboxylic acid;

(2R, 3S)-ethyl 1-((S)-2-(1-aminoisoquinolin-6-ylamino)-2-(4-fluoro-3-rnethoxyphenyl)acetyl)-2-(2-(isopropylsulfonyl)phenyl)pyrrolidine3-carhoxylate;

(2R, 3S)-ethyl 1-((R)-2-(1-aminoisoquinolin-6-ylamino)-2-(4-fluoro-3-methoxyphenyl)acetyl)-2-(2-(isopropylsulfonyl)phenyl)pyrrolidine3-carboxylate;

(2S, 3R)-ethyl 1-((S)-2-(1-aminoisoquinolin-6-ylarnino)-2-(4chloro-3-methoxyphenyl)acetyl)-2-(2-(isopropylsulfonyl)pheny)pyrrolidine-3-carboxylate;

(2S, 3R)-ethyl 1-((R)-2-(1-aminoisoquinolin-6-ylamino)-2-(4-fluoro-3-methoxyphenyl)acetyl)-2-(2-(isopropysulfonyl)phenyl)pyrrolidine-3-carboxylate;

(2R, 3S)-ethyl 1((R)-2-(1-aminoisoquinolin-6-ylamino)-2-(4-chloro-3-methoxyphenyl)acetyl)-2-(2-(isopropylsulfony)phenyl)pyrrolidine3-carboxylate;

(2R, 3S)-ethyl 1-((R)-2-(1-aminoisoquinolin-6-ylamino)-2-(4-chloro-3-rnethoxyphenyl)acetyl)-2-(2-(isopropylsulfonyl)phenyl)pyrrolidine-3-carboxylate;

(2R, 3R)-ethyl 2(R)-2-(1-aminoisoquinolin-6-yiarnino)-2-(4-fluoro-3-methoxyphenyl)acetyl)-2-(2-(cyclopropylsulfonyl)phenyl)pyrrolidine-3-carboxylate;

(2R, 3S)-1-((R)-2-(1-aminoisoquinolin-6-ylamino)-2-(4-fluoro-3-methoxyphenyl)acetyl)-2-(2-(isopropylsulfonyl)phenyl)pyrrolidine-3-carboxylic acid;

(2S, 3R)-1-((R)-2-(1-aminoisoquinolin-6-ylamino)-2-(4-fluoro-3methoxyphenyl)acetyl)-2-(2-(isopropylsulfonyl)phenyl)pyrrolidine-3-carboxylic acid;

(2R, 3S)-1-((R)-2-(1-aminoisoquinolin-6-ylamino)-2-(4-chloro-3-methoxyphenyl)acetyl)-2-(2-(isopropylsulfonyl)phenyl)pyrrolidine-3-carboxylic acid;

(2R, 3S)-1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid;

(2R, 3R)-1-((R)-2-(1-aminoisoquinolin-6-ylamino)-2-(4-fluoro-3-rnethoxyphenyl)acetyl)-2-(2-(cyclopropylsulfonyl)phenyl)pyrrolidine-3-carboxylic acid; (2S, 3S) ((R)-2-(1-aminoisoquinolin-6-ylamino)-2-(4-fluoro-3-rnethoxyphenyl)acetyl-2-(2-(cyclopropylsulfonyl)pheny)pyrrolidine-3-carboxylic acid;

(2S, 3R)-1-((R)-2-(1-aminoisoquinolin-6-ylamino)-2-(4-fluoro-3-methoxyphenyl)acetyl)-2-(2cyclopropylsulfonyl)phenyl)pyrrolidine-3-carboxylic acid;

(2R, 3S)-1-((R)-2-(1-aminoisoquinolin-6-ylamino)-2-(3-ethoxy-4-fluorophenyl)acetyl)-2-(2-(ethylsulfonyl)phenyl)-N,N-dimethylpyrrolidine-3-carboxamide;

3-(3-((R)-1-((R)-2-(1-aminoisoquinolin-6-ylamino)-2-(4-fluoro-3-methoxyphenyl)acetyl)pyrrolidin-2-yl)-4-(isopropylsulfonyl)phenyl) 1,1-dimethylurea; and 3(3-((R)-1-((S)-2-(1-aminoisoquinolin-6-ylamino)-2-(4-fluoro-3-methoxyphenyl)acetyl)pyrrolidin-2-yl)-4-(isopropylsulfonyl)phenyl)-1,1dimethylurea; or a stereoisomer a tautomer, or a pharmaceutically acceptable salt thereof.

13. A pharmaceutical composition, comprising: a pharmaceutically acceptable carrier and a therapeutically effective amount of a compound of claim 1.

14. A pharmaceutical composition, comprising: a pharmaceutically acceptable carrier and a therapeutically effective amount of a compound of claim 5.

15. A pharmaceutical composition, comprising: a pharmaceutically acceptable carrier and a therapeutically effective amount of a compound of claim 11.

16. A pharmaceutical composition, comprising: a pharmaceutically acceptable carrier and a therapeutically effective amount of a compound of claim 12.

17. A phannaceutical composition, comprising: a pharmaceutically acceptable carrier and a therapeutically effective amount of a compound of claim 3.

18. A pharmaceutical composition, comprising: a pharmaceutically acceptable carrier and a therapeutically effective amount of a compound of claim 4.

19. A pharmaceutical composition, comprising: a pharmaceutically acceptable carrier and a therapeutically effective amount of a compound of claim 6.

20. A pharmaceutical composition, comprising: a pharmaceutically acceptable carrier and a therapeutically effective amount of a compound of claim 7.

21. A pharmaceutical composition, comprising: a pharmaceutically acceptable carrier and a therapeutically effective amount of a compound of claim 8.

22. A pharmaceutical composition, comprising: a pharmaceutically acceptable cater and a therapeutically effective amount of a compound of claim 9.

23. A pharmaceutical composition, comprising: a pharmaceutically acceptable carrier and a therapeutically effective amount of a compound of claim 10.

\* \* \* \* \*

UNITED STATES PATENT AND TRADEMARK OFFICE
CERTIFICATE OF CORRECTION

PATENT NO. : 7,622,585 B2  
APPLICATION NO. : 11/328479  
DATED : November 24, 2009  
INVENTOR(S) : Xiaojun Zhang et al.

Page 1 of 4

It is certified that error appears in the above-identified patent and that said Letters Patent is hereby corrected as shown below:

Column 2 (Other Publications) First Page  
Line 9, "Vlla" should read -- VIIa --.

Column 2 (Abstract) First Page  
Line 2, "it0"should read -- it --.

Column 242

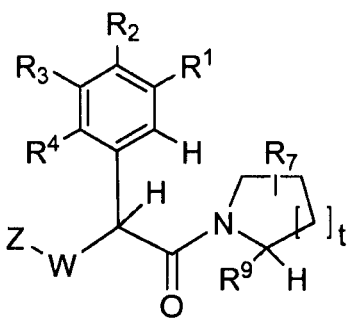

Line 5-15, " 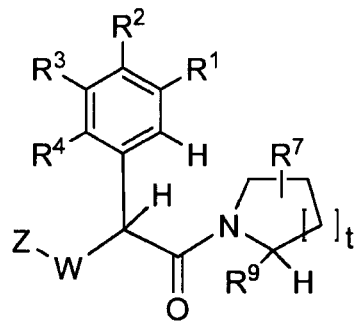 " should read -- --.

Line 48, "04" should read -- 0-4 --.

Column 249  
Line 23, "pyrrohdin" should read -- pyrrolidin --;  
Line 28, "aminoisoquinohn" should read -- aminoisoquinolin --;  
Line 31, "ylaminol)" should read -- ylamino) --;  
Line 32, "2-yI)" should read -- 2-yl) --;  
Line 38, "pyrrohdin" should read -- pyrrolidin --;  
Line 47, "aininoisoquinolin" should read -- aminoisoquinolin --;  
Line 54, "sopropoxyphenyl" should read -- isopropoxyphenyl --; and  
Line 56, "6ylamino" should read -- 6-ylamino --.

Signed and Sealed this

Twenty-ninth Day of June, 2010

David J. Kappos  
*Director of the United States Patent and Trademark Office*

Column 250
Line 2, "cthoxy" should read -- ethoxy --;
Line 7, "2isopropylsulfonyl" should read -- 2-(isopropylsulfonyl --;
Line 19, "sulfoflyl" should read -- sulfonyl --;
Line 22, "carboxylatc;" should read -- carboxylate; --;
Line 23, "6-ylarnino)" should read -- 6-ylamino) --;
Line 26, "2isopropylsulfonyl)" should read -- 2-(isopropylsulfonyl) --;
Line 44, "aminoisoquinoliu" should read -- aminoisoquinolin --.
Line 47, "6-ylarnino)" should read -- 6-ylamino) --;
Line 49, "sulfony)" should read -- sulfonyl) --;
Line 59, "(metboxycarbonyl)" should read -- (methoxycarbonyl) --;
Line 65, "arninoisoquino" should read -- aminoisoquinolin --; and
Line 66, "fluoropheny)" should read -- fluorophenyl) --.

Column 251
Line 6, "pheny)" should read -- phenyl) --;
Line 8, "phenyt)" should read -- phenyl) --;
Line 11, "pyrrolidin" should read -- pyrrolidin --;
Line 12, "phenyI)" should read -- phenyl) --;
Line 16, "1-((5)" should read -- 1-((S) --;
Line 23, "isopropoxyphenyi)" should read -- isopropoxyphenyl) --;
Line 24, "phenycarbamate;" should read -- phenylcarbamate; --;
Line 25, "3-1-" should read -- 3-((S)-1- --;
Line 27, "(isopropylsulfony)" should read -- (isopropylsulfonyl) --;
Line 28, "3-((R)-1" should read -- 3-((S)-1 --;
Line 30, "yI)" should read -- yl) --;
Line 33, "4-isopropylsulfonyl)" should read -- 4-(isopropylsulfonyl) --;
Line 33, "phenylearbamate;" should read -- phenylcarbamate; --;
Line 40, "phenylcarbamate;" should read -- phenylcarbamate; --;
Line 45, "(isopropylsuifonyl)" should read -- (isopropylsulfonyl) --;
Line 50, "aminoisoquinohn" should read -- aminoisoquinolin --;
Line 51, "methoxypheny)" should read -- methoxyphenyl) --;
Line 52, "phenycarbamate;" should read -- phenylcarbamate; --; and
Line 61, "ylarnino" should read -- ylamino --.

Column 252
Line 1, "2(-acetarnido-2" should read -- 2-(5-acetamido-2 --;
Line 5, "2-isopropylsulfonyl)" should read -- 2-(isopropylsulfonyl) --;
Line 6, "arninoisoquinolin" should read -- aminoisoquinolin --;
Line 11, "(2isopropylsulfonyl)" should read -- (2-(isopropylsulfonyl) --;
Line 14, "(isopropylsulfony)" should read -- (isopropylsulfonyl) --;
Line 17, "2-yI)" should read -- 2-yl) --;
Line 18, "6ylamino)-" should read -- 6-ylamino)- --;
Line 23, "(isopropyisulfonyl)" should read -- (isopropylsulfonyl) --;
Line 34-35, "(isopropylsuifonyl)" should read -- (isopropylsulfonyl) --;
Line 36, "aminoisoquinohn" should read -- aminoisoquinolin --;
Line 38, "sulfony)" should read -- sulfonyl) --;

CERTIFICATE OF CORRECTION (continued)
U.S. Pat. No. 7,622,585 B2

Column 252 (continued)
Line 39, "(1aminoisoquinolin" should read -- (1-aminoisoquinolin --;
Line 62, "2-amino" should read -- 2-(5-amino --;
Line 64, "(ethoxy" should read -- (5-ethoxy --;
Line 65, "2-(aminoisoquinolin" should read -- 2-(1-aminoisoquinolin --; and
Line 65, "2-yI-" should read -- 2-yl)- --.

Column 253
Line 4, "3((R)-1-((R)-2" should read -- 3-((R)-1-((S)-2 --;
Line 11, "2-(fluoro" should read -- 2-(2-fluoro --;
Line 17, "ylainino" should read -- ylamino --;
Line 17-18, "2(isopropylsulfonyl)" should read -- 2-(2-(isopropylsulfonyl) --;
Line 21, "(isopropylsulfony)" should read -- (isopropylsulfonyl) --;
Line 22, "1-((5)-2" should read -- 1-((S)-2 --;
Line 24, "(isopropylsulfonyl)" should read -- (2-(isopropylsulfonyl) --;
Line 26, "acetyi)" should read -- acetyl) --;
Line 27, "(isopropylsulfonyl)pheny)" should read -- (2-(isopropylsulfonyl)phenyl) --;
Line 34, "(isopropylsulfony)" should read -- (isopropylsulfonyl) --;
Line 35, "1-((R)-2-(1-ammnoisoquinolin" should read -- 1-((S)-2-(1-aminoisoquinolin --;
Line 43, "2-ethoxy" should read -- 2-(5-ethoxy --;
Line 43, "2-yI)-" should read -- 2-yl)- --;
Line 44, "(isopropylsulfonyt)" should read -- (isopropylsulfonyl) --;
Line 50, "(metboxycarbonyl)" should read -- (methoxycarbonyl) --;
Line 53, "pyyrrolidin" should read -- pyrrolidin --; and
Line 66, "2-yI)-" should read -- 2-yl)- --.

Column 254
Line 11, "acety)pyrroIidin" should read -- acetyl)pyrrolidin --;
Line 15, "sulfony)" should read -- sulfonyl) --;
Line 39, "fluoro" should read -- (2-fluoro --;
Line 39, "2-(ethyl" should read -- 2-(2-(ethyl --;
Line 51, "2-yI)-" should read -- 2-yl)- --;
Line 57, "4ethyl" should read -- 4-(ethyl --;
Line 60-61, "(ethylsuifonyl)" should read -- (ethylsulfonyl) --;
Line 63, "(2ethyl" should read -- (2-(ethyl --; and
Line 66, "2-ethyl" should read -- 2-(5-ethyl --.

Column 255
Line 7, "(2R, 3)" should read -- (2R, 3S) --;
Line 8, "2-(2-)ethyl" should read -- 2-(2-(ethyl --;
Line 9-12, after "acid;" delete "methyl 3-((R).......phenylcarbamate;" and insert the same on Col. 255, Line 13 as a new line;
Line 13, "1((R)" should read -- 1-((R) --;
Line 18, "2-yI)-" should read -- 2-yl)- --;
Line 33, "(3 4-" should read -- (3, 4- --;
Line 41, "aminoisoquino" should read -- aminoisoquinolin --;

Column 255 (continued)
Line 43, "(isopropylsalfonyl)" should read -- (isopropylsulfonyl) --;
Line 56, "6-ylarnino)-" should read -- 6-ylamino)- --;
Line 58, "phenyI)" should read -- phenyl) --;
Line 58, "3-carboxyIate;" should read -- 3-carboxylate; --;
Line 59, "arninoisoquinolin" should read -- aminoisoquinolin --;
Line 62, "-2-" should read -- -1- --;
Line 62, "aminoisoquinolim" should read -- aminoisoquinolin --;
Line 63, "2-(ethysulfonyl)" should read -- 2-(2-(ethylsulfonyl) --; and
Line 66, "fluoro" should read -- (4-fluoro --.

Column 256
Line 8, "rnethoxyphenyl)" should read -- methoxyphenyl) --;
Line 14, "rnethoxyphenyl)" should read -- methoxyphenyl) --;
Line 15, "pyrrolidine3-carhoxylate;" should read -- pyrrolidine-3-carboxylate; --;
Line 18, "pyrrolidine3" should read -- pyrrolidine-3 --;
Line 19, "6-ylarnino)-" should read -- 6-ylamino)- --;
Line 21, "pheny)" should read -- phenyl) --;
Line 23, "(isopropy-" should read -- (isopropyl- --;
Line 25, "1((R)" should read -- 1-((S) --;
Line 27, "sulfony)" should read -- sulfonyl) --;
Line 27, "pyrrolidine3" should read -- pyrrolidine-3 --;
Line 30, "rnethoxyphenyl)" should read -- methoxyphenyl) --;
Line 32, "ethyl 2(R)" should read -- ethyl 1-((R) --;
Line 32, "6-yiarnino)-" should read -- 6-ylamino)- --;
Line 42-43, "(isopropylsulfonyI)" should read -- (isopropylsulfonyl) --;
Line 48, "rnethoxyphenyl)" should read -- methoxyphenyl) --;
Line 49-52, "(2S, 3S) ((R)-2-(1-aminoisoquinolin-6-ylamino)-2-(4-fluoro-3-rnethoxyphenyl)acetyl-2-(2-(cyclopropylsulfonyl)pheny)pyrrolidine-3-carboxylic acid;" should read
-- (2S, 3S)-1-((R)-2-(1-aminoisoquinolin-6-ylamino)-2-(4-fluoro-3-methoxyphenyl)acetyl)-2-(2-(cyclopropylsulfonyl)phenyl)pyrrolidine-3-carboxylic acid; -- on Col. 256, Line 51 as a new line; and
Line 61, "2-yI)-" should read -- 2-yl)- --.

Column 257
Line 13, "phannaceutical" should read -- pharmaceutical --.

Column 258
Line 11, "cater" should read -- carrier --.